United States Patent
Kobayashi et al.

(10) Patent No.: US 6,451,796 B1
(45) Date of Patent: Sep. 17, 2002

(54) FUSED PYRAZINE COMPOUNDS

(75) Inventors: Kaoru Kobayashi; Tadashi Tatsumi; Kiyoyuki Sato; Hiroyuki Ohno, all of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/554,166

(22) PCT Filed: Oct. 30, 1998

(86) PCT No.: PCT/JP98/04931
§ 371 (c)(1),
(2), (4) Date: May 10, 2000

(87) PCT Pub. No.: WO99/24434
PCT Pub. Date: May 20, 1999

(30) Foreign Application Priority Data

Nov. 11, 1997 (JP) ............................................. 9-323945

(51) Int. Cl.$^7$ ..................... A01N 43/58; A61K 31/495; C07D 497/00; C07D 471/00
(52) U.S. Cl. ........................ 514/249; 514/250; 544/346; 544/350
(58) Field of Search ................................ 514/249, 250; 544/346, 350

(56) References Cited

U.S. PATENT DOCUMENTS

| | | | |
|---|---|---|---|
| 3,979,387 A | 9/1976 | Dreikorn et al. | 260/250 |
| 3,987,196 A | 10/1976 | Dreikorn | 424/250 |
| 4,160,097 A | 7/1979 | Warner, Jr. et al. | 548/346 |
| 4,191,766 A | 3/1980 | Warner, Jr. et al. | 424/250 |
| 4,191,767 A | 3/1980 | Warner, Jr. et al. | 424/250 |
| 4,198,508 A | 4/1980 | Warner, Jr. et al. | 544/346 |
| 4,200,750 A | 4/1980 | Warner, Jr. et al. | 544/346 |
| 4,254,123 A | 3/1981 | Ramm et al. | 424/250 |
| 5,095,018 A | 3/1992 | Kelley | 514/249 |
| 5,283,244 A | 2/1994 | Sakamoto et al. | 514/249 |
| 5,532,236 A | 7/1996 | Jacobsen et al. | 514/228.5 |
| 6,001,832 A | 12/1999 | Nielsen | 514/250 |

FOREIGN PATENT DOCUMENTS

| | | |
|---|---|---|
| EP | WO 95/35296 | 12/1995 |
| EP | 0705834 A1 | 10/1996 |
| FR | 2 662 163 A1 | 11/1991 |
| FR | 2662163 | 11/1991 |
| GB | 1146770 | 2/1967 |
| GB | 1235910 | 12/1968 |
| JP | 51-149299 | 12/1976 |
| JP | 51-151329 | 12/1976 |
| JP | 57 59872 | 4/1982 |
| JP | 57-59872 | 4/1982 |
| JP | 3-20276 | 1/1991 |
| JP | WO 95 35296 A | 12/1995 |
| WO | WO 94/21639 | 9/1994 |
| WO | WO 9608493 A1 | 3/1996 |

OTHER PUBLICATIONS

Ohmori, Junya et al., 8-(1H-Imidazol-1-yl)-7-nitro-4(5H)-imidazo[1,2-a]quinoxalinone and Related CompoundsL Synthesis and Structure–Activity Relationships for the AMPA–type Non–NMDA Receptor., J. Med. Chem., Jun. 1997, vol. 40, No. 13, pp. 2053–2063.

PLE, Nelly et al., A new route to aminodiazines via metalation reaction. Synthesis of an aza analog of nevirapine. Diazines. Part XV.., Synthesis, 1996, vol. 7, pp. 838–842.

Chem. Abstr. vol. 123, 1995, the abstract No. 339992, Zayed, Salem E. et al., Synthesis of some azaheterocycles condensed to and fused with quinoxaline., Mansoura J. Pharm. Sci., 1995, 11(2), 266–84.

Chem. Abstr., vol. 123, 1995, the abstract No. 9412, GAD, Laila, M., Further investigation of quinoxalines, synthesis an characterization., Mansoura J. Pharm. Sci., 1995, 10(2), 237–53.

Chem. Abstr., vol. 116, 1992, the abstract No. 59325, El–Kerdawy, M. et al., Synthesis and characterization of 1,2,4–triazolo[4,3–a]quinoxalines and 1,2,4–triazolo–s–triazines as potential antimicrobial agents., Zhonghua Yaoxue Zazhi, 1991, 43(5), 355–64.

Lippmann, E. et al., Quinoxalines. Part 28. Reactions of 3–chloroquinoxaline–2–carboxaldehyde., Z. Chem., 1990, vol. 30, No. 7, pp. 251–52.

(List continued on next page.)

*Primary Examiner*—Mukund J. Shah
*Assistant Examiner*—Tamthom N. Truong
(74) *Attorney, Agent, or Firm*—Sughrue Mion, PLLC

(57) ABSTRACT

The compound of the formula (I):

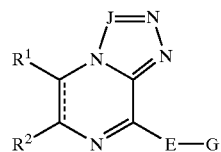

wherein all the symbols are meaning the same as descriptions of the specification; and salts thereof.

The compounds of the formula (I) have inhibitory activity of adhesion molecules expression, and are useful for prevention and/or treatment of inflammation, rheumatoid arthritis, allergies, asthma, atopic dermatitis, psoriasis, suppression of ischemia reperfusion injury, nephritis, hepatitis, multiple sclerosis, ulcerative colitis, adult respiratory distress syndrome (ARDS), suppression of transplant rejection, sepsis, diabetes, autoimmune diseases, tumor metastasis, arteriosclerosis and AIDS.

8 Claims, No Drawings

OTHER PUBLICATIONS

Sarges, Reinhard et al., 4–Amino[1,2,4]triazolo[4,3–a]quinoxalines. A novel class of potent adenosine receptor antagonists and potential rapid–onset antidepressants., J. Med. Chem., 1990, vol. 33, No. 8, pp. 2240–2254.

Vogel, M. et al., Quinoxalines. XXVII. Synthesis of bis–azolo[a,c]–fused quinoxalines. II. Synthesis from azolo[a]quinoxaline–4–carboxaldehydes., J. Prakt. Chem., 1989, vol. 331, No. 1, pp. 75–81.

Nagarajan K. et al., Displacement reactions of 2,3–dichloro–6–nitroquinoxaline: synthesis of s–triazolo[4,3–a]quinoxaline., Indian J. Chem., Sect. B, 1986, vol. 25B, No. 7, pp. 739–40.

Lippmann, Eberhard et al., Quinoxalines. XX. Synthesis and reactions of 6–nitroquinoxalines., Z. Chem., 1985, vol. 25, No. 12, p. 431.

Koren, Bozidar et al., A novel synthesis and transformations of 1H–pyrazino[2,3–e]–1,3,4–thiadiazine derivatives., Heterocycles, 1985, vol. 23, No. 4, pp. 913–25.

Campaigne, E. et al., Some 4–alkyl s–triazolo[4,3–a]quinoxalines., 1983, J. Heterocycl. Chem., vol. 20, No. 3, pp. 781–2.

Lippmann, E. et al., Synthesis and reactions of tetrazolo[1,5–a]quinoxalines., J. Prakt. Chem., 1982, vol. 324, No. 2, pp. 329–334.

Wentrup, Curt et al., Hetarylnitrenes. 7. Cyclic carbodiimides by rearrangements of nitrenes., Agnew. Chem., 1980, vol. 92, No. 7, pp. 556–557.

Polson, James B. et al., Analysis of the relation between pharmacological inhibition of cyclic nucleotide phosphodiesterase and relaxation of canine tracheal smooth muscle., Biochem. Pharmacol., 1979, vol. 28, No. 8, pp. 1391–1395.

Stoesser, R. et al., EPR and emission spectroscopy examination of quinoxalines and s–triazolo[4,3a]quinoxalines., Tetrahedron, 1978, vol. 34, No. 17, pp. 2701–2704.

Schneller, S.W. et al., Formycin analogs. I. Model studies in the preparation of an isomer of formycin and related derivatives (s–triazolo[4,3–a]pyrazines)., J. Heterocycl. Chem., 1978, vol. 15, No. 6, pp. 987–992.

Koennecke, Andreas et al., Tetrazoles. XXVI. Syntheses with tetrazolo[1,5–a]quinoxalines., Z. Chem., 1978, vol. 18, No. 7, pp. 257–258.

Chem. Abstr., vol. 88, 1978, the abstract No. 136565 No. 136565, Shadrina, L.P. et al., Studies in the field of nitrogen–containing heterocycles. III. Some reactions of 3–(2–thienyl)quinoxal–2–ones., Org. Khim., 1976, 70–2.

Bradac, Jernej et al., Telesubstitution and other transformations of imidazo[1,2–a]–and s–triazolo[4,3–a]pyrazines., 1977, J. Org. Chem., vol. 42, No. 26, pp. 4197–4201.

Chem. Abstr., vol. 87, 1977, the abstract No. 106, Barry, V.C. et al., Antitumor activity of tetrazolopyridazines and tetrazolophthalazines., Chemother., Proc. Int. Congr. Chemother., 9th, Meeting Date 1975, vol. 8, 103–6.

Chem. Abstr., vol. 86, 1977, the abstract No. 171378, Conalty, M.L. et al., Anticancer agents. XII. Pyridazine and benxodiazine derivatives., Proc. R. lr. Acad., Sect. B, 1976, 76(10), 151–63.

Yurugi, Shojiro et al., Syntheses of N–heterocyclic compounds. XVI. Reaction of fused s–triazolo derivatives. II., Takeda Kenyusho Ho, 1973, vol. 32, No. 2, pp. 111–117.

Chem. Abstr., vol. 74, 1971, the abstract No. 76394, Postovskii, I. Ya. et al., Benzodiazines. XVI. Synthesis of 2–quinoxalones, containing methoxy groups on the benzene rings., Khim. Geterotsikl. Soedin. 1970, (7), 981–5.

Chem. Abstr., vol. 71, 1969, the abstract No. 49891, Maguire, J. et al., s–Triazolopyrazines., J. Chem. Soc. C. 1969, (11), 1593–7.

Chem. Abstr., vol. 69, 1968, the abstract No. 77232, Potts, K.T. et al., 1,2,4–Triazoles. XX. Pyrolytic decomposition of ketone hydrazones derived from pyrid–2–ylhydrazine and related bases. Some further examples of the s–triazolo[4,3–a]pyrazine and s–triazolo[4,3–a]quinoxaline series., J. Heterocycl. Chem., 1968, 5(4), 485–95.

Komatsu et al.; "Inhibition of Leukocyte Adhesion to Endothelial Cells of Human Umbilical Vein by Y–24180" Int. J. Immunopharmacol., vol. 15, No. 6, 1993, pp. 737–744, XPO00983191.

Potts, K.T. et al., 1,2,4,–Triazoles. XX. Pyrolytic Decomposition of Ketone Hydrazones Derived from Pyrid–2–ylhydrazine and Related Bases. Some Further Examples of the s–Triazolo[4,3–α]pyrazine and s–Triazolo [4,3–α] quinoxaline Series (1), Chem., 1968, 5(4), 485–95.

Maguire, J. et al., s–Triazolopyrazines., J. Chem. Soc. C, 1969, (11), 1593–7.

Yurugi, Shojiro et al., Syntheses of N–Heterocyclic Compounds. XVI. Reaction of Fused s–Triazolo derivatives. II., Takeda Kenkyusho Ho, 1973, vol. 32, No. 2, pp. 111–117.

Conalty, M.L. et al., Anticancer Agents. XII. Pyridazine and Benzodiazine Derivatives., Proc. R. Ir. Acad., Sect. B, 1976, 76(10), 151–63.

Bradac, Jernej et al., Telesubstitution and Other Transformations of Imidazo [1,2–a]–and s–Triazolo [4,3–a]Pyrazines., 1977, J. Org. Chem., vol. 42, No. 26, pp. 4197–4201.

FUSED PYRAZINE COMPOUNDS

SUMMARY

This invention is related to fused pyrazine derivatives and adhesion molecules expression inhibitors containing fused pyrazine derivatives as active ingredient. More particularly, this invention is related to adhesion molecules expression inhibitors containing fused pyrazine derivatives of the formula (I):

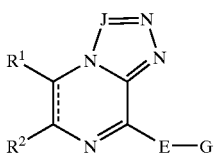

wherein all the symbols are the same meaning as hereinafter defined, and non-toxic salts thereof, and novel fused pyrazine derivatives of the above formula (I) and non-toxic salts thereof, and processes for the preparation thereof.

BACKGROUND

Cellular adhesions are basic responses in the organism and relate to various biological phenomenon deeply. In diseases, there are various examples which are mediated by excess reactions or disordered reactions. Inflammatory reaction, which protect a host from a foreign matter, is essentially one of the defensive response in the organism and it is thought that acceleration of leukocytes adhesion to endothelial cells is a central process in the early step in this reaction. Leukocytes are one of the major cells in inflammation and migrate into the inflammatory tissues and secrete chemical mediators, cytokines or enzymes and develop inflammation. Therefore, it has been thought leukocytes extravasation from the vascular flow is an important process in inflammatory development and the process, which is leukocytes-endothelial cells adhesion, is essential in the early step in transmigration.

Cellular migration is at least classified following 4 steps:
1) tethering of leukocytes to endothelial cells,
2) rolling of leukocytes,
3) firm adhesion of leukocytes to endothelial cells,
4) transmigration of leukocytes.

Recently, it has been reported these various cellular adhesions are mediated by cell surface molecular groups which are called adhesion molecules and explained the distinct molecular groups specifically play a central role in the previous each adhesion step. That is to say, it has been explained tethering and rolling process are induced by interaction of carbohydrate and selectin, such as E-selectin, and subsequent firm adhesion and extravasation processes are mediated by interaction of integrin family on leukocytes and immunoglobulin superfamily, such as ICAM-1 (Intercellular Adhesion Molecule-1) and VCAM-1 (Vascular Cell Adhesion Molecule-1).

Any of endothelial adhesion molecules which are E-selectin, VCAM-1 and ICAM-1 are induced molecules stimulated by inflammatory cytokines, such as TNF and IL-1. In fact, it has been reported that these adhesion molecules expression are upregulated in the various lesional sites. Therefore the upregulation of adhesion molecules develops cellular adhesion and participates in disease formation, such as chronic inflammation.

It has been suggested these cellular adhesions to endothelial cells participate not only inflammatory reaction but also tumor metastasis, allergic reaction and immune reaction. Furthermore, the reports which showed the upregulation of VCAM-1 and the increase of ICAM-1 concentration in HIV infected patients have suggested the relation between adhesion molecules expression and HIV infection [Clinical Immunology and Immunopathology, 81, 6–21 (1996)].

From these viewpoints, it is expected the inhibition of adhesion molecules expression which are E-selectin, VCAM-1 and ICAM-1 suppresses the cellular adhesion and links the treatment for various diseases.

The present invitation provides a useful new therapeutic agent which has inhibitory activity on these adhesion molecules expression According to a further aspect, the present invitation provides the use of the compounds for treatment and/or prevention of disorders mediated by cellular adhesion and infiltration, such as inflammation, rheumatoid arthritis, allergies, asthma, atopic dermatitis, psoriasis, suppression of ischemia reperfusion injury, nephritis, hepatitis, multiple sclerosis, ulcerative colitis, adult respiratory distress syndrome (ARDS), suppression of transplant rejection, sepsis, diabetes, autoimmune diseases, tumor metastasis, arteriosclerosis and AIDS [The Hand Book of Immunopharmacology, Adhesion Molecule, Academic Press, (1994), Trends in Pharmacological Science 16, 418–423, (1995), Molecular Medicine Today, 3, 418–423 (1997), Molecular Medicine Today, 3, 310–321 (1997), Japanese Journal of Inflammation, 17, 459–467 (1997)].

For example, 1,2,4-triazolo-[4,3-a]pyrazine derivatives of the formula (X):

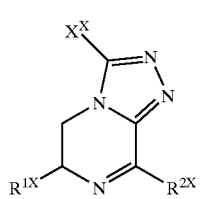

in the specification of GB 1235910,
and the formula (Y):

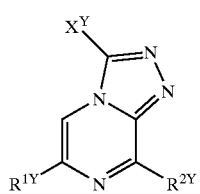

in the specification of GB 1146770, are disclosed to be useful as treatment of bronchial disorder.

In the specification of U.S. Pat. Nos. 4,200,750, 4,198, 508, 4,191,767, 4,191,766, BE 878028 and BE 862608, imidazo-[1,2-a]quinoxaline derivatives are disclosed to be useful as immunosuppressants, anti-inflammatory agents, antifungal agents, antiyeast agents, treatment of bronchial disorder.

Besides, in the specification of WO 9535296, fused imidazole derivatives of the formula (Z):

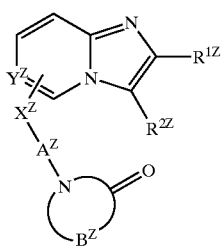

are disclosed to have an inhibitory activity of adhesion molecules expression.

DISCLOSURE OF THE INVENTION

Energetic investigations have been carried out in order to make adhesion molecules expression inhibitors. The present inventors have found that fused pyrazine derivatives of the formula (I) accomplished the present purpose.

Fused pyrazine derivatives of the formula (I) of the present invention are not known as adhesion molecules expression inhibitors at all. Besides, a lot of fused pyrazine derivatives of the formula (I) are novel compounds.

The present invention is related to:
(i) adhesion molecules expression inhibitors containing fused pyrazine derivatives of the formula (I):

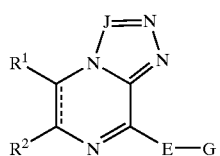

wherein $R^1$ and $R^2$ each, independently, is (i) hydrogen, (ii) C1–8 alkyl, (iii) C1–8 alkoxy, (iv) C1–8 alkylthio, (v) Cyc1, (vi) nitrile, (vii) formyl, (viii) —COOR$^{14}$, in which R$^{14}$ is hydrogen or C1–8 alkyl, (ix) —CONR$^{15}$R$^{16}$, in which R$^{15}$ and R$^{16}$ each, independently, is hydrogen, C1–8 alkyl or phenyl, (x) C1–8 alkyl or C2–8 alkenyl substituted by 1 or 2 of hydroxy, C1–4 alkoxy, phenoxy, halogen atom, nitrile, C2–5 acyl, —COOR$^{14}$, —CONR$^{15}$R$^{16}$, or —NR$^{17}$R$^{18}$, in which R$^{17}$ and R$^{18}$ each, independently, is hydrogen, C1–8 alkyl or acetyl, (xi) C1–8 alkyl, C1–8 alkoxy or C1–8 alkylthio substituted by Cyc1, or $R^1$ and $R^2$, taken together with carbon atoms which are attached to each of them, is

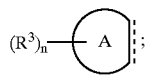

in which Cyc1 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —NR$^{101}$R$^{102}$, in which R$^{101}$ and R$^{102}$ each, independently, is hydrogen or C1–8 alkyl, (ix) —COOR$^{103}$, in which R$^{103}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —NR$^{101}$R$^{102}$ or —COOR$^{103}$;

is C3–7 mono-carbocyclic ring or 3–7 membered mono-heterocyclic ring containing 1–4 of nitrogen(s), 1–2 of oxygen(s) and/or 1 of sulfur;

$R^3$ is
1) hydrogen,
2) C1–8 alkyl,
3) C2–8 alkenyl,
4) C1–8 alkoxy,
5) C1–8 alkylthio,
6) halogen atom,
7) nitro,
8) cyano,
9) hydroxy,
10) formyl,
11) C2–5 acyl,
12) —NR$^4$R$^5$, in which R$^4$ and R$^5$ each, independently, is hydrogen, C1–8 alkyl or acetyl,
13) —COOR$^6$, in which R$^6$ is hydrogen or C1–8 alkyl,
14) —CONR$^{19}$R$^{20}$, in which R$^{19}$ and R$^{20}$ each, independently, is hydrogen, C1–8 alkyl, phenyl, or C1–4 alkyl substituted by hydroxy, 5–7 membered mono-heterocyclic ring containing 1–2 of nitrogen (s), or 1 of nitrogen and 1 of oxygen, or R$^{19}$ and R$^{20}$, taken together is =CH—NR$^{21}$R$^{22}$, in which R$^{21}$ and R$^{22}$ each, independently, is hydrogen or C1–4 alkyl,
15) trihalomethyl,
16) trihalomethoxy,
17) phenyl,
18) phenyloxy,
19) phenylthio, or
20) C1–8 alkyl, C1–8 alkoxy, C1–8 alkylthio or C1–8 alkylamino substituted by phenyl, or
21) C1–8 alkyl or C2–8 alkenyl substituted by 1 or 2 of hydroxy, C1–4 alkoxy, phenoxy, halogen atom, nitrile, C2–5 acyl, —COOR$^6$, —CONR$^{19}$R$^{20}$ or —NR$^4$R$^5$;

n is 0 or 1–5;

J is nitrogen atom or C—R$^7$;

R$^7$ is
1) hydrogen,
2) C1–8 alkyl,
3) Cyc2,
4) C1–8 alkyl substituted by Cyc2,
5) C1–8 alkyl or C1–8 alkoxy substituted by 1–17 of halogen atom, or
6) halogen atom,
  in which Cyc2 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —NR$^{201}$R$^{202}$, in which R$^{201}$ and R$^{202}$ each, independently, is hydrogen or C1–8 alkyl, (ix) —COOR$^{203}$, in which R$^{203}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —NR$^{201}$R$^{202}$ or —COOR$^{203}$;

E is a single bond, C1–4 alkylene, oxygen atom, sulfur atom, —SO—, —SO$_2$—, C1–4 alkylene-M—, with the proviso that alkylene bond to ring and M is bond to G;

M is oxygen atom, sulfur atom, —SO—, —SO$_2$—;

G is
1) C1–8 alkyl,
2) C2–8 alkenyl,
3) C2–8 alkynyl,
4) Cyc3, or
5) C1–8 alkyl substituted by —OR$^8$, —SR$^8$, —NR$^9$R$^{10}$, —COR$^{11}$ or Cyc3, with the proviso that (i) one carbon atom in C1–8 alkyl, which is a component atom of cycloalkyl, may represent 3–7 membered cycloalkyl, or (ii) neighboring two carbon atom in C1–8 alkyl, which are component atoms of cycloalkyl, may represent 3–7 membered cycloalkyl;
in which Cyc3 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —NR$^{301}$R$^{302}$, in which R$^{301}$ and R$^{302}$ each, independently, is hydrogen or C1–8 alkyl, (ix) —COOR$^{303}$, in which R$^{303}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —NR$^{301}$R$^{302}$ or —COOR$^{303}$;

R$^8$ is hydrogen, C1–8 alkyl, C2–8 alkenyl, C1–8 alkyl substituted by phenyl or C1–8 alkoxy, or —S—(C1–8 alkylene)-OR$^{23}$, in which R$^{23}$ is hydrogen or C1–8 alkyl; with the proviso that (i) one carbon atom in C1–8 alkylene, which is a component atom of cycloalkyl, may represent 3–7 membered cycloalkyl, or (ii) neighboring two carbon atom in C1–8 alkylene, which are component atoms of cycloalkyl, may represent 3–7 membered cycloalkyl;

R$^9$ is hydrogen, C1–8 alkyl, C2–8 alkenyl, C1–8 alkyl substituted by phenyl or C1–8 alkoxy;

R$^{10}$ is hydrogen, C1–8 alkyl, C2–8 alkenyl, C1–8 alkyl substituted by phenyl, or C2–5 acyl;

R$^{11}$ is (i) C1–8 alkyl, (ii) C1–8 alkoxy, (iii) hydroxy, (iv) C1–8 alkyl or C1–8 alkoxy substituted by phenyl, or (v) —NR$^{12}$R$^{13}$, in which R$^{12}$ and R$^{13}$ each, independently, is hydrogen, C1–8 alkyl or C1–8 alkyl substituted by phenyl; === is a single bond or a double bond;

with the proviso that the compounds in which R$^2$ is C1–8 alkyl, E is a single bond or C1–4 alkylene and G is C1–8 alkyl are excluded;

or non-toxic acid thereof as active ingredient, (ii) novel fused pyrazine derivatives of the formula (I):

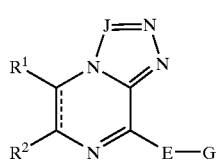

(I)

wherein R$^1$ and R$^2$ each, independently, is (i) hydrogen, (ii) C1–8 alkyl, (iii) C1–8 alkoxy, (iv) C1–8 alkylthio, (v) Cyc$_1$, (vi) nitrile, (vii) formyl, (viii) —COOR$^{14}$, in which R$^{14}$ is hydrogen or C1–8 alkyl, (ix) —CONR$^{15}$R$^{16}$, in which R$^{15}$ and R$^{16}$ each, independently, is hydrogen, C1–8 alkyl or phenyl, (x) C1–8 alkyl or C2–8 alkenyl substituted by 1 or 2 of hydroxy, C1–4 alkoxy, phenoxy, halogen atom, nitrile, C2–5 acyl, —COOR$^{14}$, —CONR$^{15}$R$^{16}$, or —NR$^{17}$R$^{18}$, in which R$^{17}$ and R$^{18}$ each, independently, is hydrogen, C1–8 alkyl or acetyl, (xi) C1–8 alkyl, C1–8 alkoxy or C1–8 alkylthio substituted by Cyc1, or R$^1$ and R$^2$, taken together with carbon atoms which are attached to each of them, is

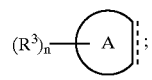

in which Cyc1 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —NR$^{101}$R$^{102}$, in which R$^{101}$ and R$^{102}$ each, independently, is hydrogen or C1–8 alkyl, (ix) —COOR$^{103}$, in which R$^{103}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —NR$^{101}$R$^{102}$ or —COOR$^{103}$;

is C3–7 mono-carbocyclic ring or 3–7 membered mono-heterocyclic ring containing 1–4 of nitrogen(s), 1–2 of oxygen(s) and/or 1 of sulfur;

R$^1$ is
1) hydrogen,
2) C1–8 alkyl,
3) C2–8 alkenyl,
4) C1–8 alkoxy,
5) C1–8 alkylthio,
6) halogen atom,
7) nitro,
8) cyano,
9) hydroxy,
10) formyl,
11) C2–5 acyl,
12) —NR$^4$R$^5$, in which R$^4$ and R$^5$ each, independently, is hydrogen, C1–8 alkyl or acetyl,
13) —COOR$^6$, in which R$^6$ is hydrogen or C1–8 alkyl,
14) —CONR$^{19}$R$^{20}$, in which R$^{19}$ and R$^{20}$ each, independently, is hydrogen, C1–8 alkyl, phenyl, or C1–4 alkyl substituted by hydroxy, 5–7 membered mono-heterocyclic ring containing 1–2 of nitrogen(s), or 1 of nitrogen and 1 of oxygen, or R$^{19}$ and R$^{20}$, taken together is =CH—NR$^{21}$R$^{22}$, in which R$^{21}$ and R$^{22}$ each, independently, is hydrogen or C1–4 alkyl,
15) trihalomethyl,
16) trihalomethoxy,
17) phenyl,
18) phenyloxy,
19) phenylthio, or
20) C1–8 alkyl, C1–8 alkoxy, C1–8 alkylthio or C1–8 alkylamino substituted by phenyl, or
21) C1–8 alkyl or C2–8 alkenyl substituted by 1 or 2 of hydroxy, C1–4 alkoxy, phenoxy, halogen atom, nitrile, C2–5 acyl, —COOR$^6$, —CONR$^{19}$R$^{20}$ or —NR$^4$R$^5$;

n is 0 or 1–5;
J is nitrogen atom or C—$R^7$;
$R^7$ is
1) hydrogen,
2) C1–8 alkyl,
3) Cyc2,
4) C1–8 alkyl substituted by Cyc2,
5) C1–8 alkyl or C1–8 alkoxy substituted by 1–17 of halogen atom, or
6) halogen atom,
   in which Cyc2 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —$NR^{201}R^{202}$, in which $R^{201}$ and $R^{202}$ each, independently, is hydrogen or C1–8 alkyl, (ix) —$COOR^{203}$, in which $R^{203}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —$NR^{201}R^{202}$ or —$COOR^{203}$;
E is a single bond, C1–4 alkylene, oxygen atom, sulfur atom, —SO—, —$SO_2$—, C1–4 alkylene-M—, with the proviso that alkylene bond to ring and M is bond to G;
M is oxygen atom, sulfur atom, —SO—, —$SO_2$—;
G is
1) C1–8 alkyl,
2) C2–8 alkenyl,
3) C2–8 alkynyl,
4) Cyc3, or
5) C1–8 alkyl substituted by —$OR^8$, —$SR^8$, —$NR^9R^{10}$, —$COR^{11}$ or Cyc3, with the proviso that (i) one carbon atom in C1–8 alkyl, which is a component atom of cycloalkyl, may represent 3–7 membered cycloalkyl, or (ii) neighboring two carbon atom in C1–8 alkyl, which are component atoms of cycloalkyl, may represent 3–7 membered cycloalkyl;
   in which Cyc3 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —$NR^{301}R^{302}$, in which $R^{301}$ and $R^{302}$ each, independently, is hydrogen or C1–8 alkyl, (ix) —$COOR^{303}$, in which $R^{303}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —$NR^{301}R^{302}$ or —$COOR^{303}$;
$R^8$ is hydrogen, C1–8 alkyl, C2–8 alkenyl, C1–8 alkyl substituted by phenyl or C1–8 alkoxy, or —S—(C1–8 alkylene)-$OR^{23}$, in which $R^{23}$ is hydrogen or C1–8 alkyl; with the proviso that (i) one carbon atom in C1–8 alkylene, which is a component atom of cycloalkyl, may represent 3–7 membered cycloalkyl, or (ii) neighboring two carbon atom in C1–8 alkylene, which are component atoms of cycloalkyl, may represent 3–7 membered cycloalkyl;
$R^9$ is hydrogen, C1–8 alkyl, C2–8 alkenyl, C1–8 alkyl substituted by phenyl or C1–8 alkoxy;

$R^{10}$ is hydrogen, C1–8 alkyl, C2–8 alkenyl, C1–8 alkyl substituted by phenyl, or C2–5 acyl;
$R^{11}$ is (i) C1–8 alkyl, (ii) C1–8 alkoxy, (iii) hydroxy, (iv) C1–8 alkyl or C1–8 alkoxy substituted by phenyl, or (v) —$NR^{12}R^{13}$, in which $R^{12}$ and $R^{13}$ each, independently, is hydrogen, C1–8 alkyl or C1–8 alkyl substituted by phenyl; === is a single bond or a double bond;
with the proviso that the compounds in which $R^2$ is C1–8 alkyl, E is a single bond or C1–4 alkylene and G is C1–8 alkyl and the following compounds of (1)–(14) are excluded;
(1) 4-(4-Chlorophenyl)thio(1,2,4-triazolo)-[4,3-a]quinoxaline,
(2) 4-(Pyrimidine-2-yl)thio(1,2,4-triazolo)-[4,3-a]quinoxaline,
(3) 4-Methoxycarbonylmethylthio(5-methyl-1,2,4-triazolo)-[4,3-a]quinoxaline,
(4) 4-Phenylthio-8-chloro(5-trifluoromethyl-1,2,4-triazolo)-[4,3-a]quinoxaline,
(5) 4-Phenylmethylthio(1,2,4-triazolo)-[4,3-a]quinoxaline,
(6) 4-(2-Chlorophenyl)thio(1,2,4-triazolo)-[4,3-a]quinoxaline,
(7) 4-(4-Methoxyphenyl)thio(1,2,4-triazolo)-[4,3-a]quinoxaline,
(8) 4-Allylthio(1,2,4- triazolo)-[4,3-a]quinoxaline,
(9) 4-(4-Chlorophenyl)thio(5-trifluoromethyl-1,2,4-triazolo)-[4,3-a]quinoxaline,
(10) 4-Phenylmethylthio(5-trifluoromethyl-1,2,4-triazolo)-[4,3-a]quinoxaline,
(11) 4-(Pyridin-2-yl)thio(5-trifluoromethyl-1,2,4-triazolo)-[4,3-a]quinoxaline,
(12) 4-Phenylthio(5-trifluoromethyl-1,2,4-triazolo)-[4,3-a]quinoxaline,
(13) 4-(4-Methoxyphenyl)thio(5-trifluoromethyl-1,2,4-triazolo)-[4,3-a]quinoxaline, and
(14) 4-Phenyl(5-methyl-1,2,4-triazolo)-[4,3-a]quinoxaline;
or non-toxic salts thereof, and
(iii) a process for the preparation of fused pyrazine derivatives of the formula (I) and non-toxic salts thereof.

DETAILED DESCRIPTION OF INVENTION

Unless otherwise specified, all isomers are included in the present invention. For example, alkyl, alkoxy and alkylene include straight and branched isomers. Double bond in alkenylene includes structure of configurations E, Z and EZ mixture. Isomers resulting from the presence of asymmetric carbon(s) e.g. branched alkyl, alkoxy and alkylene are also included within the present invention.

In the present invention, C1–4 alkyl is methyl, ethyl, propyl, butyl and isomeric groups thereof.

C1–8 alkyl is methyl, ethyl, propyl, butyl, pentyl, hexyl, heptyl, octyl and isomeric groups thereof.

C1–8 alkoxy is methoxy, ethoxy, propoxy, butoxy, pentyloxy, hexyloxy, heptyloxy, octyloxy and isomeric groups thereof.

C1–8 alkylthio is methylthio, ethylthio, propylthio, butylthio, pentylthio, hexylthio, heptylthio, octylthio and isomeric groups thereof.

Halogen atom is chlorine, bromine, fluorine, or iodine.

Trihalomethyl is methyl tri-substituted by chlorine, bromine, fluorine, or iodine.

Trihalomethoxy is methoxy tri-substituted by chlorine, bromine, fluorine, or iodine.

C1–8 alkylamino is methylamino, ethylamino, propylamino, butylamino, pentylamino, hexylamino, heptylamino, octylamino and isomeric groups thereof.

C1–8 alkyl substituted by 1–17 of halogen atom is methyl, ethyl, propyl, butyl, pentyl, hexyl, heptyl, octyl and isomeric groups thereof substituted by 1–17 of chlorine, bromine, fluorine, or iodine.

C1–8 alkoxy substituted by 1–17 of halogen atom is methoxy, ethoxy, propoxy, butoxy, pentyloxy, hexyloxy, heptyloxy, octyloxy and isomeric groups thereof substituted by 1–17 of chlorine, bromine, fluorine, or iodine.

C1–4 alkylene is methylene, ethylene, trimethylene, tetramethylene and isomeric groups thereof.

C2–8 alkenyl is vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and isomeric groups thereof.

C2–8 alkynyl is ethynyl, propynyl, butynyl, pentynyl, hexynyl, heptynyl, octynyl and isomeric groups thereof.

C2–5 acyl is acetyl, propionyl, butyryl, pentanoyl and isomeric groups thereof.

C3–7 mono-carbocyclic ring is, for example, cyclopropane, cyclobutane, cyclopentane, cyclohexane, cycloheptane, cyclopentene, cyclohexene, cyclopentadiene, cyclohexadiene, benzene.

3–7 membered mono-heterocyclic ring containing 1–4 of nitrogen(s), 1–2 of oxygen(s) and/or 1 of sulfur is 3–7 membered mono-heterocyclic aryl containing 1–4 of nitrogen(s), 1–2 of oxygen(s) and/or 1 of sulfur, partially or fully saturated thereof.

3–7 membered mono-heterocyclic aryl containing 1–4 of nitrogen(s), 1–2 of oxygen(s) and 1 or 1 of sulfur is, for example, pyrrole, imidazole, triazole, tetrazole, pyrazole, pyridine, pyrazine, pyrimidine, pyridazine, azepine, diazepine, furan, pyran, oxepin, oxazepine, thiophene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine.

Partially or fully saturated 3–7 membered mono-heterocyclic ring containing 1–4 of nitrogen(s), 1–2 of oxygen(s) and/or 1 of sulfur is, for example, oxirane, aziridine, azetidine, pyrroline, pyrrolidine, imidazoline, imidazolidine, triazoline, triazolidine, tetrazoline, tetrazolidine, pyrazoline, pyrazolidine, piperidine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, oxolane, oxane.

C3–15 mono-, bi- or tri-carbocyclic ring is, for example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene.

5–18 membered mono-, bi- or tri-heterocyclic ring containing 1–4 of nitrogen(s), 1–2 of oxygen(s) and/or 1 of sulfur is 5–18 membered mono-, bi- or tri-heterocyclic aryl containing 1–4 of nitrogen(s), 1–2 of oxygen(s) and/or 1 of sulfur, partially or fully saturated thereof.

5–18 membered mono-, bi- or tri-heterocyclic aryl containing 1–4 of nitrogen(s), 1–2 of oxygen(s) and/or 1 of sulfur, is, for example, pyrrole, imidazole, triazole, tetrazole, pyrazole, pyridine, pyrazine, pyrimidine, pyridazine, azepine, diazepine, furan, pyran, oxepin, oxazepine, thiophene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, carbazole or acridine.

Partially or fully saturated 5–18 membered mono-, bi- or tri-heterocyclic ring containing 1–4 of nitrogen(s), 1–2 of oxygen(s) and/or 1 of sulfur, for example, pyrroline, pyrrolidine, imidazoline, imidazolidine, triazoline, triazolidine, tetrazoline, tetrazolidine, pyrazoline, pyrazolidine, piperidine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, oxolane, oxane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, benzoxazepine, benzoxadiazepine, benzothiazepine, benzothiadiazepine, benzoazepine, benzodiazepine, indolooxazepine, indolotetrahydrooxazepine, indolooxadiazepine, indolotetrahydrooxadiazepine, indolothiazepine, indolotetrahydrothiazepine, indolothiadiazepine, indolotetrahydrothiadiazepine, indoloazepine, indolotetrahydroazepine, indolodiazepine, indolotetrahydrodiazepine, benzofurazan, benzothiadiazole, benzotriazole, camphor, imidazothiazole, dihydrocarbazole, tetrahydrocarbazole, perhydrocarbazole, dihydroacridine, tetrahydroacridine, perhydroacridine.

5–7 membered mono-heterocyclic ring containing 1–2 of nitrogen(s), or 1 of nitrogen and 1 of oxygen is, for example, pyrrole, pyrroline, pyrrolidine, imidazole, pyrazole, imidazoline, imidazolidine, pyrazoline, pyrazolidine, pyridine, pyridazine, pyrimidine, pyrazine, piperidine, piperazine, oxazole, isoxazole, oxazine, morpholine.

C3–7 cycloalkyl represented by one carbon atom in C1–8 alkyl or C1–8 alkylene, which is a component atom of cycloalkyl, is, for example, in case of C2 alkyl or alkylene,

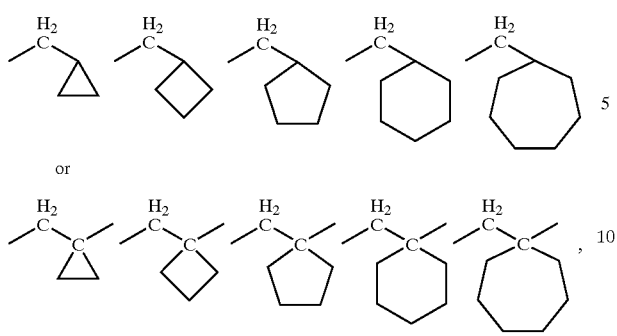

in case of C3 alkyl or alkylene,

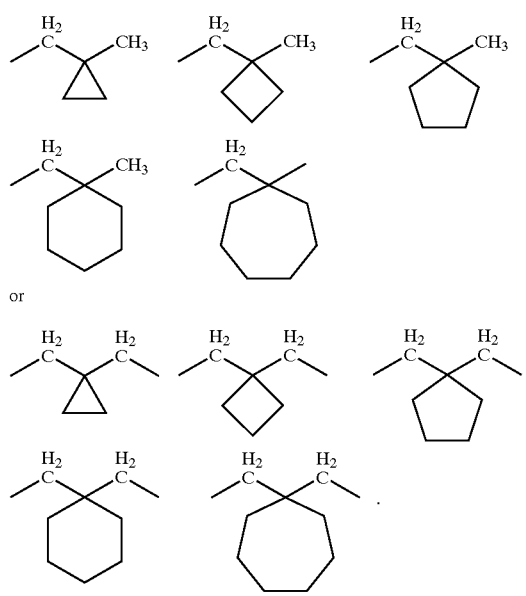

C3–7 cycloalkyl represented by neighboring two carbon atoms in C1–8 alkyl or C1–8 alkylene, which is component atoms of cycloalkyl, is, for example, in case of C4 alkyl or alkylene,

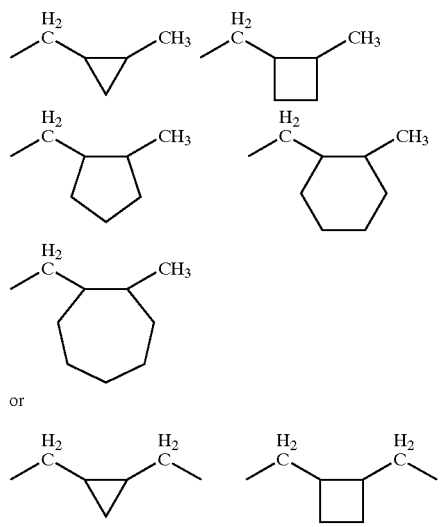

-continued

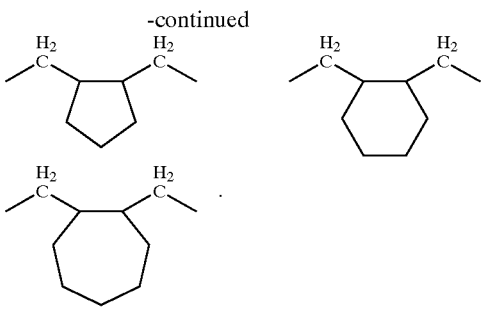

Salts

Non-toxic salts of the present invention include all pharmaceutically acceptable salts, for example, general salts, acid addition salts, hydrate salts.

The compounds of formulae (I) of the present invention may be converted into the corresponding salts. Non-toxic salts and water-soluble salts are preferred. Suitable salts, for example, include: salts of alkali metals (e.g. potassium, sodium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine).

The compounds of formulae (I) may be converted into the corresponding acid addition salts. Non-toxic acid addition salts and water-soluble acid addition salts are preferred. Suitable salts, for example, include: salts of inorganic acids e.g. hydrochloride, hydrobromide, sulfate, phosphate, nitrate; salts of organic acids e.g. acetate, trifluoroacetate, lactate, tartarate, oxalate, fumarate, maleate, citrate, benzoate, methanesulphonate, ethanesulphonate, benzenesulphonate, toluenesulphonate, isethionate, glucuronate, gluconate.

The compounds of formulae (I) and salts thereof may be converted into the corresponding hydrates by conventional means.

In the compounds of the present invention of formulae (1), the following compounds of the formulae are preferred:

the formula (I-A):

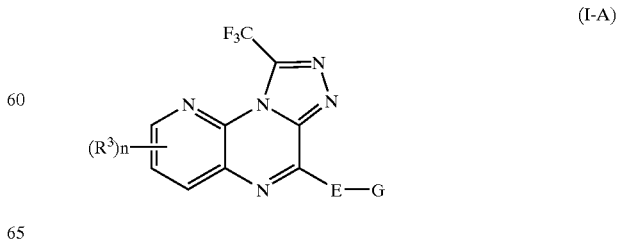

wherein all the symbols are as hereinbefore defined;

the formula (I-B):

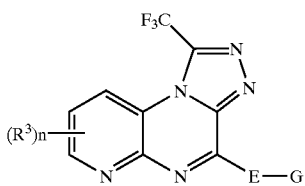
(I-B)

wherein all the symbols are as hereinbefore defined;

the formula (I-C):

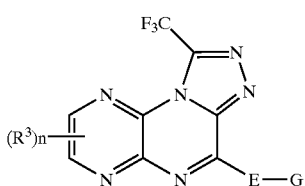
(I-C)

wherein all the symbols are as hereinbefore defined;

the formula (I-D):

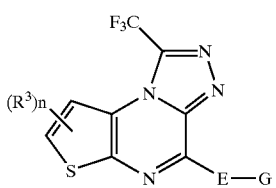
(I-D)

wherein all the symbols are as hereinbefore defined;

the formula (I-E):

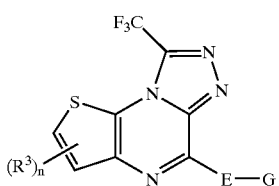
(I-E)

wherein all the symbols are as hereinbefore defined;

the formula (I-F):

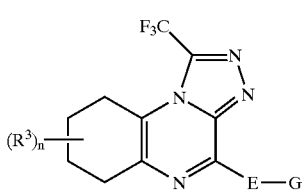
(I-F)

wherein all the symbols are as hereinbefore defined;

the formula (I-G):

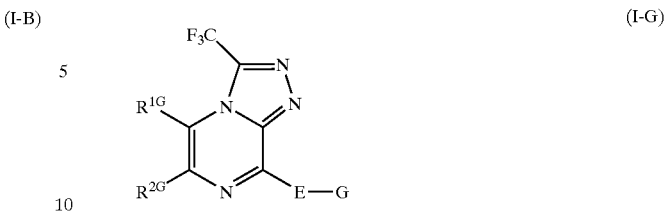
(I-G)

wherein $R^{1G}$ and $R^{2G}$ each, independently, is (i) hydrogen, (ii) C1–8 alkyl, (iii) C1–8 alkoxy, (iv) C1–8 alkylthio, (v) Cyc1, (vi) nitrile, (vii) formyl, (viii) —COOR$^{14}$, (ix) —CONR$^{15}$R$^{16}$, (x) C1–8 alkyl or C2–8 alkenyl substituted by 1 or 2 of hydroxy, C1–4 alkoxy, phenoxy, halogen atom, nitrile, C2–5 acyl, —COOR$^{14}$, —CONR$^{15}$R$^{16}$, or —NR$^{17}$R$^{18}$, (xi) C1–8 alkyl, C1–8 alkoxy or C1–8 alkylthio substituted by Cyc1, and the other symbols are as hereinbefore defined;

the formula (I-H):

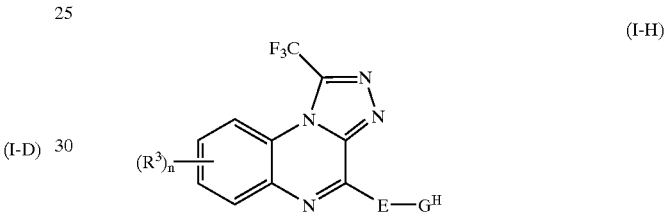
(I-H)

wherein $G^H$ is substituted or unsubstituted C3–15 mono-, bi- or tri-carbocyclic ring, and the other symbols are as hereinbefore defined;

the formula (I-J):

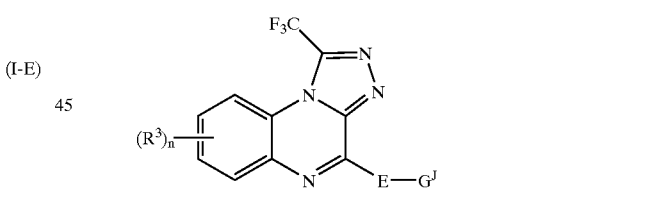
(I-J)

wherein $G^J$ is C1–8 alkyl, and the other symbols are as hereinbefore defined;

the formula (I-K):

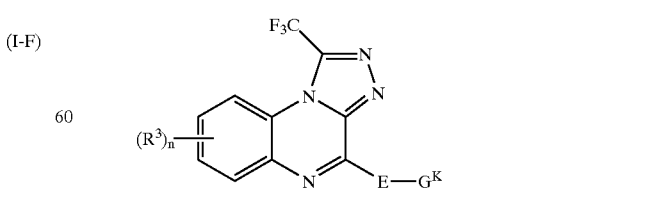
(I-K)

wherein $G^K$ is C1–8 alkyl substituted by hydroxy, and the other symbols are as hereinbefore defined;

the formula (I-L):

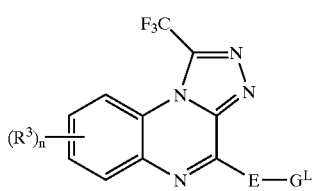

wherein $G^L$ is substituted or unsubstituted 5–18 membered mono-, bi- or tri-heterocyclic ring containing 1–4 of nitrogen(s), 1 of oxygen and/or 1 of sulfur, and the other symbols are as hereinbefore defined.

The following compounds, the compounds described in Table 1–Table 15 and the compounds described in the Examples or non-toxic salts thereof are more preferred.

The following known compounds of (1)–(14) are on the market, but they are not known as adhesion molecules expression inhibitors at all.

Compound (1):

4-(4-Chlorophenyl)thio(1,2,4-triazolo)-[4,3-a]quinoxaline (Bionet; a catalog No. 10E-957)

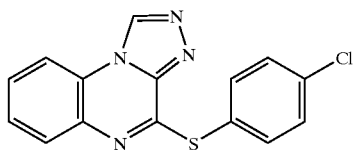

Compound (2):

4-(Pyrimidine-2-yl)thio(1,2,4-triazolo)-[4,3-a]quinoxaline (Bionet; a catalog No. 11E-909)

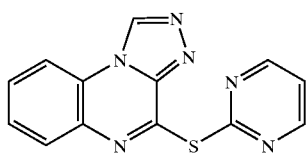

Compound (3):

4-Methoxycarbonylmethylthio(5-methyl-1,2,4-triazolo)-[4,3-a]quinoxaline (Bionet; a catalog No. 12E-941)

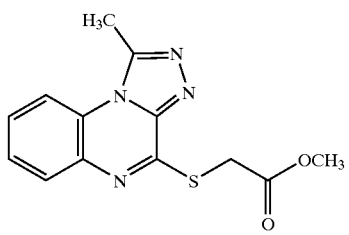

Compound (4):

4-Phenylthio-8-chloro(5-trifluoromethyl-1,2,4-triazolo)-[4,3-a]quinoxaline (Bionet; a catalog No. 12E-954)

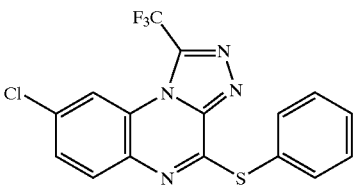

Compound (5):

4-Phenylmethylthio(1,2,4-triazolo)-[4,3-a]quinoxaline (Bionet; a catalog No. 4G-912)

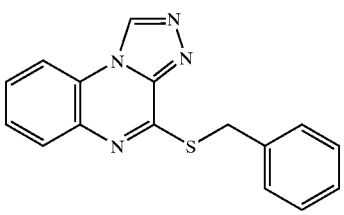

Compound (6):

4-(2-Chlorophenyl)thio(1,2,4-triazolo)-[4,3-a]quinoxaline (Bionet; a catalog No. 4G-913)

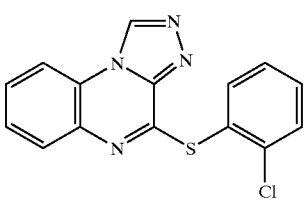

Compound (7):

4-(4-Methoxyphenyl)thio(1,2,4-triazolo)-[4,3-a]quinoxaline (Bionet; a catalog No. 4G-914)

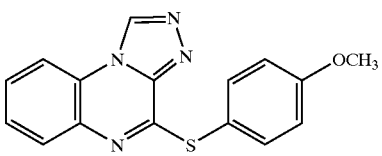

Compound (8):

4-Allylthio(1,2,4-triazolo)-[4,3-a]quinoxaline (Bionet; a catalog No. 4G-922)

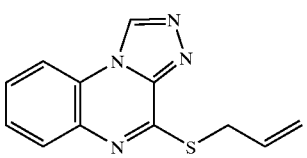

Compound (9):
4-(4-Chlorophenyl)thio(5-trifluoromethyl-1,2,4-triazolo)-[4,3-a]quinoxaline (Bionet a catalog No. 4G-937)

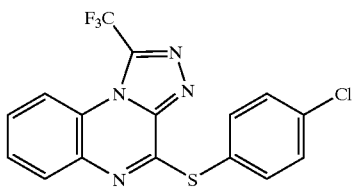

Compound (10):
4-Phenylmethylthio(5-trifluoromethyl-1,2,4-triazolo)-[4,3-a]quinoxaline (Bionet; a catalog No. 4G-938)

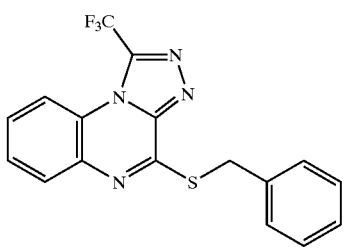

Compound (11):
4-(Pyridin-2-yl)thio(5-trifluoromethyl-1,2,4-triazolo)-[4,3-a]quinoxaline (Bionet; a catalog No. 4G-943)

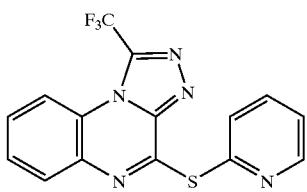

Compound (12):
4-Phenylthio(5-trifluoromethyl-1,2,4-triazolo)-[4,3-a]quinoxaline (Bionet; a catalog No. 4G-944)

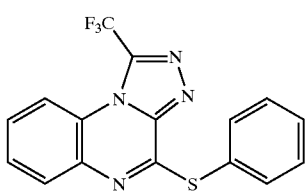

Compound (13):
4-(4-Methoxyphenyl)thio(5-trifluoromethyl-1,2,4-triazolo)-[4,3-a]quinoxaline (Bionet; a catalog No. 4G-945)

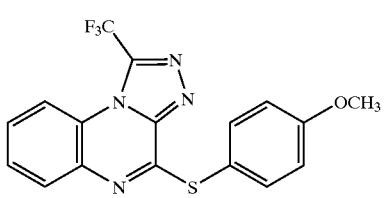

Compound (14):
4-Phenyl(5-methyl-1,2,4-triazolo)-[4,3-a]quinoxaline (Labotest; a catalog No. LT-2 VO 14)

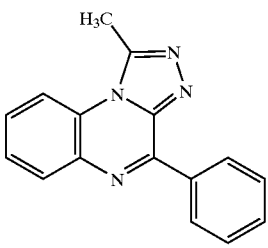

TABLE 1-1

(I-A1)

| No. | R³ | —E—G |
|---|---|---|
| 1 | H | —S—phenyl |
| 2 | H | —S—isobutyl |
| 3 | H | —S—CH₂CH₂CH₂OH |
| 4 | H | —S—(pyridin-2-yl) |
| 5 | H | —O—phenyl |
| 6 | H | —O—isobutyl |
| 7 | H | —O—CH₂CH₂CH₂OH |
| 8 | H | —O—(pyridin-2-yl) |
| 9 | Cl | —S—phenyl |
| 10 | Cl | —S—isobutyl |
| 11 | Cl | —S—CH₂CH₂CH₂OH |

TABLE 1-1-continued
(I-A1)
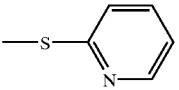
| No. | R³ | —E—G |
|---|---|---|
| 12 | Cl | 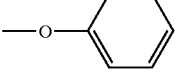 |
| 13 | Cl | 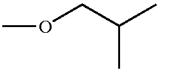 |
| 14 | Cl |  |
| 15 | Cl | 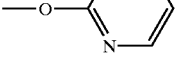 |
| 16 | Cl | 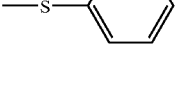 |
| 17 | COOCH₃ | 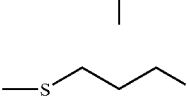 |
| 18 | COOCH₃ |  |
| 19 | COOCH₃ | 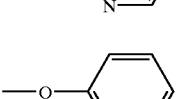 |
| 20 | COOCH₃ | 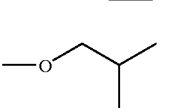 |
| 21 | COOCH₃ | 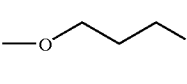 |
| 22 | COOCH₃ | 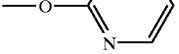 |
| 23 | COOCH₃ |  |
| 24 | COOCH₃ | 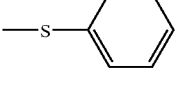 |
TABLE 1-2
(I-A1)
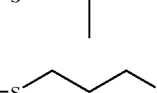
| No. | R³ | —E—G |
|---|---|---|
| 25 | CONH₂ | 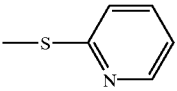 |
| 26 | CONH₂ | 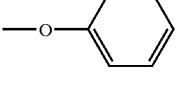 |
| 27 | CONH₂ | 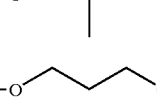 |
| 28 | CONH₂ | 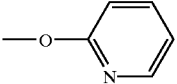 |
| 29 | CONH₂ | 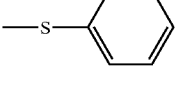 |
| 30 | CONH₂ | 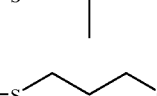 |
| 31 | CONH₂ | 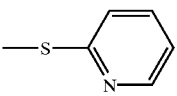 |
| 32 | CONH₂ | 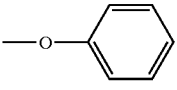 |
| 33 | CH₂OH | 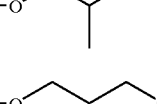 |
| 34 | CH₂OH | |
| 35 | CH₂OH | |
| 36 | CH₂OH |  |
| 37 | CH₂OH | |
| 38 | CH₂OH | |
| 39 | CH₂OH |  |

TABLE 1-2-continued
(I-A1)
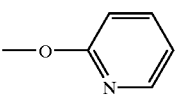
| No. | R³ | —E—G |
|---|---|---|
| 40 | CH₂OH | 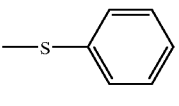 |
| 41 | CN | 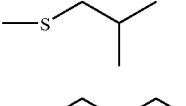 |
| 42 | CN | 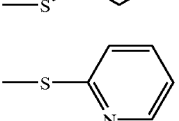 |
| 43 | CN | 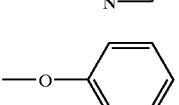 |
| 44 | CN | 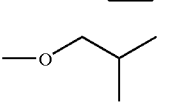 |
| 45 | CN | 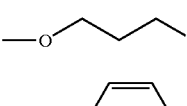 |
| 46 | CN | 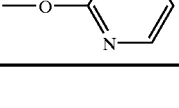 |
| 47 | CN | 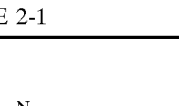 |
| 48 | CN | 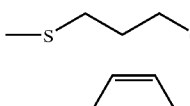 |
TABLE 2-1
(I-B1)
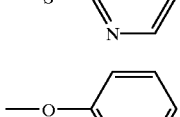
| No. | R³ | —E—G |
|---|---|---|
| 1 | H | 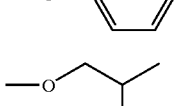 |
| 2 | H | 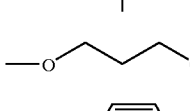 |
TABLE 2-1-continued
(I-B1)
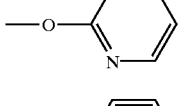
| No. | R³ | —E—G |
|---|---|---|
| 3 | H | 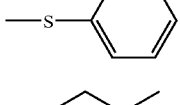 |
| 4 | H | 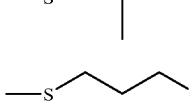 |
| 5 | H | 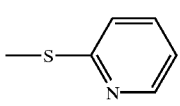 |
| 6 | H | 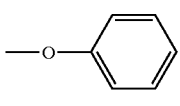 |
| 7 | H | 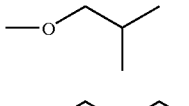 |
| 8 | H | 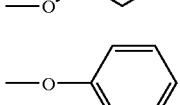 |
| 9 | Cl | 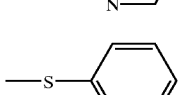 |
| 10 | Cl | 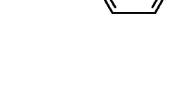 |
| 11 | Cl |  |
| 12 | Cl | 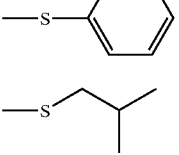 |
| 13 | Cl |  |
| 14 | Cl | —O—CH₂CH(CH₃)₂ |
| 15 | Cl | —O—CH₂CH₂CH₂OH |
| 16 | Cl | —O—(2-pyridyl) |
| 17 | COOCH₃ | —S—C₆H₅ |

TABLE 2-1-continued (I-B1)

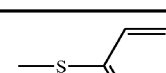

| No. | R³ | —E—G |
|---|---|---|
| 18 | COOCH₃ | —S—CH₂CH(CH₃)₂ (isobutylthio) |
| 19 | COOCH₃ | —S—CH₂CH₂CH₂OH |
| 20 | COOCH₃ | —S—(2-pyridyl) |
| 21 | COOCH₃ | —O—phenyl |
| 22 | COOCH₃ | —O—CH₂CH(CH₃)₂ |
| 23 | COOCH₃ | —O—CH₂CH₂CH₂OH |
| 24 | COOCH₃ | —O—(2-pyridyl) |

TABLE 2-2

(I-B1)

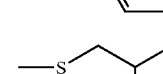

| No. | R³ | —E—G |
|---|---|---|
| 25 | CONH₂ | —S—phenyl |
| 26 | CONH₂ | —S—CH₂CH(CH₃)₂ |
| 27 | CONH₂ | —S—CH₂CH₂CH₂OH |
| 28 | CONH₂ | —S—(2-pyridyl) |

TABLE 2-2-continued (I-B1)

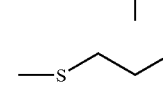

| No. | R³ | —E—G |
|---|---|---|
| 29 | CONH₂ | —O—phenyl |
| 30 | CONH₂ | —O—CH₂CH(CH₃)₂ |
| 31 | CONH₂ | —O—CH₂CH₂CH₂OH |
| 32 | CONH₂ | —O—(2-pyridyl) |
| 33 | CH₂OH | —S—phenyl |
| 34 | CH₂OH | —S—CH₂CH(CH₃)₂ |
| 35 | CH₂OH | —S—CH₂CH₂CH₂OH |
| 36 | CH₂OH | —S—(2-pyridyl) |
| 37 | CH₂OH | —O—phenyl |
| 38 | CH₂OH | —O—CH₂CH(CH₃)₂ |
| 39 | CH₂OH | —O—CH₂CH₂CH₂OH |
| 40 | CH₂OH | —O—(2-pyridyl) |
| 41 | CN | —S—phenyl |
| 42 | CN | —S—CH₂CH(CH₃)₂ |
| 43 | CN | —S—CH₂CH₂CH₂OH |

TABLE 2-2-continued
(I-B1)
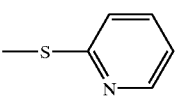
| No. | R³ | —E—G |
|---|---|---|
| 44 | CN | 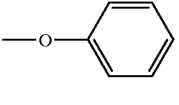 |
| 45 | CN | 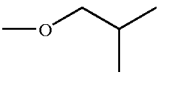 |
| 46 | CN | 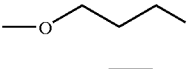 |
| 47 | CN | 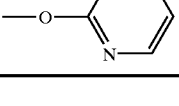 |
| 48 | CN | 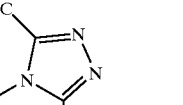 |
TABLE 3-1
(I-C1)
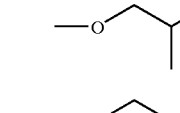
| No. | R³ | —E—G |
|---|---|---|
| 1 | H | 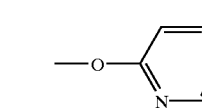 |
| 2 | H | 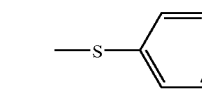 |
| 3 | H | 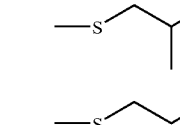 |
| 4 | H | 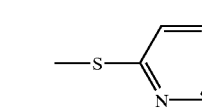 |
| 5 | H | 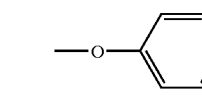 |
| 6 | H |  |
TABLE 3-1-continued
(I-C1)
| No. | R³ | —E—G |
|---|---|---|
| 7 | H | —O—CH₂CH₂CH₂OH |
| 8 | H | —O-(2-pyridyl) |
| 9 | Cl | —S-phenyl |
| 10 | Cl | —S-isobutyl |
| 11 | Cl | —S-CH₂CH₂CH₂OH |
| 12 | Cl | —S-(2-pyridyl) |
| 13 | Cl | —O-phenyl |
| 14 | Cl | —O-isobutyl |
| 15 | Cl | —O-CH₂CH₂CH₂OH |
| 16 | Cl | —O-(2-pyridyl) |
| 17 | COOCH₃ | —S-phenyl |
| 18 | COOCH₃ | —S-isobutyl |
| 19 | COOCH₃ | —S-CH₂CH₂CH₂OH |
| 20 | COOCH₃ | —S-(2-pyridyl) |
| 21 | COOCH₃ | —O-phenyl |

TABLE 3-1-continued (I-C1)

| No. | R³ | —E—G |
|---|---|---|
| 22 | COOCH₃ | —O—CH₂CH(CH₃)₂ (isobutoxy) |
| 23 | COOCH₃ | —O—CH₂CH₂CH₂OH |
| 24 | COOCH₃ | —O—(2-pyridyl) |

TABLE 3-2

(I-C1)

| No. | R³ | —E—G |
|---|---|---|
| 25 | CONH₂ | —S—phenyl |
| 26 | CONH₂ | —S—CH₂CH(CH₃)₂ |
| 27 | CONH₂ | —S—CH₂CH₂CH₂OH |
| 28 | CONH₂ | —S—(2-pyridyl) |
| 29 | CONH₂ | —O—phenyl |
| 30 | CONH₂ | —O—CH₂CH(CH₃)₂ |
| 31 | CONH₂ | —O—CH₂CH₂CH₂OH |
| 32 | CONH₂ | —O—(2-pyridyl) |

TABLE 3-2-continued (I-C1)

| No. | R³ | —E—G |
|---|---|---|
| 33 | CH₂OH | —S—phenyl |
| 34 | CH₂OH | —S—CH₂CH(CH₃)₂ |
| 35 | CH₂OH | —S—CH₂CH₂CH₂OH |
| 36 | CH₂OH | —S—(2-pyridyl) |
| 37 | CH₂OH | —O—phenyl |
| 38 | CH₂OH | —O—CH₂CH(CH₃)₂ |
| 39 | CH₂OH | —O—CH₂CH₂CH₂OH |
| 40 | CH₂OH | —O—(2-pyridyl) |
| 41 | CN | —S—phenyl |
| 42 | CN | —S—CH₂CH(CH₃)₂ |
| 43 | CN | —S—CH₂CH₂CH₂OH |
| 44 | CN | —S—(2-pyridyl) |
| 45 | CN | —O—phenyl |
| 46 | CN | —O—CH₂CH(CH₃)₂ |
| 47 | CN | —O—CH₂CH₂CH₂OH |

TABLE 3-2-continued (I-C1)

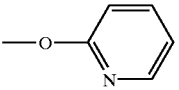

| No. | R³ | —E—G |
|---|---|---|
| 48 | CN | —O-(2-pyridyl) |

TABLE 4-1

(I-D1)

| No. | R³ | —E—G |
|---|---|---|
| 1 | H | —S-phenyl |
| 2 | H | —S-isobutyl |
| 3 | H | —S-CH₂CH₂CH₂OH |
| 4 | H | —S-(2-pyridyl) |
| 5 | H | —O-phenyl |
| 6 | H | —O-isobutyl |
| 7 | H | —O-CH₂CH₂CH₂OH |
| 8 | H | —O-(2-pyridyl) |
| 9 | Cl | —S-phenyl |
| 10 | Cl | —S-isobutyl |

TABLE 4-1-continued (I-D1)

| No. | R³ | —E—G |
|---|---|---|
| 11 | Cl | —S-CH₂CH₂CH₂OH |
| 12 | Cl | —S-(2-pyridyl) |
| 13 | Cl | —O-phenyl |
| 14 | Cl | —O-isobutyl |
| 15 | Cl | —O-CH₂CH₂CH₂OH |
| 16 | Cl | —O-(2-pyridyl) |
| 17 | COOCH₃ | —S-phenyl |
| 18 | COOCH₃ | —S-isobutyl |
| 19 | COOCH₃ | —S-CH₂CH₂CH₂OH |
| 20 | COOCH₃ | —S-(2-pyridyl) |
| 21 | COOCH₃ | —O-phenyl |
| 22 | COOCH₃ | —O-isobutyl |
| 23 | COOCH₃ | —O-CH₂CH₂CH₂OH |
| 24 | COOCH₃ | —O-(2-pyridyl) |

TABLE 4-2
(I-D1)
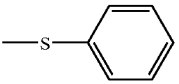
| No. | R³ | —E—G |
|---|---|---|
| 25 | CONH₂ | 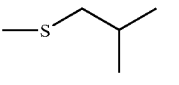 |
| 26 | CONH₂ | 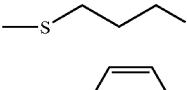 |
| 27 | CONH₂ | 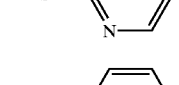 |
| 28 | CONH₂ | 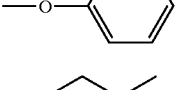 |
| 29 | CONH₂ | 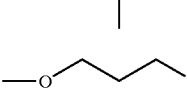 |
| 30 | CONH₂ | 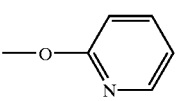 |
| 31 | CONH₂ | 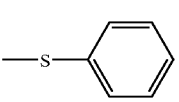 |
| 32 | CONH₂ | 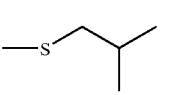 |
| 33 | CH₂OH | 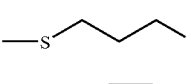 |
| 34 | CH₂OH | 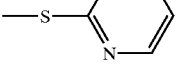 |
| 35 | CH₂OH | 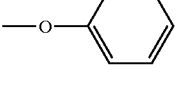 |
| 36 | CH₂OH | 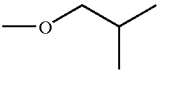 |
| 37 | CH₂OH | 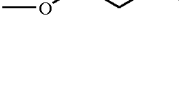 |
| 38 | CH₂OH |  |
| 39 | CH₂OH | 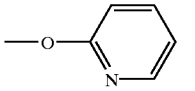 |
TABLE 4-2-continued
(I-D1)
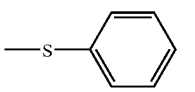
| No. | R³ | —E—G |
|---|---|---|
| 40 | CH₂OH | 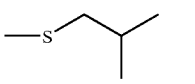 |
| 41 | CN | 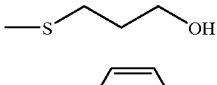 |
| 42 | CN | 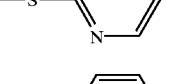 |
| 43 | CN | 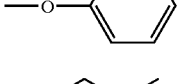 |
| 44 | CN | 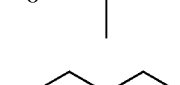 |
| 45 | CN | 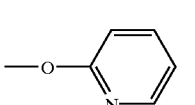 |
| 46 | CN | 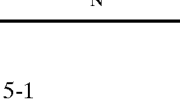 |
| 47 | CN | 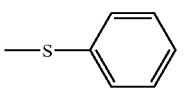 |
| 48 | CN | 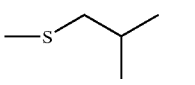 |
TABLE 5-1
(I-E1)
| No. | R³ | —E—G |
|---|---|---|
| 1 | H |  |
| 2 | H |  |

TABLE 5-1-continued (I-E1)

Structure: Thieno-triazolo-pyrazine core with F₃C, R³, and —E—G substituents

| No. | R³ | —E—G |
|---|---|---|
| 3 | H | —S—CH₂CH₂CH₂—OH |
| 4 | H | —S-(2-pyridyl) |
| 5 | H | —O-phenyl |
| 6 | H | —O—CH₂CH(CH₃)₂ |
| 7 | H | —O—CH₂CH₂CH₂—OH |
| 8 | H | —O-(2-pyridyl) |
| 9 | Cl | —S-phenyl |
| 10 | Cl | —S—CH₂CH(CH₃)₂ |
| 11 | Cl | —S—CH₂CH₂CH₂—OH |
| 12 | Cl | —S-(2-pyridyl) |
| 13 | Cl | —O-phenyl |
| 14 | Cl | —O—CH₂CH(CH₃)₂ |
| 15 | Cl | —O—CH₂CH₂CH₂—OH |
| 16 | Cl | —O-(2-pyridyl) |
| 17 | COOCH₃ | —S-phenyl |
| 18 | COOCH₃ | —S—CH₂CH(CH₃)₂ |
| 19 | COOCH₃ | —S—CH₂CH₂CH₂—OH |
| 20 | COOCH₃ | —S-(2-pyridyl) |
| 21 | COOCH₃ | —O-phenyl |
| 22 | COOCH₃ | —O—CH₂CH(CH₃)₂ |
| 23 | COOCH₃ | —O—CH₂CH₂CH₂—OH |
| 24 | COOCH₃ | —O-(2-pyridyl) |

TABLE 5-2

(I-E1)

Structure: Thieno-triazolo-pyrazine core with F₃C, R³, and —E—G substituents

| No. | R³ | —E—G |
|---|---|---|
| 25 | CONH₂ | —S-phenyl |
| 26 | CONH₂ | —S—CH₂CH(CH₃)₂ |
| 27 | CONH₂ | —S—CH₂CH₂CH₂—OH |
| 28 | CONH₂ | —S-(2-pyridyl) |

TABLE 5-2-continued (I-E1)

| No. | R³ | —E—G |
|---|---|---|
| 29 | CONH₂ | —O—phenyl |
| 30 | CONH₂ | —O—CH₂CH(CH₃)₂ |
| 31 | CONH₂ | —O—(CH₂)₃—OH |
| 32 | CONH₂ | —O—(2-pyridyl) |
| 33 | CH₂OH | —S—phenyl |
| 34 | CH₂OH | —S—CH₂CH(CH₃)₂ |
| 35 | CH₂OH | —S—(CH₂)₃—OH |
| 36 | CH₂OH | —S—(2-pyridyl) |
| 37 | CH₂OH | —O—phenyl |
| 38 | CH₂OH | —O—CH₂CH(CH₃)₂ |
| 39 | CH₂OH | —O—(CH₂)₃—OH |
| 40 | CH₂OH | —O—(2-pyridyl) |
| 41 | CN | —S—phenyl |
| 42 | CN | —S—CH₂CH(CH₃)₂ |
| 43 | CN | —S—(CH₂)₃—OH |
| 44 | CN | —S—(2-pyridyl) |
| 45 | CN | —O—phenyl |
| 46 | CN | —O—CH₂CH(CH₃)₂ |
| 47 | CN | —O—(CH₂)₃—OH |
| 48 | CN | —O—(2-pyridyl) |

TABLE 6

(I-F1)

| No. | f | —E—G |
|---|---|---|
| 1 | 1 | —S—phenyl |
| 2 | 1 | —S—CH₂CH(CH₃)₂ |
| 3 | 1 | —S—(CH₂)₃—OH |
| 4 | 1 | —S—(2-pyridyl) |
| 5 | 1 | —O—phenyl |
| 6 | 1 | —O—CH₂CH(CH₃)₂ |

TABLE 6-continued (I-F1)

Structure: triazolo-fused bicyclic with CF$_3$, (CH$_2$)$_f$ chain, and —E—G substituent

| No. | f | —E—G |
|---|---|---|
| 7 | 1 | —O—CH$_2$CH$_2$CH$_2$—OH |
| 8 | 1 | —O-(2-pyridyl) |
| 9 | 2 | —S-phenyl |
| 10 | 2 | —S—CH$_2$CH(CH$_3$)$_2$ |
| 11 | 2 | —S—CH$_2$CH$_2$CH$_2$—OH |
| 12 | 2 | —S-(2-pyridyl) |
| 13 | 2 | —O-phenyl |
| 14 | 2 | —O—CH$_2$CH(CH$_3$)$_2$ |
| 15 | 2 | —O—CH$_2$CH$_2$CH$_2$—OH |
| 16 | 2 | —O-(2-pyridyl) |

TABLE 7-1

(I-G1)

Structure: triazolopyrazine with CF$_3$, R$^{1G}$, R$^{2G}$, and —E—G substituents

| No. | R$^{1G}$ | R$^{2G}$ | —E—G |
|---|---|---|---|
| 1 | CH$_2$CH$_3$ | H | —S-phenyl |
| 2 | CH$_2$CH$_3$ | H | —S—CH$_2$CH(CH$_3$)$_2$ |
| 3 | CH$_2$CH$_3$ | H | —S—CH$_2$CH$_2$CH$_2$—OH |
| 4 | CH$_2$CH$_3$ | H | —S-(2-pyridyl) |
| 5 | CH$_2$CH$_3$ | H | —O-phenyl |
| 6 | CH$_2$CH$_3$ | H | —O—CH$_2$CH(CH$_3$)$_2$ |
| 7 | CH$_2$CH$_3$ | H | —O—CH$_2$CH$_2$CH$_2$—OH |
| 8 | CH$_2$CH$_3$ | H | —O-(2-pyridyl) |
| 9 | OCH$_3$ | H | —S-phenyl |
| 10 | OCH$_3$ | H | —S—CH$_2$CH(CH$_3$)$_2$ |
| 11 | OCH$_3$ | H | —S—CH$_2$CH$_2$CH$_2$—OH |
| 12 | OCH$_3$ | H | —S-(2-pyridyl) |
| 13 | OCH$_3$ | H | —O-phenyl |
| 14 | OCH$_3$ | H | —O—CH$_2$CH(CH$_3$)$_2$ |
| 15 | OCH$_3$ | H | —O—CH$_2$CH$_2$CH$_2$—OH |
| 16 | OCH$_3$ | H | —O-(2-pyridyl) |

TABLE 7-2
(I-G1)
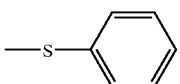
| No. | R$^{1G}$ | R$^{2G}$ | —E—G |
|---|---|---|---|
| 17 | CN | H | 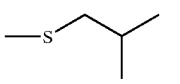 |
| 18 | CN | H | 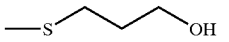 |
| 19 | CN | H | 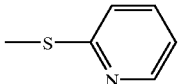 |
| 20 | CN | H | 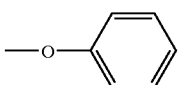 |
| 21 | CN | H | 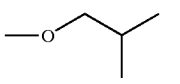 |
| 22 | CN | H | 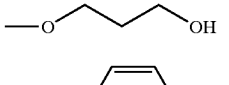 |
| 23 | CN | H | 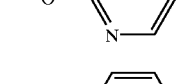 |
| 24 | CN | H | 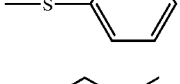 |
| 25 | Ph | H | 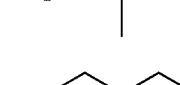 |
| 26 | Ph | H | 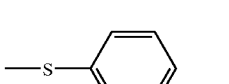 |
| 27 | Ph | H | 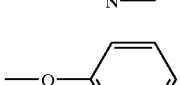 |
| 28 | Ph | H | 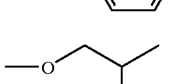 |
| 29 | Ph | H | 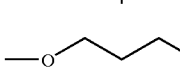 |
| 30 | Ph | H |  |
| 31 | Ph | H | 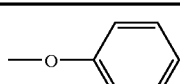 |
TABLE 7-2-continued
(I-G1)
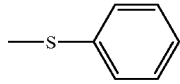
| No. | R$^{1G}$ | R$^{2G}$ | —E—G |
|---|---|---|---|
| 32 | Ph | H | 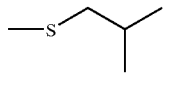 |
TABLE 7-3
(I-G1)
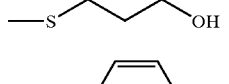
| No. | R$^{1G}$ | R$^{2G}$ | —E—G |
|---|---|---|---|
| 33 | CH$_2$OH | H | 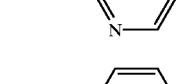 |
| 34 | CH$_2$OH | H | 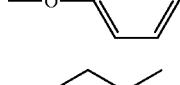 |
| 35 | CH$_2$OH | H | 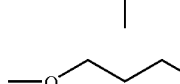 |
| 36 | CH$_2$OH | H | 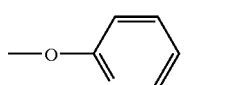 |
| 37 | CH$_2$OH | H | 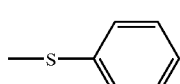 |
| 38 | CH$_2$OH | H | 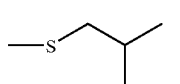 |
| 39 | CH$_2$OH | H | |
| 40 | CH$_2$OH | H | |
| 41 | COOCH$_3$ | H | |
| 42 | COOCH$_3$ | H |  |

TABLE 7-3-continued (I-G1) structure: 3-CF₃-[1,2,4]triazolo[4,3-a]pyrazine with R¹ᴳ at 5-position, R²ᴳ at 6-position, E—G at 8-position.

| No. | R¹ᴳ | R²ᴳ | —E—G |
|---|---|---|---|
| 43 | COOCH₃ | H | —S(CH₂)₃OH |
| 44 | COOCH₃ | H | —S-(2-pyridyl) |
| 45 | COOCH₃ | H | —O-phenyl |
| 46 | COOCH₃ | H | —OCH₂CH(CH₃)₂ |
| 47 | COOCH₃ | H | —OCH₂CH₂CH₂OH |
| 48 | COOCH₃ | H | —O-(2-pyridyl) |

TABLE 7-4

(I-G1) structure as above.

| No. | R¹ᴳ | R²ᴳ | —E—G |
|---|---|---|---|
| 49 | CONH₂ | H | —S-phenyl |
| 50 | CONH₂ | H | —SCH₂CH(CH₃)₂ |
| 51 | CONH₂ | H | —S(CH₂)₃OH |
| 52 | CONH₂ | H | —S-(2-pyridyl) |
| 53 | CONH₂ | H | —O-phenyl |

TABLE 7-4-continued

| No. | R¹ᴳ | R²ᴳ | —E—G |
|---|---|---|---|
| 54 | CONH₂ | H | —OCH₂CH(CH₃)₂ |
| 55 | CONH₂ | H | —OCH₂CH₂CH₂OH |
| 56 | CONH₂ | H | —O-(2-pyridyl) |
| 57 | H | CH₂CH₃ | —S-phenyl |
| 58 | H | CH₂CH₃ | —SCH₂CH(CH₃)₂ |
| 59 | H | CH₂CH₃ | —S(CH₂)₃OH |
| 60 | H | CH₂CH₃ | —S-(2-pyridyl) |
| 61 | H | CH₂CH₃ | —O-phenyl |
| 62 | H | CH₂CH₃ | —OCH₂CH(CH₃)₂ |
| 63 | H | CH₂CH₃ | —OCH₂CH₂CH₂OH |
| 64 | H | CH₂CH₃ | —O-(2-pyridyl) |

TABLE 7-5
(I-G1)
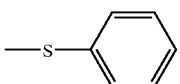
| No. | R¹ᴳ | R²ᴳ | —E—G |
|---|---|---|---|
| 65 | H | OCH₃ | 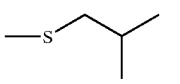 |
| 66 | H | OCH₃ | 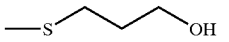 |
| 67 | H | OCH₃ | 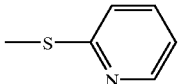 |
| 68 | H | OCH₃ | 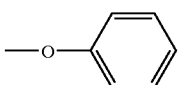 |
| 69 | H | OCH₃ | 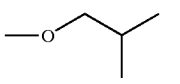 |
| 70 | H | OCH₃ | 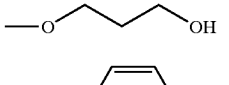 |
| 71 | H | OCH₃ | 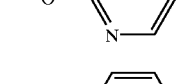 |
| 72 | H | OCH₃ | 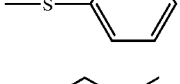 |
| 73 | H | CN | 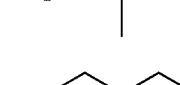 |
| 74 | H | CN | 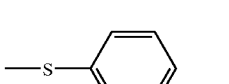 |
| 75 | H | CN | 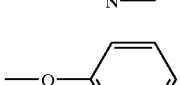 |
| 76 | H | CN | 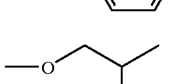 |
| 77 | H | CN | 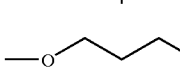 |
| 78 | H | CN |  |
| 79 | H | CN | 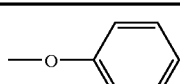 |
TABLE 7-5-continued
(I-G1)
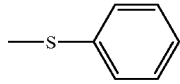
| No. | R¹ᴳ | R²ᴳ | —E—G |
|---|---|---|---|
| 80 | H | CN | 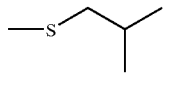 |
TABLE 7-6
(I-G1)
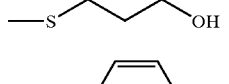
| No. | R¹ᴳ | R²ᴳ | —E—G |
|---|---|---|---|
| 81 | H | Ph | 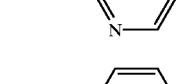 |
| 82 | H | Ph | 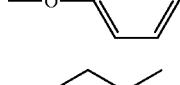 |
| 83 | H | Ph | 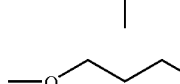 |
| 84 | H | Ph | 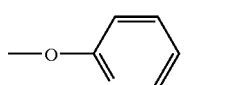 |
| 85 | H | Ph | 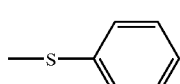 |
| 86 | H | Ph | 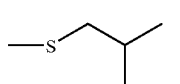 |
| 87 | H | Ph |  |
| 88 | H | Ph | |
| 89 | H | CH₂OH | |
| 90 | H | CH₂OH | |

TABLE 7-6-continued (I-G1)

Structure: triazolo-pyrazine core with F₃C, R¹G, R²G, E—G substituents

| No. | R¹G | R²G | —E—G |
|---|---|---|---|
| 91 | H | CH₂OH | —S—CH₂CH₂CH₂—OH |
| 92 | H | CH₂OH | —S—(2-pyridyl) |
| 93 | H | CH₂OH | —O—phenyl |
| 94 | H | CH₂OH | —O—CH₂CH(CH₃)₂ |
| 95 | H | CH₂OH | —O—CH₂CH₂CH₂—OH |
| 96 | H | CH₂OH | —O—(2-pyridyl) |

TABLE 7-7

(I-G1)

| No. | R¹G | R²G | —E—G |
|---|---|---|---|
| 97 | H | COOCH₃ | —S—phenyl |
| 98 | H | COOCH₃ | —S—CH₂CH(CH₃)₂ |
| 99 | H | COOCH₃ | —S—CH₂CH₂CH₂—OH |
| 100 | H | COOCH₃ | —S—(2-pyridyl) |

TABLE 7-7-continued (I-G1)

| No. | R¹G | R²G | —E—G |
|---|---|---|---|
| 101 | H | COOCH₃ | —O—phenyl |
| 102 | H | COOCH₃ | —O—CH₂CH(CH₃)₂ |
| 103 | H | COOCH₃ | —O—CH₂CH₂CH₂—OH |
| 104 | H | COOCH₃ | —O—(2-pyridyl) |
| 105 | H | CONH₂ | —S—phenyl |
| 106 | H | CONH₂ | —S—CH₂CH(CH₃)₂ |
| 107 | H | CONH₂ | —S—CH₂CH₂CH₂—OH |
| 108 | H | CONH₂ | —S—(2-pyridyl) |
| 109 | H | CONH₂ | —O—phenyl |
| 110 | H | CONH₂ | —O—CH₂CH(CH₃)₂ |
| 111 | H | CONH₂ | —O—CH₂CH₂CH₂—OH |
| 112 | H | CONH₂ | —O—(2-pyridyl) |

TABLE 7-8

(I-G1)

[Structure: triazolopyrazine core with F₃C, R¹ᴳ, R²ᴳ, and E—G substituents]

| No. | R¹ᴳ | R²ᴳ | —E—G |
|---|---|---|---|
| 113 | CH₂CH₃ | CH₂CH₃ | —S—phenyl |
| 114 | CH₂CH₃ | CH₂CH₃ | —S—CH₂CH(CH₃)₂ |
| 115 | CH₂CH₃ | CH₂CH₃ | —S—(CH₂)₃—OH |
| 116 | CH₂CH₃ | CH₂CH₃ | —S—(2-pyridyl) |
| 117 | CH₂CH₃ | CH₂CH₃ | —O—phenyl |
| 118 | CH₂CH₃ | CH₂CH₃ | —O—CH₂CH(CH₃)₂ |
| 119 | CH₂CH₃ | CH₂CH₃ | —O—(CH₂)₃—OH |
| 120 | CH₂CH₃ | CH₂CH₃ | —O—(2-pyridyl) |
| 121 | CN | CN | —S—phenyl |
| 122 | CN | CN | —S—CH₂CH(CH₃)₂ |
| 123 | CN | CN | —S—(CH₂)₃—OH |
| 124 | CN | CN | —S—(2-pyridyl) |
| 125 | CN | CN | —O—phenyl |
| 126 | CN | CN | —O—CH₂CH(CH₃)₂ |
| 127 | CN | CN | —O—(CH₂)₃—OH |

TABLE 7-8-continued (I-G1)

| No. | R¹ᴳ | R²ᴳ | —E—G |
|---|---|---|---|
| 128 | CN | CN | —O—(2-pyridyl) |

TABLE 8-1

(I-H1)

[Structure: triazoloquinoxaline with F₃C, R³⁻¹, R³⁻², R³⁻³ on the benzene ring, and —S—phenyl—Rᴴ]

| No. | R³⁻¹ | R³⁻² | R³⁻³ | Rᴴ |
|---|---|---|---|---|
| 1 | H | H | H | H |
| 2 | Cl | H | H | H |
| 3 | COOCH₃ | H | H | H |
| 4 | CONH₂ | H | H | H |
| 5 | —(CH₂)₃—OH | H | H | H |
| 6 | NH₂ | H | H | H |
| 7 | OH | H | H | H |
| 8 | OCH₃ | H | H | H |
| 9 | H | H | H | F |
| 10 | Cl | H | H | F |
| 11 | COOCH₃ | H | H | F |
| 12 | CONH₂ | H | H | F |
| 13 | —(CH₂)₃—OH | H | H | F |
| 14 | NH₂ | H | H | F |
| 15 | OH | H | H | F |
| 16 | OCH₃ | H | H | F |

TABLE 8-2

(I-H1)

[Structure: triazoloquinoxaline with F₃C, R³⁻¹, R³⁻², R³⁻³, and —S—phenyl—Rᴴ]

| No. | R³⁻¹ | R³⁻² | R³⁻³ | Rᴴ |
|---|---|---|---|---|
| 17 | H | Cl | H | H |
| 18 | H | COOCH₃ | H | H |

TABLE 8-2-continued (I-H1)

| No. | $R^{3-1}$ | $R^{3-2}$ | $R^{3-3}$ | $R^H$ |
|---|---|---|---|---|
| 19 | H | CONH$_2$ | H | H |
| 20 | H | ∼∼OH | H | H |
| 21 | H | NH$_2$ | H | H |
| 22 | H | OH | H | H |
| 23 | H | OCH$_3$ | H | H |
| 24 | H | Cl | H | F |
| 25 | H | COOCH$_3$ | H | F |
| 26 | H | CONH$_2$ | H | F |
| 27 | H | ∼∼OH | H | F |
| 28 | H | NH$_2$ | H | F |
| 29 | H | OH | H | F |
| 30 | H | OCH$_3$ | H | F |

TABLE 8-3

(I-H1)

| No. | $R^{3-1}$ | $R^{3-2}$ | $R^{3-3}$ | $R^H$ |
|---|---|---|---|---|
| 31 | H | H | Cl | H |
| 32 | H | H | COOCH$_3$ | H |
| 33 | H | H | CONH$_2$ | H |
| 34 | H | H | ∼∼OH | H |
| 35 | H | H | NH$_2$ | H |
| 36 | H | H | OH | H |
| 37 | H | H | OCH$_3$ | H |
| 38 | H | H | Cl | F |
| 39 | H | H | COOCH$_3$ | F |
| 40 | H | H | CONH$_2$ | F |
| 41 | H | H | ∼∼OH | F |
| 42 | H | H | NH$_2$ | F |
| 43 | H | H | OH | F |
| 44 | H | H | OCH$_3$ | F |

TABLE 8-4

(I-H1)

| No. | $R^{3-1}$ | $R^{3-2}$ | $R^{3-3}$ | $R^H$ |
|---|---|---|---|---|
| 45 | Cl | Cl | H | H |
| 46 | Cl | NH$_2$ | H | H |
| 47 | Cl | COOCH$_3$ | H | H |
| 48 | Cl | CH$_2$OH | H | H |
| 49 | Cl | Cl | H | F |
| 50 | Cl | NH$_2$ | H | F |
| 51 | Cl | COOCH$_3$ | H | F |
| 52 | Cl | CH$_2$OH | H | F |
| 53 | Cl | H | Cl | H |
| 54 | Cl | H | NH$_2$ | H |
| 55 | Cl | H | COOCH$_3$ | H |
| 56 | Cl | H | CH$_2$OH | H |
| 57 | Cl | H | Cl | F |
| 58 | Cl | H | NH$_2$ | F |
| 59 | Cl | H | COOCH$_3$ | F |
| 60 | Cl | H | CH$_2$OH | F |

TABLE 9-1

(I-H2)

| No. | $R^{3-1}$ | $R^{3-2}$ | $R^{3-3}$ | $R^H$ |
|---|---|---|---|---|
| 1 | H | H | H | H |
| 2 | Cl | H | H | H |
| 3 | COOCH$_3$ | H | H | H |
| 4 | CONH$_2$ | H | H | H |
| 5 | ∼∼OH | H | H | H |
| 6 | NH$_2$ | H | H | H |
| 7 | OH | H | H | H |
| 8 | OCH$_3$ | H | H | H |
| 9 | H | H | H | F |
| 10 | Cl | H | H | F |
| 11 | COOCH$_3$ | H | H | F |
| 12 | CONH$_2$ | H | H | F |
| 13 | ∼∼OH | H | H | F |
| 14 | NH$_2$ | H | H | F |
| 15 | OH | H | H | F |
| 16 | OCH$_3$ | H | H | F |

TABLE 9-2

(I-H2)

| No. | R³⁻¹ | R³⁻² | R³⁻³ | Rᴴ |
|---|---|---|---|---|
| 17 | Cl | H | H | H |
| 18 | H | COOCH₃ | H | H |
| 19 | H | CONH₂ | H | H |
| 20 | H | ~~~OH (propyl-OH) | H | H |
| 21 | H | NH₂ | H | H |
| 22 | H | OH | H | H |
| 23 | H | OCH₃ | H | H |
| 24 | H | Cl | H | F |
| 25 | H | COOCH₃ | H | F |
| 26 | H | CONH₂ | H | F |
| 27 | H | ~~~OH (propyl-OH) | H | F |
| 28 | H | NH₂ | H | F |
| 29 | H | OH | H | F |
| 30 | H | OCH₃ | H | F |

TABLE 9-3

(I-H2)

| No. | R³⁻¹ | R³⁻² | R³⁻³ | Rᴴ |
|---|---|---|---|---|
| 31 | H | H | Cl | H |
| 32 | H | H | COOCH₃ | H |
| 33 | H | H | CONH₂ | H |
| 34 | H | H | ~~~OH (propyl-OH) | H |
| 35 | H | H | NH₂ | H |
| 36 | H | H | OH | H |
| 37 | H | H | OCH₃ | H |
| 38 | H | H | Cl | F |
| 39 | H | H | COOCH₃ | F |
| 40 | H | H | CONH₂ | F |
| 41 | H | H | ~~~OH (propyl-OH) | F |
| 42 | H | H | NH₂ | F |
| 43 | H | H | OH | F |
| 44 | H | H | OCH₃ | F |

TABLE 9-4

(I-H2)

| No. | R³⁻¹ | R³⁻² | R³⁻³ | Rᴴ |
|---|---|---|---|---|
| 45 | Cl | Cl | H | H |
| 46 | Cl | NH₂ | H | H |
| 47 | Cl | COOCH₃ | H | H |
| 48 | Cl | CH₂OH | H | H |
| 49 | Cl | Cl | H | F |
| 50 | Cl | NH₂ | H | F |
| 51 | Cl | COOCH₃ | H | F |
| 52 | Cl | CH₂OH | H | F |
| 53 | Cl | H | Cl | H |
| 54 | Cl | H | NH₂ | H |
| 55 | Cl | H | COOCH₃ | H |
| 56 | Cl | H | CH₂OH | H |
| 57 | Cl | H | Cl | F |
| 58 | Cl | H | NH₂ | F |
| 59 | Cl | H | COOCH₃ | F |
| 60 | Cl | H | CH₂OH | F |

TABLE 10-1

(I-J1)

| No. | R³⁻¹ | R³⁻² | R³⁻³ |
|---|---|---|---|
| 1 | H | H | H |
| 2 | Cl | H | H |
| 3 | COOCH₃ | H | H |
| 4 | CONH₂ | H | H |
| 5 | ~~~OH (propyl-OH) | H | H |
| 6 | NH₂ | H | H |
| 7 | OH | H | H |
| 8 | OCH₃ | H | H |
| 9 | H | Cl | H |
| 10 | H | COOCH₃ | H |
| 11 | H | CONH₂ | H |
| 12 | H | ~~~OH (propyl-OH) | H |
| 13 | H | NH₂ | H |
| 14 | H | OH | H |
| 15 | H | OCH₃ | H |

TABLE 10-2

(I-J1)

Structure: triazoloquinoxaline with $F_3C$, $R^{3-1}$, $R^{3-2}$, $R^{3-3}$ substituents and S-isobutyl group

| No. | $R^{3-1}$ | $R^{3-2}$ | $R^{3-3}$ |
|---|---|---|---|
| 16 | H | H | Cl |
| 17 | H | H | COOCH₃ |
| 18 | H | H | CONH₂ |
| 19 | H | H | ~~~OH (butanol chain) |
| 20 | H | H | NH₂ |
| 21 | H | H | OH |
| 22 | H | H | OCH₃ |
| 23 | Cl | Cl | H |
| 24 | Cl | NH₂ | H |
| 25 | Cl | COOCH₃ | H |
| 26 | Cl | CH₂OH | H |
| 27 | Cl | H | Cl |
| 28 | Cl | H | NH₂ |
| 29 | Cl | H | COOCH₃ |
| 30 | Cl | H | CH₂OH |

TABLE 11-1

(I-J2)

Structure: triazoloquinoxaline with $F_3C$, $R^{3-1}$, $R^{3-2}$, $R^{3-3}$ substituents and O-isobutyl group

| No. | $R^{3-1}$ | $R^{3-2}$ | $R^{3-3}$ |
|---|---|---|---|
| 1 | H | H | H |
| 2 | Cl | H | H |
| 3 | COOCH₃ | H | H |
| 4 | CONH₂ | H | H |
| 5 | ~~~OH (butanol chain) | H | H |
| 6 | NH₂ | H | H |
| 7 | OH | H | H |
| 8 | OCH₃ | H | H |
| 9 | H | Cl | H |
| 10 | H | COOCH₃ | H |
| 11 | H | CONH₂ | H |
| 12 | H | ~~~OH (butanol chain) | H |
| 13 | H | NH₂ | H |
| 14 | H | OH | H |
| 15 | H | OCH₃ | H |

TABLE 11-2

(I-J2)

Structure: triazoloquinoxaline with $F_3C$, $R^{3-1}$, $R^{3-2}$, $R^{3-3}$ substituents and O-isobutyl group

| No. | $R^{3-1}$ | $R^{3-2}$ | $R^{3-3}$ |
|---|---|---|---|
| 16 | H | H | Cl |
| 17 | H | H | COOCH₃ |
| 18 | H | H | CONH₂ |
| 19 | H | H | ~~~OH (butanol chain) |
| 20 | H | H | NH₂ |
| 21 | H | H | OH |
| 22 | H | H | OCH₃ |
| 23 | Cl | Cl | H |
| 24 | Cl | NH₂ | H |
| 25 | Cl | COOCH₃ | H |
| 26 | Cl | CH₂OH | H |
| 27 | Cl | H | Cl |
| 28 | Cl | H | NH₂ |
| 29 | Cl | H | COOCH₃ |
| 30 | Cl | H | CH₂OH |

TABLE 12-1

(I-K1)

Structure: triazoloquinoxaline with $F_3C$, $R^{3-1}$, $R^{3-2}$, $R^{3-3}$ substituents and S-(3-hydroxypropyl) group

| No. | $R^{3-1}$ | $R^{3-2}$ | $R^{3-3}$ |
|---|---|---|---|
| 1 | H | H | H |
| 2 | Cl | H | H |
| 3 | COOCH₃ | H | H |
| 4 | CONH₂ | H | H |
| 5 | ~~~OH (butanol chain) | H | H |
| 6 | NH₂ | H | H |
| 7 | OH | H | H |
| 8 | OCH₃ | H | H |
| 9 | H | Cl | H |
| 10 | H | COOCH₃ | H |
| 11 | H | CONH₂ | H |
| 12 | H | ~~~OH (butanol chain) | H |
| 13 | H | NH₂ | H |
| 14 | H | OH | H |
| 15 | H | OCH₃ | H |

TABLE 12-2

(I-K1)

[Structure: 1-trifluoromethyl-[1,2,4]triazolo[4,3-a]quinoxaline with R³⁻¹, R³⁻², R³⁻³ substituents on benzene ring and S-CH₂CH₂CH₂-OH at 4-position]

| No. | R³⁻¹ | R³⁻² | R³⁻³ |
|-----|------|------|------|
| 16 | H | H | Cl |
| 17 | H | H | COOCH₃ |
| 18 | H | H | CONH₂ |
| 19 | H | H | ~~~OH (propyl-OH) |
| 20 | H | H | NH₂ |
| 21 | H | H | OH |
| 22 | H | H | OCH₃ |
| 23 | Cl | Cl | H |
| 24 | Cl | NH₂ | H |
| 25 | Cl | COOCH₃ | H |
| 26 | Cl | CH₂OH | H |
| 27 | Cl | H | Cl |
| 28 | Cl | H | NH₂ |
| 29 | Cl | H | COOCH₃ |
| 30 | Cl | H | CH₂OH |

TABLE 13-1

(I-K2)

[Structure: 1-trifluoromethyl-[1,2,4]triazolo[4,3-a]quinoxaline with R³⁻¹, R³⁻², R³⁻³ substituents on benzene ring and O-CH₂CH₂CH₂-OH at 4-position]

| No. | R³⁻¹ | R³⁻² | R³⁻³ |
|-----|------|------|------|
| 1 | H | H | H |
| 2 | Cl | H | H |
| 3 | COOCH₃ | H | H |
| 4 | CONH₂ | H | H |
| 5 | ~~~OH (propyl-OH) | H | H |
| 6 | NH₂ | H | H |
| 7 | OH | H | H |
| 8 | OCH₃ | H | H |
| 9 | H | Cl | H |
| 10 | H | COOCH₃ | H |
| 11 | H | CONH₂ | H |
| 12 | H | ~~~OH (propyl-OH) | H |
| 13 | H | NH₂ | H |
| 14 | H | OH | H |
| 15 | H | OCH₃ | H |

TABLE 13-2

(I-K2)

[Structure: 1-trifluoromethyl-[1,2,4]triazolo[4,3-a]quinoxaline with R³⁻¹, R³⁻², R³⁻³ substituents on benzene ring and O-CH₂CH₂CH₂-OH at 4-position]

| No. | R³⁻¹ | R³⁻² | R³⁻³ |
|-----|------|------|------|
| 16 | H | H | Cl |
| 17 | H | H | COOCH₃ |
| 18 | H | H | CONH₂ |
| 19 | H | H | ~~~OH (propyl-OH) |
| 20 | H | H | NH₂ |
| 21 | H | H | OH |
| 22 | H | H | OCH₃ |
| 23 | Cl | Cl | H |
| 24 | Cl | NH₂ | H |
| 25 | Cl | COOCH₃ | H |
| 26 | Cl | CH₂OH | H |
| 27 | Cl | H | Cl |
| 28 | Cl | H | NH₂ |
| 29 | Cl | H | COOCH₃ |
| 30 | Cl | H | CH₂OH |

TABLE 14-1

(I-L1)

[Structure: 1-trifluoromethyl-[1,2,4]triazolo[4,3-a]quinoxaline with R³⁻¹, R³⁻², R³⁻³ substituents on benzene ring and S-(2-pyridyl) at 4-position]

| No. | R³⁻¹ | R³⁻² | R³⁻³ |
|-----|------|------|------|
| 1 | H | H | H |
| 2 | Cl | H | H |
| 3 | COOCH₃ | H | H |
| 4 | CONH₂ | H | H |
| 5 | ~~~OH (propyl-OH) | H | H |
| 6 | NH₂ | H | H |
| 7 | OH | H | H |
| 8 | OCH₃ | H | H |
| 9 | H | Cl | H |
| 10 | H | COOCH₃ | H |
| 11 | H | CONH₂ | H |
| 12 | H | ~~~OH (propyl-OH) | H |
| 13 | H | NH₂ | H |
| 14 | H | OH | H |
| 15 | H | OCH₃ | H |

TABLE 14-2

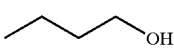

(I-L1)

| No. | R³⁻¹ | R³⁻² | 3-3 |
|---|---|---|---|
| 16 | H | H | Cl |
| 17 | H | H | COOCH₃ |
| 18 | H | H | CONH₂ |
| 19 | H | H | ~~~OH |
| 20 | H | H | NH₂ |
| 21 | H | H | OH |
| 22 | H | H | OCH₃ |
| 23 | Cl | Cl | H |
| 24 | Cl | NH₂ | H |
| 25 | Cl | COOCH₃ | H |
| 26 | Cl | CH₂OH | H |
| 27 | Cl | H | Cl |
| 28 | Cl | H | NH₂ |
| 29 | Cl | H | COOCH₃ |
| 30 | Cl | H | CH₂OH |

TABLE 15-1

(I-L2)

| No. | R³⁻¹ | R³⁻² | R³⁻³ |
|---|---|---|---|
| 1 | H | H | H |
| 2 | Cl | H | H |
| 3 | COOCH₃ | H | H |
| 4 | CONH₂ | H | H |
| 5 | ~~~OH | H | H |
| 6 | NH₂ | H | H |
| 7 | OH | H | H |
| 8 | OCH₃ | H | H |
| 9 | H | Cl | H |
| 10 | H | COOCH₃ | H |
| 11 | H | CONH₂ | H |
| 12 | H | ~~~OH | H |
| 13 | H | NH₂ | H |
| 14 | H | OH | H |
| 15 | H | OCH₃ | H |

TABLE 15-2

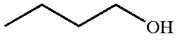

(I-L2)

| No. | R³⁻¹ | R³⁻² | R³⁻³ |
|---|---|---|---|
| 16 | H | H | Cl |
| 17 | H | H | COOCH₃ |
| 18 | H | H | CONH₂ |
| 19 | H | H | ~~~OH |
| 20 | H | H | NH₂ |
| 21 | H | H | OH |
| 22 | H | H | OCH₃ |
| 23 | Cl | Cl | H |
| 24 | Cl | NH₂ | H |
| 25 | Cl | COOCH₃ | H |
| 26 | Cl | CH₂OH | H |
| 27 | Cl | H | Cl |
| 28 | Cl | H | NH₂ |
| 29 | Cl | H | COOCH₃ |
| 30 | Cl | H | CH₂OH |

Process for the Preparation

The compounds of the present invention of the formula (I), may be prepared by following methods or the methods described in the Examples.

[1] In the compounds of the present invention of the formula (I), the compound in which $R^3$ is not —NH₂, that is the compound of the formula (I-1):

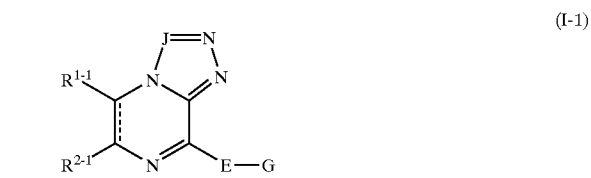

(I-1)

wherein $R^{1-1}$ and $R^{2-1}$ each, independently, is the a same meaning as $R^1$ and $R^2$, with the proviso that, $R^3$ in $R^{1-1}$ and $R^{2-1}$ is not —NH₂, the other symbols are as hereinbefore defined;
may be prepared by following methods (a)–(d).

(a) The compound in which E is oxygen atom, sulfur atom, —(C1–4 alkylene)-O— or —(C1–4 alkylene)-S—, that is the compound of the formula (I-1-a):

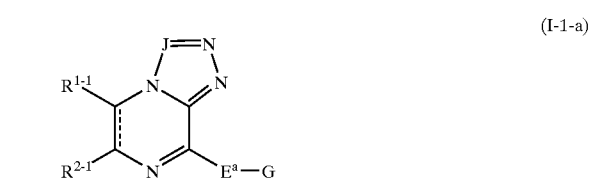

(I-1-a)

wherein $E^a$ is oxygen atom, sulfur atom, —(C1–4 alkylene)-O— or —(C1–4 alkylene)-S—, and the other symbols are as hereinbefore defined;
may be prepared by reacting the compound of the formula (II-a-1):

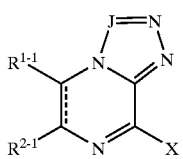

(II-a-1)

wherein X is an ordinary elimination group (e.g. chloride, bromide, iodide, mesyl or tosyl), and the other symbols are as hereinbefore defined;

or the compound of the formula (II-a-2):

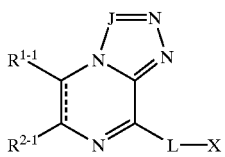

(II-a-2)

wherein L is C1–4 alkylene, and the other symbols are as hereinbefore defined;

with the compound of the formula (III-a):

 (III-a)

wherein all the symbols are as hereinbefore defined.

The reaction of the compound of the formula (II-a-1) or the formula (II-a-2), and the compound of the formula (III-a) was known, for example, it may be carried out by reacting alcohol or thiol of the formula (III-a) in an inactive organic solvent (e.g. dimethylformamide, dimethyl sulfoxide, acetonitrile, tetrahydrofuran or acetone), using an alkali metal hydride, an alkali metal hydroxide, (e.g. sodium hydroxide, potassium hydroxide or lithium hydroxide), an alkaline earth metal hydroxide (e.g. barium hydroxide or calcium hydroxide) or a carbonate (e.g. sodium carbonate or potassium carbonate), an aqueous solution thereof or mixture thereof at 0–40° C., and reacting the obtained alkoxide ion or thiolate ion and the compound of the formula (II-a-1) or the formula (II-a-2) at 0–40° C.

This reaction may be carried out under an inert gas (e.g. argon, nitrogen) to avoid water in order to obtain a preferable result.

(b) The compound in which J is C—$R^7$ and E is a single bond or C1–4 alkylene, that is the compound of the formula (I1-b):

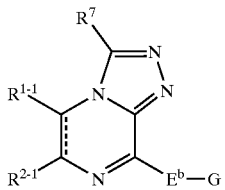

(I-1-b)

wherein $E^b$ is a single bond or C1–4 alkylene, the other symbols are as hereinbefore defined;

may be prepared by reacting the compound (II-b):

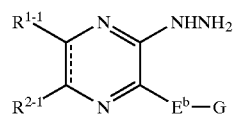

(II-b)

wherein all the symbols are as hereinbefore defined;
with the compound of the formula (III-b-1):

$R^7$—COOH (III-b-1)

wherein all the symbols are as hereinbefore defined;
or the compound of the formula (III-b-2):

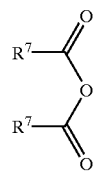

(III-b-2)

wherein all the symbols are as hereinbefore defined;
or the compound of the formula (III-b-3):

$R^7$—C(OT)$_3$ (III-b-3)

wherein T is C1–8 alkyl, the other symbols are as hereinbefore defined.

The reaction of the compound of the formula (II-b) and the compound of the formula (III-b-1), the formula (III-b-2) or the formula (III-b-3) was known (See J Med. Chem., 33, 2240 (1990), J. Heterocyclic Chem. 31, 549 (1994).), for example, it may be carried out in organic solvent (e.g. pyridine, toluene, benzene, dichloromethane, 1,2-dichloroethane, methanol, ethanol) or without a solvent at 20–150° C.

(c) The compound in which J is nitrogen atom and E is a single bond or C1–4 alkylene, that is the compound of the formula (I-1-c):

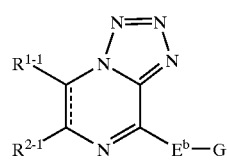

(I-1-c)

wherein all the symbols are as hereinbefore defined;
may be prepared by reacting the compound (II-c):

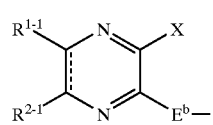

(II-c)

wherein all the symbols are as hereinbefore defined;
with an alkali metal azide.

The reaction of the compound of the formula (II-c) and an alkali metal azide was known (See J. Med. Chem. 35, 3323 (1992).), for example, it may be carried out in an alcohol solvent (e.g. methanol, ethanol), in the presence of an inorganic acid (e.g. hydrochloric acid or sulfuric acid) using an alkali metal azide (e.g. sodium azide) at 40–120° C.

(d) The compound in which E is —SO—, —SO$_2$—, —(C1–4 alkylene)-SO— or —(C1–4 alkylene)-SO$_2$—, that is the compound of the formula (I-1-d):

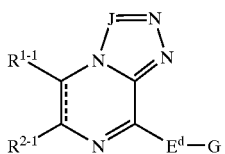

(I-1-d)

wherein E$^d$ is —SO—, —SO$_2$—, —(C1–4 alkylene)-SO— or —(C1–4 alkylene)-SO$_2$—, and the other symbols are as hereinbefore defined;

may be prepared by subjecting the compound in which E is sulfur atom or —(C1–4 alkylene)-S— in the above compound of the formula (I-1-a), that is the compound of the formula (I-1-a-1):

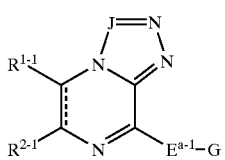

(I-1-a-1)

wherein E$^{a-1}$ is sulfur atom or —(C1–4 alkylene)-S—, and the other symbols are as hereinbefore defined;

to oxidation reaction.

The oxidation reaction was known, for example, in case of the compound in which E$^d$ is —SO— or —(C1–4 alkylene)-SO—, it may be carried out in a suitable organic solvent (e.g. dichloromethane, chloroform, benzene, hexane, t-butyl alcohol), in the presence of 1 equivalent oxidizing agent (e.g. hydrogen peroxide, sodium periodate, acyl nitrite, sodium perborate, peroxide (such as 3-chloroperbenzoic acid, peracetic acid)) at −78–0° C.

In case of the compound in which E$^d$ is —SO$_2$— or —(C1–4 alkylene)-SO$_2$—, it may be carried out in a suitable organic solvent (e.g. dichloromethane, chloroform, benzene, hexane, t-butyl alcohol), in the presence of an excess amount of oxidizing agent (e.g. hydrogen peroxide, sodium periodate, acyl nitrite, sodium perborate, peroxide (such as 3-chloroperbenzoic acid, peracetic acid)) at 0–40° C.

[2] In the compounds of the present invention of the formula (I), the compound in which R$^3$ is —NH$_2$, that is the compound of the formula (I2):

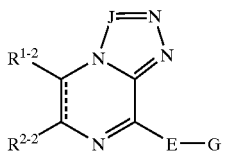

(I-2)

wherein R$^{1-2}$ and R$^{2-2}$ each, independently, is the a same meaning as R$^1$ and R$^2$, with the proviso that, R$^3$ in R$^{1-2}$ and R$^{2-2}$ is —NH$_2$, the other symbols are as hereinbefore defined;

may be prepared by subjecting the compound in which R$^3$ is nitro in the compound of formula (I-1), that is the compound of the formula (I-1-2):

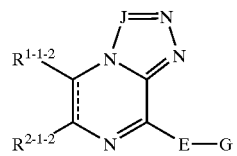

(I-1-2)

wherein R$^{1-1-2}$ and R$^{2-1-2}$ each, independently, is the a same meaning as R$^1$ and R$^2$, with the proviso that, R$^3$ in R$^{1-1-2}$ and R$^{2-1-2}$ is nitro, the other symbols are as hereinbefore defined;

to reduction.

The reduction of nitro was known, for example, it may be carried out by hydrogenolysis and reduction using an organic metal.

Hydrogenolysis was known, for example, it may be carried out in an inactive solvent [e.g. ether (such as tetrahydrofuran, dioxane, dimethoxyethane or diethyl ether), alcohol (such as methanol or ethanol), benzene (such as benzene or toluene), ketone (such as acetone or methyl ethyl ketone), nitrile (such as acetonitrile), amide (such as dimethylformamide), water, ethyl acetate, acetic acid or two more mixture thereof], in the presence of a catalyst (e.g. palladium on carbon, palladium black, palladium, palladium hydroxide, platinum dioxide, nickel or Raney-nickel), optionally in the presence of an inorganic acid (e.g. hydrochloric acid, sulfuric acid, hypochlorous acid, boric acid or tetrafluoroboric acid) or an organic acid (e.g. acetic acid, p-toluenesulfonic acid, oxalic acid, trifluoroacetic acid or formic acid), at ordinary or elevated pressure of hydrogen gas or in the presence of ammonium formate at 0–200° C. It does not matter using a salt of acid, when it is carried out in the presence of an acid.

The reduction using an organic metal was known, for example, it may be carried out in a water miscible solvent (such as ethanol or methanol), optionally in the presence of an aqueous solution of hydrochloric acid using an organic metal (such as zinc, iron, tin, tin chloride, iron chloride) at 0–150° C.

[3] In the compounds of the present invention of the formula (I), the compound in which R$^3$ is —NR$^{4-3}$R$^{5-3}$, in which R$^{4-3}$ and R$^{5-3}$ each, independently, is the a same meaning as R$^4$ and R$^5$, with the proviso that, they are not hydrogen at same time, that is the compound of the formula (I3):

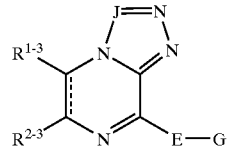

(I-3)

wherein R$^{1-3}$ and R$^{2-3}$ each, independently, is the a same meaning as R$^1$ and R$^2$, with the proviso that, R$^3$ in R$^{1-3}$ and R$^{2-3}$ is —NR$^{4-3}$R$^{5-3}$, and the other symbols are as hereinbefore defined;

may be prepared by subjecting the above compound of the formula (I-2) to alkylation or acetylation also.

The reaction of alkylation was known, for example, it may be carried out in a solvent (such as tetrahydrofuran dimethylformamide or a mixture thereof) using alkyl iodide (such as methyl iodide), in the presence of sodium hydride at 0–40° C.

The reaction of acetylation was known, for example, it may be carried out in the presence of tertiary amine or pyridine, using anhydrous acetic acid at 0–80° C.

[4] The compound in which $R^1$ is (i) COOH, (ii) $CONR^{15}R^{16}$, (iii) formyl, (iv) nitrile, (v) C2–8 alkenyl, (vi) methyl substituted by halogen atom, hydroxy or phenoxy, (vii) ethenyl substituted by $COOR^{14a}$, in which $R^{14a}$ is C1–8 alkyl; nitrile, halogen atom, acetyl, C1–6 alkyl or C2–6 alkenyl, and $R^2$ is hydrogen, may be prepared by following methods described in scheme 1(1) and scheme 1(2) also.

In the schemes, X is halogen atom, Ph is phenyl, s is 0 or 1–6, $R^x$ is hydrogen, halogen atom, C1–6 alkyl, C2–6 alkenyl, $COOR^{14a}$, nitrile or acetyl, $R^Y$ is hydrogen, C1–6 alkyl, halogen atom or nitrile, and the other symbols are as hereinbefore defined.

All reactions in scheme were known.

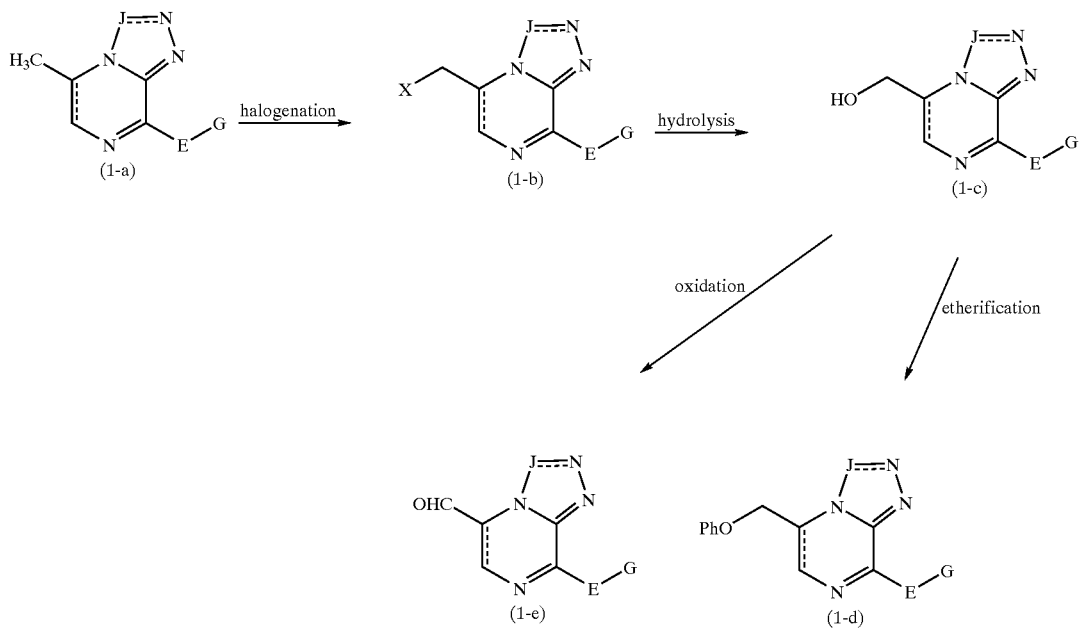

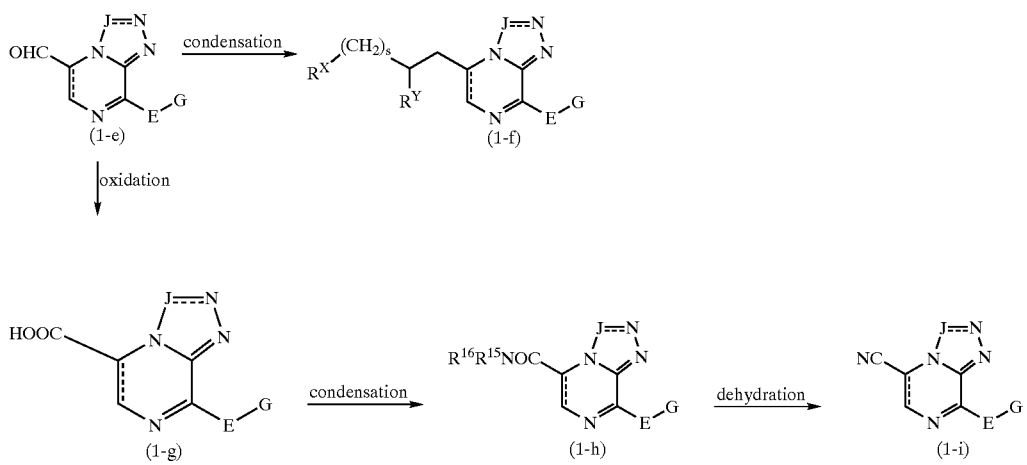

[5] The compound in which n is 1, $R^3$ is (i) formyl, (ii) C1–8 alkanoyl, (iii) C2–8 alkenyl, (iv) methyl substituted by halogen atom or $-NR^4R^5$, (v) C1–8 alkyl substituted by hydroxy, (vi) C2–8 alkenyl substituted by $COOR^6$, hydroxy, halogen atom, nitrile, may be prepared by following methods described in scheme 2(1) and scheme 2(2) also.

In the schemes, t is 0 or 1–6, $R^W$ is hydrogen, C1–6 alkyl, C2–6 alkenyl, halogen atom, nitrile, $COOR^{6a}$, in which $R^{6a}$ is C1–8 alkyl; $R^Z$ is hydrogen, C1–6 alkyl, halogen atom or nitrile, and the other symbols are as hereinbefore defined.

All reactions in scheme were known.

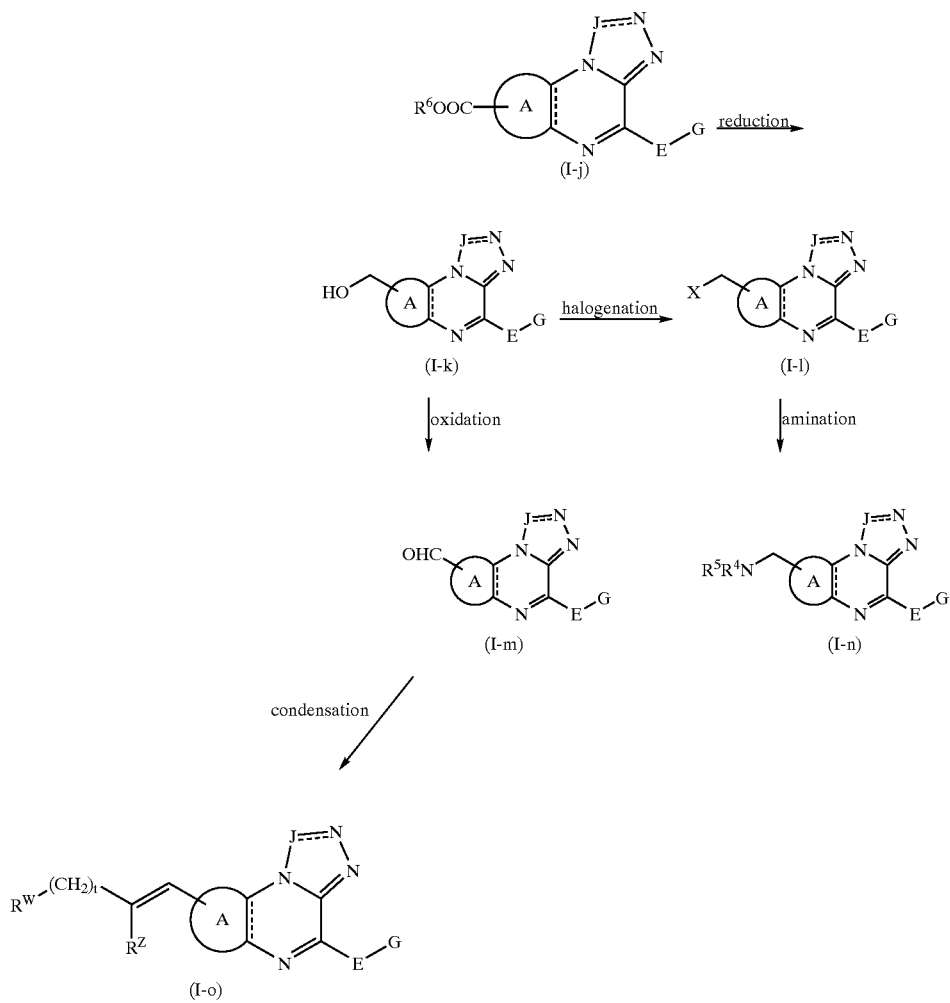

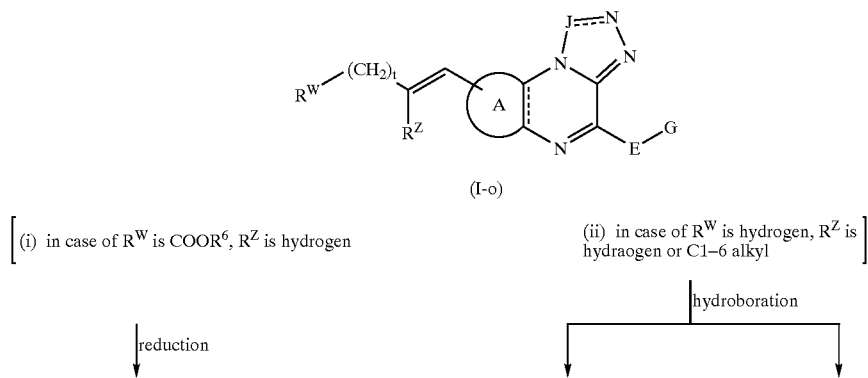

[(i) in case of $R^W$ is $COOR^6$, $R^Z$ is hydrogen]   [(ii) in case of $R^W$ is hydrogen, $R^Z$ is hydraogen or C1–6 alkyl]

↓ reduction         hydroboration

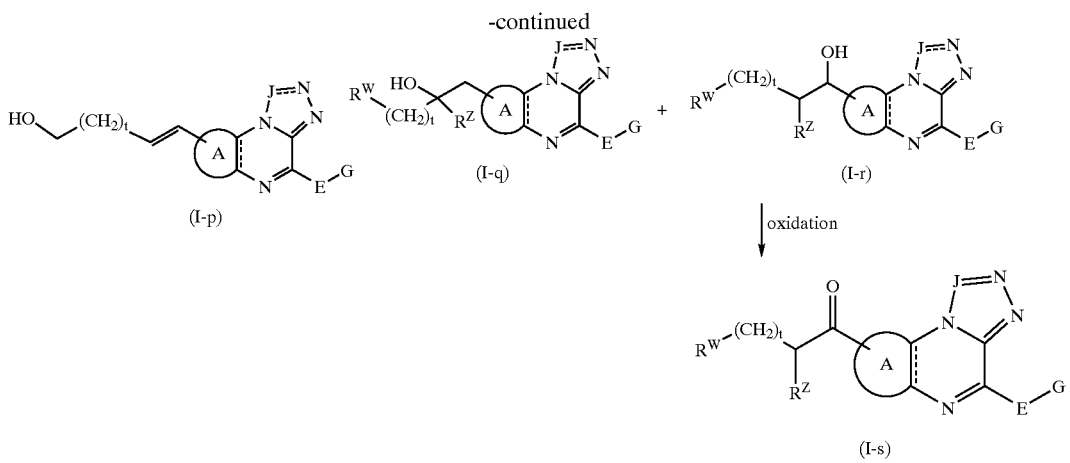

The compounds of the formulae (II-a), (III-a), (II-b), (III-b-1), (III-b-2) are known per se or may be prepared by known methods (See J. Med. Chem. 33, 2240 (1990) or J. Med. Chem. 35, 3323 (1992).).

In each reaction in the present specification, products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reactions or after a series of reactions.

Pharmacological Activities

The inhibitory activity of adhesion molecules expression of the compound of the formula (I) was confirmed as below.

(1) Inhibition of Adhesion Molecules Expression in HUVEC

Human umbilical vein endothelial cells were cultured using MCDB104 medium (Nissui) containing 5% Fetal bovine serum supplemented antibiotics (100 U/ml penicillin, 100 µg/ml streptomycin (Gibco)), 0.01 mg/ml heparin (Nissui) and 0.005 mg/ml endothelial cells (EC) growth factor (Nissui) in gelatin coated 96-well microtiter plates by resulting in confluent monolayers.

The compounds were dissolved in dimethyl sulfoxide and prepared final 0.2% concentration in the medium and then added 50 µl into the well. Cytokine stimulation of EC was performed by adding 50 µl of 10 ng/ml TNFα (Genzyme) (for E-selectin. and ICAM-1 expression) or 50 µl of 10 ng/ml TNFα plus 1 ng/ml IL-4 (Genzyme)(for VCAM-expression).

After stimulation for 6 hours, the wells were washed with PBS(-) once and EC monolayers were fixed by incubating with methanol containing 0.3% hydrogen peroxide for 10 minutes at room temperature. After washing with PBS(-) three times, an ELISA was used to measure the expression of adhesion molecules on EC surface. The ELISA was performed at room temperature with three times washes with PBS(-) between each step. EC were incubated for 30 minutes in turn with 100 µl primary antibody which were anti-ICAM-1 antibody (BBA4), anti-E-selectin antibody (BBA2) or anti-VCAM-1 antibody (BBA6) (mouse IgG1, 1.25 µl/ml; R&D), with 100 µl of secondary antibody which was goat anti-mouse IgG conjugated peroxidase (dilution (1/400); Nordic Immunological laboratories). The enzyme substrate 1 mg/ml o-phenylenediamine/2HCl and 0.1% hydrogen peroxide of 100 µl was added and incubated for 4 minutes at room temperature.

Reaction was stopped with 50 µl of 8N sulfuric acid and optical density (OD) of each well read at 490 nm in immunoreder. Inhibitory percentage was calculated as follows and IC$_{50}$ value was estimated by percentage for control.

Inhibitory percentage (%)=[(C-S)/(C-B)]×100

C: OD of the sample stimulated by cytokines
S: OD of the sample stimulated by cytokines in the presence of test compound
B: OD of the nonstimulated sample These results are shown in Table 16.

TABLE 16

|  | IC50 (µM) | | |
| --- | --- | --- | --- |
|  | E-selectin | VCAM-1 | ICAM-1 |
| Compound (12) | 1.04 | 0.95 | 0.95 |
| Example 3(16) | 0.103 | 0.032 | 0.073 |
| Example 3(73) | 0.60 | 0.20 | 0.40 |

Furthermore, MTT [3-(4,5-dimethyl-2-thiazolyl)-2,5-diphenyl-2H-tetrazolium bromide] assay was enforced and the number of living cells was counted in order to estimate the effect of compound not to depend cytotoxicity on the above evaluation system.

(2) Cytotoxicity Test by MTT Assay

[Method]

EC Were treated under conditions identical to those employed for measurement of adhesion molecules expression. After incubation, the wells were washed with PBS(-) once, added 100 µl of MTT solution (1 mg/ml) and incubated for 3 hours. After incubation supernatants were discarded and 100 µl of methanol added. After stirring, OD of each well read at 570 nm/690 nm in immunoreader. Inhibitory percentage was calculated as follows and IC$_{50}$ value was estimated by percentage for control.

Inhibitory percentage (%)=[(C-S)/C]×100

C: OD of the sample stimulated by cytokines
S: OD of the sample stimulated by cytokines in the presence of test compound As the result, IC$_{50}$ values of compound (12), Example 3 (16) and Example 3 (73) were more than 50 µM, 100 µM and 25 µM respectively.

Toxicity

The toxicity of the compounds of the present invention is very low and therefore, the compounds may be considered safe for pharmaceutical use.

Application for Pharmaceuticals

Inhibition of adhesion molecules expression is useful for prevention and or treatment of diseases, for example, inflammation, rheumatoid arthritis, allergies, asthma, atopic dermatitis, psoriasis, suppression of ischemia reperfusion injury, nephritis, hepatitis, multiple sclerosis, ulcerative colitis, ARDS, suppression of transplant rejection, sepsis, diabetes, autoimmune diseases, tumor metastasis, arteriosclerosis and AIDS in animals including human beings, especially human beings.

For the purpose above described, the compounds of formulae (I) of the present invention, non-toxic salts, acid addition salt or hydrates thereof may be normally by administered systematically or locally, usually by oral or parenteral administration.

The doses to be administered are determined depending upon, for example, age, body weight, symptom, the desired therapeutic effect, the route of administration, and the duration of the treatment In the human adult, the doses per person are Generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid forms for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof.

Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se. Sprays may comprise additional substances other than diluents, such as stabilizing agents (such as sodium sulfate), isotonic buffers (such as sodium chloride, sodium citrate or citric acid). For preparation of such sprays, for example, the method described in the U.S. Pat. Nos. 2,868,691 or 3,095,355 may be used.

The Best Form in Order to Conduct a Present Invention

The following Reference Examples and Examples illustrate the present invention, but do not limit the present invention.

The solvents in the parentheses show the developing or eluting solvents and the ratios of the solvents used are by volume in chromatographic separations or TLC.

The solvents in the parentheses in NMR show the solvents used in measurement.

EXAMPLE 1

4-Isopropylthio-(5-trifluoromethyl-1,2,4-triazolo)[4,3-a]quinoxaline

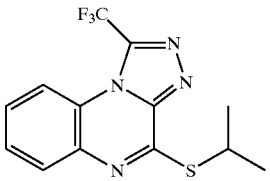

60% Sodium hydride (44 mg) was added to a solution of 2-propanthiol (0.94 ml) in dimethylformamide (10 ml) at 0° C. The mixture was stirred for 30 minutes at room temperature. 4-Chloro-(5-trifluoromethyl-1,2,4-triazolo)[4,3-a]quinoxaline (The compound is described in J. Med. Chem., 33, 2240 (1990).) (250 mg) was added to the mixture at 0° C. The mixture was stirred for 30 minutes at room temperature. Water with ice was added to the reaction mixture and the mixture was extracted with chloroform. The extract was washed with a saturated aqueous solution of sodium chloride, dried over anhydrous sodium sulfate and concentrated. The residue was purified by column chromatography on silica gel (hexane:ethyl acetate=9:1→4:1) to give the present compound (0.203 g) having the following physical data.

TLC: Rf 0.61 (Hexane:Ethyl acetate=4:1);

NMR (d6-DMSO): δ8.10–7.97 (2H, m), 7.84–7.70 (2H, m), 4.40 (1H, sept, J=6.8 Hz), 1.50 (6H, d, J=6.8 Hz).

EXAMPLE 1(1)–1(84)

The following present compounds were obtained by the same procedure as a series of reaction of Example 1, using a corresponding thiol or alcohol instead of 2-propanthiol, if necessary by converting into the corresponding salts by a known method.

EXAMPLE 1(1)

4-Phenyloxy-(5-trifluoromethyl-1,2,4-triazolo)[4,3-a]quinoxaline

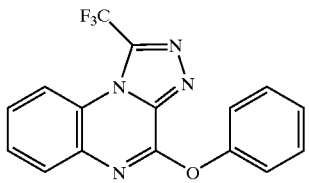

TLC: Rf 0.53 (Hexane:Ethyl acetate=2:1);

NMR (CDCl3): δ8.22–8.10 (1 H, m), 7.89–7.78 (1 H, m), 7.69–7.58 (2H, m), 7.57–7.45 (2H, m), 7.44–7.31 (3H, m).

EXAMPLE 1(2)

4-(Pyrimidin-2-yl)thio-(5-trifluoromethyl-1,2,4-triazolo)[4,3-a]quinoxaline

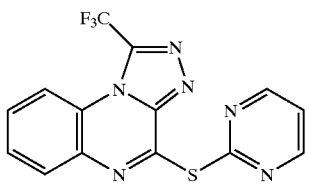

TLC: Rf 0.38 (Chloroform:Methanol=10:1);

NMR (d6-DMSO): δ8.69 (2H, d, J=5.0 Hz), 8.23–8.08 (2H, m), 8.04–7.81 (2H, m), 7.42 (1H, t, J=5.0 Hz).

EXAMPLE 1(3)

4-Allylthio-(5-trifluoromethyl-1,2,4-triazolo)[4,3-a]quinoxaline

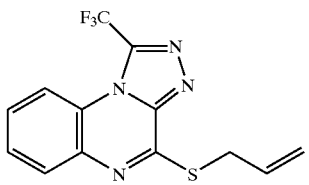

TLC: Rf 0.49 (Hexane:Ethyl acetate 4:1);

NMR (d6-DMSO): δ8.17–7.94 (2H, m), 7.86–7.69 (2H, m), 6.14–5.94 (1H, m), 5.47 (1H, d, J=15.6 Hz), 5.21 (1H, d, J=10.0 Hz), 4.11 (1H, d, J=7.0 Hz).

EXAMPLE 1(4)

4-(Thiophen-2-yl)thio-(5-trifluoromethyl-1,2,4-triazolo)[4,3-a]quinoxaline

TLC: Rf 0.46 (Hexane:Ethyl acetate 4:1);

NMR (d6-DMSO): δ8.09–7.97 (2H, m), 7.88–7.66 (3H, m), 7.56 (1H, d, J=5.3 Hz), 7.30 (1H, dd, J=5.3, 3.4 Hz).

EXAMPLE 1(5)

4-Cyclohexylthio-(5-trifluoromethyl-1,2,4-triazolo)[4,3-a]quinoxaline

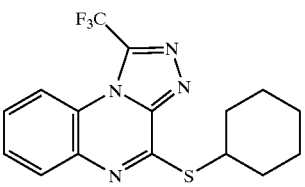

TLC: Rf 0.63 (Hexane:Ethyl acetate=4:1);

NMR(d6-DMSO): δ8.10–7.94 (2H, m), 7.84–7.68 (2H, m), 4.33–4.12 (1H, m), 2.26–1.98 (2H, m), 1.93–1.19 (8H, m).

EXAMPLE 1(6)

4-(4-Trifluoromethylphenyl)thio-(5-trifluoromethyl-1,2,4-triazolo)[4,3-a]quinoxaline

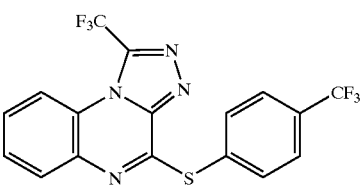

TLC: Rf 0.53 (Hexane:Ethyl acetate=4:1);

NMR (CDCl3): δ8.18–8.07 (1H, m), 7.90–7.72 (5H, m), 7.70–7.59 (2H, m).

EXAMPLE 1(7)

4-(4-Trifluoromethoxyphenyl)thio-(5-trifluoromethyl-1,2,4-triazolo)[4,3-a]quinoxaline

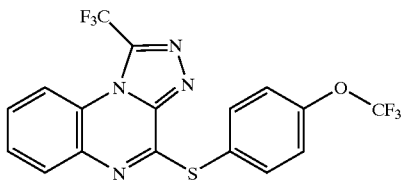

TLC: Rf 0.43 (Chloroform);

NMR (CDCl3): δ8.15–8.10 (1H, m), 7.87–7.82 (1H, m), 7.75 (2H, d, J=8.8 Hz), 7.68–7.62 (2H, m), 7.37 (2H, d, J=8.8 Hz).

EXAMPLE 1(8)

4-(Pyridin-4-yl)thio-(5-trifluoromethyl-1,2,4-triazolo)[4,3-a]quinoxaline

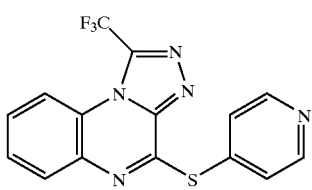

TLC: Rf 0.23 (Hexane:Ethyl acetate=2:1);

NMR (CDCl3): δ8.76 (2H, d, J=6.2 Hz), 8.21–8.10 (1H, m), 7.94–7.88 (1H, m), 7.75–7.65 (4H, m).

EXAMPLE 1(9)

4-(Pyridin-4-yl)thio-(5-trifluoromethyl-1,2,4-triazolo)[4,3-a]quinoxaline-hydrochloride

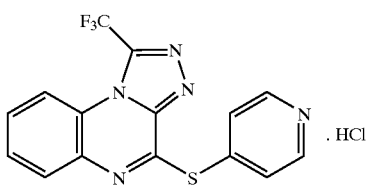

TLC: Rf 0.69 (Chloroform:Methanol=10:1);

NMR (CDCl3): δ8.83 (2H, d, J=6.6 Hz), 8.14 (2H, d, J=6.6 Hz), 8.12–7.77 (4H, m).

EXAMPLE 1(10)

4-(2-Methoxyphenyl)thio-(5-trifluoromethyl-1,2,4-triazolo)[4,3-a]quinoxaline

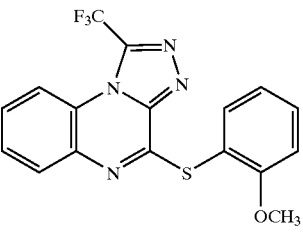

TLC: Rf 0.56 (Hexane:Ethyl acetate=2:1);

NMR (CDCl3): δ8.13–8.08 (1H, m), 7.83–7.75 (1H, m), 7.67 (1H, dd, J=7.8, 6.0 Hz), 7.62–7.57 (2H, m), 7.53 (1H, dd, J=7.8, 6.0 Hz), 7.09 (2H, dd, J=7.8, 7.8 Hz), 3.80 (3H, s).

EXAMPLE 1(11)

4-(3-Methoxyphenyl)thio-(5-trifluoromethyl-1,2,4-triazolo)[4,3-a]quinoxaline

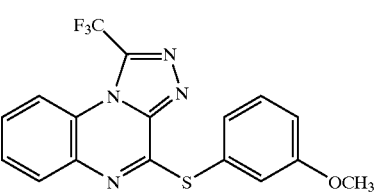

TLC: Rf 0.62 (Hexane:Ethyl acetate=2:1);

NMR (CDCl3): δ8.14–8.09 (1H, m), 7.89–7.84 (1H, m), 7.68–7.58 (2H, m), 7.43 (1H, dd, J=8.0, 8.0 Hz), 7.30 (1H, dd, J=8.0, 5.6 Hz), 7.28 (1H, s), 7.07 (1H, dd, J=8.0, 5.6 Hz), 3.86 (3H, s).

EXAMPLE 1(12)

4-(2-Chlorophenyl)thio-(5-trifluoromethyl-1,2,4-triazolo)[4,3-a]quinoxaline

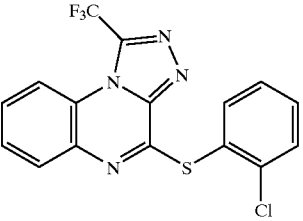

TLC: Rf 0.61 (Hexane:Ethyl acetate=2:1);

NMR (CDCl3) : δ8.15–8.10 (1H, m), 7.83–7.77 (2H, m), 7.68–7.59 (3H, m), 7.51 (1H, ddd, J=7.6, 7.6, 2.0 Hz), 7.41 (1H, ddd, J=7.6, 7.6, 2.0 Hz).

EXAMPLE 1(13)

4-(3-Chlorophenyl)thio-(5-trifluoromethyl-1,2,4-triazolo)[4,3-a]quinoxaline

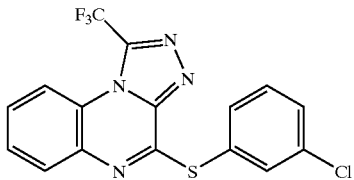

TLC: Rf 0.68 (Hexane:Ethyl acetate=2:1);

NMR (CDCl3): δ8.15–8.10 (1H, m), 7.89–7.84 (1H, m), 7.74 (1H, s), 7.67–7.41 (5H, m).

EXAMPLE 1(14)

4-(2-Aminophenyl)thio-(5-trifluoromethyl-1,2,4-triazolo)[4,3-a]quinoxaline

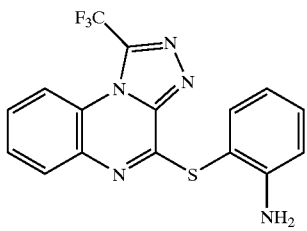

TLC: Rf 0.56 (Hexane:Ethyl acetate 2:1);

NMR (d6-DMSO): δ8.03 (1H, d, J=8.0 Hz), 7.81–7.63 (3H, m), 7.38 (1H, dd, J=8.0, 1.4 Hz), 7.27 (1H, ddd, J=8.0, 8.0, 1.4 Hz), 6.84 1H, dd, J=8.0, 1.4 Hz), 6.65 (1H, ddd, J=8.0, 8.0, 1.4 Hz), 5.42 (2H, brs).

EXAMPLE 1(15)

4-(2-Aminophenyl)thio-(5-trifluoromethyl-1,2,4-triazolo)[4,3-a]quinoxaline.hydrochloride

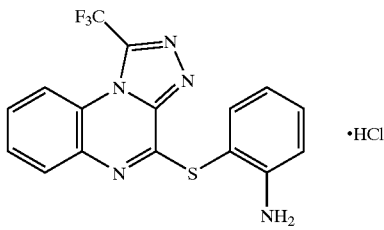

TLC: Rf 0.56 (Hexane:Ethyl acetate=2:1);

NMR (d6-DMSO): δ8.19–8.15 (1H, m), 7.89–7.84 (1H, m), 7.55–7.50 (2H, m), 7.31–7.22 (2H, m), 6.82 (1H, d, J=8.0 Hz), 6.62 (1H, dd, J=8.0, 7.2 Hz), 5.52 brs).

EXAMPLE 1(16)

4-(3-Carboxyphenyl)thio-(5-trifluoromethyl-1,2,4-triazolo)[4,3-a]quinoxaline

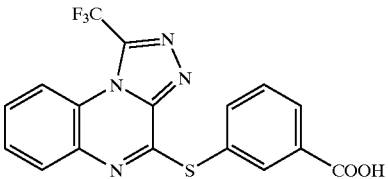

TLC: Rf 0.33 (Chloroform:Methanol=10:1);

NMR (d6-DMSO): δ8.24 (1H, s), 8.11 (1H, d, J=8.0 Hz), 8.03 (1H, d, J=8.4 Hz), 7.92 (1H, d, J=8.0 Hz), 7.84–7.64 (4H, m).

EXAMPLE 1(17)

4-(4-Carboxyphenyl)thio-(5-trifluoromethyl-1,2,4-triazolo)[4,3-a]quinoxaline

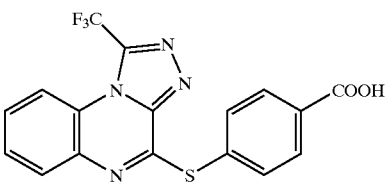

TLC: Rf 0.31 (Chloroform:Methanol=10:1);

NMR (d6-DMSO): δ8.10–8.02 (1H, m), 8.08 (2H, d, J=8.6 Hz), 7.85 (2H, d, J=8.6 Hz), 7.84–7.69 (3H, m).

EXAMPLE 1 (18)

4-(4-Aminophenyl)thio-(5-trifluoromethyl-1,2,4-triazolo)[4,3-a]quinoxaline

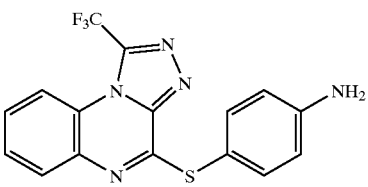

TLC: Rf 0.22 (Chloroform);

NMR (d6-DMSO): δ8.00 (1H, d, J=8.5 Hz), 7.77–7.73 (2H, m), 7.67 (1H, dd, J=8.5, 7.0 Hz), 7.28 (2H, d, J=8.0 Hz), 6.69 (2H, d, J=8.0 Hz), 5.66 (2H, brs).

EXAMPLE 1(19)

4-(4-Aminophenyl)thio-(5-trifluoromethyl-1,2,4-triazolo)[4,3-a]quinoxaline hydrochloride

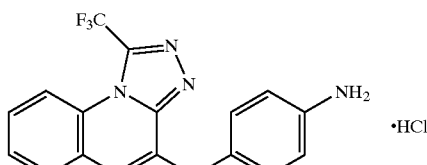

TLC: Rf 0.22 (Chloroform);

NMR (d6-DMSO): δ8.02 (1H, d, J=8.0 Hz), 7.79–7.75 (2H, m), 7.68 (1H, dd, J=8.0, 7.0 Hz), 7.55 (2H, d, J=8.0 Hz), 7.11 (2H, d, J=8.0 Hz), 5.00–2.80 (3H, br).

EXAMPLE 1(20)

4-(4-(2-Carboxyethyl)phenyl)thio-(5-trifluoromethyl-1,2,4-triazolo)[4,3-a]quinoxaline

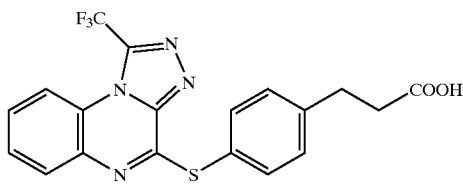

TLC: Rf 0.41 (Chloroform:Methanol=10:1);

NMR (d6-DMSO): δ8.02 (1H, d, J=7.8 Hz), 7.81–7.69 (3H, m), 7.63 (2H, d, J=8.4 Hz), 7.43 (2H, d, J=8.4 Hz), 2.93 (2H, t, J=7.8 Hz), 2.62 (2H, t, J=7.8 Hz).

EXAMPLE 1(21)

4-(N,N,-Dimethylamino)ethylthio-(5-trifluoromethyl-1,2,4-triazolo)[4,3-a]quinoxaline

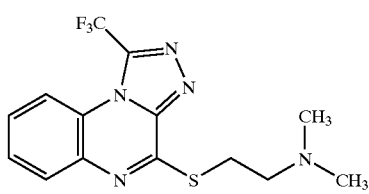

TLC: Rf 0.49 (Chloroform:Methanol=10:1);

NMR (d6-DMSO): δ8.07–8.00 (2H, m), 7.83–7.74 (2H, m), 3.54 (2H, t, J=7.0 Hz), 2.66 (2H, t, J=7.0 Hz), 2.26 (6H, s).

EXAMPLE 1(22)

4-(N,N,-Dimethylamino)ethylthio-(5-trifluoromethyl-1,2,4-triazolo)[4,3-a]quinoxaline.hydrochloride

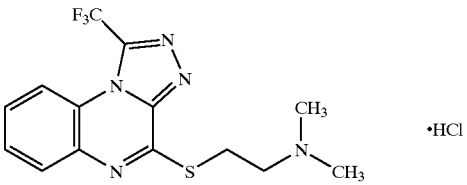

TLC: Rf 0.49 (Chloroform:Methanol=10:1);

NMR (d6-DMSO): δ10.8 (1H, brs), 8.24–8.20 (1H, m), 8.08–8.03 (1H, m), 7.85–7.80 (2H, m), 3.80 (2H, t, J=7.4 Hz), 3.43 (2H, t, J=7.4 Hz), 2.88 (6H, s).

EXAMPLE 1(23)

4-(3-Methoxycarbonylphenyl)thio-(5-trifluoromethyl-1,2,4-triazolo)[4,3-a]quinoxaline

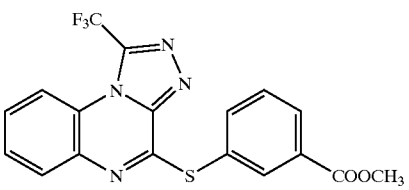

TLC: Rf 0.32 (Chloroform);

NMR (d6-DMSO): δ8.27 (1H, s), 8.15 (1H, d, J=7.6 Hz), 8.06–7.99 (2H, m), 7.85–7.69 (4H, m), 3.88 (3H, s).

EXAMPLE 1(24)

4-(4-Methoxycarbonylphenyl)thio-(5-trifluoromethyl-1,2,4-triazolo)[4,3-a]quinoxaline

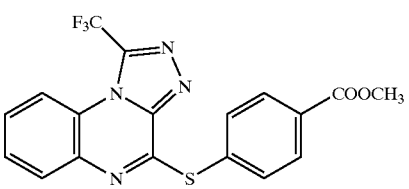

TLC: Rf 0.25 (Chloroform);

NMR (d6-DMSO): δ8.11 (2H, d, J=8.4 Hz), 8.08–8.03 (1H, m), 7.90 (2H, d, J=8.4 Hz), 7.86–7.67 (3H, m), 3.91 (3H, s).

EXAMPLE 1(25)

4-(4-(2-Methoxycarbonyethyl)phenyl)thio-(5-trifluoromethyl-1,2,4-triazolo)[4,3-a]quinoxaline

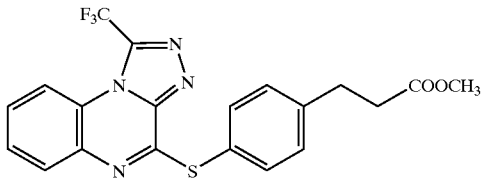

TLC: Rf 0.30 (Chloroform);

NMR (CDCl3): δ8.13–8.09 (1H, m), 7.86–7.81 (1H, m), 7.67–7.59 (2H, m), 7.63 (2H, d, J=8.0 Hz), 7.35 (2H, d, J=8.0 Hz), 3.71 (3H, s), 3.06 (2H, t, J=7.8 Hz), 2.72 (2H, t, J=7.8 Hz).

EXAMPLE 1(26)

4-(3-Aminophenyl)thio-(5-trifluoromethyl-1,2,4-triazolo)[4,3-a]quinoxaline

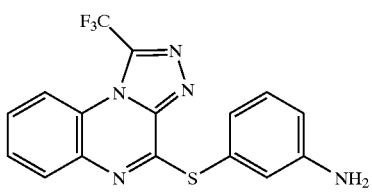

TLC: Rf 0.21 (Hexane:Ethyl acetate=2:1);

NMR (d6-DMSO): δ8.02 (1H, d, J=7.8 Hz), 7.83–7.65 (3H, m), 7.19 (1H, dd, J=7.8, 7.8 Hz), 6.91 (1H, s), 6.82 (1H, d, J=7.8 Hz), 6.73 (1H, d, J=7.8 Hz), 5.39 (2H, brs).

EXAMPLE 1(27)

4-(3-Aminophenyl)thio-(5-trifluoromethyl-1,2,4-triazolo)[4,3-a]quinoxaline.hydrochloride

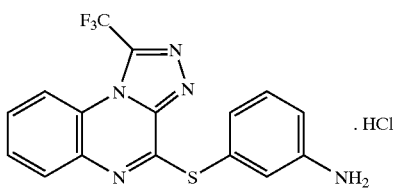

TLC: Rf 0.21 (Hexane:Ethyl acetate=2:1);

NMR (d6-DMSO): δ8.04 (1H, d, J=8.8 Hz), 7.84–7.70 (3H, m), 7.45 (1H, dd, J=7.8, 7.8 Hz), 7.36 (1H, s), 7.31 (1H, d, J=7.8 Hz), 7.17 (1H, d, J=7.8 Hz), 4.00–3.00 (3H, br).

EXAMPLE 1(28)

4-Isopropyloxy-(5-trifluoromethyl-1,2,4-triazolo)[4,3-a]quinoxaline

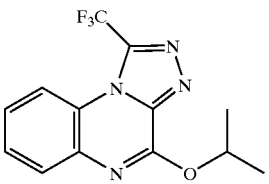

TLC: Rf 0.54 (Hexane:Ethyl acetate=3:1);

NMR (CDCl3): δ8.10 (1H, d, J=8.5 Hz), 7.92 (1H, dd, J=7.5, 1.5 Hz), 7.67–7.63 (1H, m), 7.59–7.55 (1H, m), 5.78 (1H, seq, J=6.5 Hz), 1.56 (6H, d, J=6.5 Hz).

EXAMPLE 1(29)

4-Allyloxy-(5-trifluoromethyl-1,2,4-triazolo)[4,3-a]quinoxaline

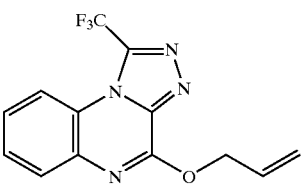

TLC: Rf 0.38 (Hexane:Ethyl acetate=3:1);

NMR (CDCl3): δ8.12 (1H, d, J=8.5 Hz), 7.94 (1H, dd, J=8.5, 1.5 Hz), 7.68–7.65 (1H, m), 7.61–7.58 (1H, m), 6.27–6.19 (1H, m), 5.57 (1H, dd, J=17.0, 1.5 Hz), 5.39 (1H, dd, J=10.5, 1.5 Hz), 5.24 (2H, d, J=6.0 Hz).

EXAMPLE 1(30)

4-Methoxycarbonylmethylthio-(5-trifluoromethyl-1,2,4-triazolo)[4,3-a]quinoxaline

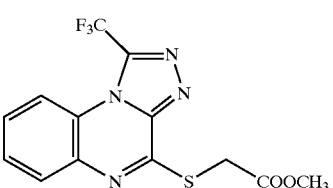

TLC: Rf 0.28 (Hexane:Ethyl acetate=2:1);

NMR (CDCl3): δ8.15–8.11 (1H, m), 8.07–8.02 (1H, m), 7.72–7.66 (2H, m), 4.22 (2H, s), 3.80 (3H, s).

EXAMPLE 1(31)

4-(1-Ethoxycarbonylethyl)thio-(5-trifluoromethyl-1,2,4-triazolo)[4,3-a]quinoxaline

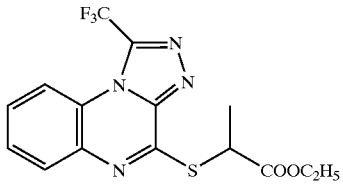

TLC: Rf 0.52 (Hexane:Ethyl acetate=2:1 );

NMR (CDCl3): δ8.15–8.10 (1H, m), 8.06–8.01 (1H, m), 7.75–7.62 (2H, m), 4.84 (1H, q, J=7.4 Hz), 4.25 (2H, q, J=7.2Hz), 1.77 (3H, d, J=7.4Hz), 1.29–3H, t, J=7.2 Hz).

EXAMPLE 1(32)

4-(2-Thiazolin-2-yl)thio-(5-trifluoromethyl-1,2,4-triazolo)[4,3-a]quinoxaline

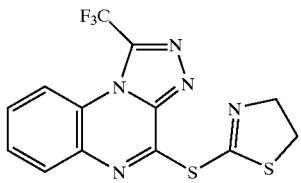

TLC: Rf 0.64 (Hexane:Ethyl acetate=2:1);

NMR (CDCl3): δ8.18–8.10 (2H, m), 7.78–7.69 (2H, m), 4.00 (2H, t, J=6.8 Hz), 3.76 (2H, t, J=6.8 Hz).

EXAMPLE 1(33)

4-(Thiazol-2-yl)thio-(5-trifluoromethyl-1,2,4-triazolo)[4,3-a]quinoxaline

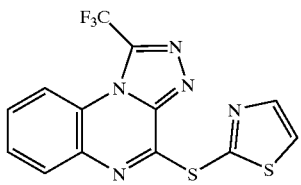

TLC: RF 0.56 (Hexane:Ethyl acetate=2:1);

NMR (CDCl3): δ8.20–8.15 (1H. m), 8.10–8.05 (1H, m), 8.04 (1H. d, J=3.6 Hz) 7.77–7.69 (2H, m), 7.68 (1H, d, J=3.6 Hz).

EXAMPLE 1(34)

4-(1-Methyltetrazol-5-yl)thio-(5-trifluoromethyl-1,2,4-triazolo)[4,3-a]quinoxaline

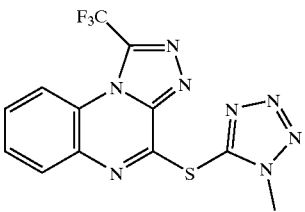

TLC: Rf 0.21 (Hexane:Ethyl acetate=2:1);

NMR (d6-DMSO): δ8.07 (1H, d, J=8.4 Hz), 7.92–7.70 (3H, m), 4.11 (3H, s).

EXAMPLE 1(35)

4-(1-Phenyltetrazol-5-yl)thio-(5-trifluoromethyl-1;2, 4-triazolo)[4,3-a]quinoxaline

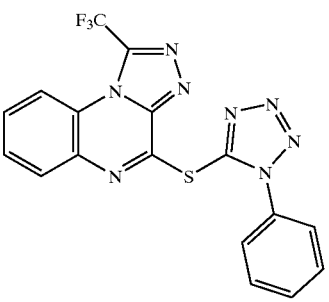

TLC: Rf 0.41 (Hexane:Ethyl acetate=2:1);

NMR (d6-DMSO): δ8.01 (1H, d, J=7.6 Hz), 7.88–7.73 (5H, m), 7.55–7.51 (3H, m).

EXAMPLE 1(36)

4-(2-Hydroxyethyl)thio-(5-trifluoromethyl-1,2,4-triazolo)[4,3-a]quinoxaline

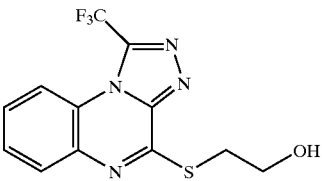

TLC: Rf 0.26 (Hexane:Ethyl acetate=1:1);

NMR (CDCl3): δ8.16–8.05 (2H, m), 7.76–7.64 (2H, m), 4.08 (2H, t, J=5.8 Hz), 3.68 (2H, t, J=5.8 Hz), 3.00–2.90 (1H, br).

EXAMPLE 1(37)

4-(2-Hydroxypropyl)thio-(5-trifluoromethyl-1,2,4-triazolo)[4,3-a]quinoxaline

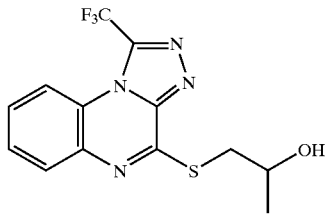

TLC: Rf 0.38 (Hexane:Ethyl acetate=1:1);

NMR (CDCl3): δ8.16–8.04 (2H, m), 7.76–7.64 (2H, m), 4.33–4.22 (1H, m), 3.71 (1H, dd, J=14.0, 3.7 Hz), 3.48 (1H, dd, J=14.0, 6.8 Hz), 1.42 (3H, d, J=6.0 Hz).

EXAMPLE 1(38)

4-(3-Hydroxypropyl)thio-(5-trifluoromethyl-1,2,4-triazolo)[4,3-a]quinoxaline

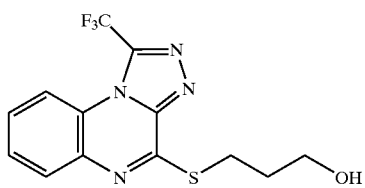

TLC: Rf 0.35 (Hexane:Ethyl acetate=1:1);

NMR (CDCl3): δ8.16–8.03 (2H, m), 7.73–7.65 (2H, m), 3.81 (2H, t, J=5.6 Hz), 3.62 (2H, t, J=6.6 Hz), 2.12 (2H, tt, J=6.6, 5.6 Hz).

EXAMPLE 1(39)

4-(2-Methylfuran-3-yl)thio-(5-trifluoromethyl-1,2,4-triazolo)[4,3-a]quinoxaline

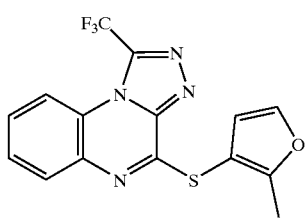

TLC: Rf 0.57 (Hexane:Ethyl acetate=3:1);

NMR (CDCl3): δ8.15–8.10 (1H, m), 7.97–7.92 (1H, m), 7.69–7.63 (2H, m), 7.49 (1H, d, J=2.2 Hz), 6.55 (1H, d, J=2.2 Hz), 2.40 (3H, s).

EXAMPLE 1(40)

4-(6-Methyl-4H, 5H-1,3-thiazine)thio-(5-trifluoromethyl-1,2,4-triazolo)[4,3-a]quinoxaline

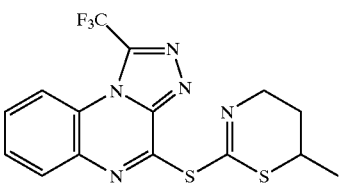

TLC: Rf 0.56 (Hexane:Ethyl acetate=2:1);

NMR (CDCl3): δ8.21 (1H, dd, J=7.4, 2.2 Hz), 8.13 (1H, d, J=8.4 Hz), 7.77–7.63 (2H, m), 4.65–4.50 (1H, m), 3.83–3.74 (2H, m), 2.34–2.15 (2H, m), 1.62 (3H, d, J=7.0 Hz).

EXAMPLE 1(41)

4-(Imidazol-2-yl)thio-(5-trifluoromethyl-1,2,4-triazolo)[4,3-a]quinoxaline

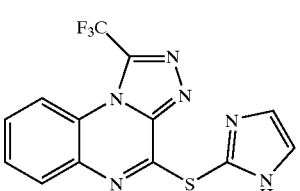

TLC: Rf 0.54 (Ethyl acetate);

NMR (d6-DMSO): δ13.0 (1H, br s), 8.05 (1H, d, J=7.8 Hz), 7.90–7.72 (3H, m), 7.55 (1H, br s), 7.26 (1H, br s).

EXAMPLE 1(42)

4-[3-(Methoxymethoxy)propyl]thio-(5-trifluoromethyl-1,2,4-triazolo)[4,3-a]quinoxaline

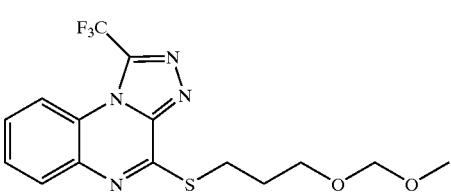

TLC: Rf 0.19 (Toluene:Ethyl acetate=9:1);

NMR (CDCl3): δ8.17–8.03 (2H, m), 7.76–7.59 (2H, m), 4.68 (2H, s), 3.74 (2H, t, J=6.0 Hz), 3.57 (2H, t, J=7.0 Hz), 3.41 (3H, s), 2.25–2.09 (2H, m).

EXAMPLE 1(43)

4-(3-Methylpropoxy)-(5-trifluoromethyl-1,2,4-triazolo)[4,3-a]quinoxaline

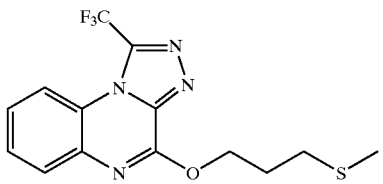

TLC: Rf 0.53 (Toluene:Ethyl acetate=4:1);

NMR (CDCl3): δ8.17–8.07 (1H, m), 8.00–7.90 (1H, m), 7.74–7.54 (2H, m), 4.84 (2H, t, J=6.3 Hz), 2.78 (2H, t, J=7.1 Hz), 2.37–2.22 (2H, m), 2.16 (3H, s).

EXAMPLE 1(44)

4-(3-Methoxypropyl)thio-(5-trifluoromethyl-1,2,4-triazolo)[4,3-a]quinoxaline

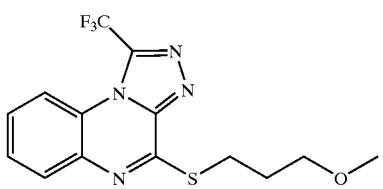

TLC: Rf 0.70 (Toluene:Ethyl acetate=2:1);

NMR (CDCl3): δ8.16–8.03 (2H, m), 7.75–7.59 (2H, m), 3.59 (2H, t, J=6.1 Hz), 3.54 (2H, t, J=7.1 Hz), 3.39 (3H, s), 2.22–2.06 (2H, m).

EXAMPLE 1(45)

4-(2-Methoxyethyl)thio-(5-trifluoromethyl-1,2,4-tniazolo)[4,3-a]quinoxaline

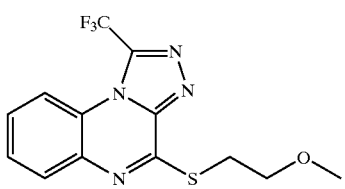

TLC: Rf 0.66 (Toluene:Ethyl acetate=2:1);

NMR (CDCl3): δ8.13 (1H, d, J=8.1 Hz), 8.07 (1H. m), 7.75–7.62 (2H, m), 3.83–3.76 (2H, m), 3.72–3.67 (2H, m), 3.45 (3H, s).

EXAMPLE 1(46)

(±)-4-(2-Methoxypropyl)thio-(5-trifluoromethyl-1,2,4-triazolo)[4,3-a]quinoxaline

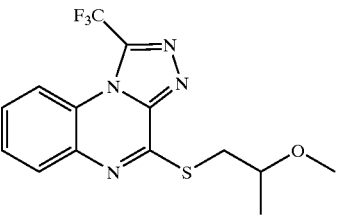

TLC: Rf 0.68 (Toluene:Ethyl acetate=2:1);

NMR (CDCl3): δ8.13 (1H, d, J=8.1 Hz), 8.06 (1H. m), 7.75–7.61 (2H, m), 3.77–3.64 (2H, m), 3.58–3.48 (1H, m), 3.48 (3H, s), 1.37 (3H, d, J=6.0 Hz).

EXAMPLE 1(47)

4-[2-(Methoxymethoxy)ethyl]thio-(5-trifluoromethyl-1,2,4-triazolo)[4,3-a]quinoxaline

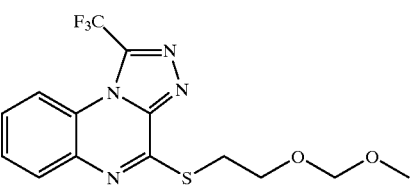

TLC: Rf 0.64 (Toluene:Ethyl acetate=2:1);

NMR (CDCl3): δ8.13 (1H, d, J=8.1 Hz), 8.07 (1H, m), 7.75–7.62 (2H, m), 4.72 (2H, s), 3.95 (2H, t, J=6.3 Hz), 3.71 (2H, t, J=6.3 Hz), 3.43 (3H, s).

EXAMPLE 1(48)

(±)-4-[2-(Methoxymethoxy)propyl]thio-(5-trifluoromethyl-1,2,4-triazolo)[4,3-a]quinoxaline

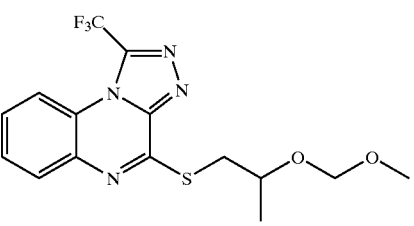

TLC: Rf 0.68 (Toluene:Ethyl acetate=2:1);

NMR (CDCl3): δ8.13 (1H, d, J=8.1 Hz), 8.06 (1H, m), 7.75–7.61 (2H, m), 4.82 and 4.76 (each 1H, ABq, J=6.9 Hz), 4.14 (1H, m), 3.66 (1H, dd, J=6.0, 13.5 Hz), 3.58 (1H, dd, J=5.7, 13.5 Hz), 3.44 (3H, s), 1.41 (3H, d, J=6.3 Hz).

EXAMPLE 1(49)

4-(2-Ethoxyethoxy)-(5-trifluoromethyl-1,2,4-triazolo)[4,3-a]quinoxaline

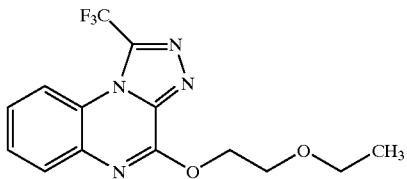

TLC: Rf 0.35 (Hexane:Ethyl acetate=2:1);

NMR (CDCl3): δ8.12 (m, 1H), 7.94 (m, 1H), 7.72–7.54 (m, 2H), 4.88 (m, 2H), 3.98 (m, 2H), 3.65 (q, J=7.0 Hz, 2H), 1.24 (t, J=7.0 Hz, 3H).

EXAMPLE 1(50)

4-(3-Hydroxypropoxy)-(5-trifluoromethyl-1,2,4-triazolo)[4,3-a]quinoxaline

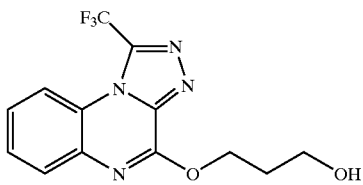

TLC: Rf 0.50 (Toluene:Ethyl acetate=1:1);

NMR (CDCl3): δ8.12 (d, J=8.1 Hz, 1H), 7.93 (dd, J=8.1, 1.8 Hz, 1H), 7.72–7.57 (m, 2H), 4.92 (t, J=6.0 Hz, 2H), 3.89 (m, 2H), 2.26 (m, 1H), 2.23 (quintet, J=6.0 Hz, 2H).

EXAMPLE 1(51)

4-Cyclopentyloxy-(5-trifluoromethyl-1,2,4-triazolo)[4,3-a]quinoxaline

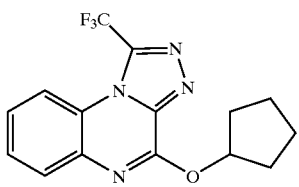

TLC: Rf 0.72 (Hexane:Ethyl acetate=2:1);

NMR (CDCl3): δ8.10 (d, J=8.0 Hz, 1H), 7.93 (dd, J=8.0, 2.0 Hz, 1H), 7.66 (ddd, J=8.0, 8.0, 2.0 Hz, 1H), 7.57 (ddd, J=8.0, 8.0, 2.0 Hz, 1H), 5.88–5.82 (m, 1H), 2.22–2.04 (m, 4H), 2.00–1.86 (m, 2H), 1.78–1.68 (m, 2H).

EXAMPLE 1(52)

4-Cyclopentylmethyloxy-(5-trifluoromethyl-1,2,4-triazolo)[4,3-a]quinoxaline

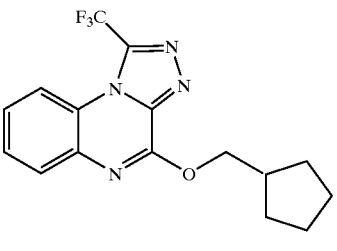

TLC: Rf 0.73 (Hexane:Ethyl acetate=2:1);

NMR (CDCl3): δ8.11 (d, J=8.0 Hz, 1H), 7.93 (dd, J=8.0, 2.0 Hz, 1H), 7.66 (ddd, J=8.0, 8.0, 2.0 Hz, 1H), 7.58 (ddd, J=8.0, 8.0, 2.0 Hz, 1H), 4.60 (d, J=7.0 Hz, 2H), 2.61 (hept, J=7.0 Hz, 1H), 2.00–1.88 (m, 2H), 1.79–1.60 (m, 4H), 1.56–1.40 (m, 2H).

EXAMPLE 1(53)

4-Cyclobutyloxy-(5-trifluoromethyl-1,2,4-triazolo)[4,3-a]quinoxaline

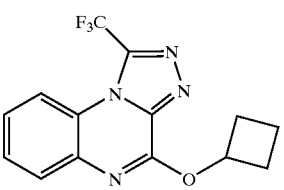

TLC: Rf 0.53 (Hexane:Ethyl acetate=4:1);

NMR (CDCl3): δ8.10 (d, J=8.8 Hz, 1H), 7.92 (dd, J=8.0, 1.6 Hz, 1H), 7.71–7.52 (m, 2H), 5.60 (quintet, J=7.6 Hz, 1H), 2.72–2.52 (m, 2H), 2.52–2.32 (m, 2H), 2.07–1.66 (m, 2H).

EXAMPLE 1(54)

4-Cyclohexylmethyloxy-(5-trifluoromethyl-1,2,4-triazolo)[4,3-a]quinoxaline

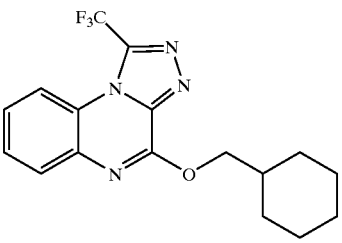

TLC: Rf 0.39 (Hexane:Ethyl acetate=8:1);

NMR (CDCl3): δ8.11 (d, J=7.8 Hz, 1H), 7.94 (dd, J=7.8, 1.8 Hz, 1H), 7.62 (m, 2H), 4.52 (d, J=6.6 Hz, 2H), 2.18–1.60 (m, 5H), 1.45–1.00 (m, 6H).

EXAMPLE 1(55)

4-Cyclopropylmethyloxy-(5-trifluoromethyl-1,2,4-triazolo)[4,3-a]quinoxaline

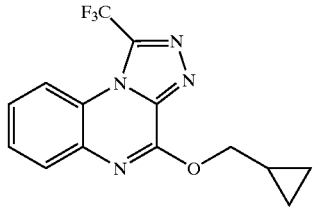

TLC: Rf 0.46 (Hexane:Ethyl acetate=4:1);

NMR (CDCl3): δ8.11 (d, J=8.1 Hz, 1H), 7.91 (dd, J=7.5, 1.8 Hz, 1H), 7.66 (td, J=7.5, 1.5 Hz, 1H), 7.58 (ddd, J=8.1, 7.5, 1.5 Hz, 1H), 4.57 (d, J=7.2 Hz, 2H), 1.59–1.45 (m, 1H), 0.75–0.62 (m, 2H), 0.54–0.47 (m, 2H).

EXAMPLE 1(56)

4-Cycloheptyloxy-(5-trifluoromethyl-1,2,4-triazolo)[4,3-a]quinoxaline

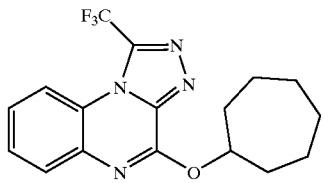

TLC: Rf 0.52 (Hexane:Ethyl acetate=4:1);

NMR (d6-DMSO): δ8.02–7.95 (m, 1H), 7.93–7.86 (m, 1H), 7.74–7.64 (m, 2H), 5.66–5.56 (m,1H), 2.21–2.09 (m, 2H), 2.00–1.86 (m, 2H), 1.81–1.47 (m, 8H).

EXAMPLE 1(57)

4-(4-Fluorophenoxy)-(5-trifluoromethyl-1,2,4-triazolo)[4,3-a]quinoxaline

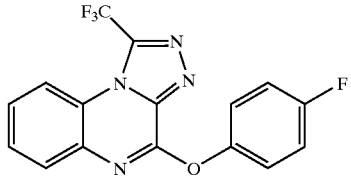

TLC: Rf 0.47 (Hexane:Ethyl acetate=4:1);

NMR (CDCl3): δ8.22–8.12 (m, 1H), 7.87–7.79 (m, 1H), 7.70–7.60 (m,2H), 7.41–7.33 (m, 2H), 7.24–7.15 (m, 2H).

EXAMPLE 1(58)

4-(4-Chlorophenoxy)-(5-trifluoromethyl-1,2,4-triazolo)[4,3-a]quinoxaline

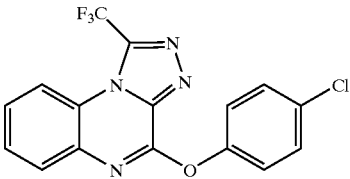

TLC: Rf 0.56 (Toluene:Ethyl acetate=9:1);

NMR (CDCl3): δ8.20–8.12 (m, 1H), 7.87–7.80 (m, 1H), 7.69–7.62 (m, 2H), 7.50–7.44 (m, 2H), 7.38–7.32 (m, 2H).

EXAMPLE 1(59)

4-(2-Hydroxyethoxy)-(5-trifluoromethyl-1,2,4-triazolo)[4,3-a]quinoxaline

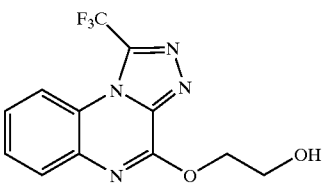

TLC: Rf 0.29 (Toluene:Ethyl acetate=1:1);

NMR (CDCl3): δ8.12 (d, J=8.0 Hz, 1H), 7.94 (dd, J=8.0, 2.0 Hz, 1H), 7.68 (ddd, J=8.0, 8.0, 2.0 Hz, 1H), 7.62 (ddd, J=8.0, 8.0, 2.0 Hz, 1H), 4.86–4.83 (m, 2H), 4.19–4.12 (m, 2H), 3.16 (br s, 1H).

EXAMPLE 1(60)

4-(3-Hydroxy-3-methylbutyl)thio-(5-trifluoromethyl-1,2,4-triazolo)[4,3-a]quinoxaline

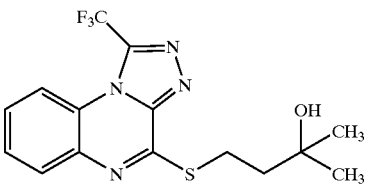

TLC: Rf 0.20 (Hexane:Ethyl acetate=2:1);

NMR (CDCl3): δ8.16–8.02 (m, 2H), 7.75–7.60 (m, 2H), 3.57–3.49 (m, 2H), 2.09–2.00 (m, 2H), 1.97 (brs, 1H), 1.38 (s, 6H).

EXAMPLE 1(61)

(±)-4-(3-Hydroxybutyl)thio-(5-trifluoromethyl-1,2,4-triazolo)[4,3-a]quinoxaline

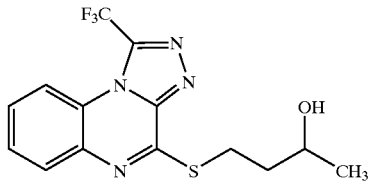

TLC: Rf 0.44 (Hexane:Ethyl acetate=1:1);

NMR (CDCl3): δ8.13 (m, 1H), 8.06 (m, 1H), 7.76–7.61 (m, 2H), 4.00 (m, 1H), 3.75 (ddd, J=14.0, 7.4, 7.0 Hz, 1H), 3.45 (ddd, J=l14.0, 5.8, 5.6 Hz,1H), 3.14 (brs, 1H), 2.03–1.93 (m, 2H), 1.27 (d, J=6.2 Hz, 3H).

EXAMPLE 1(62)

4-(3-Hydroxy-2,2-dimethylpropyl)thio-(5-trifluoromethyl-1,2,4-triazolo)[4,3-a]quinoxaline

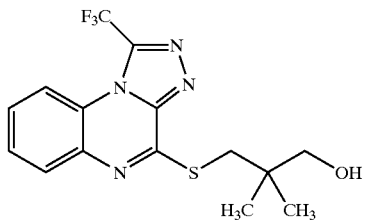

TLC: Rf 0.52 (Hexane:Ethyl acetate=2:1);

NMR (CDCl3): δ8.14 (d, J=7.8 Hz, 1H), 8.04 (dd, J=7.0, 2.4 Hz, 1H), 7.75–7.65 (m, 2H), 3.90 (t, J=6.9 Hz, 1H), 3.50 (s, 2H), 3.38 (d, J=6.9Hz, 2H), 1.15 (s, 6H).

EXAMPLE 1(63)

4-(2-Hydroxy-2-methylpropyl)thio-(5-trifluoromethyl-1,2,4-triazolo)[4,3-a]quinoxaline

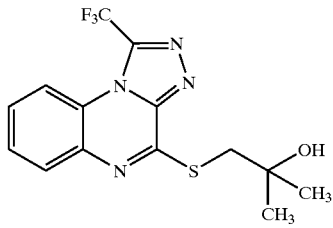

TLC: Rf 0.27 (Hexane:Ethyl acetate=2:1);

NMR (CDCl3): δ8.16–8.11 (m, 1H), 8.08–8.04 (m, 1H), 7.74–7.64 (m, 2H), 3.67 (s, 2H), 3.17 (brs, 1H), 1.46 (s, 6H).

EXAMPLE 1(64)

4-(4-Hydroxybutyl)thio-(5-trifluoromethyl-1,2,4-triazolo)[4,3-a]quinoxaline

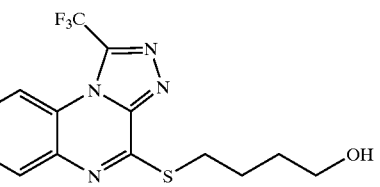

TLC: Rf 0.15 (Hexane:Ethyl acetate=2:1);

NMR (CDCl3): δ8.15–8.06 (m, 2H), 7.74–7.61 (m, 2H), 3.77 (brt, 2H), 3.50 (t, J=7.2 Hz, 2H), 1.98 (m, 2H), 1.81 (m, 2H).

EXAMPLE 1(65)

4-(5-Hydroxypentyl)thio-(5-trifluoromethyl-1,2,4-triazolo)[4,3-a]quinoxaline

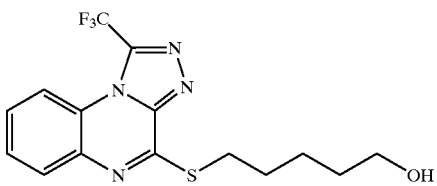

TLC: Rf 0.43 (Hexane:Ethyl acetate=1:2);

NMR (CDCl3): δ8.15–8.05 (2H, m), 7.75–7.60 (2H, m), 3.70 (2H, t, J=6.2 Hz), 3.47 (2H, t, J=7.0 Hz), 1.98–1.80 (2H, m), 1.75–1.40 (5H, m).

EXAMPLE 1(66)

4-(6-Hydroxyhexyl)thio-(5-trifluoromethyl-1,2,4-triazolo)[4,3-a]quinoxaline

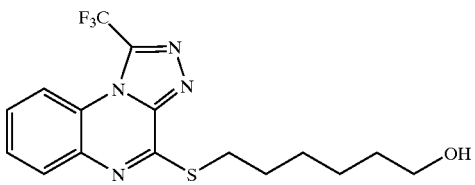

TLC: Rf 0.49 (Hexane:Ethyl acetate=1:2);

NMR (CDCl3): δ8.14–8.05 (2H, m), 7.75–7.59 (2H, m), 3.67 (2H, t, J=6.2 Hz), 3.46 (2H, t, J=7.0 Hz), 1.98–1.80 (2H, m), 1.70–1.40 (7H, m).

EXAMPLE 1(67)

4-[1-(Hydroxymethyl)cyclopropyl-1-yl]methylthio-(5-trifluoromethyl-1,2,4-triazolo)[4,3-a]quinoxaline

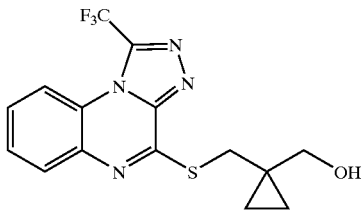

TLC: Rf 0.20 (Hexane:Ethyl acetate=2:1);

NMR (CDCl3): δ8.16–8.10 (m, 1H), 8.06–8.00 (m, 1H), 7.76–7.61 (m, 2H), 3.61 (s, 2H), 3.49 (s, 2H), 1.65 (brs, 1H) 0.77–0.65 (m, 4H).

EXAMPLE 1(68)

(±)-4-(3-Hydroxy-2-methylpropyl)thio-(5-trifluoromethyl-1,2,4-triazolo)[4,3-a]quinoxaline

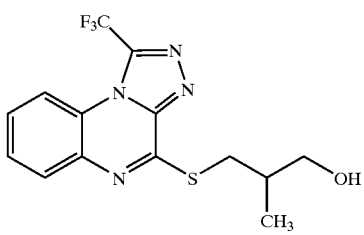

TLC: Rf 0.12 (Hexane:Ethyl acetate=2:1);

NMR (CDCl3): 8.13 (m, 1H), 8.03 (m, 1H), 7.76–7.61 (m, 1H), 3.72–3.46 (m, 4H), 3.31 (m, 2H), 2.24 (m, 1H), 1.14 (d, J=7.0 Hz, 4H).

EXAMPLE 1(69)

(±)-4-(4-Hydroxy-2-butyl)thio-(5-trifluoromethyl-1,2,4-triazolo)[4,3-a]quinoxaline

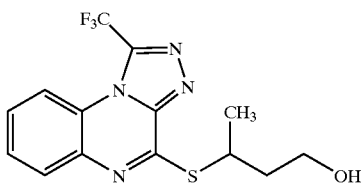

TLC: Rf 0.45 (Hexane:Ethyl acetate=1:1);

NMR (CDCl3): δ8.18–8.10 (m, 1H), 8.06–7.95 (m, 1H), 7.77–7.62 (m, 2H), 4.62–4.41 (m, 1H), 3.85–3.73 (m, 2H), 3.38–3.24 (brs, 1H), 2.30–2.15 (m, 1H), 2.07–1.85 (m, 1H), 1.63 (d, J=7.0 Hz, 3H).

EXAMPLE 1(70)

(±)-4-(3-Hydroxy-2-propyl)thio-(5-trifluoromethyl-1,2,4-triazolo)[4,3-a]quinoxaline

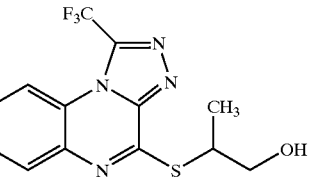

TLC: Rf 0.55 (Hexane:Ethyl acetate=1:1);

NMR (CDCl3): δ8.13 (d, J=8.7 Hz, 1H), 8.05 (d, J=8.1 Hz, 1H), 7.74–7.64 (m, 2H), 4.54–4.42 (m, 2H), 4.06–3.87 (m, 2H), 2.77 (brs, 1H), 1.58 (d, J=7.2Hz, 3H).

EXAMPLE 1(71)

(±)-4-(1-Hydroxy-2-butyl)thio-(5-trifluoromethyl-1,2,4-triazolo)[4,3-a]quinoxaline

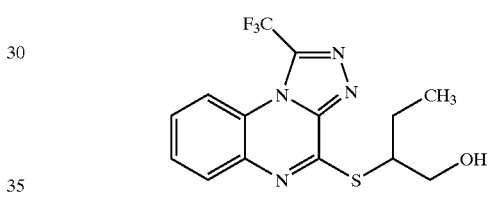

TLC: Rf 0.57 (Hexane:Ethyl acetate=1:1);

NMR (CDCl3): δ8.13 (d, J=9.0 Hz, 1H), 8.05 (d, J=7.5 Hz, 1H), 7.75–7.64 (m, 2H), 4.42–4.32 (m, 1H), 4.09–3.92 (m, 2H), 2.72 (brs, 1H), 2.10–1.81 (m, 2H), 1.17 (t, J=7.5 Hz, 3H).

EXAMPLE 1(72)

(±)-4-(1-Hydroxy-3-pentyl)thio-(5-trifluoromethyl-1,2,4-triazolo)[4,3-a]quinoxaline

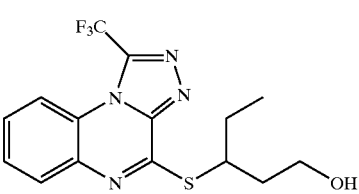

TLC: Rf 0.65 (Hexane:Ethyl acetate=1:1);

NMR (CDCl3): δ8.15–8.12 (m, 1H), 8.02–7.99 (m, 1H), 7.74–7.64 (m, 2H), 4.44–4.33 (m, 1H), 3.83–3.74 (m, 2H), 3.59 (brs, 1H), 2.32–2.18 (m, 1H), 2.06–1.82 (m 3H), 1.54 (t, J=7.2 Hz, 3H).

EXAMPLE 1(73)

(±)-4-(2-Hydroxybutyl)thio-(5-trifluoromethyl-1,2,4-triazolo)[4,3-a]quinoxaline

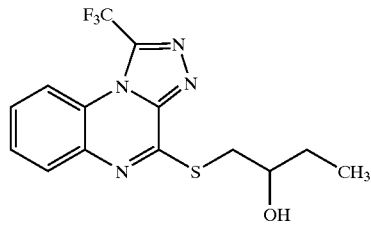

TLC: Rf 0.54 (Hexane:Ethyl acetate=1:1);

NMR (CDCl3): δ8.15–8.12 (m, 1H), 8.08–8.04 (m, 1H), 7.74–7.64 (m, 2H), 3.98–3.92 (m,1H), 3.75 (dd, J=14.1, 3.3 Hz, 1H), 3.46 (dd, J=14.1, 7.5 Hz, 1H), 3.23 (brs, 1H), 1.78–1.57 (m, 2H), 1.08 (t, J=7.2 Hz, 3H).

EXAMPLE 1(74)

(±)-4-(4-Hydroxypentyl)thio-(5-trifluoromethyl-1,2,4-triazolo)[4,3-a]quinoxaline

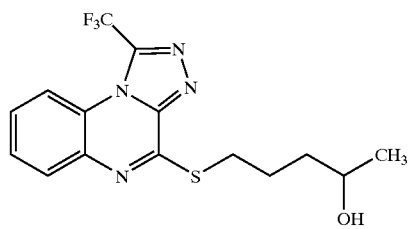

TLC: Rf 0.51 (Hexane:Ethyl acetate=1:1);

NMR (CDCl3): δ8.13–8.05 (m, 2H), 7.74–7.58 (m, 2H), 4.01–3.85 (m, 1H), 3.52–3.40 (m, 2H), 2.09–1.89 (m, 2H), 1.75–1.62 (m, 3H), 1.24 (d, J=6.2 Hz, 3H).

EXAMPLE 1(75)

4-(4-Hydroxy-2-cis-butenyl)thio-(5-trifluoromethyl-1,2,4-triazolo)[4,3-a]quinoxaline

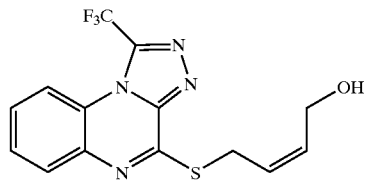

TLC: Rf 0.35 (Hexane:Ethyl acetate=1:1)

NMR (CDCl3): δ8.13 (d, J=8.1 Hz, 2H), 7.75–7.64 (m, 2H), 5.87–5.73 (m, 2H), 4.49 (d, J=5.1 Hz, 2H), 4.19 (d, J=6.9 Hz, 2H), 2.36 (brs, 1H).

EXAMPLE 1(76)

(±)-4-(1-Hydroxy-3-methylbutyl)thio-(5-trifluoromethyl-1,2,4-triazolo)[4,3-a]quinoxaline

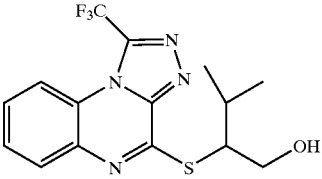

TLC: Rf 0.65 (Hexane:Ethyl acetate=1:1);

NMR (CDCl3): δ8.12 (d, J=7.5 Hz, 1H), 8.04 (d, J=7.5 Hz, 1H), 7.73–7.63 (m, 2H), 4.48–4.42 (m,1H), 4.10–3.48 (m, 2H), 2.76 (brs, 1H), 2.42–2.30 (m, 1H), 1.16 (t, J=6.6 Hz, 6H).

EXAMPLE 1(77)

(±)-cis-4-[2-(Hydroxymethyl)cyclopropylmethyl]thio-(5-trifluoromethyl-1,2,4-triazolo)[4,3-a]quinoxaline

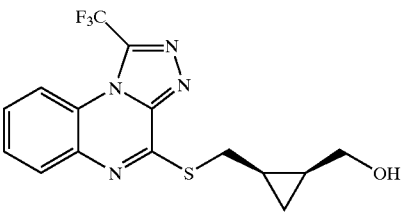

TLC: Rf 0.45 (Hexane:Ethyl acetate=1:1)

NMR (CDCl3): δ8.11 (t, J=9.0 Hz, 2H), 7.73–7.62 (m, 2H), 3.93 (dd, J=11.7, 6.0 Hz, 1H), 3.75–3.65 (m, 2H), 3.48 (dd, J=13.8, 8.4 Hz, 1H), 1.82 (brs, 1H), 1.61–1.36 (m, 2H), 1.00–0.94 (m, 1H), 0.45–0.39 (dd, J=11.1, 5.7, 1H).

EXAMPLE 1(78)

4-(4-Hydroxy-2-trans-butenyl)thio-(5-trifluoromethyl-1,2,4-triazolo)[4,3-a]quinoxaline

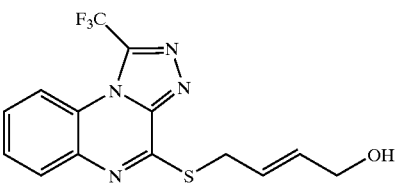

TLC: Rf 0.45 (Hexane:Ethyl acetate=1:1);

NMR (CDCl3): δ8.11 (d, J=7.8 Hz, 1H), 8.07 (d, J=7.8 Hz, 1H), 7.73–7.61 (m, 2H), 6.08 (dt, J=15.3, 5.1 Hz, 1H), 5.94 (dt, J=15.3, 6.6 Hz, 1H), 4.16 (d, J=5.1 Hz, 2H), 4.11 (d, J=6.6 Hz, 2H), 1.52 (brs, 1H).

EXAMPLE 1(79)

4-(Cyclopropylmethyl)thio-(5-trifluoromethyl-1,2,4-triazolo)(4,3-a]quinoxaline

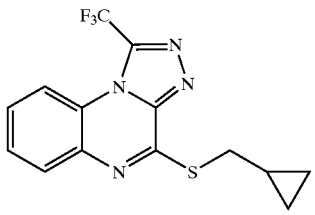

TLC: Rf 0.40 (Hexane:Ethyl acetate=9:1);

NMR (CDCl3): δ8.12 (d, J=8.4 Hz, 1H), 8.06 (d, J=7.8 Hz, 1H), 7.72–7.61 (m, 2H), 3.41 (d, J=7.5 Hz, 2H), 1.37–1.22 (m, 1H), 0.71–0.65 (m, 2H), 0.47–0.43 (m,2H).

EXAMPLE 1(80)

(±)-4-(2,2-Dimethyl-1,3-dioxolan-4-yl)methylthio-(5-trifluoromethyl-1,2,4-triazolo)[4,3-a]quinoxaline

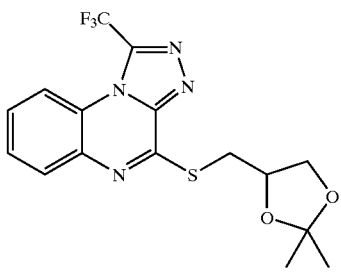

TLC: Rf 0.36 (Hexane:Ethyl acetate=4:1);

NMR (CDCl3): δ8.16–8.07 (m, 2H), 7.74–7.63 (m, 2H), 4.58–4.50 (m, 1H), 4.17 (dd, J=8.7, 6.0 Hz, 1H), 3.89 (dd, J=8.7, 6.0 Hz, 1H), 3.85 (dd, J=13.5, 6.0 Hz, 1H), 3.53 (dd, J=13.5, 6.0 Hz, 1H), 1.51 (s, 3H), 1.38 (s, 3H).

EXAMPLE 1(81)

(±)-4-(2,3-Dihydroxypropyl)thio-(5-trifluoromethyl-1,2,4-triazolo)[4,3-a]quinoxaline

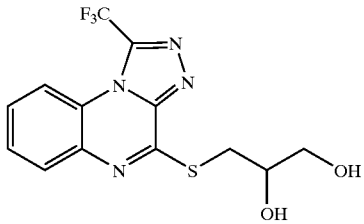

TLC: Rf 0.20 (Hexane:Ethyl acetate=1:1);

NMR (CDCl3): δ8.08 (d, J=8.1 Hz, 1H), 7.98 (dd, J=6.9, 2.1 Hz, 1H), 7.69–7.60 (m, 2H), 4.09 (m, 1H), 3.80–3.49(m, 4H), 3.37 (brs, 1H), 2.63 (brs, 1H).

EXAMPLE 1(82)

(±)-trans-4-[2-(Hydroxymethyl)cyclopropyl]methoxy-(5-trifluoromethyl-1,2,4-triazolo)[4,3-a]quinoxaline

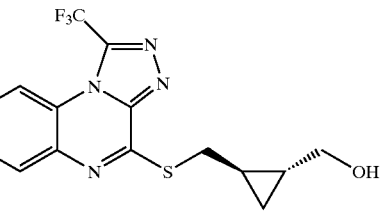

TLC: Rf 0.38 (Hexane:Ethyl acetate=1:1);

NMR (CDCl3): δ8.12 (brd, J=8.2 Hz, 1H), 8.06 (dd, J=7.4, 1.5 Hz, 1H), 7.76–7.59 (m,2H), 3.60–3.35 (m, 4H), 1.42 (brs, 1H), 1.34–1.18 (m, 2H), 0.80–0.62 (m, 2H).

EXAMPLE 1(83)

(±)-4-(3-Hydroxy-1-trifluoromethylpropyl)thio-(5-trifluoromethyl-1,2,4-triazolo)[4,3-a]quinoxaline

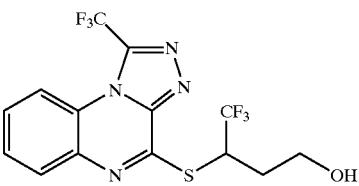

TLC: Rf 0.62 (Hexane:Ethyl acetate=1:1);

NMR (CDCl3): δ8.16–8.08 (m, 2H), 7.77–7.69 (m, 2H), 5.33 (m, 1H), 3.93–3.83 (m, 2H), 2.51 (m, 1H), 2.41 (brs, 1H), 2.03 (m, 1H).

EXAMPLE 1(84)

(±)-4-(2-Hydroxymethylbutyl)thio-(5-trifluoromethyl-1,2,4-triazolo)[4,3-a]quinoxaline

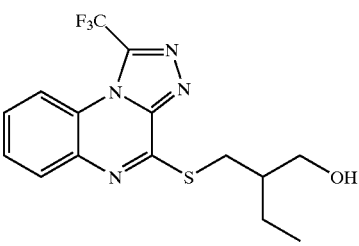

TLC: Rf 0.29 (Toluene:Ethyl acetate=4:1);

NMR (CDCl3): δ8.18–8.10 (1H, m), 8.07–8.01 (1H, m), 7.77–7.62 (2H, m), 3.75–3.40 (3H, m), 3.71 (1H, dd, J=14.2, 4.4 Hz), 3.53 (1H, dd, J=14.2, 6.6 Hz), 2.04–1.92 (1H, m), 1.60–1.45 (2H, m), 1.05 (3H, t, J=7.2 Hz).

EXAMPLE 2(1)–2(10)

The following present compounds were obtained by the same procedure as a series of reaction of Example 1, using 4-Chloro-(5-methyl-1,2,4-triazolo)[4,3-a]quinoxaline, 4-Chloro-(5-phenyl-1,2,4-triazolo)[4,3-a]quinoxaline, 4-Chloro-(5-ethyl-1,2,4-triazolo)[4,3-a]quinoxaline, 4-Chloro-(5-propyl-1,2,4-triazolo)[4,3-a]quinoxaline, 4-Chloro-(1,2,4-triazolo)[4,3-a]quinoxaline or 4-Chloro-(5-pentafluoroethyl-1,2,4-triazolo)[4,3-a]quinoxaline (They were described in J. Med. Chem., 33, 2240 (1990).) instead of 4-Chloro-(5-trifluoromethyl-1,2,4-triazolo)[4,3-a] quinoxaline, and using a corresponding thiol or alcohol.

EXAMPLE 2(1)

4-Phenylthio-(5-methyl-1,2,4-triazolo)[4,3-a]quinoxaline

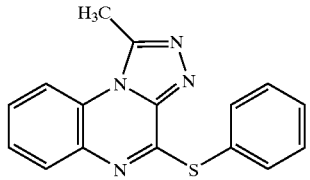

TLC: Rf 0.20 (Toluene:Ethyl acetate=3:1);

NMR (CDCl3): δ8.11–8.06 (1H, m), 7.79–7.69 (3H, m), 7.56–7.48 (5H, m), 3.17 (3H, s).

EXAMPLE 2(2)

4-Phenyloxy-(5-methyl-1,2,4-triazolo)[4,3-a]quinoxaline

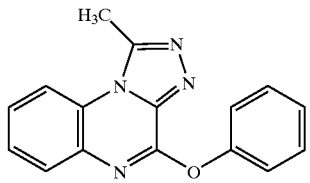

TLC: Rf 0.48 (Chloroform:Methanol=10:1);

NMR (d6-DMSO): δ8.30 (1H, d, J=7.7 Hz), 7.70–7.47 (5H, m), 7.46–7.27 (3H, m), 3.11 (3H, s).

EXAMPLE 2(3)

4-(Pyrimidin-2-yl)thio-(5-methyl-1,2,4-triazolo)[4,3-a]quinoxaline

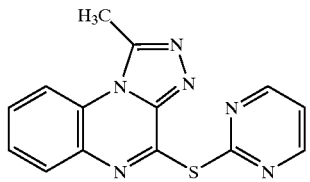

TLC: Rf 0.1 8 (Chloroform:Methanol=10:1);

NMR (d6-DMSO): δ8.64 (1H, d, J=5.0 Hz), 8.38 (1H, d, J=8.4 Hz), 8.05 (1H, dd, J=7.8, 1.4 Hz), 7.90–7.66 (2H, m), 7.36 (1H, t, J=5.0 Hz), 3.10 (3H, s).

EXAMPLE 2(4)

4-(4-Trifluoromethylphenyl)thio-(5-methyl-1,2,4-triazolo)[4,3-a]quinoxaline

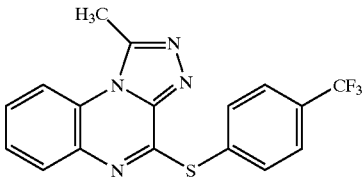

TLC: Rf 0.60 (Chloroform:Methanol=10:1);

NMR (CDCl3): δ8.16–8.06 (1H, m), 7.91–7.71 (5H, m), 7.64–7.48 (2H, m), 3.17 (3H, s).

EXAMPLE 2(5)

4-Phenylthio-(5-phenyl-1,2,4-triazolo)[4,3-a]quinoxaline

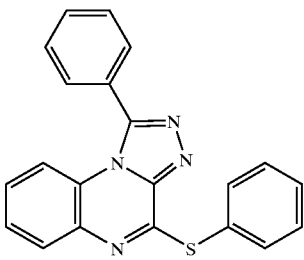

TLC: Rf 0.47 (Chloroform:Methanol=20:1);

NMR (d6-DMSO): δ7.82–7.56 (11H, m), 7.49 (1H, dt, J=1.6, 7.2 Hz), 7.42–7.26 (3H, m).

EXAMPLE 2(6)

4-Phenylthio-(5-ethyl-1,2,4-triazolo)[4,3-a]quinoxaline

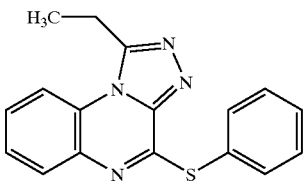

TLC: Rf 0.26 (Chloroform:Methanol 20:1);

NMR (CDCl3): δ8.07–8.00 (1H, m), 7.79–7.66 (3H, m), 7.59–7.44 (5H, m), 3.50 (2H, q, J=7.4 Hz), 1.64 (3H, t, J=7.4 Hz).

EXAMPLE 2(7)

4-Phenylthio-(5-propyl-1,2,4-triazolo)[4,3-a]quinoxaline

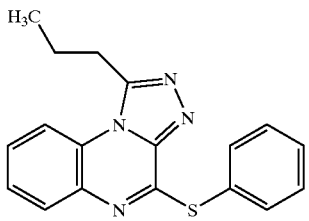

TLC: Rf 0.34 (Chloroform:Methanol=20:1);

NMR (CDCl3): δ8.04–7.97 (1H, m), 7.79–7.66 (3H, m), 7.60–7.43 (5H, m), 3.44 (2H, t, J=7.6 Hz), 2.07 (2H, m), 1.18 (3H, t, J=7.4 Hz).

EXAMPLE 2(8)

4-Propylthio-(1,2,4-triazolo)[4,3-a]quinoxaline

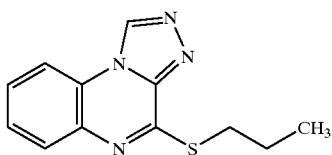

TLC: Rf 0.51 (Chloroform:Methanol=10:1);

NMR (CDCl3): δ9.22 (1H, s), 8.02–7.97 (1H, m), 7.89–7.84 (1H, m), 7.67–7.52 (2H, m), 3.43 (2H, t, J=7.2Hz), 1.89 (2H, qt, J=7.2, 7.2 Hz), 1.31 (3H, t, J=7.2 Hz).

EXAMPLE 2(9)

4-Isopropylthio-(1,2,4-triazolo)[4,3-a]quinoxaline

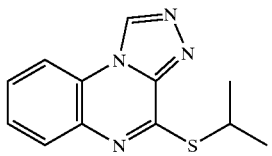

TLC: Rf 0.54 (Chloroform:Methanol=10:1);

NMR (CDCl3): δ9.22 (1H, s), 8.02–7.97 (1H, m), 7.89–7.84 (1H, m), 7.67–7.52 (2H, m), 4.40 (1H, sept, J=6.8 Hz), 1.56 (6H, d, J=6.8 Hz).

EXAMPLE 2(10)

4-Phenylthio-(5-pentafluoroethyl-1,2,4-triazolo)[4,3-a]quinoxaline

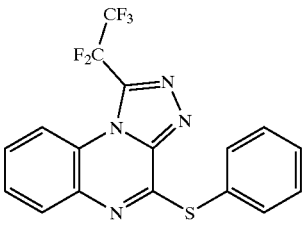

TLC: Rf 0.58 (Hexane:Ethyl acetate=4:1);

NMR (CDCl3): δ8.26–8.14 (1H, m), 7.88–7.78 (1H, m), 7.76–7.67 (2H, m), 7.67–7.58 (2H, m), 7.58–7.48 (3H, m).

Reference Example 1(1)–1(34)

The following compounds were obtained by the same procedure as a series of reaction in J. Med. Chem., 33, 2240 (1990), using a corresponding benzopyrazine derivative or pyrazine derivative instead of 2,3-Dichlorobenzopyrazine.

Reference Example 1(1)

4-Chloro-(5-trifluoromethyl-1,2,4-triazolo)[3,4-c]1,4,5-triazanaphthalene

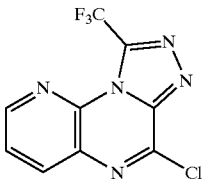

TLC: Rf 0.60 (Hexane:Ethyl acetate=1:1);

NMR (CDCl3): δ8.87 (1H, dd, J=1.6, 4.6 Hz), 8.50 (1H, dd, J=1.6, 8.0 Hz), 7.81 (1H, dd, J=4.6, 8.0 Hz).

Reference Example 1(2)

4-Chloro-7-nitro-(5-trifluoromethyl-1,2,4-triazolo)[4,3-a]quinoxaline

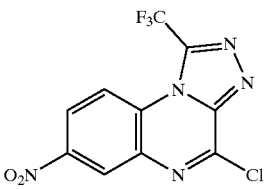

TLC: Rf 0.13 (Toluene);

NMR (CDCl3): δ9.04 (1H, d, J=2.8 Hz), 8.67 (1H, dd, J=2.8, 9.2 Hz), 8.39 (1H, d, J=9.2 Hz).

Reference Example 1(3)

4-Chloro-7,8-dimethoxy-(5-trifluoromethyl-1,2,4-triazolo)[4,3-a]quinoxaline

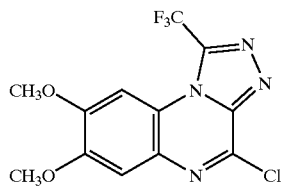

TLC: Rf 0.27 (Hexane:Ethyl acetate=3:1);
NMR (d6-DMSO): δ7.70 (1H, s), 7.39 (1H, s), 3.96 (6H, s).

Reference Example 1(4)

4,7,8-Trichloro-(5-trifluoromethyl-1,2,4-triazolo)[4,3-a]quinoxaline

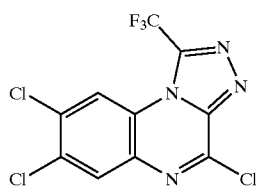

TLC: Rf 0.43 (Toluene).

Reference Example 1(5)

4-Chloro-7-methoxycarbonyl-(5-trifluoromethyl-1,2,4-triazolo)[4,3-a]quinoxaline

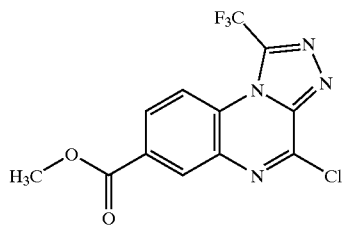

TLC: Rf 0.46 (Hexane:Ethyl acetate=5:1);
NMR (CDCl3): δ8.83 (1H, d, J=2.1 Hz), 8.47 (1H, dd, J=9.0, 2.0 Hz), 8.27 (1H, d, J=9.0 Hz), 4.04 (3H, s).

Reference Example 1(6)

4-Chloro-6,7,8,9-tetrahydro-(5-trifluoromethyl-1,2,4-triazolo)[4,3-a]quinoxaline

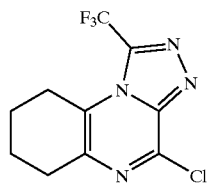

TLC: Rf 0.28 (Hexane:Ethyl acetate=4:1).

Reference Example 1(7)

4-Chloro-(5-trifluoromethyl-1,2,4-triazolo)[4,3-a]pyrazine

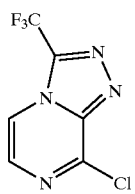

TLC: Rf 0.65 (Chloroform:Methanol=9:1).

Reference Example 1(8)

4-Chloro-6,7-dimethyl-(5-trifluoromethyl-1,2,4-triazolo)[4,3-a]pyrazine

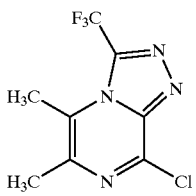

TLC: Rf 0.33 (Hexane:Ethyl acetate=4:1).

Reference Example 1(9)

4-Chloro-8-nitro-(5-trifluoromethyl-1,2,4-triazolo)(4,3-a]quinoxaline

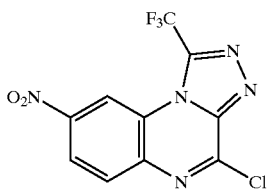

TLC: Rf 0.49 (Hexane:Ethyl acetate=2:1)
NMR (CDCl3): δ9.18 (1H, d, J=2.2 Hz), 8.65 (1H, dd, J=2.2, 9.2 Hz), 8.37 (1H, d, J=9.2 Hz).

Reference Example 1(10)

4-Chloro-8-methoxycarbonyl-(5-trifluoromethyl-1,2,4-triazolo)[4,3-a]quinoxaline

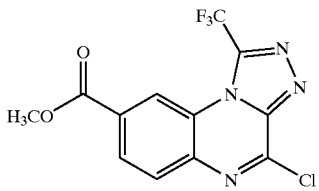

TLC: Rf 0.35 (Hexane:Ethyl acetate=3:1).

Reference Example 1(11)

4-Chloro-6-ethoxycarbonyl-(5-trifluoromethyl-1,2,4-triazolo)[4,3-a]quinoxaline

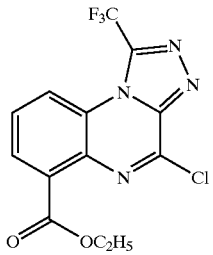

TLC: Rf 0.37 (Hexane:Ethyl acetate=2:1).

Reference Example 1(12)

4,8-Dichloro-6-methoxycarbonyl-(5-trifluoromethyl-1,2,4-triazolo)[4,3-a]quinoxaline

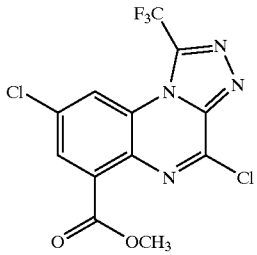

TLC: Rf 0.39 (Hexane:Ethyl acetate=4:1).

Reference Example 1(13)

8-Carboxy-4-Chloro-(5-trifluoromethyl-1,2,4-triazolo)[4,3-a]quinoxaline

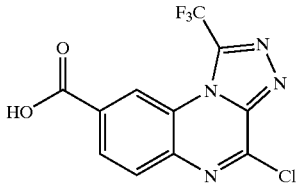

TLC: Rf 0.40 (Chloroform:Methanol=2:1).

Reference Example 1(14)

4-Chloro-6-nitro-(5-trifluoromethyl-1,2,4-triazolo)[4,3-a]quinoxaline

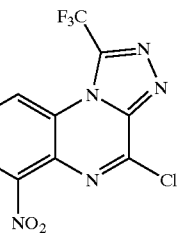

TLC: Rf 0.55 (Toluene:Ethyl acetate=9:1).

Reference Example 1(15)

4-Chloro-(5-trifluoromethyl-1,2,4-triazolo)[4,3-a]1,4,5-triazanaphthalene

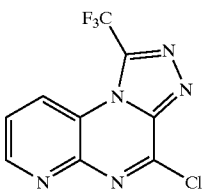

TLC: Rf 0.76 (Hexane:Ethyl acetate=1:1).

Reference Example 1(16)

4-Chloro-6-phenyl-(5-trifluoromethyl-1,2,4-triazolo)[4,3-a]pyrazine

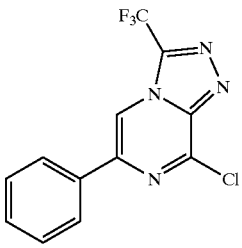

TLC: Rf 0.52 (Toluene:Ethyl acetate=9:1).

Reference Example 1(17)

4-Chloro-7-methyl-(5-trifluoromethyl-1,2,4-triazolo)[4,3-a]pyrazine

TLC: Rf 0.29 (Toluene:Ethyl acetate=9:1).

Reference Example 1(18)

4-Chloro-7-ethyl-(5-trifluoromethyl-1,2,4-triazolo)[4,3-a]pyrazine

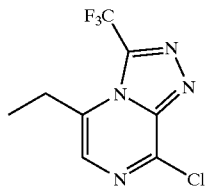

TLC: Rf 0.27 (Hexane:Ethyl acetate=4:1).

Reference Example 1(19)

4,7-Dichloro-(5-trifluoromethyl-1,2,4-triazolo)[4,3-a]quinoxaline

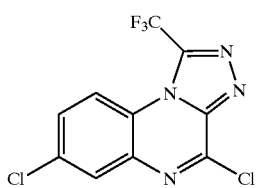

TLC: Rf 0.64 (Hexane:Ethyl acetate=4:1).

Reference Example 1(20)

4,8-Dichloro-(5-trifluoromethyl-1,2,4-triazolo)[4,3-a]quinoxaline

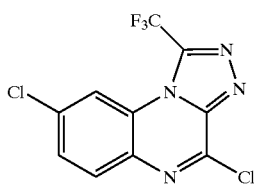

TLC: Rf 0.59(Hexane:Ethyl acetate=4:1).

Reference Example 1(21)

4,6-Dichloro-(5-trifluoromethyl-1,2,4-triazolo)[4,3-a]quinoxaline

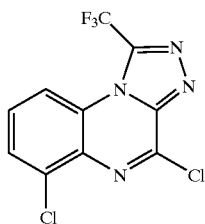

TLC: Rf 0.47 (Hexane:Ethyl acetate=4:1).

Reference Example 1(22)

4,6,8-Trichloro-(5-trifluoromethyl-1,2,4-triazolo)[4,3-a]quinoxaline

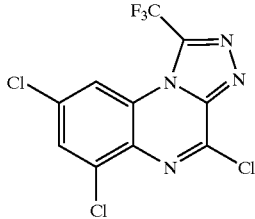

TLC: Rf 0.35 (Toluene).

Reference Example 1(23)

8-Bromo-4-chloro-(5-trifluoromethyl-1,2,4-triazolo)[4,3-a]quinoxaline

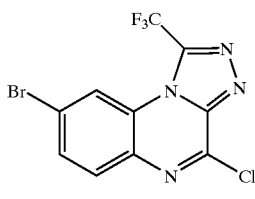

TLC: Rf 0.36 (Hexane:Ethyl acetate=4:1).

Reference Example 1(24)

4-Chloro-6,8-dibromo-(5-trifluoromethyl-1,2,4-triazolo)[4,3-a]quinoxaline

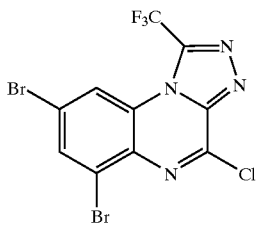

TLC: Rf 0.38 (Hexane:Ethyl acetate=10:1).

Reference Example 1(25)

4-Chloro-8-trifluoromethyl-(5-trifluoromethyl-1,2,4-triazolo)[4,3-a]quinoxaline

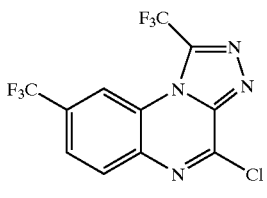

TLC: Rf 0.34 (Chloroform).

Reference Example 1(26)

4-Chloro-8-fluoro-(5-trifluoromethyl-1,2,4-triazolo)[4,3-a]quinoxaline

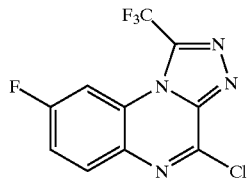

TLC: Rf 0.42 (Hexane:Ethyl acetate=4:1).

Reference Example 1(27)

4-Chloro-7-propyl-(5-trifluoromethyl-1,2,4-triazolo)[4,3-a]pyrazine

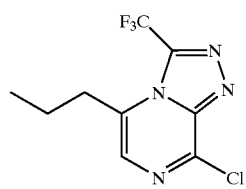

TLC: Rf 0.30 (Hexane:Ethyl acetate=3:1).

Reference Example 1(28)

7-Butyl-4-chloro-(5-trifluoromethyl-1,2,4-triazolo)[4,3-a]pyrazine

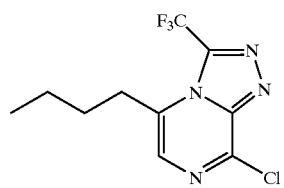

TLC: Rf 0.31 (Hexane:Ethyl acetate=4:1).

Reference Example 1(29)

4-Chloro-7-pentyl-(5-trifluoromethyl-1,2,4-triazolo)[4,3-a]pyrazine

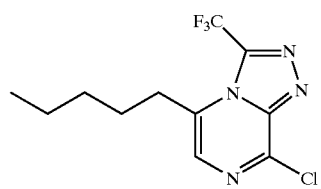

TLC: Rf 0.35 (Hexane:Ethyl acetate=4:1).

Reference Example 1(30)

4-Chloro-8-fluoro-6-methoxycarbonyl-(5-trifluoromethyl-1,2,4-triazolo)[4,3-a]quinoxaline

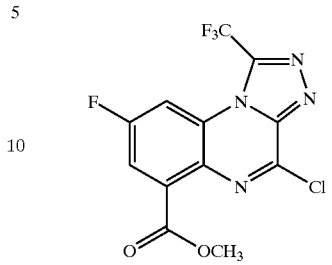

TLC: Rf 0.35 (Hexane:Ethyl acetate=4:1).

Reference Example 1(31)

4-Chloro-7-methoxycarbonyl-(5-trifluoromethyl-1,2,4-triazolo)[3,4-c]1,4,5-triazanaphthalene

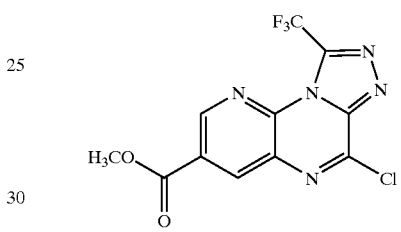

TLC: Rf 0.16 (Chloroform).

Reference Example 1(32)

4-Chloro-8-hydroxymethyl-(5-trifluoromethyl-1,2,4-triazolo)[4,3-a]quinoxaline

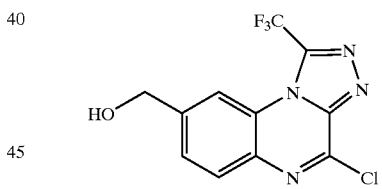

A solution of the compound prepared in Reference Example 1(10) (2.47 g) in anhydrous tetrahydrofuran (THF) (70 ml) was cooled to −78° C. under an atmosphere of argon. Diisobutylaluminum hydride (22.5 ml; 1.0M toluene solution) was added to the solution. The mixture was stirred for 3 hours. The reaction mixture was warmed to 0° C. The mixture was diluted with diethyl ether. A saturated aqueous solution of anhydrous sodium sulfate was added to the mixture, and the mixture was stirred enough. Insoluble material was removed by filtration. The filtrate was concentrated. The residue was purified by column chromatography on silica gel (methylene chloride:ethyl acetate=20:1) to give the title compound (1.80 g) having the following physical data.

TLC: Rf 0.49 (Toluene:Ethyl acetate=1:1).

Reference Example 1(33)–1(35)

The following compounds were obtained by the same procedure as a series of reaction of Reference Example 1(32), using the compounds prepared in Reference Example 1(11), 1(12), 1(30).

Reference Example 1(33)

4-Chloro-6-hydroxymethyl-(5-trifluoromethyl-1,2,4-triazolo)[4,3-a]quinoxaline

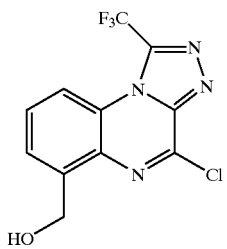

TLC: Rf 0.53 (Methylene chloride:Ethyl acetate=100:1).

Reference Example 1(34)

4,8-Dichloro-6-hydroxymethyl-(5-trifluoromethyl-1,2,4-triazolo)[4,3-a]quinoxaline

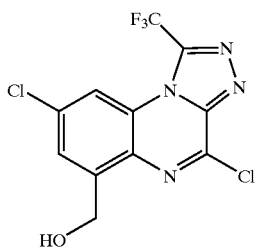

TLC: Rf 0.45 (Chloroform:Methanol=10:1).

Reference Example 1(35)

4-Chloro-8-fluoro-6-hydroxymethyl-(5-trifluoromethyl-1,2,4-triazolo)[4,3-a]quinoxaline

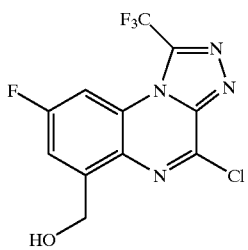

TLC: Rf 0.42 (Chloroform:Methanol=10:1).

EXAMPLE 3(1)–3(135)

The following present compounds were obtained by the same procedure as a series of reaction of Example 1, using the compound prepared in Reference Example 1(1)–1(37) instead of 4-Chloro-(5-trifluoromethyl-1,2,4-triazolo)[4,3-a]quinoxaline, and using a corresponding thiol or alcohol.

EXAMPLE 3(1)

4-Phenylthio-(5-trifluoromethyl-1,2,4-triazolo)[3,4-c]1,4,5-triazanaphthalene

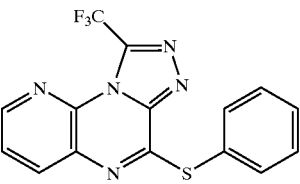

TLC: Rf 0.30 (Chloroform);

NMR (CDCl3): δ8.66 (1H, dd, J=1.8, 4.8 Hz), 8.13 (1H, dd, J=1.8, 8.0 Hz), 7.74–7.50 (6H, m).

EXAMPLE 3(2)

4-Phenylthio-7-nitro-(5-trifluoromethyl-1,2,4-triazolo)[4,3-a]quinoxaline

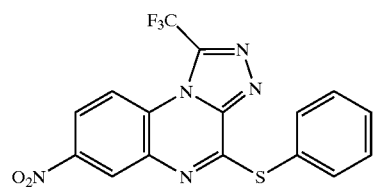

TLC: Rf 0.51 (Hexane:Ethyl acetate=3:1);

NMR (CDCl3): δ8.63 (1H, d, J=2.6 Hz), 8.45 (1H, dd, J=2.6, 9.2 Hz), 8.25 (1H, d, J=9.2 Hz), 7.74–7.54 (5H, m).

EXAMPLE 3(3)

4-Phenylthio-7,8-dimethoxy-(5-trifluoromethyl-1,2,4-triazolo)[4,3-a]quinoxaline

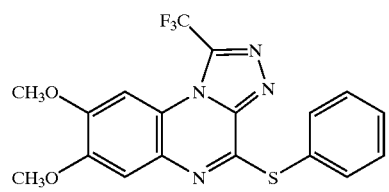

TLC: Rf 0.22 (Chloroform);

NMR (CDCl3): δ7.75–7.69 (2H, m), 7.57–7.50 (4H, m), 7.21 (1H, s), 4.02 (3H, s), 3.95 (3H, s).

EXAMPLE 3(4)

4-Phenylthio-7,8-dichloro-(5-trifluoromethyl-1,2,4-triazolo)[4,3-a]quinoxaline

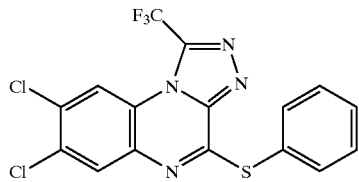

TLC: Rf 0.60 (Hexane:Ethyl acetate=4:1);

NMR (CDCl3): δ8.19 (1H, s), 7.90 (1H, s), 7.70–7.63 (2H, m), 7.58–7.50 (3H, m).

EXAMPLE 3(5)

4-Phenylthio-7-methoxycarbonyl-(5-trifluoromethyl-1,2,4-triazolo)[4,3-a]quinoxaline

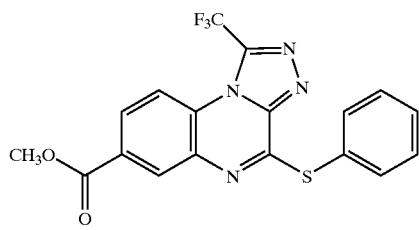

TLC: Rf 0.42 (Hexane:Ethyl acetate=3:1);

NMR (CDCl3): δ8.54 (1H, d, J=1.8 Hz), 8.26 (1H, dd, J=8.6, 1.8 Hz), 8.15 (1H, d, J=8.6 Hz), 7.73–7.68 (2H, m), 7.60–7.51 (3H, m), 3.97 (3H, s).

EXAMPLE 3(6)

4-Phenyloxy-7-methoxycarbonyl-(5-trifluoromethyl-1,2,4-triazolo)[4,3-a]quinoxaline

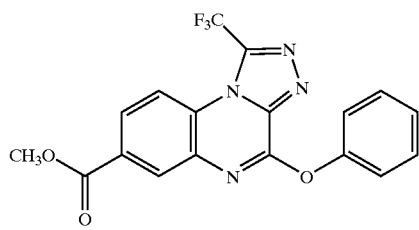

TLC: Rf 0.34 (Hexane:Ethyl acetate=3:1);

NMR (CDCl3): δ8.28 (1H, dd, J=8.8, 2.0 Hz), 8.17 (1H, d, J=8.8 Hz), 8.15 (1H, d, J=2.0 Hz), 7.63–7.51 (2H, m), 7.48–7.34 (3H, m), 3.88 (3H, s).

EXAMPLE 3(7)

4-Phenylthio-6,7,8,9-tetrahydro-(5-trifluoromethyl-1,2,4-triazolo)[4,3-a]quinoxaline

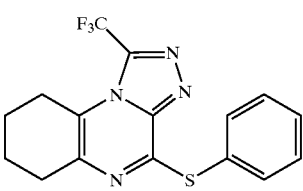

TLC: Rf 0.77 (Hexane:Ethyl acetate=4:1);

NMR (CDCl3): δ7.69–7.59 (2H, m), 7.50–7.41 (3H, m), 3.06–2.93 (2H, m), 2.75 (2H, t, J=6.1 Hz), 2.07–1.75 (4H, m).

EXAMPLE 3(8)

4-Phenylthio-(5-trifluoromethyl-1,2,4-triazolo)[4,3-a]pyrazine

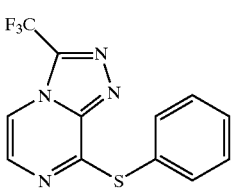

TLC: Rf 0.35 (Toluene:Ethyl acetate=15:1);

NMR (CDCl3): δ7.85 (1H, d, J=4.6 Hz), 7.75 (1H, d, J=5.0 Hz), 7.70–7.63 (2H, m), 7.57–7.48 (3H, m).

EXAMPLE 3(9)

4-Allylthio-(5-trifluoromethyl-1,2,4-triazolo)[4,3-a]pyrazine

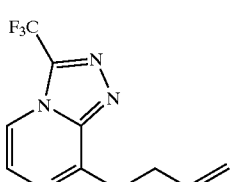

TLC: Rf 0.30 (Hexane:Ethyl acetate=5:1);

NMR (CDCl3): δ7.87 (2H, m), 6.11–5.90 (1H, m), 5.42 (1H, dd, J=1.4, 17.0 Hz), 5.22 (1H, dd, J=1.4, 10.0 Hz), 4.03 (2H, dt, J=1.1, 6.8 Hz).

EXAMPLE 3(10)

4-(3-Allylthiopropyl)thio-(5-trifluoromethyl-1,2,4-triazolo)[4,3-a]pyrazine

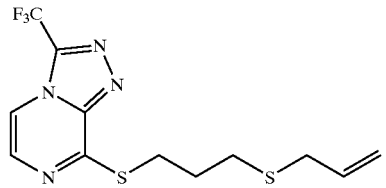

TLC: Rf 0.26 (Hexane:Ethyl acetate=5:1);

NMR (CDCl3): δ7.89 (2H, s), 5.90–5.70 (1H, m), 5.17–5.05 (2H, m), 3.48 (2H, t, J=7.2 Hz), 3.17 (2H, dd, J=1.0, 7.0 Hz), 2.65 (2H, t, J=7.2 Hz), 2.07 (2H, m).

EXAMPLE 3(11)

4-Phenylthio-6,7-dimethyl-(5-trifluoromethyl-1,2,4-triazolo)[4,3-a]pyrazine

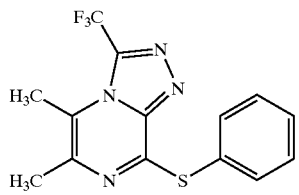

TLC: Rf 0.37 (Hexane:Ethyl acetate=4:1);

NMR (CDCl3): δ7.72–7.57 (2H, m), 7.53–7.40 (3H, m), 2.64 (3H, s), 2.39 (3H s).

EXAMPLE 3(12)

4-Phenylthio-8-nitro-(5-trifluoromethyl-1,2,4-triazolo)[4,3-a]quinoxaline

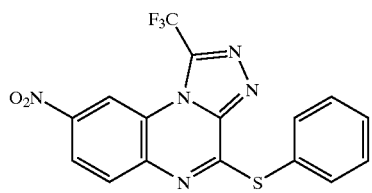

TLC: Rf 0.57 (Hexane:Ethyl acetate=2:1);

NMR (CDCl3): δ9.08 (1H, d, J=2.2 Hz), 8.43 (1H, dd, J=2.2, 9.0 Hz), 7.94 (1H. d, J=9.0 Hz), 7.72–7.50 (5H, m).

EXAMPLE 3(13)

4,8-Diphenylthio-(5-trifluoromethyl-1,2,4-triazolo)[4,3-a]quinoxaline

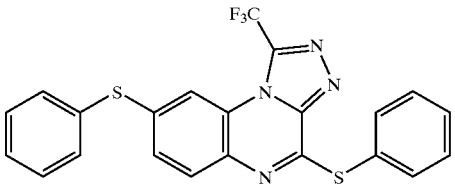

TLC: Rf 0.63 (Hexane:Ethyl acetate=1:1);

NMR (CDCl3): δ7.72–7.64 (3H, m), 7.61–7.44 (9H, m), 7.44 (1H, dd, J=1.4, 8.4 Hz).

EXAMPLE 3(14)

8-Methoxycarbonyl-4-phenylthio-(5-trifluoromethyl-1,2,4-triazolo)[4,3-a]quinoxaline

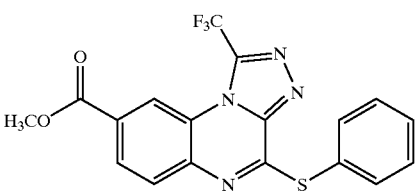

TLC: Rf 0.39 (Hexane:Ethyl acetate=3:1);

NMR (CDCl3): δ8.84 (1H, s), 8.23 (1H, dd, J=8.6, 1.4 Hz), 7.84 (1H, d, J=8.6 Hz), 7.76–7.62 (2H, m), 7.60–7.47 (3H, m), 4.01 (3H, s).

EXAMPLE 3(15)

8-Methoxycarbonyl-4-phenoxy-(5-trifluoromethyl-1,2,4-triazolo)[4,3-a]quinoxaline

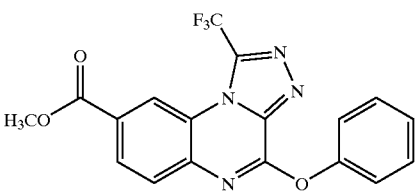

TLC: Rf 0.37 (Hexane:Ethyl acetate=3:1);

NMR (CDCl3): δ8.89 (1H, s), 8.27 (1H, dd, J=8.6, 1.7 Hz), 7.87 (1H, d, J=8.6 Hz), 7.59–7.46 (2H, m), 7.44–7.33 (3H, m), 4.02 (3H, s).

EXAMPLE 3(16)

4-Isopropylthio-(5-trifluoromethyl-1,2,4-triazolo)[3,4-c]1,4,5-triazanaphthalene

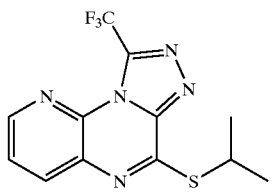

TLC: Rf 0.39 (Hexane:Ethyl acetate=4:1);

NMR (CDCl3): δ8.67 (1H, dd, J=4.6, 1.8 Hz), 8.34 (1H, dd, J=8.2, 1.8 Hz), 7.68 (1H. dd, J=8.2, 4.6 Hz), 4.39 (1H, quint., J=6.8 Hz), 1.57 (6H, d, J=6.8 Hz).

EXAMPLE 3(17)

4-Isobutylthio-(5-trifluoromethyl-1,2,4-triazolo)[3,4-c]1,4,5-triazanaphthalene

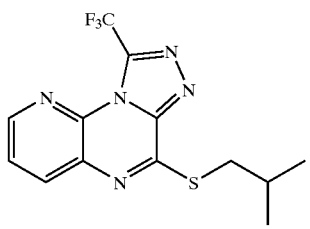

TLC: Rf 0.52 (Hexane:Ethyl acetate=4:1);

NMR (CDCl3): δ8.67 (1H, dd, J=4.8, 1.5 Hz), 8.34 (1H, dd, J=8.1, 1.5 Hz), 7.68 (1H, dd, J=8.1, 4.8 Hz), 3.39 (2H, d, J=6.9 Hz), 2.14 (1H, m), 1.14 (6H, d, J=6.6 Hz).

EXAMPLE 3(18)

4-Butylthio-(5-trifluoromethyl-1,2,4-triazolo)[3,4-c]1,4,5-triazanaphthalene

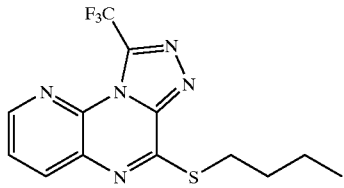

TLC: Rf 0.46 (Hexane:Ethyl acetate=4:1);

NMR (CDCl3): δ8.67 (1H, dd, J=4.6, 1.6 Hz), 8.34 (1H, dd, J=8.4, 1.6 Hz), 7.68 (1H, dd, J=8.4, 4.6 Hz), 3.47 (2H, t, J=7.4 Hz), 1.85 (2H, m), 1.57 (2H, m), 1.01 (3H, t, J=7.4 Hz).

EXAMPLE 3(19)

4-Cyclopentylthio-(5-trifluoromethyl-1,2,4-triazolo)[3,4-c]1,4,5-triazanaphthalene

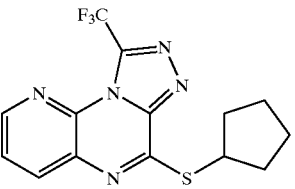

TLC: Rf 0.44 (Hexane:Ethyl acetate=4:1);

NMR (CDCl3): δ8.67 (1H, dd, J=4.6, 1.8 Hz), 8.34 (1H, dd, J=8.0, 1.8 Hz), 7.67 (1H, dd, J=8.0, 4.6 Hz), 4.40 (1H, m), 2.35 (2H, m), 1.80 (6H, m).

EXAMPLE 3(20)

6-Nitro-4-phenylthio-(5-trifluoromethyl-1,2,4-triazolo)[4,3-a]quinoxaline

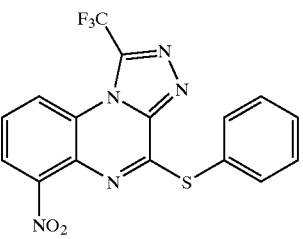

TLC: Rf 0.29 (Hexane:Ethyl acetate=4:1);

NMR (CDCl3): δ8.28 (1H, dd, J=9.0, 0.9 Hz), 7.85 (1H, dd, J=8.1, 0.9 Hz), 7.71 (1H, dd, J=9.0, 8.1 Hz), 7.68–7.50 (5H, m).

EXAMPLE 3(21)

6-Ethoxycarboyl-4-phenylthio-(5-trifluoromethyl-1,2,4-triazolo)[4,3-a]quinoxaline

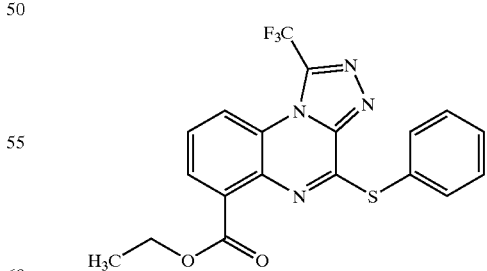

TLC: Rf 0.38 (Hexane:Ethyl acetate=3:1);

NMR (CD3OD): δ8.19 (1H, d, J=6.8 Hz), 7.76–7.60 (4H, m), 7.57–7.47 (3H, m), 3.97 (2H, q, J=7.0 Hz), 1.11 (3H, t, J=7.0 Hz).

EXAMPLE 3(22)

6-Ethoxycarbonyl-4-isopropylthio-(5-trifluoromethyl-1,2,4-triazolo)[4,3-a]quinoxaline

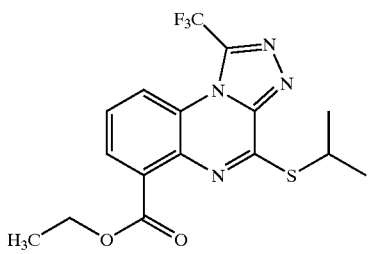

TLC: Rf 0.51 (Hexane:Ethyl acetate=3:1);

NMR (CD3OD): δ8.20 (1H, d, J=8.6 Hz), 7.86 (1H, dd, J=7.6, 1.2 Hz), 7.66 (1H, dd, J=8.6, 7.6 Hz), 4.50 (2H, q, J=7.0 Hz), 4.29 (1H, sept, J=6.8 Hz), 1.56 (6H, d, J=6.8 Hz), 1.44 (3H, t, J=7.0 Hz).

EXAMPLE 3(23)

8-Carboxy-4-phenylthio-(5-trifluoromethyl-1,2,4-triazolo)[4,3-a]quinoxaline

TLC: Rf 0.55 (Chloroform:Methanol=2:1);

NMR (d6-DMSO): δ8.64 (1H, s), 8.16 (1H, d, J=8.6 Hz), 7.79 (1H, d, J=8.6 Hz), 7.77–7.71 (2H, m), 7.66–7.58 (3H, m).

EXAMPLE 3(24)

8-Carboxy-4-isopropylthio-(5-trifluoromethyl-1,2,4-triazolo)[4,3-a]quinoxaline

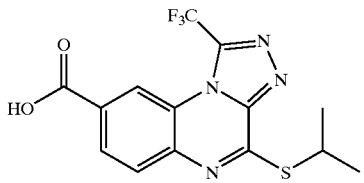

TLC: Rf 0.47 (Chloroform:Methanol=3:1);

NMR (d6-DMSO): δ8.64 (1H, brs), 8.24 (1H, dd, J=8.7, 1.8 Hz), 8.12 (1H, d, J=8.7 Hz), 4.33 (1H, hept, J=6.9 Hz), 1.52 (6H, d, J=6.9 Hz).

EXAMPLE 3(25)

4-Isopropylthio-8-methoxycarbonyl-(5-trifluoromethyl-1,2,4-triazolo)[4,3-a]quinoxaline

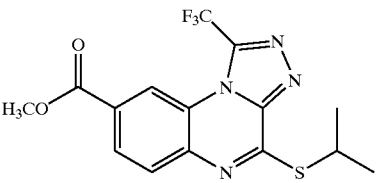

TLC: Rf 0.79 (Hexane:Ethyl acetate 2:1);

NMR (CDCl3): δ8.83 (d, J=1.5 Hz, 1H), 8.33 (dd, J=8.4, 1.5 Hz, 1H), 8.00 (d, J=8.4 Hz, 1H), 4.40 (sept, J=6.9 Hz, 1H), 4.03 (s, 3H), 1.58 (d, J=6.9 Hz, 6H).

EXAMPLE 3(26)

4-(4-Fluorophenyl)thio-8-methoxycarbonyl-(5-trifluoromethyl-1,2,4-triazolo)[4,3-a]quinoxaline

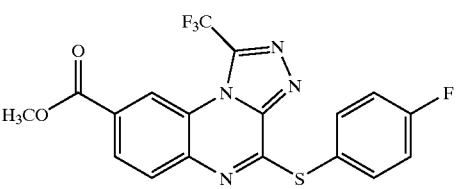

TLC: Rf 0.59 (Chloroform:Methanol 10:1);

NMR (CDCl3): δ8.85 (d, J=1.5 Hz, 1H), 8.25 (dd, J=8.5, 1.5 Hz, 1H), 7.86 (d, J=8.5 Hz, 1H), 7.72–7.63 (m, 2H), 7.29–7.20 (m, 3H), 4.01 (s, 3H).

EXAMPLE 3(27)

4-(3-Hydroxypropyl)thio-8-methoxycarbonyl-(5-trifluoromethyl-1,2,4-triazolo)[4,3-a]quinoxaline

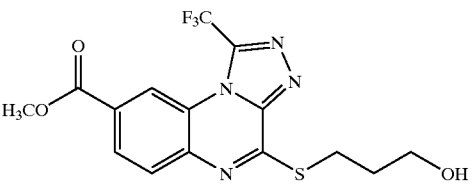

TLC: Rf 0.46 (Chloroform:Methanol 10:1);

NMR (CDCl3): δ8.86 (d, J=1.2 Hz, 1H), 8.33 (dd, J=8.1, 1.2 Hz, 1H), 8.09 (d, J=8.1 Hz,1H), 4.04 (s, 3H), 3.82 (t, J=5.7 Hz, 1H), 3.62 (t, J=6.6 Hz, 1H 2.34 (br, 1H, OH), 2.17–2.09 (m, 1H).

EXAMPLE 3(28)

4-(Imidazol-2-yl)thio-8-methoxycarbonyl-(5-trifluoromethyl-1,2,4-triazolo)[4,3-a]quinoxaline

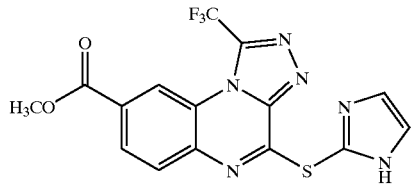

TLC: Rf 0.28 (Chloroform:Methanol=10:1);

NMR (CD3OD+CDCl3): δ8.98 (s, 1H), 8.46 (dd, J=8.4, 1.2 Hz, 1H), 8.38 (d, J=8.4 Hz, 1H), 7.46 (d, J=2.7 Hz, 1H), 7.10 (d, J=2.7 Hz, 1H), 4.04 (s, 3H

EXAMPLE 3(29)

4-Isopropylthio-6-phenyl-(5-trifluoromethyl-1,2,4-triazolo)[4,3-a]pyrazine

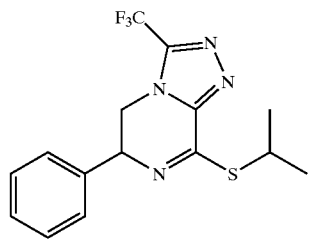

TLC: Rf 0.61 (Toluene:Ethyl acetate=9:1);

NMR (CDCl3): δ8.12 (s, 1H), 7.99–7.93 (m, 2H), 7.58–7.46 (m, 3H), 4.41 (heptet, J=6.6 Hz, 1H), 1.60 (d, J=6.6 Hz, 6H).

EXAMPLE 3(30)

7-Chloro-4-isopropylthio-(5-trifluoromethyl-1,2,4-triazolo)[4,3-a]quinoxaline

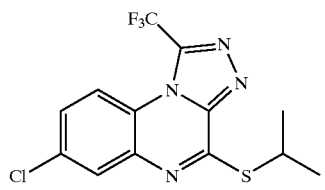

TLC: Rf 0.53 (Hexane:Ethyl acetate=4:1);

NMR (CDCl3): δ8.07 (d, J=2.4 Hz, 1H), 8.03 (d, J=9.0 Hz, 1H), 7.59 (dd, J=9.0, 2.4 Hz, 1H), 4.36 (sept, J=6.9 Hz, 1H), 1.56 (d, J=6.9 Hz, 6H).

EXAMPLE 3(31)

8-Chloro-4-isopropylthio-(5-trifluoromethyl-1,2,4-triazolo)[4,3-a]quinoxaline

TLC: Rf 0.53 (Hexane:Ethyl acetate=10:1);

NMR (CDCl3): δ8.09 (d, J=2.1 Hz, 1H), 8.00 (d, J=8.4 Hz, 1H), 7.65 (dd, J=8.4, 2.1 Hz, 1H), 4.36 (sept, J=6.9 Hz, 1H), 1.56 (d, J=6.9 Hz, 6H).

EXAMPLE 3(32)

4-Isobutylthio-7-methyl-(5-trifluoromethyl-1,2,4-triazolo)[4,3-a]pyrazine

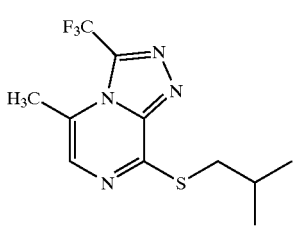

TLC: Rf 0.52 (Hexane:Ethyl acetate 4:1);

NMR (CDCl3): δ7.63–7.61 (m, 1H), 3.25 (d, J=6.6 Hz, 2H), 2.70–2.68 (m, 3H), 2.15–1.97 (m, 1H), 1.10 (d, J=6.6 Hz, 6H).

EXAMPLE 3(33)

4-(4-Fluorophenyl)thio-(5-trifluoromethyl-1,2,4-triazolo)[3,4-c]1,4,5-triazanaphthalene

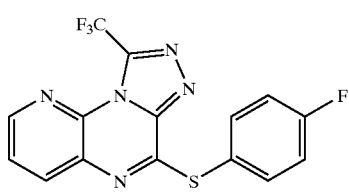

TLC: Rf 0.43 (Hexane:Ethyl acetate 4:1);

NMR (CDCl3): δ8.67 (dd, J=4.8, 1.8 Hz, 1H), 8.13 (dd, J=8.0, 1.8 Hz, 1H), 7.73–7.57 (m, 3H), 7.30–7.18 (m, 2H).

EXAMPLE 3(34)

4-(3-Hydroxypropyl)thio-(5-trifluoromethyl-1,2,4-triazolo)[3,4-c]1,4,5-triazanaphthalene

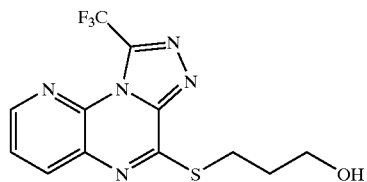

TLC: Rf 0.31 (Hexane:Ethyl acetate=1:1);

NMR (CDCl3+CD3OD(2 drops)): δ8.70 (dd, J=4.4, 1.8 Hz, 1H), 8.36 (dd, J=8.0, 1.8 Hz, 1H), 7.71 (dd, J=8.0, 4.4 Hz, 1H), 3.81 (t, J=5.8 Hz, 2H), 3.61 (t, J=7.0 Hz, 2H), 2.12 (m, 2H).

EXAMPLE 3(35)

8-Chloro-4-(4-fluorophenyl)thio-(5-trifluoromethyl-1,2,4-triazolo)[4,3-a]quinoxaline

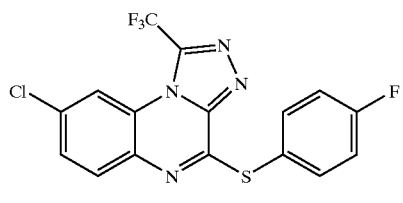

TLC: Rf 0.52 (Hexane:Ethyl acetate=4:1);

NMR (CDCl3): δ8.09 (d, J=2.1 Hz, 1H), 7.75 (d, J=8.7 Hz, 1H), 7.70–7.63 (m, 2H), 7.58 (dd, J=8.7, 2.1 Hz, 1H), 7.27–7.18 (m, 3H).

EXAMPLE 3(36)

8-Chloro-4-(3-Hydroxypropyl)thio-(5-trifluoromethyl-1,2,4-triazolo)[4,3-a]quinoxaline

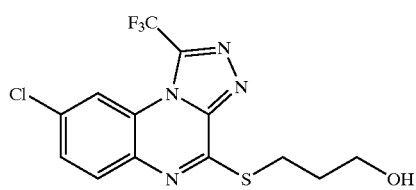

TLC: Rf 0.49 (Chloroform:Methanol=10:1);

NMR (CDCl3): δ8.11 (d, J=2.1 Hz, 1H), 7.98 (d, J=8.7 Hz, 1H), 7.67 (dd, J=8.7, 2.1 Hz, 1H), 3.86–3.77 (m, 2H), 3.59 (t, J=6.6 Hz, 2H), 2.52–2.41 (m, 1H), 2.15–2.07 (m, 2H).

EXAMPLE 3(37)

4-Isobutyloxy-(5-trifluoromethyl-1,2,4-triazolo)[3,4-c]1,4,5-triazanaphthalene

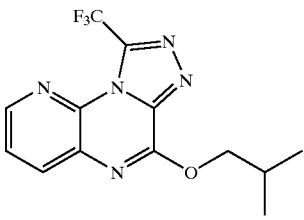

TLC: Rf 0.44 (Hexane:Ethyl acetate=4:1);

NMR (CDCl3): δ8.63 (dd, J=4.8, 1.8 Hz, 1H), 8.22 (dd, J=8.4, 1.8 Hz, 1H), 7.65 (dd, J=8.4, 4.8 Hz, 1H), 4.51 (d, J=7.0 Hz, 2H), 2.36 (sept., J=6.6 Hz, 1H), 1.13 (d, J=6.6 Hz, 6H).

EXAMPLE 3(38)

6-Chloro-4-isobutylthio-(5-trifluoromethyl-1,2,4-triazolo)[4,3-a]quinoxaline

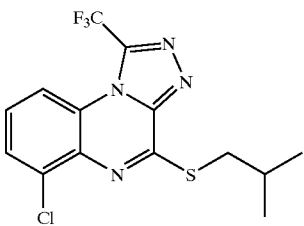

TLC: Rf 0.67 (Hexane:Ethyl acetate=3:1);

NMR (CDCl3): δ8.04 (d, J=8.8 Hz, 1H), 7.81 (dd, J=8.0, 1.0 Hz, 1H), 7.54 (dd, J=8.8, 8.0 Hz, 1H), 3.43 (d, J=6.8 Hz, 2H), 2.31–2.08 (m, 1H), 1.14 (d, J=6.6 Hz, 6H).

EXAMPLE 3(39)

6,8-Dichloro-4-isobutylthio-(5-trifluoromethyl-1,2,4-triazolo)[4,3-a]quinoxaline

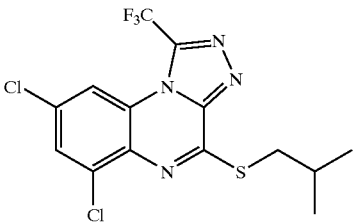

TLC: Rf 0.46 (Toluene:Ethyl acetate 99:1);

NMR (CDCl3) δ8.01 (d, J=1.5 Hz, 1H), 7.79 (d, J=1.5 Hz, 1H), 3.40 (d, J=6.6 Hz, 2H), 2.26–2.12 (m, 1H), 1.14 (d, J=6.9 Hz, 6H).

EXAMPLE 3(40)

4-Isobutylthio-8-trifluoromethyl-(5-trifluoromethyl-1,2,4-triazolo)[4,3-a]quinoxaline

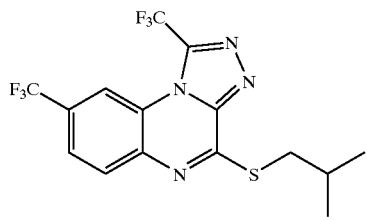

TLC: Rf 0.42 (Hexane:Ethyl acetate=10:1);

NMR (CDCl3): δ8.39 (s, 1H), 8.18 (d, J=8.8 Hz, 1H), 7.92 (dd, J=8.8, 1.8 Hz, 1H), 3.40 (d, J=7.0 Hz, 2H), 2.15 (sept., J=6.6 Hz, 1H), 1.15 (d, J=6.6 Hz, 6H)

EXAMPLE 3(41)

8-Fluoro-4-isobutylthio-(5-trifluoromethyl-1,2,4-triazolo)[4,3-a]quinoxaline

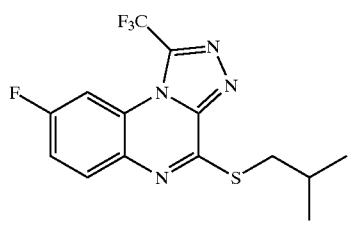

TLC: Rf 0.44 (Hexane:Ethyl acetate=10:1);

NMR (CDCl3): δ8.07 (dd, J=8.8, 6.0 Hz, 1H), 7.83 (dd, J=9.0, 2.6 Hz, 1H), 7.44 (ddd, J=8.8, 7.8, 2.6 Hz, 1H), 3.36 (d, J=6.6 Hz, 2H), 2.13 (sept., J=6.6 Hz, 1H), 1.14 (d, J=6.6 Hz, 6H).

EXAMPLE 3(42)

6,8-Dibromo-4-isobutylthio-(5-trifluoromethyl-1,2,4-triazolo)[4,3-a]quinoxaline

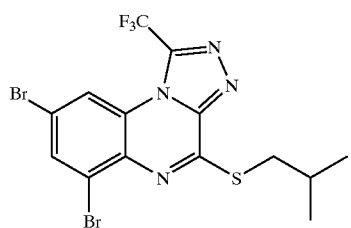

TLC: Rf 0.30 (Hexane:Ethyl acetate=20:1);

NMR (CDCl3): δ8.21 (d, J=2.0 Hz, 1H), 8.14 (d, J=2.0 Hz, 1H), 3.42 (d, J=7.0 Hz, 2H), 2.21 (sept., J=6.6 Hz, 1H), 1.15 (d, J=6.6 Hz, 6H).

EXAMPLE 3(43)

4-(4-Fluorophenyl)thio-8-fluoro-(5-trifluoromethyl-1,2,4-triazolo)[4,3-a]quinoxaline

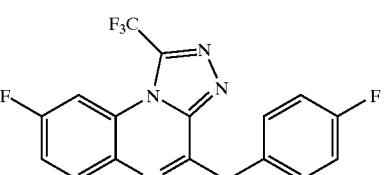

TLC: Rf 0.33 (Hexane:Ethyl acetate=10:1);

NMR (CDCl3): δ7.84 (dd, J=8.8, 2.6 Hz, 1H), 7.83 (dd, J=8.8, 5.8 Hz, 1H), 7.73–7.61 (m, 1H) 7.67 (dd, J=8.8, 5.0 Hz, 1H), 7.37 (ddd, J=8.8, 7.8, 2.6 Hz, 1H), 7.29–7.15 (m, 2H).

EXAMPLE 3(44)

8-Fluoro-4-(3-hydroxypropyl)thio-(5-trifluoromethyl-1,2,4-triazolo)[4,3-a]quinoxaline

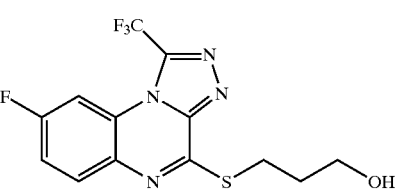

TLC: Rf 0.31 (Hexane:Ethyl acetate=1:1);

NMR (CDCl3): δ8.06 (dd, J=9.2, 5.8 Hz, 1H), 7.85 (dd, J=9.2, 2.6 Hz, 1H), 7.46 (ddd, J=9.2, 7.4, 2.6 Hz, 1H) 3.81 (brt, J=5.4 Hz, 2H), 3.60 (t, J=7.0 Hz, 2H), 2.56 (br, 1H; OH), 2.12 (m, 2H).

EXAMPLE 3(45)

4-(3-Hydroxy-3-methylbutyl)thio-(5-trifluoromethyl-1,2,4-triazolo)[3,4-c]1,4,5-triazanaphthalene

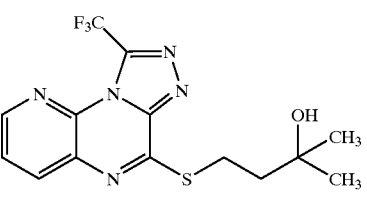

TLC: Rf 0.10 (Hexane:Ethyl acetate=2:1);

NMR (CDCl3): δ8.68 (dd, J=4.4, 1.8 Hz, 1H), 8.34 (dd, J=8.0, 1.8 Hz, 1H), 7.69 (dd, J=8.0, 4.4 Hz, 1H), 3.59–3.50 (m, 2H), 2.08–2.00 (m, 2H), 1.92 (brs, 1H), 1.38 (s, 6H).

EXAMPLE 3(46)

8-Chloro-4-(3-hydroxy-3-methylbutyl)thio-(5-trifluoromethyl-1,2,4-triazolo)[4,3-a]quinoxaline

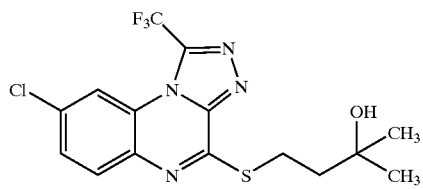

TLC: Rf 0.23 (Hexane:Ethyl acetate=2:1);

NMR (CDCl3): δ8.10 (d, J=1.8 Hz, 1H), 7.98 (d, J=8.8Hz, 1H), 7.66 (dd, J=8.8, 1.8 Hz, 1H), 3.56–3.48 (m, 2H), 2.07–1.99 (m, 2H), 1.82 (brs, 1H), 1.37 (brs, 6H).

EXAMPLE 3(47)

(±)-8-Chloro-4-(3-hydroxybutyl)thio-(5-trifluoromethyl-1,2,4-triazolo)[4,3-a]quinoxaline

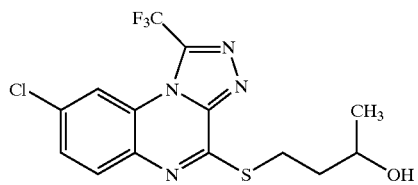

TLC: Rf 0.48 (Hexane:Ethyl acetate=1:1);

NMR (CDCl3): δ8.10 (d, J=2.0 Hz, 1H), 7.98 (d, J=8.8 Hz, 1H), 7.67 (dd, J=8.8, 2.0 Hz, 1H), 3.99 (m, 1H), 3.69 (m, 1H), 3.47 (ddd, J=1 4.0, 6.2, 5.4 Hz, 1H), (brs, 1H), 2.03–1.92 (m, 2H), 1.27 (d, J=6.4 Hz, 3H).

EXAMPLE 3(48)

4-Isobutylthio-6-methyl-(5-trifluoromethyl-1,2,4-triazolo)[4,3-a]pyrazine

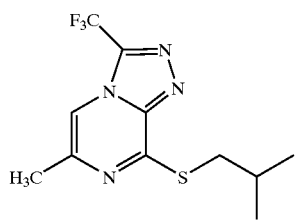

TLC: Rf 0.61 (Toluene:Ethyl acetate=9:1);

NMR (CDCl3): δ7.61 (brs, 1H), 3.29 (d, J=6.6 Hz, 2H), 2.51 (d, J=1.2 Hz, 3H), 2.17–1.98 (m, 1H), 1.10 (d, J=6.9 Hz, 6H).

EXAMPLE 3(49)

8-Chloro-4-(3-hydroxy-2, 2-dimethylpropyl)thio-(5-trifluoromethyl-1,2,4-triazolo)[4,3-a]quinoxaline

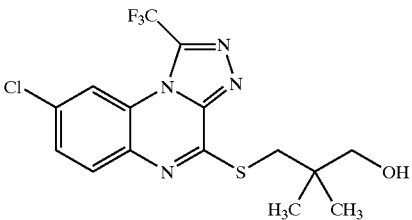

TLC: Rf 0.59 (Hexane:Ethyl acetate=2:1);

NMR (CDCl3): δ8.11 (d, J=1.8 Hz, 1H), 7.97 (d, J=8.7 Hz, 1H), 7.67 (dd, J=8.7, 1.8 Hz, 1H), 3.53 (t, J=6.9 Hz, 1H), 3.49 (s, 2H), 3.38 (d, J=6.9 Hz, 2H), 1.14 (s, 6H).

EXAMPLE 3(50)

8-Chloro-4-(2-hydroxy-2-methylpropyl)thio-(5-trifluoromethyl-1,2,4-triazolo)[4,3-a]quinoxaline

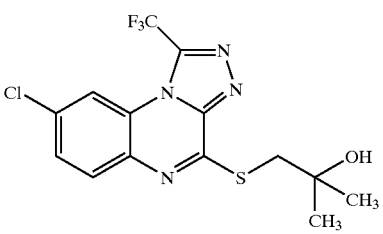

TLC: Rf 0.29 (Hexane:Ethyl acetate=2:1);

NMR (CDCl3): δ8.11 (d, J=1.8 Hz, 1H), 7.99 (d, J=8.7Hz, 1H), 7.67 (dd, J=8.7, 1.8 Hz, 1H), 3.66 (s, 2H), 2.83 (brs, 1H), 1.45 (s, 6H).

EXAMPLE 3(51)

8-Chloro-4-isobutylthio-6-methoxycarbonyl-(5-trifluoromethyl-1,2,4-triazolo)[4,3-a]quinoxaline

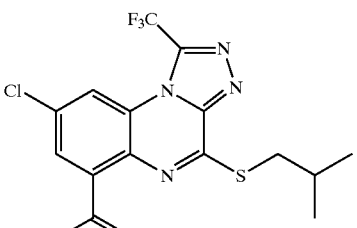

TLC: Rf 0.51 (Hexane:Ethyl acetate=4:1);

NMR (CDCl3): δ8.18 (d, J=2.2 Hz, 1H), 7.86 (d, J=2.2 Hz, 1H), 4.03 (s, 3H), 3.33 (d, J=6.8 Hz, 2H), 2.20–2.02 (m, 1H), 1.11 (d, J=6.8 Hz, 6H).

EXAMPLE 3(52)

8-Chloro-4-(4-fluorophenyl)thio-6-methoxycarbonyl-(5-trifluoromethyl-1,2,4-triazolo)[4,3-a]quinoxaline

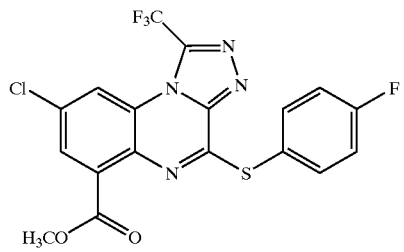

TLC: Rf 0.45 (Hexane:Ethyl acetate=4:1);

NMR (CDCl3): δ8.15 (d, J=1.6 Hz, 1H), 7.72 (d, J=1.6 Hz, 1H), 7.71–7.62 (m, 2H), 7.28–7.20 (m, 2H), 3.60 (s, 3H).

EXAMPLE 3(53)

8-Chloro-4-(4-hydroxybutyl)thio-(5-trifluoromethyl-1,2,4-triazolo)[4,3-a]quinoxaline

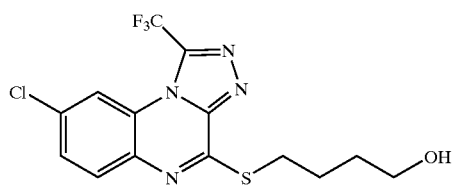

TLC: Rf 0.17 (Hexane:Ethyl acetate=2:1);

NMR (CDCl3): δ8.10 (d, J=1.8 Hz, 1H), 8.01 (d, J=8.7 Hz, 1H), 7.66 (dd, J=8.7, 1.8 Hz, 1H), 3.76 (brt, 2H), 3.48 (t, J=7.2Hz, 2H), 1.97 (m, 2H), 1.81 (m, 2H).

EXAMPLE 3(54)

8-Chloro-4-[[1-[[1-(hydroxymethyl)cyclopropyl-1-yl]methylsufanylmethyl]cyclopropyl-1-yl]methyloxy]-(5-trifluoromethyl-1,2,4-triazolo)[4,3-a]quinoxaline

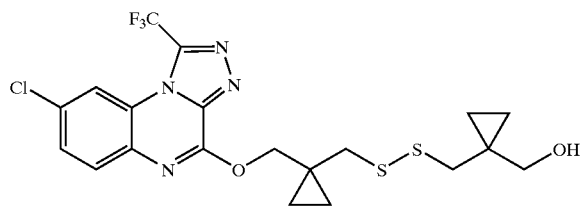

TLC: Rf 0.38 (Hexane:Ethyl acetate=2:1);

NMR (CDCl3): δ8.10 (d, J=1.8 Hz, 1H), 7.86 (d, J=8.7 Hz, 1H), 7.63 (dd, J=8.7, 1.8 Hz, 1H), 4.72 (s, 2H), 3.55 (d, J=4.2Hz, 2H), 3.12 (s, 2H), 2.97 (s, 2H), (brs, 1H), 0.92–0.89 (m, 4H), 0.54 (s, 4H).

EXAMPLE 3(55)

4-[1-(Hydroxy)cyclopropyl-1-yl]methylthio-(5-trifluoromethyl-1,2,4-triazolo)[4,3-a]quinoxaline

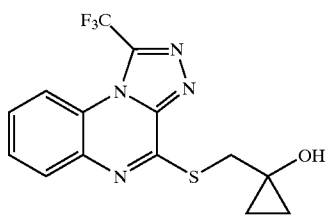

TLC: Rf 0.33 (Hexane:Ethyl acetate=2:1);

NMR (d6-DMSO): δ8.05–8.00 (m, 2H), 7.80–7.73 (m, 2H), 5.75 (s, 1H), 3.71 (s, 2H), 0.76–0.73 (m, 4H).

EXAMPLE 3(56)

4-[1-(Hydroxy)cyclopropyl-1-yl]methylthio-8-chloro-(5-trifluoromethyl-1,2,4-triazolo)[4,3-a]quinoxaline

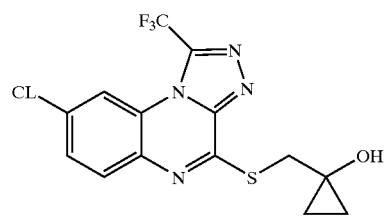

TLC: Rf 0.36 (Hexane:Ethyl acetate=2:1);

NMR (d6-DMSO): δ8.06 (d, J=8.4 Hz, 1H), 7.86 (d, J=2.1 Hz, 1H), 7.84 (dd, J=8.4, 2.1 Hz, 1H), 5.76 (s, 1H), 3.71 (s, 2H), 0.76–0.73 (m, 4H).

EXAMPLE 3(57)

4-(3-Hydroxy-2, 2-dimethylpropyl)thio-(5-trifluoromethyl-1,2,4-triazolo)[3, 4-c]1,4,5-triazanaphthalene

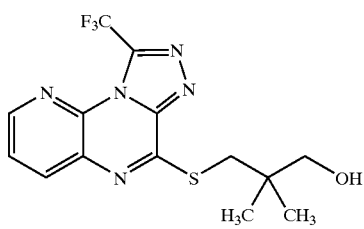

TLC: Rf 0.51 (Hexane:Ethyl acetate=2:1);

NMR (CDCl3): δ8.70 (dd, J=4.8, 1.4 Hz, 1H), 8.32 (dd, J=8.0, 1.4 Hz, 1H), 7.69 (dd, J=8.0, 4.8 Hz, 1H), 3.52 (s, 2H), 3.50–3.37 (m, 3H), 1.15 (s, 6H).

EXAMPLE 3(58)

4-(4-Hydroxybutyl)thio-(5-trifluoromethyl-1,2,4-triazolo)[3,4-c]1,4,5-triazanaphthalene

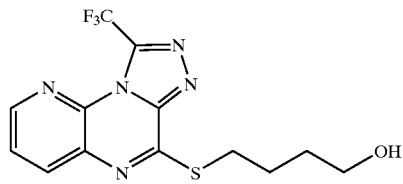

TLC: Rf 0.24 (Hexane:Ethyl acetate=1:1);

NMR (CDCl3): δ8.68 (dd, J=4.4, 1.6 Hz, 1H), 8.36 (dd, J=8.0, 1.6 Hz, 1H), 7.68 (dd, J=8.0, 4.4 Hz, 1H), 3.84–3.72 (m, 2H), 3.51 (t, J=7.2 Hz, 2H), 2.07–1.91 (m, 2H), 1.89–1.74 (m, 2 H), 1.61 (brs, 1H).

EXAMPLE 3(59)

(±)-4-(3-Hydroxybutyl)thio-(5-trifluoromethyl-1,2,4-triazolo)[3, 4-c]1,4,5-triazanaphthalene

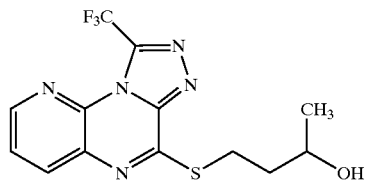

TLC:Rf 0.29 (Hexane:Ethyl acetate=1:1);

NMR (CDCl3): δ8.69 (dd, J=4.8, 1.4 Hz, 1H), 8.33 (dd, J=8.4, 1.4 Hz, 1H), 7.69 (dd, J=8.4, 4.8 Hz, 1H), 4.00 (m, 1H), 3.70 (ddd, J=14, 8.0, 7.2 Hz, 1H), 3.50 (ddd, J=14, 6.0, 5.8 Hz, 1H), 2.72 (brs, 1H), 2.03–1.93 (m, 2H), 1.27 (d, J=6.0 Hz 6H).

EXAMPLE 3(60)

4-Isobutylthio-6,7,8,9-tetrahydro-(5-trifluoromethyl-1,2,4-triazolo)[4,3-a]quinoxaline

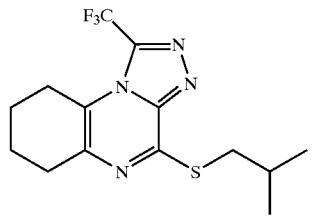

TLC: Rf 0.71 (Hexane:Ethyl acetate=3:1);

NMR (CDCl3): δ3.24 (d, J=6.9 Hz, 2H), 3.04–2.93 (m, 4H), 2.12–1.98 (m, 1H), 2.00–1.89 (m, 4H), 1.09 (d, J=6.3 Hz, 6H).

EXAMPLE 3(61)

4-(4-Hydroxybutyl)thio-6,7,8,9-tetrahydro-(5-trifluoromethyl-1,2,4-triazolo)[4,3-a]quinoxaline

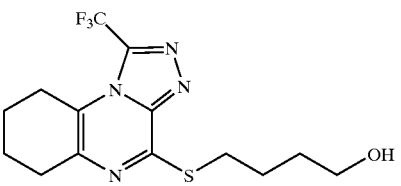

TLC: Rf 0.20 (Hexane:Ethyl acetate=1:1);

NMR (CDCl3): δ3.73 (t, J=7.2 Hz, 2H), 3.36 (t, J=7.2 Hz, 2H) 3.05–2.94 (m, 4H) 2.03–1.83 (m, 6H), 1.81–1.71 (m, 2H).

EXAMPLE 3(62)

8-Fluoro-4-(4-hydroxybutyl)thio-(5-trifluoromethyl-1,2,4-triazolo)[4,3-a]quinoxaline

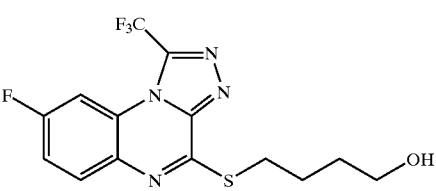

TLC: Rf 0.24 (Hexane:Ethyl acetate=1:1);

NMR (CDCl3): δ8.09 (dd, J=9.0, 5.7 Hz, 1H), 7.83 (dd, J=9.3, 2.1 Hz, 1H), 7.44 (ddd, J=9.3, 5.7, 2.1 Hz, 1H), 3.77 (t, J=6.3 Hz, 2H), 3.48 (t, J=6.3 Hz, 2H), 2.02–1.92 (m, 2H), 1.85–1.76 (m, 2H).

EXAMPLE 3(63)

7-Ethyl-4-isobutylthio-(5-trifluoromethyl-1,2,4-triazolo)[4,3-a]pyrazine

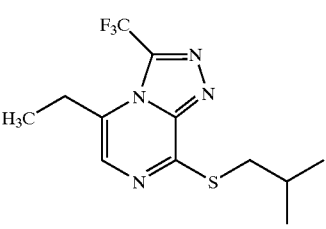

TLC: Rf 0.51 (Hexane:Ethyl acetate=4:1);

NMR (CDCl3): δ7.67 (brs, 1H), 3.26 (d, J=6.6 Hz, 2H), 3.06 (q, J=7.2 Hz, 2H), 2.16–1.96 (m, 1H), 1.46 (t, J=7.2 Hz, 3H), 1.10 (d, J=6.6 Hz, 6H).

EXAMPLE 3(64)

8-Fluoro-4-(2-hydroxyethyl)thio-(5-trifluoromethyl-1,2,4-triazolo)[4,3-a]quinoxaline

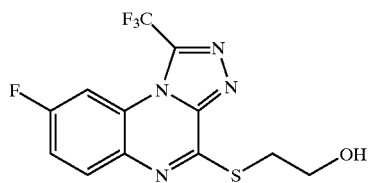

TLC: Rf 0.35 (Hexane:Ethyl acetate=1:1);

NMR (CDCl3): δ8.07 (dd, J=9.0, 5.7 Hz, 1H), 7.84 (dd, J=9.0, 2.1 Hz, 1H), 7.46 (ddd, J=9.0 5.7 2.1 Hz, 1H), 4.06 (q, J=5.7Hz, 2H), 3.67 (t, J=5.7 Hz, 2H), 2.54 (t, J=5.7 Hz, 1H).

EXAMPLE 3(65)

(±)-4-(3-Hydroxy-2-methylpropyl)thio-(5-trifluoromethyl-1,2,4-triazolo)[3,4-c]1,4,5-triazanaphthalene

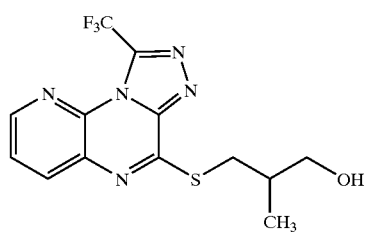

TLC: Rf 0.06 (Hexane:Ethyl acetate=2:1);

NMR (CDCl3): δ8.68 (dd, J=4.8, 1.6 Hz, 1H), 8.32 (dd, J=8.4, 1.6 Hz, 1H), 7.69 (dd, J=8.4, 4.8 Hz, 1H), 3.72–3.49 (m, 2H), 3.57 (d, J=5.8 Hz, 2H), 2.96 (brs, 1H), 2.24 (m, 1H) 1.14 (d, J=7.0 Hz, 3H).

EXAMPLE 3(66)

4-Isobutylthio-8-nitro-(5-trifluoromethyl-1,2,4-triazolo)[4,3-a]quinoxaline

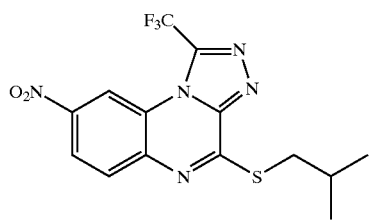

TLC: Rf 0.39 (Hexane:Ethyl acetate=4:1);

NMR (CDCl3): δ9.08 (d, J=2.1 Hz, 1H), 8.53 (dd, J=9.3, 2.1 Hz, 1H), 8.19 (d, J=9.3 Hz, 1H), 3.42 (d, J=6.9 Hz, 2H), 2.25–2.08 (m, 1H), 1.16 (d, J=6.6 Hz, 6H).

EXAMPLE 3(67)

4-(3-Hydroxypropyl)thio-8-nitro-(5-trifluoromethyl-1,2,4-triazolo)[4,3-a]quinoxaline

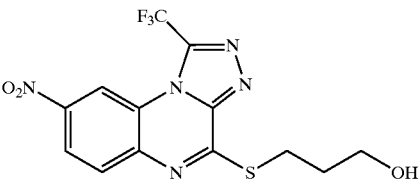

TLC: Rf 0.19 (Hexane:Ethyl acetate=1:1);

NMR (CDCl3): δ9.09 (d, J=2.1 Hz, 1H), 8.54 (dd, J=8.7, 2.1 Hz, 1H), 8.20 (d, J=8.7 Hz, 1H), 3.85 (t, J=5.7 Hz, 2H), 3.65 (t, J=6.9 Hz, 2H), 2.15 (tt, J=6.9, 5.7 Hz, 2H).

EXAMPLE 3(68)

4-(4-Hydroxybutyl)thio-8-nitro-(5-trifluoromethyl-1,2,4-triazolo)[4,3-a]quinoxaline

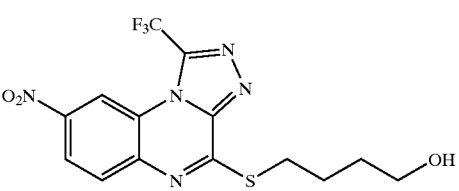

TLC: Rf 0.26 (Hexane:Ethyl acetate=1:1);

NMR (d6-DMSO): δ8.78 (d, J=2.4 Hz, 1H), 8.55 (dd, J=9.0, 2.4 Hz, 1H), 8.25 (d, J=9.0 Hz, 1H), 4.48 (t, J=4.8 Hz, 1H), 3.53–3.44 (m, 4H), 1.91–1.79 (m, 2H), 1.69–1.58 (m, 2H).

EXAMPLE 3(69)

4-(4-Hydroxybutyl)thio-7-methyl-(5-trifluoromethyl-1,2,4-triazolo)[4,3-a]pyrazine

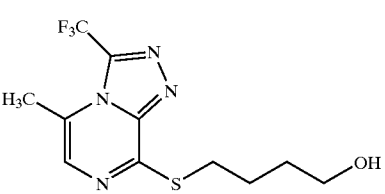

TLC: Rf 0.22 (Hexane:Ethyl acetate=1:1);

NMR (CDCl3): δ7.63 (brd, J=1.2 Hz, 1H), 3.74 (t, J=6.0 Hz, 2H), 3.37 (t, J=7.2 Hz, 2H), 2.68 (brs, 3H), 1.97–1.85 (m, 2H), 1.78–1.68 (m, 2H).

EXAMPLE 3(70)

4-Isobutylthio-(5-trifluoromethyl-1,2,4-triazolo)[4,3-a]pyrazine

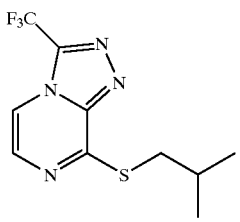

TLC: Rf 0.47 (Hexane:Ethyl acetate=4:1);

NMR (CDCl3): δ7.87–7.80 (m, 2H), 3.29 (d, J=7.0 Hz, 2H), 2.19–2.07 (m, 1H), 1.11 (d, J=6.6 Hz, 6H).

EXAMPLE 3(71)

4-(5-Hydroxypentyl)thio-(5-trifluoromethyl-1,2,4-triazolo)[3,4-c]1,4,5-triazanaphthalene

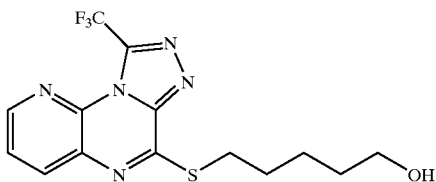

TLC: Rf 0.38 (Hexane:Ethyl acetate=1:2);

NMR (CDCl3): δ8.67 (1H, dd, J=4.8, 1.6 Hz), 8.34 (1H, dd, J=8.4, 1.6 Hz), 7.68 (1H, dd, J=8.4, 4.8 Hz), 3.70 (2H, t, J=6.2 Hz), 3.48 (2H, t, J=7.0 Hz), 1.98–1.82 (2H, m), 1.75–1.20 (5H, m).

EXAMPLE 3(72)

4-(6-Hydroxyhexyl)thio-(5-trifluoromethyl-1,2,4-triazolo)[3,4-c]1,4,5-triazanaphthalene

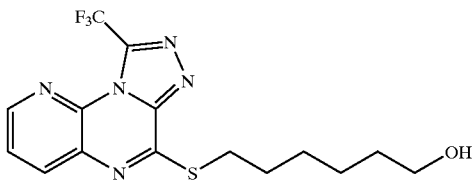

TLC: Rf 0.45 (Hexane:Ethyl acetate=1:2);

NMR (CDCl3): δ8.67 (1H, dd, J=4.4, 1.8 Hz), 8.35 (1H, dd, J=8.0, 1.8 Hz), 7.68 (1H, dd, J=8.0, 4.4 Hz), 3.67 (2H, t, J=6.2 Hz), 3.47 (2H, t, J=7.0 Hz), 1.95–1.81 (2H, m), 1.69–1.16 (7H, m).

EXAMPLE 3(73)

8-Chloro-4-(5-hydroxypentyl)thio-(5-trifluoromethyl-1,2,4-triazolo)[4,3-a]quinoxaline

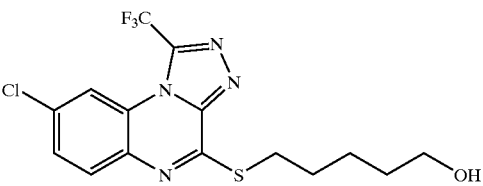

TLC: Rf 0.35 (Hexane:Ethyl acetate=1:1);

NMR (CDCl3): δ8.09 (1H, d, J=1.8 Hz), 8.00 (1H, d, J=8.8 Hz), 7.66 (1H, dd, J=8.8, 1.8 Hz), 3.69 (2H, t, J=6.2 Hz), 3.45 (2H, t, J=7.0 Hz), 1.98–1.82 (2H, m), 1.75–1.20 (5H, m).

EXAMPLE 3(74)

8-Chloro-4-(6-hydroxyhexyl)thio-(5-trifluoromethyl-1,2,4-triazolo)[4,3-a]quinoxaline

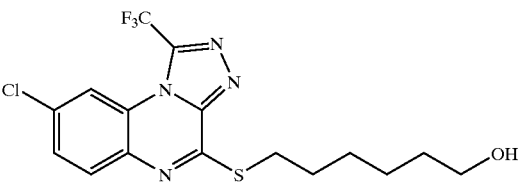

TLC: Rf 0.37 (Hexane:Ethyl acetate=1:1);

NMR (CDCl3): δ8.09 (1H, d, J=2.2 Hz), 8.00 (1H, d, J=8.8 Hz), 7.66 (1H, dd, J=8.8, 2.2 Hz), 3.67 (2H, t, J=6.2 Hz), 3.44 (2H, t, J=7.0 Hz), 1.98–1.82 (2H, m), 1.70–1.20 (7H, m).

EXAMPLE 3(75)

4-[1-(Hydroxymethyl)cyclopropyl-1-yl]methylthio-(5-trifluoromethyl-1,2,4-triazolo)[3,4-c]1, 4, 5-triazanaphthalene

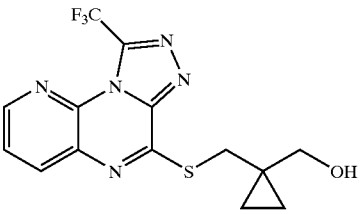

TLC: Rf 0.12 (Hexane:Ethyl acetate=2:1);

NMR (CDCl3): δ8.69 (dd, J=4.8, 1.6 Hz, 1H), 8.31 (dd, J=8.4, 1.6 Hz, 1H), 7.69 (dd, J=8.4, 4.8 Hz, 1H), 3.63 (s, 2H), 3.51 (s, 2H), 3.08 (brs, 1H), 0.79–0.68 (m, 4H).

EXAMPLE 3(76)

8-Fluoro-4-(5-hydroxypentyl)thio-(5-trifluoromethyl-1,2,4-triazolo)[4,3-a]quinoxaline

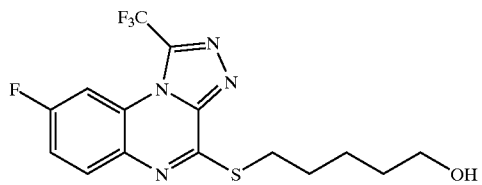

TLC: Rf 0.30 (Hexane:Ethyl acetate=1:1);

NMR (CDCl3): δ8.07 (1H, dd, J=9.2, 5.8 Hz), 7.83 (1H, dd, J=9.4, 2.6 Hz), 7.44 (1H, ddd, J=9.2, 7.6, 2.6 Hz), 3.69 (2H, t, J=6.2 Hz), 3.45 (2H, t, J=7.0 Hz), 1.98–1.82 (2H, m), 1.75–1.20 (5H, m).

EXAMPLE 3(77)

8-Fluoro-4-(6-hydroxyhexyl)thio-(5-trifluoromethyl-1,2,4-triazolo)[4,3-a]quinoxaline

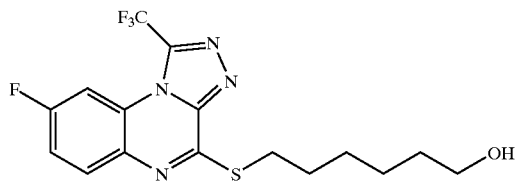

TLC: Rf 0.34 (Hexane:Ethyl acetate=1:1);

NMR (CDCl3): δ8.07 (1H, dd, J=9.2, 5.8 Hz), 7.83 (1H, dd, J=9.4, 2.6 Hz), 7.44 (1H, ddd, J=9.2, 7.6, 2.6 Hz), 3.67 (2H, t, J=6.2 Hz), 3.44 (2H, t, J=7.2 Hz), 1.98–1.82 (2H, m), 1.75–1.20 (7H, m).

EXAMPLE 3(78)

4-Isobutylthio-7-methoxycarbonyl-(5-trifluoromethyl-1,2,4-triazolo)[4,3-a]quinoxaline

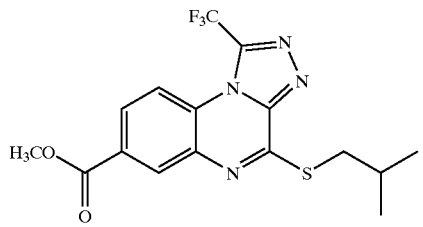

TLC: Rf 0.55 (Hexane:Ethyl acetate=5:1);

NMR (CDCl3): δ8.71 (d, J=1.8 Hz, 1H), 8.27 (dd, J=9.0, 1.8 Hz, 1H), 8.16 (d, J=9.0 Hz, 1H), 4.03 (s, 3H), 3.39 (d, J=6.6 Hz, 2H), 2.25–2.05 (m, 1H), 1.15 (d, J=6.6 Hz, 6H).

EXAMPLE 3(79)

8-Hydroxymethyl-4-isobutylthio-(5-trifluoromethyl-1,2,4-triazolo)[4,3-a]quinoxaline

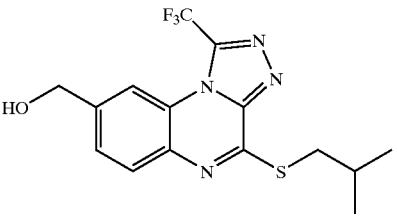

TLC: Rf 0.41 (Hexane:Ethyl acetate=1:1);

NMR (CDCl3): δ8.15 (s, 1H), 8.03 (d, J=8.4 Hz, 1H), 7.66 (d, J=8.4 Hz, 1H), 4.94 (d, J=4.0 Hz, 2H), 3.37 (d, J=7.0 Hz, 2H), 2.24–1.98 (m, 2H), 1.13 (d, J=7.0 Hz, 6H).

EXAMPLE 3(80)

8-Hydroxymethyl-4-(3-hydroxypropyl)thio-(5-trifluoromethyl-1,2,4-triazolo)[4,3-a]quinoxaline

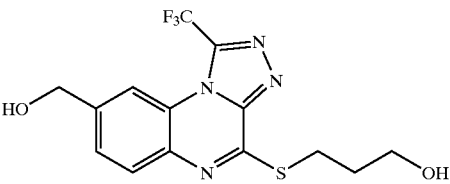

TLC: Rf 0.51 (Ethyl acetate);

NMR (d6-DMSO): δ8.08 (s, 1H), 8.01 (d, J=8.4 Hz, 1H), 7.65 (d, J=8.4 Hz, 1H), 5.65 (t, J=5.4 Hz, 1H), 4.73 (d, J=5.0 Hz, 2H), 4.70–4.60 (m, 1H), 3.62–3.53 (m, 2H), 3.45 (t, J=7.0 Hz, 2H), 2.00–1.85 (m, 2H).

EXAMPLE 3(81)

8-Chloro-4-[1-(Hydroxymethyl)cyclopropyl-1-yl]methylthio-(5-trifluoromethyl-1,2,4-triazolo)[4,3-a]quinoxaline

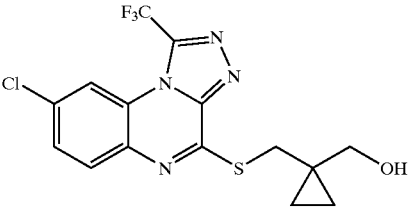

TLC: Rf 0.18 (Hexane:Ethyl acetate=2:1);

NMR (CDCl3): δ8.10 (d, J=2.2Hz, 1H), 7.95 (d, J=8.8 Hz, 1H), 7.66 (dd, J=8.8, 2.2 Hz, 1H), 3.60 (s, 2H), 3.50 (s, 2H), 2.80 (brs, 1H), 0.77–0.65 (m, 4H).

EXAMPLE 3(82)

(±)-8-Chloro-4-(3-hydroxy-2-methylpropyl)thio-(5-trifluoromethyl-1,2,4-triazolo)[4,3-a]quinoxaline

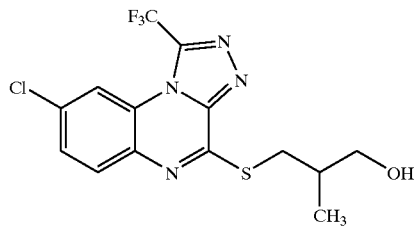

TLC: Rf 0.23 (Hexane:Ethyl acetate 2:1);

NMR (CDCl3) δ8.11 (d, J=1.8 Hz, 1H), 7.97 (d, J=8.8 Hz, 1H), 7.67 (dd, J=8.8, 1.8 Hz, 1H), 3.67 (dd, J=11.4, 4.8 Hz, 1H), 3.55 (brd, J=6.0 Hz, 1H), 3.54 (brs, 1H), 3.53 (dd, J=11.4, 7.0 Hz,1H), 2.23 (m,1H), 1.13 (d, J=7.0 Hz, 3H).

EXAMPLE 3(83)

6,7-Dimethyl-4-isobutylthio-(5-trifluoromethyl-1,2,4-triazolo)[4,3-a]pyrazine

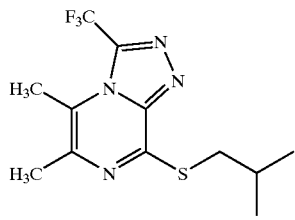

TLC: Rf 0.70 (Hexane:Ethyl acetate=2:1);

NMR (CDCl3): δ3.25 (d, J=6.6 Hz, 2H), 2.65–2.64 (m, 3H), 2.58–2.57 (m, 3H), 2.05 (m, 1H), 1.08 (d, J=6.6 Hz, 6H).

EXAMPLE 3(84)

8-Bromo-4-isobutylthio-(5-trifluoromethyl-1,2,4-triazolo)[4,3-a]quinoxaline

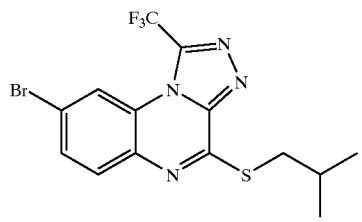

TLC: Rf 0.49 (Hexane:Ethyl acetate=4:1);

NMR (CDCl3): δ8.24 (d, J=2.1 Hz, d), 7.92 (d, J=8.7 Hz, 1H), 7.80 (dd, J=8.7, 2.1 Hz, 1H), 3.36 (d, J=6.6 Hz, 2H), 2.20–2.06 (m, 1H), 1.13 (d, J=6.9 Hz, 6H).

EXAMPLE 3(85)

8-Bromo-4-(3-hydroxypropyl)thio-(5-trifluoromethyl-1,2,4-triazolo)[4,3-a]quinoxaline

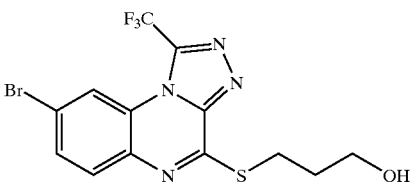

TLC: Rf 0.46 (Toluene:Ethyl acetate=1:1);

NMR (CDCl3): 8.26 (d, J=1.8 Hz, d), 7.91 (d, J=8.7 Hz, 1H), 7.81 (dd, J=8.7, 1.8 Hz, 1H), 3.85–3.77 (m, 2H), 3.59 (t, J=6.9 Hz, 2H), 2.48 (brs, 1H), 2.16–2.0 (m, 2H).

EXAMPLE 3(86)

8-Bromo-4-(4-hydroxybutyl)thio-(5-trifluoromethyl-1,2,4-triazolo)[4,3-a]quinoxaline

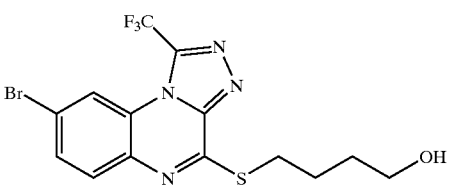

TLC: Rf 0.46 (Toluene:Ethyl acetate=1:1);

NMR (CDCl3): δ8.25 (d, J=1.8 Hz, d), 7.94 (d, J=8.7 Hz, 1H), 7.80 (dd, J=8.7, 1.8 Hz, 1H), 3.77 (t, J=6.0 Hz, 2H), 3.48 (t, J=7.2 Hz, 2H), 2.03–1.92 (m, 2H), 1.86–1.76 (m, 2H).

EXAMPLE 3(87)

4-Isobutylthio-(5-trifluoromethyl-1,2,4-triazolo)[4,3-a]1,4,5-triazanaphthalene

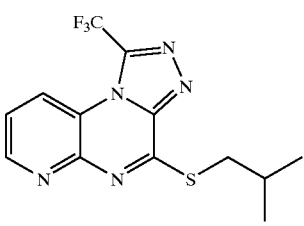

TLC: Rf 0.20 (Hexane:Ethyl acetate=2:1);

NMR (CDCl3): δ8.96 (dd, J=4.4, 1.4 Hz, 1H), 8.46 (m, 1H), 7.60 (dd, J=8.4, 4.4 Hz,1H), 3.50 (d, J=7.0 Hz, 2H), 2.17 (m,1H), 1.15 (d, J=6.6 Hz, 6H).

EXAMPLE 3(88)

4-Cyclopentylthio-6-hydroxymethyl-(5-trifluoromethyl-1,2,4-triazolo)[4,3-a]quinoxaline

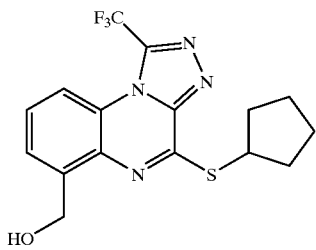

TLC: Rf 0.59 (Hexane:Ethyl acetate=1:1);

NMR (CDCl3): δ8.07 (d, J=8.4 Hz, 1H), 7.72 (d, J=6.9Hz, 1H), 7.62 (dd, J=8.4, 6.9 Hz, 1H), 5.21 (d, J=6.3 Hz, 2H), 4.37–4.25 (m, 1H), 3.28 (t, J=6.3 Hz, 1H), 2.45–2.27 (m, 2H), 1.96–1.68 (m, 6H).

EXAMPLE 3(89)

4-Cyclohexylthio-6-hydroxymethyl-(5-trifluoromethyl-1,2,4-triazolo)[4,3-a]quinoxaline

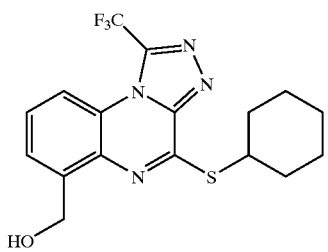

TLC: Rf 0.59 (Hexane:Ethyl acetate=1:1);

NMR (CDCl3) δ8.07 (d, J=9.0 Hz, 1H), 7.72 (d, J=6.9 Hz, 1H), 7.62 (dd, J=9.0, 6.9 Hz, 1H), 5.21 (d, J=6.0 Hz, 2H), 4.21–4.07 (m, 1H), 3.14 (t, J=6.0 Hz, 1H), 2.28–2.16 (m, 2H), 1.94–1.82 (m, 2H), 1.80–1.34 (m, 6H).

EXAMPLE 3(90)

(±)-8-Fluoro-4-(2-hydroxypropyl)thio-(5-trifluoromethyl-1,2,4-triazolo)[4,3-a]quinoxaline

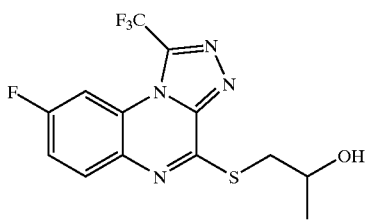

TLC: Rf 0.47 (Hexane:Ethyl acetate=1:1);

NMR (CDCl3): δ8.06 (dd, J=9.2, 6.0 Hz, 1H), 7.83 (dd, J=9.2, 2.6 Hz, 1H), 7.50–7.39 (m, 1H), 4.46–4.18 (m, 1H), 3.68 (dd, J=14.0, 4.0 Hz, 1H), 3.45 (dd, J=14.0, 6.8 Hz, 1H), 2.87 (brs, 1H), 1.40 (d, J=6.2 Hz, 3H).

EXAMPLE 3(91)

(±)-8-Fluoro-4-(3-hydroxy-2-methylpropyl)thio-(5-trifluoromethyl-1,2,4-triazolo)[4,3-a]quinoxaline

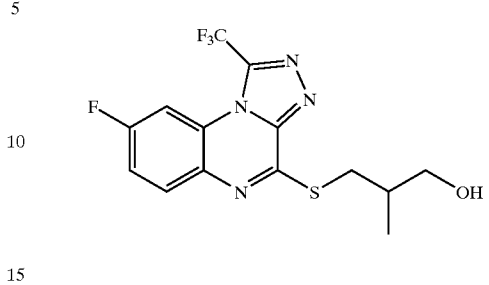

TLC:Rf 0.63 (Hexane:Ethyl acetate=1:1);

NMR (CDCl3): δ8.05 (dd, J=8.8, 5.4 Hz, 1H), 7.84 (dd, J=9.2, 2.2 Hz, 1H), 7.51–7.40 (m, 1H), 3.76–3.47 (m, 2H), 3.56 (d, J=6.0 Hz, 2H), 3.03 (brs, 1H), 2.36–2.17 (m, 1H), 1.14 (d, J=6.4 Hz, 3H).

EXAMPLE 3(92)

4-Butylthio-6-hydroxymethyl-(5-trifluoromethyl-1,2,4-triazolo)[4,3-a]quinoxaline

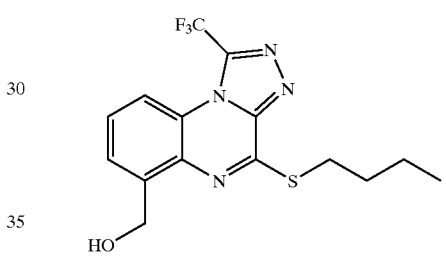

TLC: Rf 0.74 (Hexane:Ethyl acetate=1:1);

NMR (CDCl3): δ8.07 (d, J=8.4 Hz, 1H), 7.74 (d, J=7.2 Hz, 1H), 7.63 (dd, J=8.4, 7.2 Hz, 1H), 5.23 (d, J=6.0 Hz, 2H), 3.41 (t, J=7.2 Hz, 2H), 3.09 (t, J=6.0 Hz, 1H), 1.94–1.82 (m, 2H), 1.64–1.50 (m, 2H), 1.00 (t, J=7.5 Hz, 3H).

EXAMPLE 3(93)

4-(4-Fluorophenyl)thio-6-hydroxymethyl-(5-trifluoromethyl-1,2,4-triazolo)[4,3-a]quinoxaline

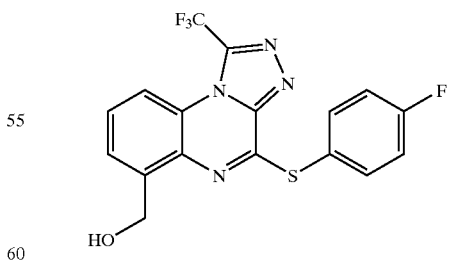

TLC: Rf 0.70 (Hexane:Ethyl acetate=1:1);

NMR (CDCl3): d 8.07 (d, J=8.7 Hz, 1H), 7.72–7.63 (m, 2H), 7.61 (d, J=7.1 Hz, 1H), 7.56 (dd, J=8.7, 7.1 Hz, 1H), 7.34–7.25 (m, 2H), 4.70 (d, J=7.2 Hz, 2H), 2.65 (t, J=7.2 Hz, 1H).

EXAMPLE 3(94)

4-Butylthio-8-chloro-6-hydroxymethyl-(5-trifluoromethyl-1,2,4-triazolo)[4,3-a]quinoxaline

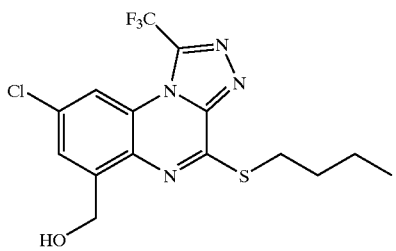

TLC: Rf 0.53 (Hexane:Ethyl acetate=2:1);

NMR (CDCl3): δ8.03 (brd, J=1.8 Hz, 1H), 7.78 (m, 1H), 5.22 (s, 2H), 3.39 (t, J=7.4 Hz, 2H), 2.86 (brs, 1H), 1.93–1.78 (m, 2H), 1.66–1.48 (m, 2H), 1.00 (t, J=7.2 Hz, 2H).

EXAMPLE 3(95)

8-Chloro-4-cyclohexylthio-6-hydroxymethyl-(5-trifluoromethyl-1,2,4-triazolo)[4,3-a]quinoxaline

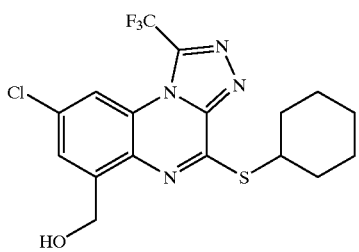

TLC: Rf 0.50 (Hexane:Ethyl acetate=2:1);

NMR (CDCl3): δ8.02 (brd, J=1.8 Hz, 1H), 7.76 (m, 1H), 5.21 (s, 2H), 4.11 (m, 1H), 2.84 (brs, 1H), 2.23–2.16 (m, 1H), 1.91–1.40 (m, 8H).

EXAMPLE 3(96)

(±)-8-Chloro-4-(2-hydroxypropyl)thio-(5-trifluoromethyl-1,2,4-triazolo)[4,3-a]quinoxaline

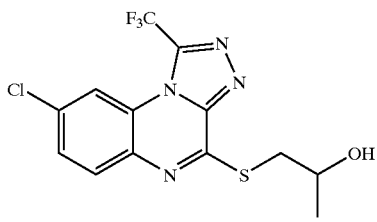

TLC: Rf 0.51 (Hexane:Ethyl acetate=1:1);

NMR (CDCl3): δ8.11 (d, J=1.8 Hz, 1H), 8.00 (d, J=9.0 Hz, 1H), 7.67 (dd, J=9.0, 1.8 Hz, 1H), 4.32–4.22 (m, 1H), 3.69 (dd, J=14.1, 3.9 Hz, 1H), 3.47 (dd, J=14.1, 6.9 Hz, 1H), 2.81 (brs, 1H), 1.41 (d, J=6.3 Hz,3H).

EXAMPLE 3(97)

(±)-4-(2-Hydroxypropyl)thio-(5-trifluoromethyl-1,2,4-triazolo)[3,4-c]1,4, 5-triazanaphthalene

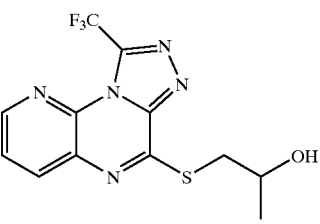

TLC: Rf 0.40 (Hexane:Ethyl acetate=1:1);

NMR (CDCl3): δ8.70 (dd, J=4.8, 1.8 Hz, 1H), 8.34 (dd, J=7.8, 1.5 Hz, 1H), 7.70 (dd, J=8.4, 4.8 Hz, 1H), 4.32–4.22 (m, 1H), 3.71 (dd, J=14.1, 4.2 Hz, 1H), 3.50 (dd, J=14.1, 6.9 Hz, 1H), 2.78 (brs, 1H), 1.42 (d, J=6.3 Hz, 3H).

EXAMPLE 3(98)

6-Hydroxymethyl-4-isobutylthio-(5-trifluoromethyl-1,2,4-triazolo)[4,3-a]quinoxaline

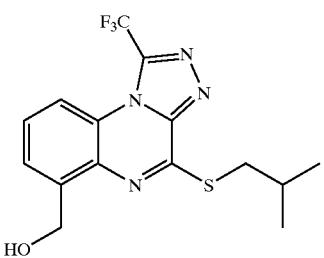

TLC: Rf 0.50 (Hexane:Ethyl acetate=2:1);

NMR (CDCl3): δ8.08 (d, J=8.0 Hz, 1H), 7.75 (d, J=7.2 Hz, 1H), 7.63 (dd, J=8.0, 7.2 Hz, 1H), 5.23 (d, J=6.0 Hz, 2H), 3.31 (d, J=7.0 Hz, 2H), 3.05 (t, J=6.0 Hz, 1H), 2.27–2.04 (m, 1H), 1.16 (d, J=6.6 Hz, 6H).

EXAMPLE 3(99)

8-Chloro-4-(4-fluorophenyl)thio-6-hydroxymethyl-(5-trifluoromethyl-1,2,4-triazolo)[4,3-a]quinoxaline

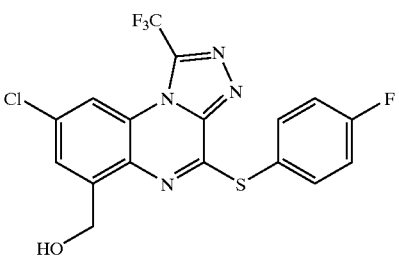

TLC: Rf 0.55 (Hexane:Ethyl acetate=2:1);

NMR (CDCl3): δ8.03 (m, 1H), 7.70–7.64 (m, 2H), 7.58 (m, 1H), 7.33–7.25 (m, 2H), 4.66 (d, J=7.0 Hz, 2H), 2.52 (t, J=7.0 Hz, 1H).

EXAMPLE 3(100)

8-Chloro-4-cyclopentylthio-6-hydroxymethyl-(5-trifluoromethyl-1,2,4-triazolo)[4,3-a]quinoxaline

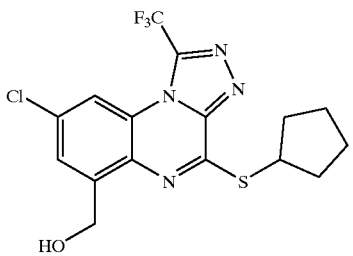

TLC: Rf 0.55 (Hexane:Ethyl acetate=2:1);

NMR (CDCl3): δ8.03 (d, J=2.2 Hz, 1H), 7.75 (m, 1H), 5.20 (brs, 2H), 4.27 (m, 1H), 3.02 (brs, 1H), 2.42–2.23 (m, 1H), 1.92–1.72 (m, 8H).

EXAMPLE 3(101)

4-Isobutylthio-7-propyl-(5-trifluoromethyl-1,2,4-triazolo)[4,3-a]pyrazine

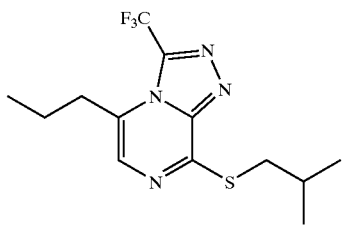

TLC: Rf 0.48 (Hexane:Ethyl acetate=3:1);

NMR (CDCl3): δ7.65 (s, 1H), 3.25 (d, J=6.9 Hz, 2H), 2.96 (t, J=7.8 Hz, 2H), 2.15–1.97 (m, 1H), 1.89–1.75 (m, 2H), 1.13 (t, J=7.5 Hz, 3H), 1.10 (d, J=6.6 Hz, 6H).

EXAMPLE 3(102)

7-Butyl-4-isobutylthio-(5-trifluoromethyl-1,2,4-triazolo)[4,3-a]pyrazine

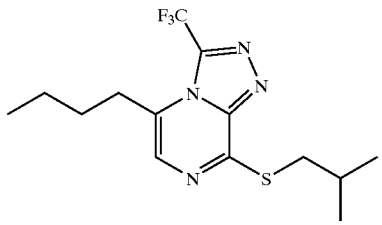

TLC: Rf 0.48 (Hexane:Ethyl acetate=4:1);

NMR (CDCl3): δ7.65 (s, 1H), 3.25 (d, J=6.6 Hz, 2H), 2.98 (t, J=7.5 Hz, 2H), 2.15–1.97 (m, 1H), 1.77 (quintet, J=7.5 Hz, 2H), 1.57–1.47 (m, 2H), 1.10 (d, J=6.6 Hz, 6H), 1.01 (t, J=7.2 Hz, 3H).

EXAMPLE 3(103)

4-Isobutylthio-7-pentyl-(5-trifluoromethyl-1,2,4-triazolo)[4,3-a]pyrazine

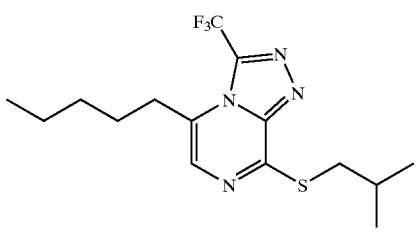

TLC: Rf 0.51 (Hexane:Ethyl acetate=4:1);

NMR (CDCl3): δ7.65 (s, 1H), 3.25 (d, J=6.6 Hz, 2H), 2.97 (t, J=7.5 Hz, 2H), 2.15–1.97 (m, 1H), 1.79 (quintet, J=7.5 Hz, 2H), 1.54–1.34 (m, 4H), 1.10 (d, J=6.6 Hz, 6H), 0.95 (t, J=6.9 Hz, 3H).

EXAMPLE 3(104)

4-(4-Hydroxypropyl)thio-8-trifluoromethyl-(5-trifluoromethyl-1,2,4-triazolo)[4,3-a]quinoxaline

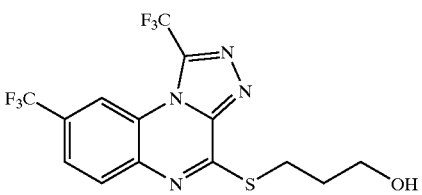

TLC: Rf 0.35 (Hexane:Ethyl acetate=1:1);

NMR (CDCl3): δ8.40 (brs, 1H), 8.17 (d, J=8.4 Hz, 1H), 7.94 (dd, J=8.4, 1.2 Hz, 1H), 3.88–3.78 (m, 2H), 3.63 (t, J=6.9 Hz, 2H), 2.32 (brs,1H), 2.13 (m, 2H).

EXAMPLE 3(105)

4-(4-Hydroxybutyl)thio-8-trifluoromethyl-(5-trifluoromethyl-1,2,4-triazolo)[4,3-a]quinoxaline

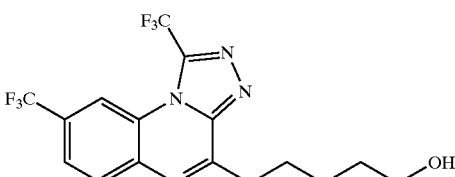

TLC: Rf 0.35 (Hexane:Ethyl acetate=1:1);

NMR (CDCl3): δ8.39 (brs, 1H), 8.19 (d, J=8.4 Hz, 1H), 7.93 (dd, J=8.4, 1.5 Hz, 1H), 3.77 (t, J=6.3 Hz, 2H), 3.52 (t, J=7.2 Hz, 2H), 2.06–1.93 (m, 2H), 1.88–1.76 (m, 2H).

EXAMPLE 3(106)

4-(4-Hydroxypentyl)thio-8-trifluoromethyl-(5-trifluoromethyl-1,2,4-triazolo)[4,3-a]quinoxaline

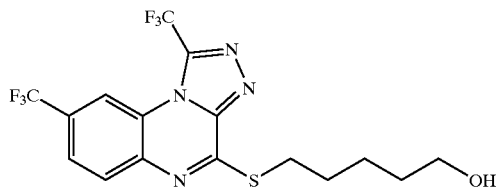

TLC: Rf 0.38 (Hexane:Ethyl acetate=1:1);

NMR (CDCl3): δ8.38 (brs, 1H), 8.18 (d, J=8.4 Hz, 1H), 7.92 (dd, J=8.4, 1.5 Hz, 1H), 3.70 (t, J=6.3 Hz, 2H), 3.49 (t, J=7.2 Hz, 2H), 1.91 (m, 2H), 1.75–1.55 (m, 4H).

EXAMPLE 3(107)

(±)-cis-8-Fluoro-4-[2-(hydroxymethyl)cyclopropyl]methylthio-(5-trifluoromethyl-1,2,4-triazolo)[4,3-a]quinoxaline

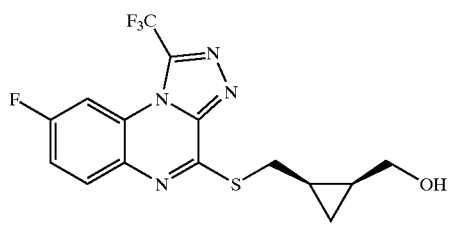

TLC: Rf 0.44 (Hexane:Ethyl acetate=1:1);

NMR (CDCl3): δ8.07 (dd, J=9.0, 5.7 Hz, 1H), 7.81 (d, J=9.6 Hz, 1H), 7.43 (dt, J=2.4, 7.8 Hz, 1H), 3.92 (dd, J=12.0, 5.7 Hz,1H), 3.71–3.63 (m, 2H), 3.45 (dd, J=13.2, 7.8 Hz, 1H), 1.92 (brs, 1H), 1.65–1.30 (m, 2H), 1.00–0.92 (m, 1H), 0.43–0.37 (m,1H).

EXAMPLE 3(108)

(±)-cis-8-Chloro-4-[2-(hydroxymethyl)cyclopropyl]methylthio-(5-trifluoromethyl-1,2,4-triazolo)[4,3-a]quinoxaline

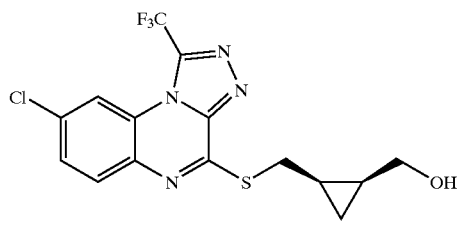

TLC: Rf 0.42 (Hexane:Ethyl acetate=1:1);

NMR (CDCl3): δ8.08 (s, 1H), 8.01 (d, J=8.7 Hz, 1H), 7.65 (d, J=8.7 Hz, 1H), 3.92 (dd, J=12.0, 6.3 Hz, 1H), 3.71–3.62 (m, 2H), 3.46 (dd, J=13.5, 8.1 Hz, 1H), 1.79 (brs, 1H), 1.56–1.32 (m, 2H), 1.00–0.93 (m, 1H), 0.43–0.38 (m, 1H).

EXAMPLE 3(109)

4-Cyclohexylthio-8-fluoro-6-hydroxymethyl-(5-trifluoromethyl-1,2,4-triazolo)[4,3-a]quinoxaline

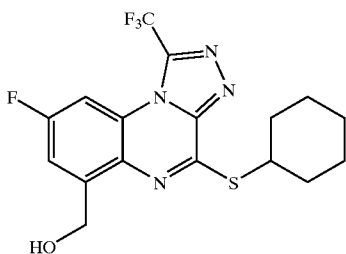

TLC: Rf 0.56 (Hexane:Ethyl acetate=2:1);

NMR (CDCl3): δ7.75 (dd, J=9.2, 2.6 Hz, 1H), 7.56 (dd, J=8.8, 2.6 Hz, 1H),5.24 (brs, 2H), 4.11 (m,1H), 2.94 (brs, 1H), 2.24–2.16 (m, 2H), 1.94–1.42 (m, 8H).

EXAMPLE 3(110)

4-Butylthio-8-fluoro-6-hydroxymethyl-(5-trifluoromethyl-1,2,4-triazolo)[4,3-a]quinoxaline

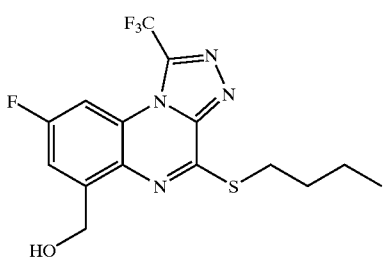

TLC: Rf 0.39 (Hexane:Ethyl acetate=2:1);

NMR (CDCl3): δ7.76 (dd, J=9.2, 2.6 Hz, 1H), 7.56 (dd, J=8.8, 2.6 Hz, 1H), 5.25 (brs, 2H), 3.38 (t, J=7.2 Hz, 2H), 2.88 (brs, 1H), 1.92–1.78 (m, 2H), 1.66–1.48 (m, 2H), 1.00 (t, 7.4 Hz, 3H).

EXAMPLE 3(111)

4-Cyclopentylthio-8-fluoro-6-hydroxymethyl-(5-trifluoromethyl-1,2,4-triazolo)[4,3-a]quinoxaline

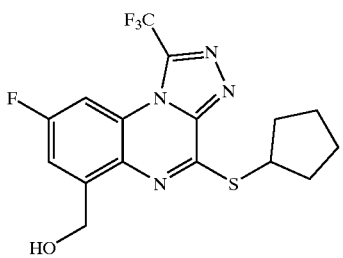

TLC: Rf 0.40 (Hexane:Ethyl acetate=2:1);

NMR (CDCl3): δ7.75 (dd, J=9.2, 2.6 Hz, 1H), 7.54 (dd, J=8.4, 2.6 Hz, 1H), 5.23 (brd, J=4.8 Hz, 2H), 4.27 (m, 1H), 3.01 (m, 1H), 2.44–2.25 (m, 2H), 1.87–1.74 (m, 6H).

EXAMPLE 3(112)

8-Fluoro-4-(4-fluorophenyl)thio-6-hydroxymethyl-(5-trifluoromethyl-1,2,4-triazolo)[4,3-a]quinoxaline

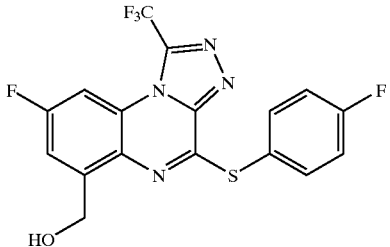

TLC: Rf 0.43 (Hexane:Ethyl acetate=2:1);

NMR (d6-DMSO): δ7.79–7.74 (m, 2H), 7.58 (m, 1H), 7.53 (m, 1H), 7.49–7.43 (m, 2H), 5.46 (d, J=5.4 Hz, 1H), 4.56 (d. J=5.4 Hz, 2H).

EXAMPLE 3(113)

8-Fluoro-6-hydroxymethyl-4-isobutylthio-(5-trifluoromethyl-1,2,4-triazolo)[4,3-a]quinoxaline

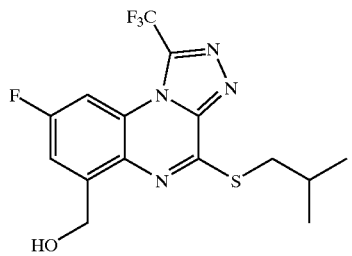

TLC: Rf 0.47 (Hexane:Ethyl acetate=2:1);

NMR (d6-DMSO): δ7.75 (dd, J=6.2, 1.6 Hz, 1H), 7.58 (dd, J=5.6, 2.6 Hz, 1H), 5.26 (s, 2H), 3.29 (d, J=4.6 Hz, 2H), 2.87 (brs, 1H), 2.14 (m, 1H),1.15 (d, J=7.4 Hz, 6H).

EXAMPLE 3(114)

8-Chloro-4-allylthio-(5-trifluoromethyl-1,2,4-triazolo)[4,3-a]quinoxaline

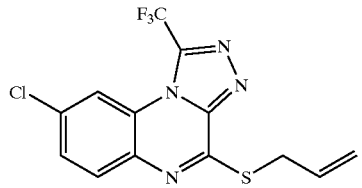

TLC: Rf 0.28 (Toluene);

NMR (CDCl3): δ8.10 (d, J=2.0 Hz, 1H), 8.02 (d, J=8.8 Hz, 1H), 7.67 (dd, J=8.8, 2.0 Hz, 1H), 6.03 (ddt, J=16.8, 9.8, 7.0 Hz, 1H), 5.46 (brd, J=16.8 Hz, 1H), 5.24 (brd, J=9.8 Hz, 1H), 4.10 (brd, J=7.0 Hz, 2H).

EXAMPLE 3(115)

4-Allylthio-8-fluoro-(5-trifluoromethyl-1,2,4-triazolo)[4,3-a]quinoxaline

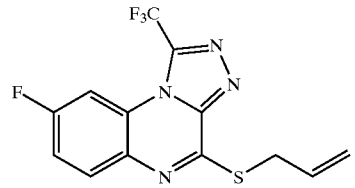

TLC: Rf 0.37 (Toluene:Ethyl acetate=99:1);

NMR (CDCl3): δ8.09 (dd, J=9.2, 5.8 Hz, 1H), 7.84 (dd, J=9.2, 2.6 Hz, 1H), 7.45 (ddd, J=9.2, 7.8, 2.6 Hz, 1H), 6.05 (ddt, J=16.8, 10.2, 7.0 Hz, 1H), 5.46 (brd, J=16.8 Hz, 1H), 5.24 (brd, J=10.2 Hz, 1H), 4.10 (brd, J=7.0 Hz, 2H).

EXAMPLE 3(116)

4-Allylthio-(5-trifluoromethyl-1,2,4-triazolo)[3,4-c]1,4,5-triazanaphthalene

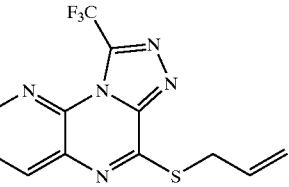

TLC: Rf 0.22 (Toluene:Ethyl acetate=99:1);

NMR (CDCl3): δ8.69 (dd, J=4.4, 1.4 Hz, 1H), 8.36 (dd, J=8.0, 1.4 Hz, 1H), 7.45 (dd, J=8.0, 4.4 Hz, 1H), 6.05 (ddt, J=17.0, 10.0, 7.0 Hz, 1H), 5.47 (brd, J=17.0 Hz, 1H), 5.25 (brd, J=10.0 Hz, 1H), 4.12 (brd, J=7.0 Hz, 2H).

EXAMPLE 3(117)

(±)-cis-4-[2-(Hydroxymethyl)cyclopropyl]methylthio-(5-trifluoromethyl-1,2,4-triazolo)[3,4-c]1,4, 5-triazanaphthalene

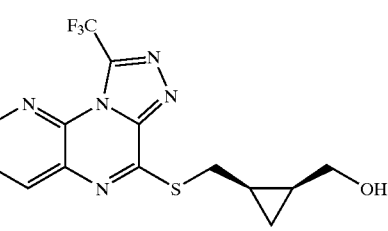

TLC: Rf 0.32 (Hexane:Ethyl acetate=1:1);

NMR (CDCl3): δ8.67 (dd, J=4.5, 1.8 Hz, 1H), 8.36 (dd, J=8.1, 1.8 Hz, 1H), 7.68 (dd, J=8.1, 4.5 Hz, 1H), 3.93 (dd, J=11.7, 6.0 Hz, 1H), 3.72–3.63 (m, 2H), 3.50 (dd, J=13.8, 8.1 Hz, 1H), 1.83 (brs, 1H), 1.56–1.24 (m, 2H), 1.00–0.93 (m, 1H), 0.44–0.38 (m, 1H).

EXAMPLE 3(118)

8-Chloro-4-(4-hydroxy-2-butenyl)thio-(5-trifluoromethyl-1,2,4-triazolo)[4,3-a]quinoxaline

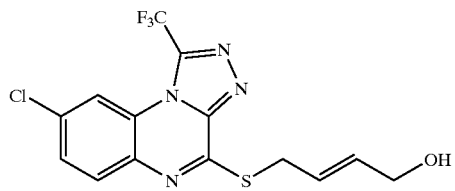

TLC: Rf 0.47 (Hexane:Ethyl acetate=1:1);

NMR (d6-DMSO): δ8.11 (d, J=9.3 Hz, 1H), 7.86 (s, 1H), 7.85 (d, J=9.3 Hz, 1H), 6.00 (dt, J=15.0, 5.4 Hz, 1H), 5.85–5.76 (m, 1H), 4.74 (t, J=6.0 Hz, 1H), 4.10 (d, J=6.9 Hz, 2H), 3.92 (brt, J=5.4 Hz, 2H).

EXAMPLE 3(119)

8-Fluoro-4-(4-hydroxy-2-butenyl)thio-(5-trifluoromethyl-1,2,4-triazolo)[4,3-a]quinoxaline

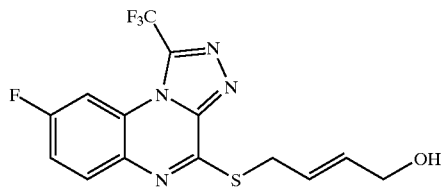

TLC: Rf 0.48 (Hexane:Ethyl acetate 1:1);

NMR (d6-DMSO): δ8.17 (dd, J=8.7, 6.0 Hz, 1H), 7.76–7.61 (m, 2H), 6.00 (dt, J=15.0, 4.5 Hz, 1H), 5.87–5.75 (m, 1H), 4.74 (t, J=5.4 Hz, 1H), 4.09 (d, J=6.9 Hz, 2H), 3.92 (s, 2H).

EXAMPLE 3(120)

4-(4-Hydroxy-2-butenyl)thio-(5-trifluoromethyl-1,2,4-triazolo)[3,4-c]1,4,5-triazanaphthalene

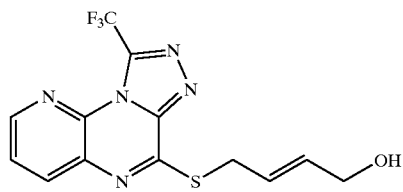

TLC: Rf 0.32 (Hexane:Ethyl acetate=1:1);

NMR (CDCl3): δ8.73 (dd, J=4.8, 1.8 Hz, 1H), 8.49 (dd, J=8.0, 1.8 Hz, 1H), 7.84 (dd, J=8.0, 4.8 Hz, 1H), 6.02 (dt, J=15.4, 4.4 Hz, 1H), 5.90–5.75 (m, 1H), 4.75 (t, J=5.4 Hz, 1H), 4.13 (d, J=6.6 Hz, 2H), 3.93 (brt, J=4.4 Hz, 2H).

EXAMPLE 3(121)

(±)-trans-8-Fluoro-4-[2-(hydroxymethyl)cyclopropyl]methylthio-(5-trifluoromethyl-1,2,4-triazolo)[4,3-a]quinoxaline

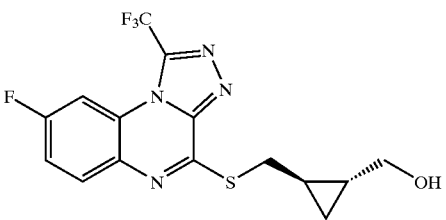

TLC: Rf 0.35 (Hexane:Ethyl acetate=1:1);

NMR (CDCl3): δ8.07 (dd, J=9.2, 6.0 Hz, 1H), 7.82 (dd, J=9.2, 2.4 Hz, 1H), 7.49–7.39 (m, 1H), 3.60–3.32 (m, 4H), 1.32–1.16 (m, 2H), 0.80–0.63 (m, 2H),

EXAMPLE 3(122)

(±)-trans-8-Chloro-4-[2-(hydroxymethyl)cyclopropyl]methylthio-(5-trifluoromethyl-1,2,4-triazolo)[4,3-a]quinoxaline

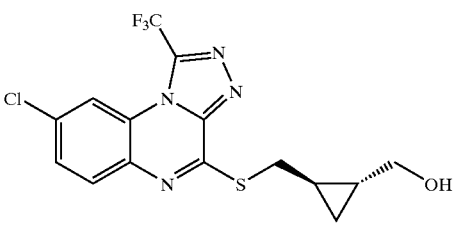

TLC: Rf 0.40 (Hexane:Ethyl acetate=1:1);

NMR (CDCl3): δ8.09 (d, J=2.2 Hz, 1H), 7.99 (d, J=8.8 Hz, 1H), 7.65 (dd, J=8.8, 2.2 Hz, 1H), 3.59–3.32 (m, 4H), 1.30–1.14 (m, 2H), 0.78–0.62 (m, 2H).

EXAMPLE 3(123)

(±)-trans-4-[2-(Hydroxymethyl)cyclopropyl]methylthio-(5-trifluoromethyl-1,2,4-triazolo)[3,4-c]1,4,5-triazanaphthalene

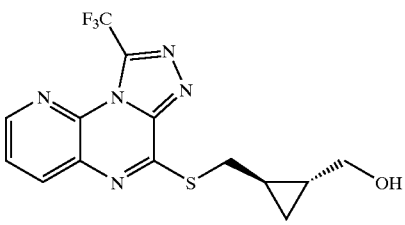

TLC: Rf 0.21 (Hexane:Ethyl acetate=1:1);

NMR (CDCl3): δ8.65 (dd, J=4.4, 1.8 Hz, 1H), 8.32 (dd, J=8.4, 1.8 Hz, 1H), 7.66 (dd, J=8.4, 4.4 Hz, 1H), 3.60–3.30 (m, 4H), 1.34–1.15 (m, 2H), 0.76–0.63 (m, 2H).

EXAMPLE 3(124)

4-Cyclopropylmethylthio-8-hydroxymethyl-(5-trifluoromethyl-1,2,4-triazolo)[4,3-a]quinoxaline

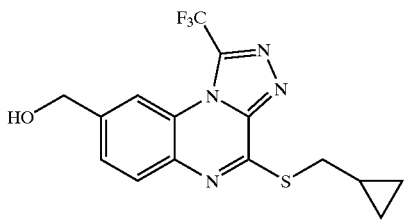

TLC: Rf 0.59 (Hexane:Ethyl acetate=1:1);

NMR (CDCl3): δ8.16 (brs, 1H), 8.04 (d, J=8.4 Hz, 1H), 7.66 (dd, J=8.4, 1.2 Hz, 1H), 4.93 (brs, 2H), 3.41 (d, J=7.4 Hz, 2H), 2.06 (m, 1H), 1.29 (m, 1H) 0.75–0.63 (m, 2H), 0.50–0.39 (m, 2H).

EXAMPLE 3(125)

(±)-8-Fluoro-4-(2-hydroxymethylbutyl)thio-(5-trifluoromethyl-1,2,4-triazolo)[4,3-a]quinoxaline

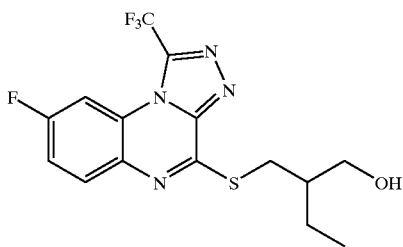

TLC: Rf 0.32 (Toluene:Ethyl acetate=4:1);

NMR (CDCl3): δ8.04 (1H, dd, J=9.2, 5.6 Hz), 7.85 (1H, dd, J=9.6, 2.4 Hz), 7.46 (1H, ddd, J=9.2, 7.8, 2.4 Hz), 3.80–3.50 (2H, m), 3.68 (1H, dd, J=13.8, 4.4 Hz), 3.52 (1H, dd, J=13.8, 6.2 Hz), 3.20–3.07 (1H, br), 2.04–1.92 (1H, m), 1.62–1.44 (2H, m), 1.05 (3H, t, J=7.2 Hz).

EXAMPLE 3(126)

(±)-8-Chloro-4-(2-hydroxymethylbutyl)thio-(5-trifluoromethyl-1,2,4-triazolo)[4,3-a]quinoxaline

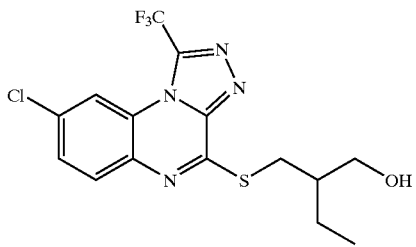

TLC: Rf 0.59 (Toluene:Ethyl acetate 1:1);

NMR (CDCl3): δ8.11 (1H, d, J=2.0 Hz), 7.97 (1H, d, J=8.4 Hz), 7.67 (1H, dd, J=8.4, 2.0 Hz), 3.80–3.44 (2H, m), 3.68 (1H, dd, J=14.2, 4.8 Hz), 3.52 (1H, dd, J=14.2, 6.6 Hz), 3.15–3.00 (1H, br), 2.06–1.90 (1H, m), 1.60–1.45 (2H, m), 1.05 (3H, t, J=7.4 Hz).

EXAMPLE 3(127)

(±)-4-(2-Hydroxymethylbutyl)thio-(5-trifluoromethyl-1,2,4-triazolo)[3,4-c]1, 4, 5-triazanaphthalene

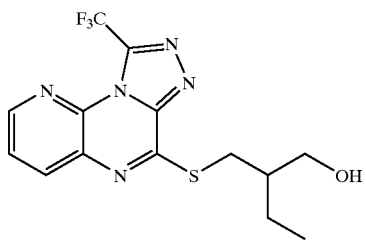

TLC: Rf 0.45 (Toluene:Ethyl acetate=1:1);

NMR (CDCl3): δ8.68 (1H, dd, J=4.4, 1.6 Hz), 8.32 (1H, dd, J=8.2, 1.6 Hz), 7.70 (1H, dd, J=8.2, 4.4 Hz), 3.80–3.55 (2H, m), 3.70 (1H, dd, J=14.0, 4.4 Hz 3.55 (1H, dd, J=14.0, 6.4 Hz), 3.15–3.00 (1H, br), 2.08–1.90 (1H, m), 1.60–1.44 (2H, m), 1.05 (3H, t, J=7.6 Hz).

EXAMPLE 3(128)

4-(Cyclopropylmethyl)thio-7-methoxycarbonyl-(5-trifluoromethyl-1,2, 4-triazolo)[3,4-c]1,4,5-triazanaphthalene

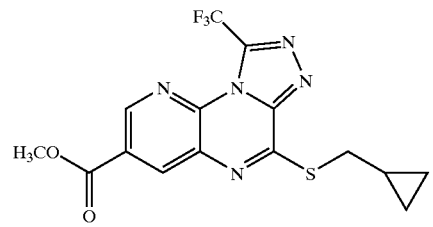

TLC: Rf 0.43 (Chloroform)

NMR (CDCl3) δ9.25 (d, J=2.1 Hz, 1H), 8.92 (d, J=2.1 Hz, 1H), 4.05 (s, 3H), 3.42 (d, J=7.5 Hz, 2H), 1.29 (m, 1H), 0.75–0.66 (m, 2H), 0.48–0.41 (m, 2H).

EXAMPLE 3(129)

4-Cyclopentylthio-8-hydroxymethyl-(5-trifluoromethyl-1,2,4-triazolo)[4, 3-a]quinoxaline

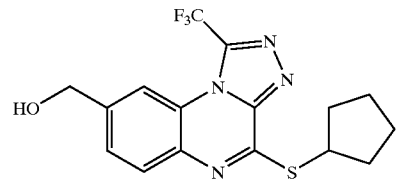

TLC: Rf 0.61 (Toluene:Ethyl acetate 1:1);

NMR (CDCl3): δ8.15 (1H, brs), 8.04 (1H, d, J=8.4 Hz), 7.67 (1H, d, J=8.4 Hz), 4.94 (2H, s), 4.46–4.30 (1H, m), 2.43–2.25 (2H, m), 2.30–1.90 (1H, br), 1.90–1.60 (6H, m).

EXAMPLE 3(130)

4-Cyclohexylthio-8-hydroxymethyl-(5-trifluoromethyl-1,2,4-triazolo)[4, 3-a]quinoxaline

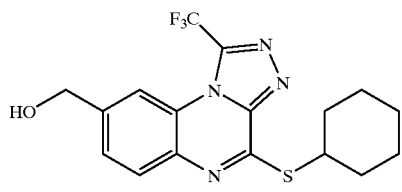

TLC: Rf 0.61 (Toluene:Ethyl acetate=1:1);

NMR (CDCl3): δ8.15 (1H, brs), 8.04 (1H, d, J=8.0 Hz), 7.66 (1H, dd, J=8.0, 1.4 Hz), 4.94 (2H, brs), 4.38–4.22 (1H, m), 2.28–2.12 (2H, m), 2.15–1.90 (1H, br), 1.90–1.40 (8H, m).

EXAMPLE 3(131)

4-Butylthio-8-hydroxymethyl-(5-trifluoromethyl-1,2,4-triazolo)[4,3-a]quinoxaline

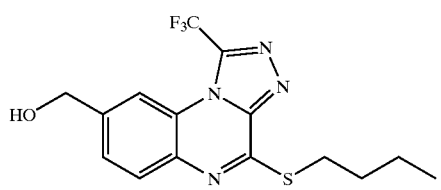

TLC: Rf 0.62 (Toluene:Ethyl acetate=1:1);

NMR (CDCl3): δ8.16 (1H, brs), 8.04 (1H, d, J=8.0 Hz), 7.67 (1H, dd, J=8.0, 1.4 Hz), 4.94 (2H, d, J=5.0 Hz), 3.46 (2H, t, J=7.4 Hz), 2.03 (1H, t, J=5.0 Hz), 1.95–1.78 (2H, m), 1.68–1.50 (2H, m), 1.01 (3H, t, J=7.2 Hz).

Example 3(132)

8-Chloro-4-(cyclopropylmethyl)thio-(5-trifluoromethyl-1,2,4-triazolo)[4, 3-a]quinoxaline

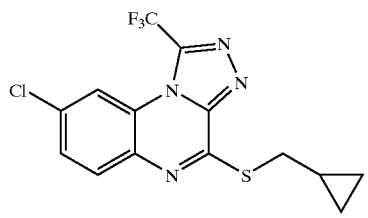

TLC: Rf 0.56 (Hexane:Ethyl acetate=4:1);

NMR (CDCl3) δ8.08 (d, J=2.2 Hz, 1H), 7.98 (d, J=8.8 Hz, 1H), 7.63 (dd, J=8.8, 2.2 Hz, 1H), 3.38 (d, J=7.4 Hz, 2H), 1.40–1.18 (m, 1H), 0.74–0.63 (m, 2H), 0.47–0.39 (m, 2H).

EXAMPLE 3(133)

4-(Cyclopropylmethyl)thio-8-fluoro-(5-trifluoromethyl-1,2,4-triazolo)[4, 3-a]quinoxaline

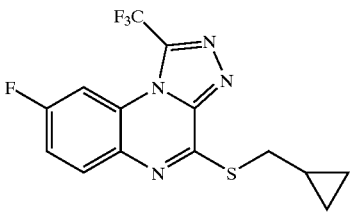

TLC: Rf 0.56 (Hexane:Ethyl acetate=4:1);

NMR (CDCl3): δ8.06 (dd, J=9.2, 5.8 Hz, 1H), 7.82 (dd, J=9.2, 2.6 Hz, 1H), 7.48–7.38 (m, 1H), 3.38 (d, J=7.4 Hz, 2H), 1.37–1.20 (m, 1H), 0.74–0.63 (m, 2H), 0.49–0.39 (m, 2H).

EXAMPLE 3(134)

4-(Cyclopropylmethyl)thio-(5-trifluoromethyl-1,2,4-triazolo)[3, 4-c]1,4, 5-triazanaphthalene

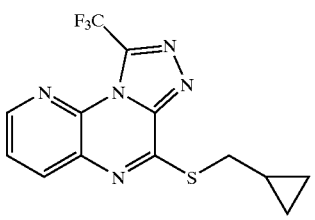

TLC: Rf 0.67 (Toluene:Ethyl acetate=4:1);

NMR (CDCl3): δ8.67 (1H, dd, J=4.8, 1.6 Hz), 8.34 (1H, dd, J=8.2, 1.6 Hz), 7.68 (1H, dd, J=8.2, 4.8 Hz), 3.42 (2H, d, J=7.4 Hz), 1.40–1.20 (1H, m), 0.75–0.63 (2H, m), 0.49–0.40 (2H, m).

EXAMPLE 3(135)

4-Cyclopropylmethylthio-8-fluoro-6-hydroxymethyl-(5-trifluoromethyl-1, 2,4-triazolo)[4,3-a]quinoxaline

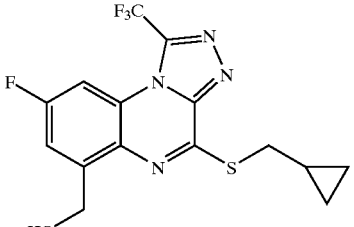

TLC: Rf 0.39 (Toluene:Ethyl acetate=4:1);

NMR (CDCl3) δ7.77 (1H, dd, J=9.2, 2.6 Hz), 7.58 (1H, dd, J=8.4, 2.6 Hz), 5.26 (2H, d, J=6.2 Hz), 3.36 (2H, d, J=7.2 Hz), 2.84 (1H, t, J=6.2 Hz), 1.18 (1H, m), 0.77–0.64 (2H, m), 0.48–0.39 (2H, m).

Example 4

4-Phenylthio-7-amino-(5-trifluoromethyl-1,2,4-triazolo)[4,3-a]quinoxaline

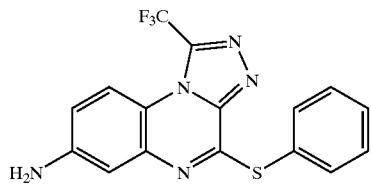

Platinum dioxide (0.054 g) was added to a solution of the compound prepared in Example 3(2) (0.33 g) in ethanol (10 ml). The mixture was stirred for 2.5 hours under an atmosphere of hydrogen gas. The reaction mixture was filtered through celite (registered trade mark). The filtrate was concentrated. The residue was purified by column chromatography on silica gel (chloroform) to give the present compound (0.044 g) having the following physical data.

TLC: Rf 0.10 (Chloroform);

NMR (CDCl3): δ7.86 (1H, d, J=9.2 Hz), 7.74–7.65 (2H, m), 7.56–7.47 (3H, m), 6.99 (1H, d, J=2.6 Hz), 6.91 (1H, dd, J=2.6, 9.2 Hz), 4.00 (2H, brs).

EXAMPLE 4(1)–4(2)

The following compounds were obtained by the same procedure as a series of reaction of Example 4, using the compound prepared in Example 3(12) or 3(20) instead of the compound prepared in Example 3(2).

Example 4(1)

6-Amino-4-phenylthio-(5-trifluoromethyl-1,2,4-triazolo)[4,3-a]quinoxaline

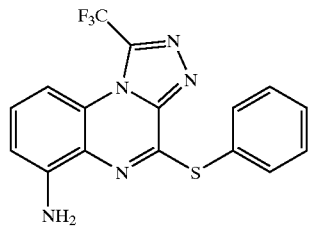

TLC: Rf 0.31 (Toluene:Ethyl acetate=19:1);

NMR (CDCl3): δ7.76–7.66 (2H, m), 7.57–7.48 (3H, m), 7.38–7.31 (2H, m), 6.84 (1H, t, J=4.6 Hz), 4.51 (2H, brs).

EXAMPLE 4(2)

8-Amino-4-phenylthio-(5-trifluoromethyl-1,2,4-triazolo)[4,3-a]quinoxaline

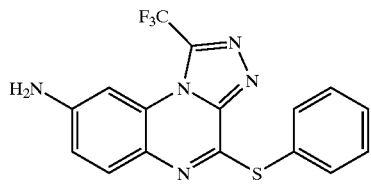

TLC: Rf 0.40 (Toluene:Ethyl acetate=4:1);

NMR (CDCl3): δ7.73–7.67 (2H, m), 7.62 (1H, d, J=9.0 Hz), 7.53–7.46 (3H, m), 7.23 (1H, d, J=2.4 Hz), 6.90 (1H, dd, J=2.4, 9.0 Hz), 4.27 (2H, brs).

Reference Example 2

2-Hydroxy-3-benzylquinoxaline

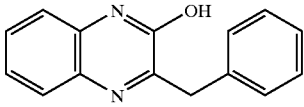

The mixture of 1,2-phenylenediamine (8.64 g), phenylpyruvic acid (13.1 g), ethanol (100 ml) and 2N hydrochloric acid (100 ml) was stirred for 1.5 hours at 50° C. The reaction mixture was cooled to room temperature. The precipitated crystals were obtained by filtration. The crystals were washed with ethanol and dried to give the title compound (15.05 g) having the following physical data.

TLC: Rf 0.62 (Chloroform:Methanol=10:1).

Reference Example 3

2-Chloro-3-benzylquinoxaline

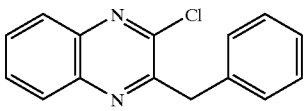

Phosphorus oxychloride (20 ml) was added to a solution of the compound prepared in Reference Example 2 (2.0 g) in dimethylformamide (1.07 ml). The mixture was stirred for 2 hours at 100°C. The reaction mixture was cooled to room temperature. Water was added to the mixture, and the mixture was extracted with ethyl acetate. The extract was washed with a saturated aqueous solution of sodium bicarbonate, a saturated aqueous solution of sodium chloride, successively, dried over anhydrous magnesium sulfate and concentrated to give the title compound (2.3 g) having the following physical data.

TLC: Rf 0.69 (Hexane:Ethyl acetate=4:1).

Reference Example 4

2-Hydrazino-3-benzylquinoxaline

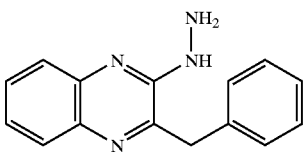

Hydrazine. monohydrate (1.01 ml) was added to a solution of the compound prepared in Reference Example 3 (2.3 g) in ethanol (50 ml). The mixture was stirred for 5 hours at 70° C. The reaction mixture was cooled to room temperature. The precipitated crystals were obtained by filtration. The crystals were washed with ethanol and dried to give the title compound (2.43 g) having the following physical data.

TLC: Rf 0.45(Chloroform:Methanol=10:1).

EXAMPLE 5

4-Benzyl-(5-trifluoromethyl-1,2,4-triazolo)[4,3-a]quinoxaline

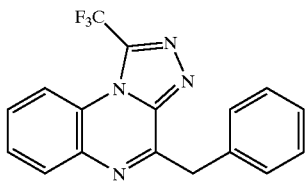

A solution of the compound prepared in Reference Example 4 (2.43 g) in trifluoroacetic acid (7.5 ml) was refluxed for 3 hours. The reaction mixture was cooled to room temperature. Water was added to the mixture. The precipitated crystals were obtained by filtration. The crystals were washed with water and dried to give the present compound (2.51 9) having the following physical data.

TLC: Rf 0.47 (Hexane:Ethyl acetate=4:1);

NMR (CDCl3): δ8.26–8.08 (2H, m), 7.79–7.67 (2H, m), 7.62 (2H, dd, J=8.0, 1.4 Hz), 7.36–7.16 (3H, m), 4.73 (2H, s).

Example 5(1)–5(7)

The following present compounds were obtained by the same procedure as a series of reaction of Reference Example 2→Reference Example 3→Reference Example 4→Example 5, using a corresponding α-ketocarboxylic acid derivative instead of penylpyruvic acid.

EXAMPLE 5(1)

4-Isobutyl-(5-trifluoromethyl-1,2,4-triazolo)[4, 3-a]quinoxaline

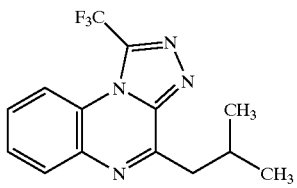

TLC: Rf 0.55 (Hexane:Ethyl acetate=4:1);

NMR (CDCl3): δ8.23–8.12 (2H, m), 7.80–7.68 (2H, m), 3.31 (2H, d, J=7.4 Hz), 2.60 (1H, sept, J=6.6 Hz), 1.08 (6H, d, J=6.6 Hz).

EXAMPLE 5(2)

4-Methyl-(5-trifluoromethyl-1,2,4-triazolo)[4,3-a]quinoxaline

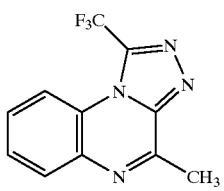

TLC: Rf 0.28 Hexane:Ethyl acetate=3:1);

NMR (CDCl3): δ8.25–8.10 (2H, m), 7.83–7.68 (2H, m), 3.09 (3H, m).

EXAMPLE 5(3)

4-Isopropyl-(5-trifluoromethyl-1,2,4-triazolo)[4,3-a]quinoxaline

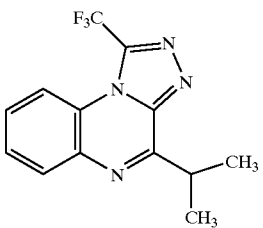

TLC: Rf 0.63 Hexane:Ethyl acetate 3:1);

NMR (CDCl3): δ8.26–8.12 (2H, m), 7.80–7.68 (2H, m), 4.07 (1H, sept, J=6.8 Hz), 1.55 (6H, d, J=6.8 Hz).

EXAMPLE 5(4)

4-Phenyl-(5-trifluoromethyl-1,2,4-triazolo)[4,3-a]quinoxaline

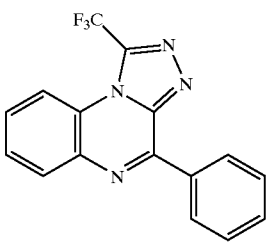

TLC: Rf 0.43 (Hexane:Ethyl acetate=4:1);

NMR (CDCl3): δ8.89–8.76 (2H, m), 8.38–8.18 (2H, m), 7.86–7.73 (2H, m), 7.69–7.57 (3H, m).

EXAMPLE 5(5)

4-(Thiophen-3-yl)-(5-trifluoromethyl-1,2,4-triazolo)[4,3-a]quinoxaline

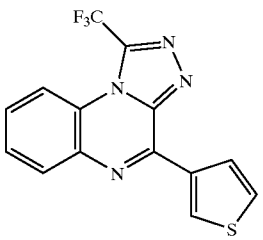

TLC: Rf 0.54 (Hexane:Ethyl acetate=4:1);

NMR (CDCl3): δ9.02 (1H, dd, J=3.8, 1.2 Hz), 8.25–8.13 (2H, m), 7.80–7.64 (3H, m), 7.29 (1H, dd, J=4.9, 3.8 Hz).

EXAMPLE 5(6)

4-(Furan-3-yl)-(5-trifluoromethyl-1,2,4-triazolo)[4,3-a]quinoxaline

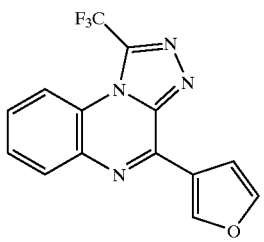

TLC: Rf 0.34 (Hexane:Ethyl acetate=3:1);

NMR (CDCl3): δ8.26–8.05 (4H, m), 7.94–7.78 (2H, m), 6.89 (1H, dd, J=3.4, 2.0 Hz).

EXAMPLE 5(7)

4(4-Dimethyaminophenyl)-(5-trifluoromethyl-1,2,4-triazolo)[4,3-a]quinoxaline

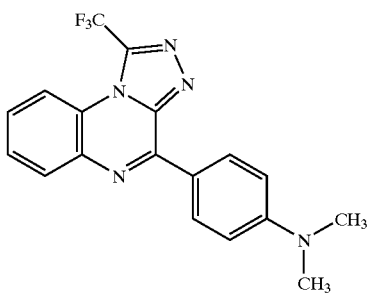

TLC: Rf 0.42 (Hexane:Ethyl acetate=3:1);

NMR (CDCl3): δ8.89 (2H, d, J=9.2 Hz), 8.21–8.12 (2H, m), 7.86–7.58 (2H, m), 6.86 (2H, d, J=9.2 Hz), 3.12 (6H, s).

Reference Example 5

4-Chloro-tetrazolo[1,5-a]quinoxaline

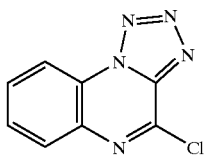

The title compound was obtained by the same procedure as a series of reaction of Reference Example 3, using 4-Hydroxy-(tetrazolo)[1,5-a]quinoxaline (It is described in J. Med. Chem., 35, 3319 (1992).) instead of the compound prepared in Reference Example 2.

TLC: Rf 0.42 (Hexane:Ethyl acetate=2:1).

EXAMPLE 6(1) and 6(2)

The following present compounds were obtained by the same procedure as a series of reaction of Example 1, using the compound prepared in Reference Example 5 instead of 4-Chloro-(5-trifluoromethyl-1,2,4-triazolo)[4,3-a]quinoxaline, and a corresponding thiol.

EXAMPLE 6(1)

4-Phenylthio-tetrazolo[1,5-a]quinoxaline

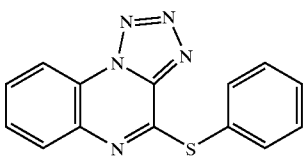

TLC: Rf 0.59 Hexane:Ethyl acetate=2:1);

NMR (CDCl3): δ8.54–8.46 (1H, m), 7.92–7.84 (1H, m), 7.80–7.62 (4H, m), 7.58–7.48 (3H, m).

EXAMPLE 6(2)

4-Allylthio-tetrazolo[1,5-a]quinoxaline

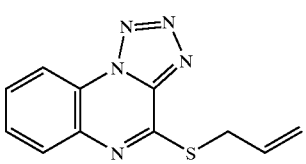

TLC: Rf 0.53 Hexane:Ethyl acetate=3:1);

NMR (CDCl3): δ8.58–8.46 (1H, m), 8.19–8.05 (1H, m), 7.86–7.68 (2H, m), 6.18–5.96 (1H, m), 5.48 (1H, d, J=1 7.1 Hz), 5.25 (1H, d, J=10.0 Hz), 4.16 J=6.8 Hz).

EXAMPLE 7

4-Phenylsulfinyl-(5-trifluoromethyl-1,2,4-triazolo)[4,3-a]quinoxaline

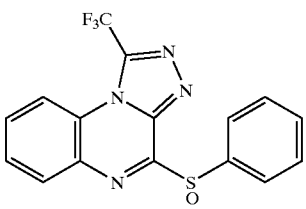

m-Chloroperoxybenzoic acid (0.6 g) was added to a solution of 4-Phenylthio-(5-trifluoromethyl-1,2,4-triazolo)[4,3-a]quinoxaline (Bionet)(0.5 g) in chloroform (30 ml) at −50° C. The mixture was stirred for 3 hours at −15° C. A saturated aqueous solution of sodium thiosulfate and the mixture was extracted with chloroform. The extract was washed with a saturated aqueous solution of sodium bicarbonate, dried over anhydrous sodium sulfate and concentrated. The residue was purified by column chromatography on silica gel (chloroform:methanol=100:1) to give the present compound (0.158 g) having the following physical data.

TLC: Rf 0.21 (Chloroform:Methanol=100:1);

NMR (CDCl3): δ8.61–8.46 (1H, m), 8.30–8.07 (3H, m), 7.98–7.76 (2H, m), 7.58–7.41 (3H, m).

EXAMPLE 7(1)

4-Isopropylsulfinyl-(5-trifluoromethyl-1,2,4-triazolo)[3,4-c]1,4, 5-triazanaphthalene

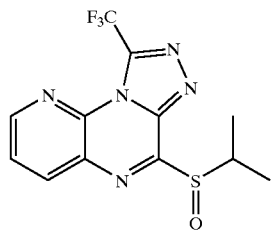

The title compound was obtained by the same procedure as a series of reaction of Example 7, using the compound prepared in Example 3(16).

TLC: Rf 0.38 (Ethyl acetate)

NMR (CDCl3): δ8.93 (dd, J=4.6, 1.6 Hz, 1H), 8.84 (dd, J=8.2, 1.6 Hz, 1H), 7.87 (dd, J=8.2, 4.6 Hz, 1H), 4.10 (quint., J=7.0 Hz, 1H), 1.70 (d, J=7.0 Hz, 3H), 1.22 (d, J=6.6 Hz, 3H).

EXAMPLE 8

6-t-Butylamino-4-phenylthio-(5-trifluoromethyl-1,2, 4-triazolo)[4, 3-a]quinoxaline

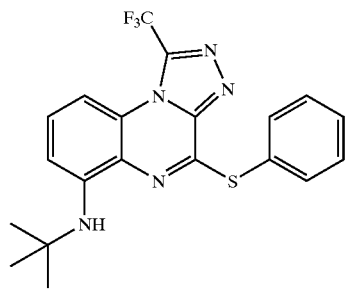

The mixture of the compound prepared in Example 3(20) (98 mg) and Tin (II) chloride (250 mg) in ethyl acetate and t-butanol (15 ml; 9:1) was stirred for 90 minutes at 60° C. Sodium borohydride (46 mg) was added to the mixture at 60° C. The mixture was stirred for 90 minutes at same temperature. The reaction solution was poured into a saturated aqueous solution of sodium bicarbonate with ice, and diluted with water. The mixture was extracted with chloroform. The organic layer was washed with water and a saturated aqueous solution of sodium chloride, successively, dried over anhydrous magnesium sulfate and concentrated. The residue was purified by column chromatography on silica gel (toluene:ethyl acetate=100:1→ 19:1) to give the present compound (24 mg) having the following physical data.

TLC: Rf 0.53 (Toluene:Ethyl acetate=19:1);

NMR (CDCl3): δ7.77–7.67 (2H, m), 7.58–7.48 (3H, m), 7.36 (1H, dd, J=8.2, 8.6 Hz), 7.22 (1H, d, J=8.6 Hz), 6.92 (1H, d, J=8.2 Hz), 5.71 (1H, brs), 1.25 (9H, s).

EXAMPLE 9

6-Acetylamino-4-phenylthio-(5-trifluoromethyl-1,2, 4-triazolo)[4, 3-a]quinoxaline

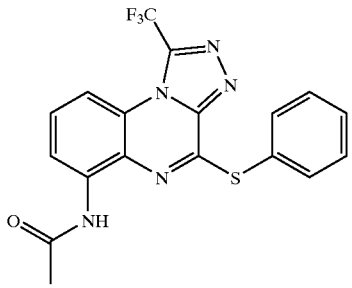

Anhydrous acetic acid (0.5 ml) was added to the compound prepared in Example 4(1) (108 mg) in pyridine (1 ml). The mixture was stirred for 4 hours at 60° C. The reaction solution was cooled with ice. Methanol was added to the mixture, and the mixture was concentrated, and distilled off an azeotropic mixture with toluene. The residue was purified by column chromatography on silica gel (toluene:ethyl acetate=9:1) to give the title compound (117 mg) having the following physical data.

TLC: Rf 0.28 (Toluene:Ethyl acetate=9:1);

NMR (CDCl3): δ7.75–7.68 (m, 2H), 7.59–7.50 (m, 3H), 7.42 (t, J=8.4 Hz, 1H), 7.24 (d, J=8.4 Hz, 1H), 6.63 (d, J=8.4 Hz, 1H), 5.35 (m, 1H), 2.80 (d, J=5.1 Hz, 3H).

EXAMPLE 10

6-Methylamino-4-phenylthio-(5-trifluoromethyl-1,2, 4-triazolo)[4,3-a]quinoxaline

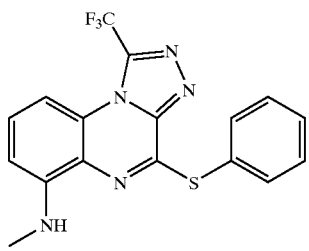

Methyl iodide (3.0 ml) was added to a mixed solution of the compound prepared in Example 4(1) (440 mg) in tetrahydrofuran (THF) (18 ml)/dimethylformamide (DMF) (2 ml). The mixture was cooled with ice, and sodium hydride (153 mg) was added to the mixture. The mixture was stirred for 3 hours at room temperature. The reaction mixture was poured into water with ice and extracted with ethyl acetate. The organic layer was washed with water and a saturated aqueous solution of sodium chloride, successively, dried over anhydrous magnesium sulfate and concentrated. The residue was purified by column chromatography on silica gel (toluene:ethyl acetate=49:1→29:1) to give the title compound (128 mg) having the following physical data.

TLC: Rf 0.66 (Toluene:Ethyl acetate=9:1);

NMR (CDCl3): δ8.70–8.64 (m, 2H), 7.78–7.70 (m, 3H), 7.66–7.54 (m, 4H), 1.94 (s, 3H).

EXAMPLE 10(1)

8-Methylamino-4-phenylthio-(5-trifluoromethyl-1,2,-triazolo)[4,3-a]quinoxaline

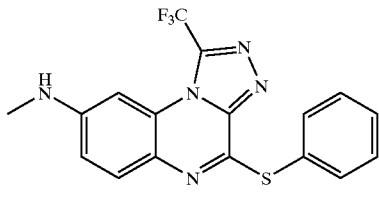

The title compound having the following physical data was obtained by the same procedure as a series of reaction of Example 10, using the compound prepared in Example 4(2).

TLC: Rf 0.38 (Toluene:Ethyl acetate=9:1);

NMR(d6-DMSO): δ7.69–7.63 (m, 2H), 7.54–7.47 (m, 4H), 7.05 (m, 1H), 6.94 (dt, J=8.7, 1.8 Hz, 1H), 6.88 (brs, 1H), 2.77 (d, J=4.8 Hz, 3H).

Reference Example 6

4-Bromomethyl-(5-trifluoromethyl-1,2,4-triazolo)[4,3-a]quinoxaline

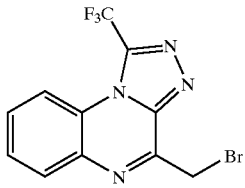

N-Bromosuccinimide (16 mg) and benzoylperoxide (a catalytic amount) were added to a solution of the compound (23 mg) prepared in Example 5(2) in carbon tetrachloride (1 ml). The mixture was stirred overnight at 100° C. The reaction solution was diluted with carbon tetrachloride. The mixture was washed with a saturated aqueous solution of sodium chloride, dried over anhydrous magnesium sulfate and concentrated. The residue was purified by column chromatography on silica gel (hexane:ethyl acetate=3:1) to give the title compound (15 mg) having the following physical data.

TLC: Rf 0.53 (Hexane:Ethyl acetate=2:1);

NMR (CDCl3): δ8.28–8.20 (m, 2H), 7.86–7.79 (m, 2H), 5.09 (s, 2H).

EXAMPLE 11

4-Isopropylthiomethyl-(5-trifluoromethyl-1,2,4triazolo)[4,3 -a]quinoxaline

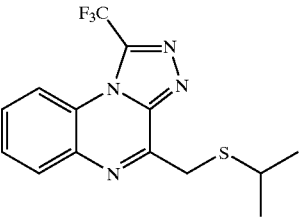

The title compound (38 mg) having the following physical data was obtained by the same procedure as a series of reaction of Example 1, using the compound (49 mg) prepared in Reference Example 6 instead of 4-Chloro-(5-trifluoromethyl-1,2,4-triazolo)[4,3-a]quinoxaline.

TLC: Rf 0.55 (Hexane:Ethyl acetate=2:1);

NMR (CDCl3): δ8.23–8.17 (2H, m), 7.81–7.72 (2H, m), 4.42 (2H, s), 3.21 (1H hept, J=7.0 Hz), 1.36 (6H, d, J=7.0 Hz).

EXAMPLE 11(1)–11(2)

The following compounds were obtained by the same procedure as a series of reaction of Example 11, using a corresponding thiol.

EXAMPLE 11(1)

4-Cyclopentylthiomethyl-(5-trifluoromethyl-1,2,4-triazolo)[4,3-a]quinoxaline

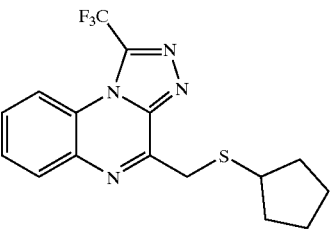

TLC: Rf 0.65 (Hexane:Ethyl acetate=2:1);

NMR (CDCl3): δ8.22–8.18 (m, 2H), 7.78–7.75 (m, 2H), 4.42 (s, 2H), 3.37 (quintet, J=7.2 Hz, 1H), 2.16–2.00 (m, 2H), 1.86–1.50 (m, 6H).

EXAMPLE 11 (2)

4-Phenylthiomethyl-(5-trifluoromethyl-1,2,4-triazolo)[4,3-a]quinoxaline

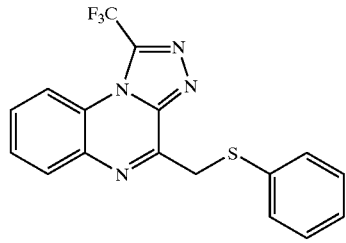

TLC: Rf 0.58 (Hexane:Ethyl acetate=2 1);

NMR (CDCl3): δ8.20–8.12 (m, 2H), 7.80–7.71 (m, 2H), 7.53–7.50 (m, 2H), 7.31–7.20 (m, 3H), 4.82 (s, 2H).

EXAMPLE 12

8-Hydroxymethyl-4-isopropylthio-(5-trifluoromethyl-1,2,4-triazolo)[4,3-a]quinoxaline

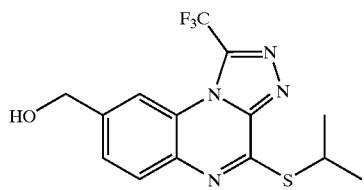

Diisobutylammonium hydride (24.7 ml; 1.0M toluene solution) was dropped to a solution of the compound (3.0 g) prepared in Example 3(25) in anhydrous methylene chloride (180 ml) under an atmosphere of argon at −78° C. The mixture was stirred for 1.5 hours at same temperature. A saturated aqueous solution of ammonium chloride was added to the reaction mixture. The mixture was warmed to room temperature. The reaction mixture was diluted with water and extracted with methylene chloride. The organic layer was washed with water and a saturated aqueous solution of sodium chloride, dried over anhydrous magnesium sulfate and concentrated. The residue was purified by column chromatography on silica gel (hexane:ethyl acetate= 3:1→2:1) to give the title compound (2.34 g) having the following physical data.

TLC: Rf 0.28 (Hexane:Ethyl acetate=2:1);

NMR (CDCl3): δ8.14 (s, 1H), 8.02 (d, J=8.4 Hz, 1H), 7.66 (dd, J=8.4, 1.4 Hz, 1H), 4.94 (d, J=5.0 Hz, 2H), 4.37 (sept, J=6.6 Hz, 1H), 2.24 (t, J=5.0, 1H), 1.56 (d, J=6.6 Hz, 6H).

EXAMPLE 12(1)–12(11)

The following compounds were obtained by the same procedure as a series of reaction of Example 12, using the compound prepared in Example 3(5), 3(6), 3(14), 3(15), 3(21), 3(22), 3(26), 3(51), 3(78) or 3(128) instead of the compound prepared in Example 3(25).

EXAMPLE 12(1)

7-Hydroxymethyl-4-phenoxy-(5-trifluoromethyl-1,2,4-triazolo)[4,3-a]quinoxaline

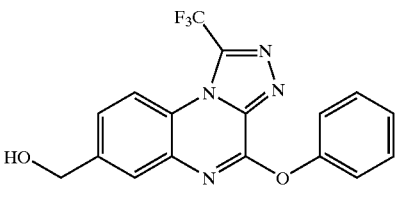

TLC: Rf 0.51 (Hexane:Ethyl acetate 1:1);

NMR (CDCl3+CD3OD): δ8.12 (1H, d, J=8.8 Hz), 7.82 (1H, d, J=2.0 Hz), 7.64 (1H, dd, J=8.8 Hz, 2.0 Hz), 7.56–7.46 (2H, m), 7.42–7.20 (3H, m), 4.80 (2H, s).

EXAMPLE 12(2)

8-Hydroxymethyl-4-phenoxy-(5-trifluoromethyl-1,2,4-triazolo)[4,3-a]quinoxaline

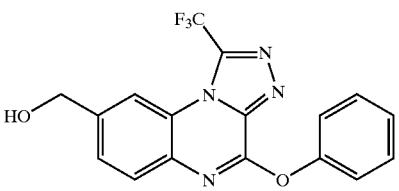

TLC: Rf 0.68 (Chloroform:Methanol=10:1);

NMR (CDCl3+CD3OD): δ8.22 (1H, s), 7.80 (1H, d, J=8.4 Hz), 7.61 (1H, dd, J=8.4, 1.5 Hz), 7.57–7.47 (2H, m), 7.44–7.35 (3H, m), 4.86 (2H, s).

EXAMPLE 12(3)

7-Hydroxymethyl-4-phenylthio-(5-trifluoromethyl-1,2,4-triazolo)[4,3-a]quinoxaline

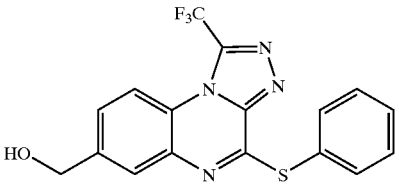

TLC: Rf 0.65 (Chloroform:Methanol=10:1);

NMR (CD3OD): δ8.11 (1H, d, J=8.8 Hz), 7.78–7.65 (4H, m), 7.59–7.50 (3H, m), 4.73 (2H, s).

EXAMPLE 12(4)

8-Hydroxymethyl-4-phenylthio-(5-trifluoromethyl-1,2,4-triazolo)[4,3-a]quinoxaline

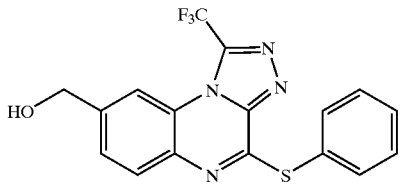

TLC: Rf 0.60 (Chloroform:Methanol=10:1);

NMR (CD3OD): δ8.22 (1H, s), 7.82–7.66 (3H, m), 7.64–7.49 (4H, m), 4.81 (2H, s).

EXAMPLE 12(5)

6-Hydroxymethyl-4-isopropylthio-(5-trifluoromethyl-1,2,4-triazolo)[4,3-a]quinoxaline

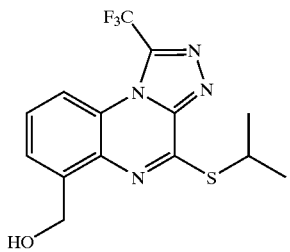

TLC: Rf 0.38 (Hexane:Ethyl acetate=2:1)

NMR (CDCl3): δ8.08 (1H, d, J=8.2 Hz), 7.74 (1H, d, J=7.4 Hz), 7.65 (1H, dd, J=8.2, 7.4 Hz), 5.23 (2H, d, J=5.8 Hz), 4.26 (1H, sept, J=6.8 Hz), 3.07 (1H, t, J=5.8 Hz), 1.60 (6H, d, J=6.8 Hz).

EXAMPLE 12(6)

6-Hydroxymethyl-4-phenylthio-(5-trifluoromethyl-1,2,4-triazolo)[4,3-a]quinoxaline

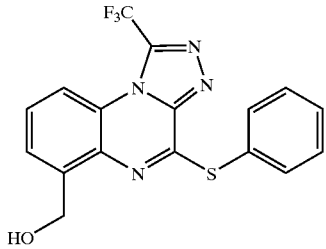

TLC: Rf 0.33 (Hexane:Ethyl acetate 2:1);

NMR (CDCl3): δ8.06 (1H, d, J=8.2 Hz), 7.76–7.48 (7H, m), 4.64 (2H, d, J=7.2 Hz), 2.67 (1H, t, J=7.2 Hz).

EXAMPLE 12(7)

6-Hydroxymethyl-4-isopropylthio-(5-trifluoromethyl-1,2,4-triazolino)[4,3-a]quinoxaline

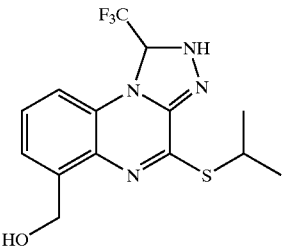

TLC: Rf 0.26 (Hexane:Ethyl acetate=2:1);

NMR (CDCl3): δ7.23 (1H, dd, J=8.0, 7.4 Hz), 7.09 (1H, d, J=7.4 Hz), 6.80 (1H, d, J=8.0 Hz), 6.17 (1H, dq, J=7.2, 4.2 Hz), 5.57 (1H, d, J=7.2 Hz, NH), 4.96 (2H, s), 4.01 (1H, sept, J=6.8 Hz), 3.34 (1H, brs, OH), 1.49 (3H, d, J=6.8 Hz), 1.48 (3H, d, J=6.8 Hz).

EXAMPLE 12(8)

4-(4-Fluorophenyl)thio-8-hydroxymethyl-(5-trifluoromethyl-1,2,4-triazolo)[4,3-a]quinoxaline

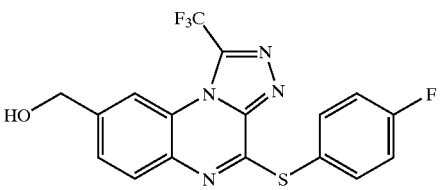

TLC: Rf 0.27 (Hexane:Ethyl acetate=2:1);

NMR (CDCl3): δ8.17 (s, 1H), 7.80 (d, J=8.4 Hz, 1H), 7.74–7.63 (m, 2H), 7.59 (dd, J=8.4, 1.8 Hz, 1H), 7.26–7.16 (m, 2H), 4.93 (d, J=5.2 Hz, 2H), 2.03 (t, J=5.2 Hz, 1H).

EXAMPLE 12(9)

8-Chloro-6-hydroxymethyl-4-isobutylthio-(5-trifluoromethyl-1,2,4-triazolo)[4,3-a]quinoxaline

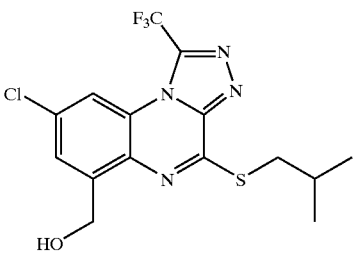

TLC: Rf 0.59 (Hexane:Ethyl acetate 2:1);

NMR (CDCl3): δ8.03 (d, J=1.6 Hz, 1H), 7.78 (d, J=1.6 Hz, 1H), 5.23 (d, J=6.2 Hz, 2H), 3.29 (d, J=6.6 Hz, 2H), 2.82 (t, J=6.2 Hz, 1H), 2.24–2.03 (m, 1H), 1.15 (d, J=6.6 Hz, 6H).

EXAMPLE 12(10)

7-Hydroxymethyl-4-isobutylthio-(5-trifluoromethyl-1,2,4-triazolo)[4,3-a]quinoxaline

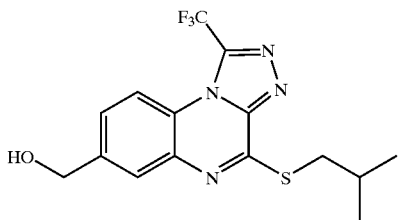

TLC: Rf 0.45 (Hexane:Ethyl acetate=2:1);

NMR (CDCl3): δ8.03 (d, J=8.7 Hz, 1H), 8.01 (d, J=1.8 Hz, 1H), 7.61 (dd, J=8.7, 1.8 Hz, 1H), 4.91 (d, J=5.4 Hz, 2H), 3.36 (d, J=6.6 Hz, 2H), 2.23–2.06 (m, 2H), 1.15 (d, J=6.6 Hz, 6H).

EXAMPLE 12(11)

4-(Cyclopropyl methyl)thio-7-hydroxymethyl-(5-trifluoromethyl-1,2,4-triazolo)[3,4-c]1,4,5-triazanaphthalene

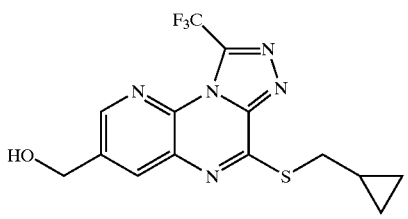

TLC: Rf 0.25 (Chloroform:Methanol=30:1);

NMR (CDCl3): δ8.66 (d, J=1.8 Hz, 1H), 8.37 (d, J=1.8 Hz, 1H), 4.98 (d, J=5.2 Hz, 2H), 3.41 (d, J=7.2 Hz, 2H), 2.06 (t, J=5.2 Hz, 2H), 1.27 (m, 1H 0.64 (m, 2H), 0.49–0.39 (m, 2H).

EXAMPLE 13

8-Formyl-4-isopropylthio-(5-trifluoromethyl-1,2,4-triazolo)[4,3-a]quinoxaline

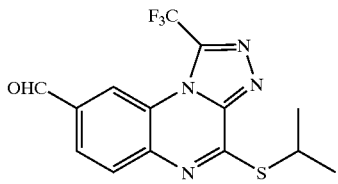

The compound (446 mg) prepared in Example 12 was added to a suspension of pyridinium dichlomate (827 mg) in methylene chloride (10 ml). The mixture was stirred overnight at room temperature. Insoluble material was removed by filtration from the reaction mixture and the material was washed with methylene chloride. A solution of the filtrate and the washings was washed with 1N hydrochloric acid, a saturated aqueous solution of sodium bicarbonate and a saturated aqueous solution of sodium chloride, successively, dried over anhydrous magnesium sulfate and concentrated. The residue was purified by column chromatography on silica gel (chloroform) to give the title compound (368 mg) having the following physical data.

TLC: Rf 0.33 (Hexane:Ethyl acetate=4:1);

NMR (CDCl3): δ10.2 (s, 1H), 8.60 (s, 1H), 8.19 (s, 2H), 4.42 (hept, J=7.2 Hz, 1H), 1.56 (d, J=7.2 Hz, 6H).

EXAMPLE 13(1)

8-Formyl-4-isobutylthio-(5-trifluoromethyl-1,2,4-triazolo)[4,3-a]quinoxaline

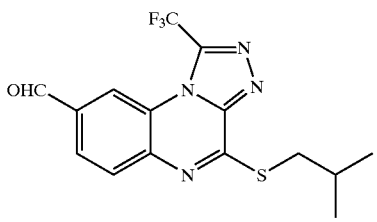

The title compound having the following physical data was obtained by the same procedure as a series of reaction of Example 13, using the compound prepared in Example 3(79) instead of the compound prepared in Example 12.

TLC: Rf 0.35 (Hexane:Ethyl acetate=4:1);

NMR (CDCl3): δ10.17 (s, 1H), 8.61 (s, 1H), 8.19 (brs, 2H), 3.41 (d, J=6.9 Hz, 2H), 2.26–2.03 (m, 1H), 1.15 (d, J=6.9 Hz, 6H).

EXAMPLE 14

4-Isopropylthio-8-(2-methoxycarbonylethenyl)-(5-trifluoromethyl-1,2,4-triazolo)[4,3-a]quinoxaline

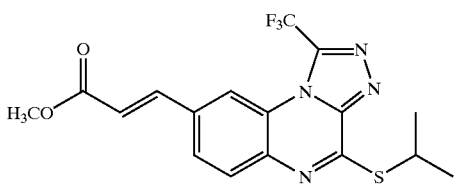

Trimethylphosphono acetate (135 μl) was added to a suspension of sodium hydride (33 mg; 60% dispersion in oil) in dimethylformamide (DMF) (5 ml) under cooling with ice. The mixture was stirred for 20 minutes. The compound (236 mg) prepared in Example 13 was added to the mixture. The mixture was stirred for 1 hour. Water was added to the reaction mixture, and the mixture was extracted with ethyl acetate. The organic layer was washed with a saturated aqueous solution of sodium chloride, dried over anhydrous magnesium sulfate and concentrated. The residue was purified by column chromatography on silica gel (chloroform) to give the title compound (250 mg) having the following physical data.

TLC: Rf 0.34 (Hexane:Ethyl acetate 4:1);

NMR (CDCl3): δ8.20 (s, 1H), 8.05 (d, J=8.7 Hz, 1H), 7.85 (d, J=8.7 Hz, 1H), 7.81 (d, J=15.6 Hz, 1H), 6.58 (d, J=15.6 Hz, 1H), 4.39 (hept, J=6.9 Hz, 1H), (s, 3H), 1.57 (d, J=6.9 Hz, 6H).

EXAMPLE 14(1)

4-Isobutylthio-8-(3-oxo-1-butenyl)-(5-trifluoromethyl-1,2,4-triazolo)[4,3-a]quinoxaline

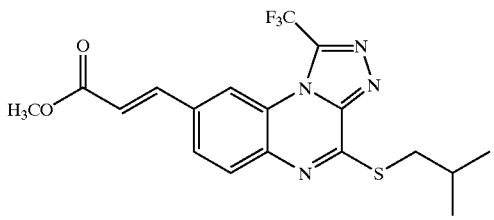

The title compound having the following physical data was obtained by the same procedure as a series of reaction of Example 14, using the compound prepared in Example 13(1) instead of the compound prepared in Example 13.

TLC: Rf 0.50 Hexane:Ethyl acetate=2:1);

NMR (CDCl3): δ8.22 (brs, 1H), 8.06 (d, J=8.4 Hz, 1H), 7.87 (dd, J=8.4, 1.8 Hz, 1H), 7.62 (d, J=16.2 Hz, 1H), 6.85 (d, J=16.2 Hz, 1H), 3.39 (d, J=6.6Hz, 2H), 2.46 (s, 3H), 2.22–2.08 (m, 1H), 1.14 (d, J=6.9 Hz, 6H).

EXAMPLE 15

8-(3-Hydroxy-1-propenyl)-4-isopropylthio-(5-trifluoromethyl-1,2,4-triazolo)[4,3-a]quinoxaline

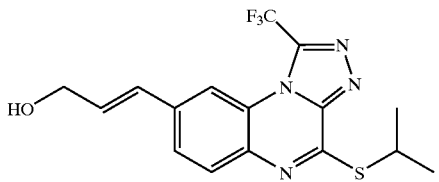

The title compound (576 mg) was obtained by the same procedure as a series of reaction of Example 12, using the compound prepared in Example 14 (809 mg).

TLC : Rf 0.12 (Toluene:Ethyl acetate=9:1);

NMR(d6-DMSO): δ7.99 (d, J=9.2 Hz, 1H), 7.94–7.90 (m, 2H), 6.78 (d, J=16.2 Hz, 1H), 6.57 (dt, J=16.2, 4.4Hz, 1H), 5.03 (t, J=5.4 Hz, 1H), 4.29 (heptet, J=7.0 Hz, 1H), 4.24–4.16 (m, 2H), 1.51 (d, J=7.0 Hz, 6H).

EXAMPLE 16

8-Vinyl-4-isobutylthio-(5-trifluoromethyl-1,2,4-triazolo)[4,3-a]quinoxaline

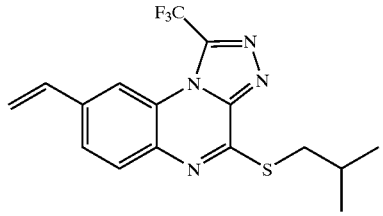

Tetrahydrofuran (60 ml) was added to a mixture of methyltriphenylphosphonium bromide (3.41 g) and potassium t-butoxide (945 mg) under an atmosphere of argon. The mixture was stirred for 1 hour at room temperature. The compound prepared in Example 13(1) (2.01 g) was added to the mixture, and the mixture was stirred for 15 minutes at room temperature. To the reaction mixture, a saturated aqueous solution of ammonium chloride, ether and a saturated aqueous solution of sodium chloride were added. The organic layer dried over anhydrous magnesium sulfate and concentrated. The residue was purified by column chromatography on silica gel (Hexane:Ethyl acetate=19:1) to give the title compound (1.433 g) having the following physical data.

TLC : Rf 0.31 (Toluene:Ethyl acetate=49:1);

NMR (CDCl3): δ8.10 (brs, 1H), 7.99 (d, J=8.4 Hz, 1H), 7.73 (dd, J=8.4, 1.8 Hz, 1H), 6.87 (dd, J=17.4, 10.8 Hz, 1H), 5.94 (d, J=17.4 Hz, 1H), 5.50 (d, J=10.8 Hz , 1H), 3.37 (d, J=6.6 Hz, 2H), 2.22–2.06 (m, 1H), 1.14 (d, J=6.6 Hz, 6H).

EXAMPLE 17(1)–17(2)

Borane dimethylsulfide (0.210 ml) was added to a solution of the compound prepared in Example 16 (776.1 mg) in THF (20 ml) under cooling with ice. The mixture was stirred for 1 hour at room temperature. Water was added to the solution under cooling with ice, and 2N aqueous solution of sodium hydroxide (2 ml) was added, continuously, 30% hydrogen peroxide (2 ml) was added slowly to the solution. The mixture was stirred for 1 hour at room temperature. The reaction solution was diluted with ethyl acetate, and washed with water a saturated aqueous solution of sodium chloride, dried over anhydrous magnesium sulfate and concentrated. The residue was purified by column chromatography on silica gel (Hexane Ethyl acetate=4 :1 →2: 1) to give following compounds of Example 17(1) (246.4 mg) and Example 17(2) (34.6 mg).

EXAMPLE 17(1)

8-(2-Hydroxyethyl)-4-isobutylthio-(5-trifluoromethyl-1,2,4-triazolo)[4,3-a]quinoxaline

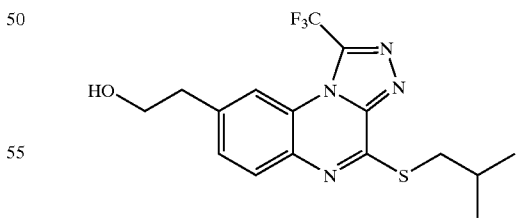

TLC: Rf 0.45 (Toluene:Ethyl acetate=2:1);

NMR (CDCl3): δ8.02–7.97 (m, 2H), 7.57 (dd, J=8.4, 1.5 Hz, 1H), 4.00 (t, J=6.0Hz, 2H), 3.36 (d, J=6.6 Hz, 2H), 3.09 (t, J=6.0 Hz, 2H), 2.20–2.05 (m, 1H), 1.13 (d, J=6.6 Hz, 6H).

EXAMPLE 17(2)

8-(1-Hydroxyethyl)-4-isobutylthio-(5-trifluoromethyl-1,2,4-triazolo)[4,3-a]quinoxaline

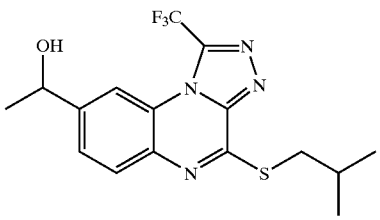

TLC Rf 0.56 (Toluene:Ethyl acetate=2:1)

NMR (CDCl3): δ8.15 (brs, 1H), 7.98 (d, J=8.1 Hz, 1H), 7.67 (brd, J=8.1 Hz, 1H), 5.14 (q, J=6.6 Hz, 1H), 3.35 (d, J=6.6 Hz, 2H), 2.22–2.04 (m, 1H), 1.59 (d, J=6.6 Hz, 3H), 1.13 (d, J=6.6 Hz, 6H).

EXAMPLE 17(3)–17(6)

The following compounds were obtained by the same procedure as a series of reaction of Example 12→Example 13→Example 16→Example 17, using the compound prepared in Example 3(98), Example 3(129), Example 3(130) or Example 3(131).

EXAMPLE 17(3)

6-(2-Hydroxyethyl)-4-isobutylthio-(5-trifluoromethyl-1,2,4-triazolo)[4,3-a]quinoxaline

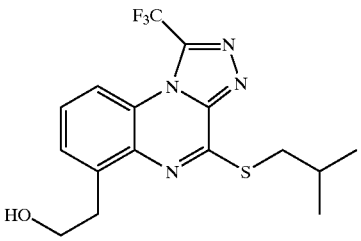

TLC: Rf 0.47 (Hexane:Ethyl acetate=1:1)

NMR (CDCl3): δ8.03 (d, J=8.1 Hz, 1H), 7.63 (dd, J=7.2, 1.2 Hz, 1H), 7.58 (dd, J=8.1, 7.2 Hz, 1H), 4.04 (t, J=6.6 Hz, 2H), 3.51 (t, J=6.6 Hz, 1H), 3.34 (d, J=6.6 Hz, 2H), 2.23–2.10 (m, 1H), 1.15 (d, J=7.2 Hz, 6H).

EXAMPLE 17(4)

4-Cyclopentylthio-8-(2-hydroxyethyl)-(5-trifluoromethyl-1,2,4-triazolo)[4,3-a]quinoxaline

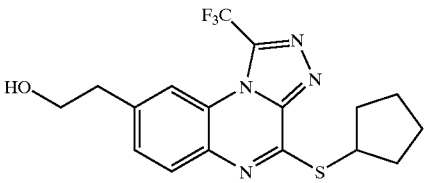

TLC: Rf 0.56 (Toluene:Ethyl acetate=1:1)

NMR (CDCl3): δ8.00 (1H, d, J=8.4 Hz), 8.00 (1H, brs), 7.57 (1H, dd, J=8.4, 1.8 Hz), 4.43–4.30 (1H, m), 3.99 (2H, t, J=6.2 Hz), 3.09 (2H, t, J=6.2 Hz), 2.42–2.25 (2H, m), 1.90–1.60 (6H, m).

EXAMPLE 17(5)

4-Cyclohexylthio-8-(2-hydroxyethyl)-(5-trifluoromethyl-1,2,4-triazolo)[4,3-a]quinoxaline

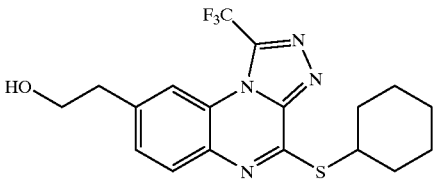

TLC : Rf 0.60 (Toluene:Ethyl acetate=1:1);

NMR (CDCl3): δ7.99 (1H, d, J=8.4 Hz), 7.99 (1H, brs), 7.57 (1H, dd, J=8.4, 1.4 Hz), 4.37–4.18 (1H, m), 3.99 (2H, t, J=6.4 Hz), 3.10 (2H, t, J=6.4 Hz), 2.30–2.12 (2H, m), 1.92–1.30 (8H, m).

EXAMPLE 17(6)

4-Butylthio-8-(2-hydroxyethyl)-(5-trifluoromethyl-1,2,4-triazolo)[4,3-a]quinoxaline

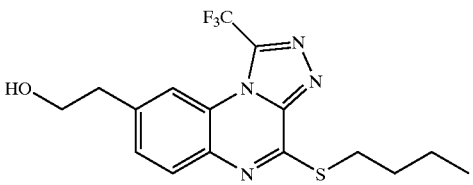

TLC Rf 0.56 (Toluene:Ethyl acetate=1:1 );

NMR (CDCl3): δ8.00 (1H, d, J=8.0 Hz), 8.00 (1H, brs), 7.58 (1H, dd, J=8.0, 1.6 Hz), 4.00 (2H, t, J=6.2 Hz), 3.45 (2H, t, J=7.0 Hz), 3.10 (2H, t, J=6.2 Hz), 1.92–1.76 (2H, m), 1.62–1.50 (2H, m), 1.00 (3H, t, J=7.2 Hz).

EXAMPLE 18

8-Acetyl-4-isobutylthio-(5-trifluoromethyl-1,2,4-triazolo)[4,3-a]quinoxaline

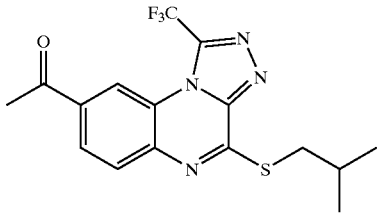

Jone's agent was added to a solution of the compound prepared in Example 17(2) (50 mg) in acetone (2 ml) in ice bath, and the mixture was stirred. 2-Propanol was added to the reaction solution, and the solution was stirred. Water was added, and the solution was extracted with ethyl acetate. The organic layer was washed with a saturated aqueous solution of sodium chloride, dried over anhydrous magnesium sulfate and concentrated. The residue was purified by column chromatography on silica gel (chloroform) to give the title compound (20.2 mg) having the following physical data.

TLC: Rf 0.28 (Chloroform)

NMR (CDCl3): δ8.76 (d, J=1.2 Hz, 1H), 8.25 (dd, J=8.7, 1.2 Hz, 1H), 8.12 (d, J=8.7Hz, 1H), 3.40 (d, J=6.6Hz, 2H), 2.74 (s, 3H), 2.25–2.05 (m, 1H), 1.15 (d, J=6.9 Hz, 6H).

EXAMPLE 19

6-Bromomethyl-4-isopropylthio-(5-trifluoromethyl-1,2,4-triazolo)[4,3-a]quinoxaline

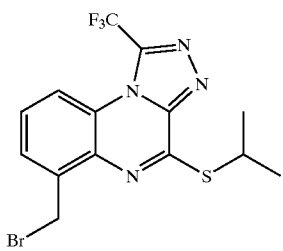

To a suspension of the compound prepared in Example 12(5) (112 mg), triphenylphosphine (102 mg) and sodium bicarbonate (92 mg) in methylene chloride (5 ml), carbon tetrabromide (162 mg) was added. The mixture was stirred for 5 minutes at room temperature. The reaction solution was diluted with methylene chloride. The solution was washed with a saturated aqueous solution of sodium bicarbonate and a saturated aqueous solution of sodium chloride, successively, dried over anhydrous magnesium sulfate and concentrated. The residue was purified by column chromatography on silica gel (methylene chloride) to give the title compound (118 mg) having the following physical data.

TLC: Rf 0.44 (Methylene chloride)

NMR (CDCl3): δ8.11 (s, 1H), 8.03 (d, J=8.4 Hz, 1H), 7.71 (dd, J=8.4, 2.0 Hz, 1H), 4.65 (s, 2H), 4.38 (sept, J=7.0 Hz, 1H, CH), 1.56 (d, J=7.0 Hz, 6H, CH3x 2).

EXAMPLE 20

6-Aminomethyl-4-isopropylthio-(5-trifluoromethyl-1,2,4-triazolo)[4,3-a]quinoxaline

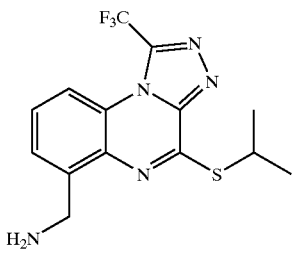

To a solution of the compound prepared in Example 19 (75 mg) in THF (5 ml), an aqueous solution of ammonia (334 μl) was added under cooling with ice. The solution was stirred for 30 minutes at same temperature. Furthermore, an excess amount of an aqueous solution of ammonia was added, the solution was stirred for 30 minutes at room temperature. The reaction solution was concentrated. The residue was purified by column chromatography on silica gel (Chloroform:Methanol =20:1 →10:1) to give the title compound (34 mg) having the following physical data.

TLC:Rf 0.25 (Chloroform:Methanol=10:1);

NMR (CDCl3): δ8.04 (1H, d, J=8.4 Hz), 7.70 (1H, d, J=7.6 Hz), 7.60 (1H, dd, J=8.4, 7.6 Hz), 4.41 (2H, s), 4.34 (1H, sept, J=6.8 Hz), 1.59 (6H, d, J=6.8 Hz).

EXAMPLE 20(1)–20(3)

The following compounds were obtained by the same procedure as a series of reaction of Example 19→Example 20, using the compound prepared in Example 12 or 12(5), and a corresponding amine.

EXAMPLE 20(1)

8-Aminomethyl-4-isopropylthio-(5-trifluoromethyl-1,2,4-triazolo)[4,3-a]quinoxaline

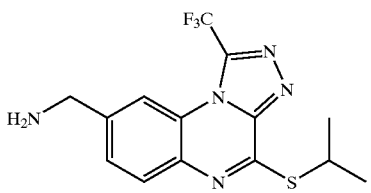

TLC: Rf 0.45 (Methylene chloride:Methanol=10:1);

NMR (CDCl3): δ8.13 (s, 1H), 8.01 (d, J=8.4 Hz, 1H), 7.66 (dd, J=8.4, 1.8 Hz, 1H), 4.37 (sept, J=6.9 Hz, 1H), 4.12 (s, 2H), 1.56 (d, J=6.9 Hz, 6H).

EXAMPLE 20(2)

6-Dimethylaminomethyl-4-isopropylthio-(5-trifluoromethyl-1,2,4-triazolo)[4,3-a]quinoxaline

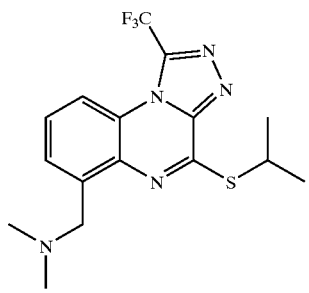

TLC: Rf 0.67 (Chloroform:Methanol=10:1);

NMR (CDCl3): δ8.04 (1H, d, J=8.4 Hz), 7.80 (1H, d, J=7.6 Hz), 7.61 (1H, dd, J=8.4, 7.6 Hz), 4.36 (1H, sept, J=6.8 Hz), 4.07 (2H, s), 2.36 (6H, s), 1.61 (6H, d, J=6.8 Hz).

EXAMPLE 20(3)

8-Dimethylaminomethyl-4-isopropylthio-(5-trifluoromethyl-1,2,4-triazolo)[4,3-a]quinoxaline

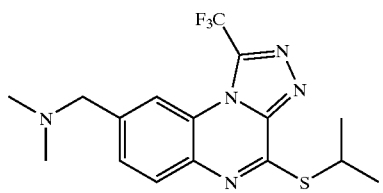

TLC: Rf 0.68 (Chloroform:Methanol=10:1)

NMR (CDCl3): δ8.08 (s, 1H), 8.01 (d, J=8.1 Hz, 1H), 7.65 (dd, J=8.1, 1.8 Hz, 1H), 4.37 (sept, J=6.9 Hz, 1H), 3.63 (s, 2H), 2.30 (s, 6H), 1.56 (d, J=6.9 Hz

EXAMPLE 21

4-Methoxy-8-methoxycarbonyl-(5-trifluoromethyl-1,2,4-triazolo)[4,3-a]quinoxaline

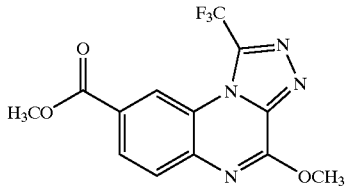

To a solution of the compound prepared in Reference Example 1(10) (9.51 g) in THF (200 ml)/methanol (50 ml), sodium methylate (3.10 g) was added under an atmosphere of argon. The mixture was stirred overnight at room temperature. The reaction solution was concentrated. The residue was diluted with chloroform, washed with water and a saturated aqueous solution of sodium chloride, successively, dried over anhydrous magnesium sulfate and concentrated. The residue was washed with ethyl acetate to give the title compound (7.62 g). Besides, the filtrate was concentrated. The residue was purified by column chromatography on silica gel (toluene:ethyl acetate=9:1) to give the title compound (0.895 g; total 8.515 g) having the following physical data.

TLC: Rf 0.21 (Toluene:Ethyl acetate=9:1);

NMR (CDCl3): δ8.87 (d, J=1.5 Hz, 1H), 8.32 (dd, J=8.4, 1.5 Hz, 1H), 8.01 (d, J=8.4 Hz, 1H), 4.36 (s, 3H), 4.03 (s, 3H).

EXAMPLE 22

4-Methoxy-8-(2-methoxycarbonylethenyl)-(5-trifluoromethyl-1,2,4-triazolo)[4,3-a]quinoxaline

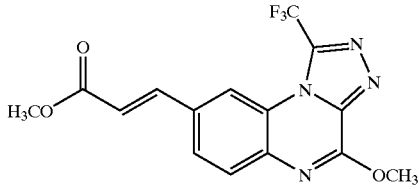

The title compound having the following physical data was obtained by the same procedure as a series of reaction of Example 12→Example 13→Example 14, using the compound prepared in Example 21.

TLC: Rf 0.49 (Chloroform:Ethyl acetate=9:1);

NMR (CDCl3): δ8.22 (brs, 1H), 7.96 (d, J=8.4 Hz, 1H), 7.83 (dd, J=8.4, 1.5 Hz, 1H), 7.81 (d, J=15.9 Hz, 1H), 6.57 (d, J=15.9 Hz, 1H), 4.34 (s, 3H), 3.87 (s

EXAMPLE 23

4-Methoxy-8-(2-methoxycarbonylethyl)-(5-trifluoromethyl-1,2,4-triazolo)[4,3-a]quinoxaline

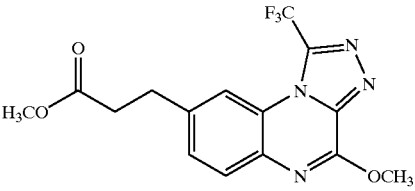

5% Palladium carbon and ammonium formate (4.50 g) were added to a suspension of the compound prepared in Example 22 (4.44 g) in acetic acid (25 ml) under an atmosphere of argon. The mixture was stirred for 15 minutes at 100° C. The cooled reaction mixture was diluted with methylene chloride. The solution was filtered trough celite (registered trade mark). The filtrate was washed with water and an aqueous solution of sodium hydroxide and water, successively, dried over anhydrous magnesium sulfate and concentrated to give the title compound (4.48 g) having the following physical data.

TLC: Rf 0.41 (Toluene:Ethyl acetate=4:1);

NMR (CDCl3): δ7.94 (brs, 1H), 7.88 (d, J=8.4 Hz, 1H), 7.53 (dd, J=8.4, 2.0 Hz, 1H), 4.31 (s, 3H), 3.69 (s, 3H), 3.16 (q, J=7.2 Hz, 2H), 2.75 (t, J=7.2 Hz, 2H).

Reference Example 7

8-(2-Carboxyethyl)-4-methoxy-(5-trifluoromethyl-1,2,4-triazolo)[4,3-a]quinoxaline

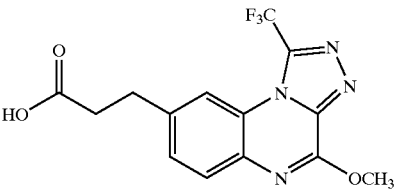

Acetic acid (15 ml) and 1N hydrochloric acid (50 ml) were added to the compound prepared in Example 23 (717 mg). The mixture was refluxed with heating for 3 hours. The cooled reaction solution was concentrated. The residue was distilled off an azeotropic mixture with toluene. To the obtained solid, phosphorus oxychloride (4.0 ml) was added. The mixture was refluxed with heating for 3 hours at 130° C. The cooled reaction solution was poured into water with ice, and stirred. The solution was extracted with ethyl acetate.

The organic layer was washed with water and a saturated aqueous solution of sodium chloride, successively, dried over anhydrous magnesium sulfate and concentrated. The residue was purified by column chromatography on silica gel (Chloroform:Methanol=9:1) to give the title compound (477 mg) having the following physical data.

TLC: Rf 0.28 (Chloroform:Methanol=9:1);

NMR (d6-DMSO): δ12.26 (brs, 1H), 8.09 (d, J=8.4 Hz, 1H), 7.91 (brs, 1H), 7.77 (dd, J=8.4, 1.5 Hz, 1H), 3.11 (t, J=7.2 Hz, 2H), 2.68 (t, J=7.2 Hz, 2H).

Reference Example 8

4-Chloro-8-(2-methoxycarbonylethyl)-(5-trifluoromethyl-1,2,4-triazolo)[4,3-a]quinoxaline

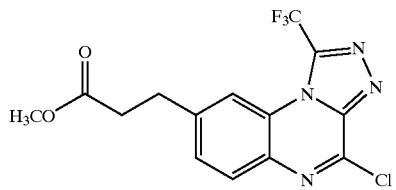

A solution of the compound prepared in Reference Example 7 (466 mg) in thionyl chloride (4.0 ml) was refluxed with heating for 1 hour at 80° C. The cooled reaction solution was concentrated. The residue was distilled off an azeotropic mixture with toluene. The obtained solid was dissolved into methylene chloride. Methanol was added to the solution under cooling with ice, and the mixture was stirred at room temperature. The reaction solution was concentrated. To the residue in acetone (10 ml), isobutyl mercaptan (160 μl) and potassium carbonate (218 mg) were added. The mixture was stirred for 5 hours at room temperature. The reaction solution was diluted with ethyl acetate, washed with water and a saturated aqueous solution of sodium chloride, successively, dried over anhydrous magnesium sulfate and concentrated. The residue was purified by column chromatography on silica gel (toluene:ethyl acetate=97:3) to give the title compound (490 mg) having the following physical data.

TLC: Rf 0.54 (Toluene:Ethyl acetate=9:1);

NMR (CDCl3): δ7.98 (d, J=8.4 Hz, 1H), 7.93 (brs, 1H), 7.54 (dd, J=8.4, 1.5 Hz, 1H), 3.69 (s, 3H), 3.36 (d, J=6.9 Hz, 2H), 3.18 (t, J=7.5 Hz, 2H), 2.75 (t, J=7.5 Hz, 2H), 2.20–2.06 (m, 1H), 1.13 (d, J=6.9 Hz, 6H).

EXAMPLE 24

4-Isobutyl-8-(2-methoxycarbonylethyl)-(5-trifluoromethyl-1,2,4-triazolo)[4,3-a]quinoxaline

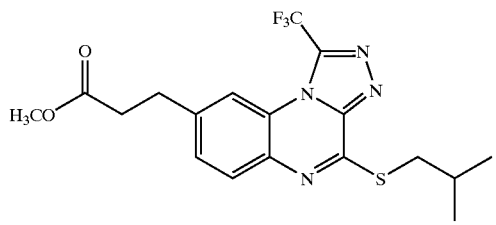

The title compound having the following physical data was obtained by the same procedure as a series of reaction of Example 1, using the compound prepared in Reference Example 8 and a corresponding thiol.

TLC: Rf 0.54 (Toluene:Ethyl acetate=9:1);

NMR (CDCl3): δ7.98 (d, J=8.4 Hz, 1H), 7.93 (brs, 1H), 7.54 (dd, J=8.4, 1.5 Hz, 1H), 3.69 (s, 3H), 3.36 (d, J=6.9 Hz, 2H), 3.18 (t, J=7.5 Hz, 2H), 2.75 (t, J=7.5 Hz, 2H), 2.20–2.06 (m, 1H), 1.13 (d, J=6.9 Hz, 6H).

Reference Example 9

4-Chloro-8-(3-hydroxypropyl)-(5-trifluoromethyl-1,2,4-triazolo)[4,3-a]quinoxaline

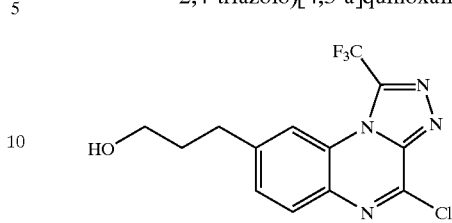

Borane dimethylsulfide complex (570 μl) was dropped into a solution of the compound prepared in Reference Example 7 (2.47 g) in THF (15 ml) at 0° C. The mixture was stirred for 2 hours at same temperature. The reaction solution was diluted with acetic acid, and a saturated aqueous solution of potassium carbonate was added. The separated organic layer was washed with water and a saturated aqueous solution of sodium chloride, successively, dried over anhydrous magnesium sulfate and concentrated. The residue was purified by column chromatography on silica gel (toluene:ethyl acetate=97:3) to give the title compound (510 mg) having the following physical data.

TLC: Rf 0.20 (Toluene:Ethyl acetate=4:1);

NMR (CDCl3): δ8.09 (d, J=8.0 Hz, 1H), 8.04 (brs, 1H), 7.66 (dd, J=8.0, 1.8 Hz, 1H), 3.75 (t, J=6.2 Hz, 2H), 3.03 (t, J=7.6 Hz, 2H), 2.45–2.30 (br, 1H), 2.08–1.95 (m, 2H).

EXAMPLE 25

8-(3-Hydroxypropyl)-4-(3-hydroxypropyl)thio-(5-trifluoromethyl-1,2,4-triazolo)[4,3-a]quinoxaline

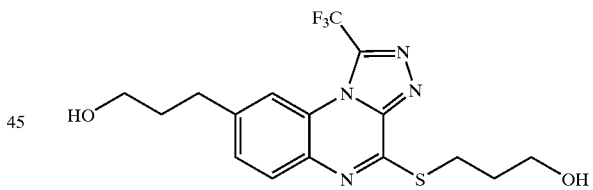

The title compound having the following physical data was obtained by the same procedure as a series of reaction of Example 1, using the compound prepared in Reference Example 9 and a corresponding thiol.

TLC: Rf 0.35 (Ethyl acetate);

NMR (CDCl3): δ7.96 (d, J=8.0 Hz, 1H), 7.95 (s, 1H), 7.56 (dd, J=8.0, 1.4 Hz, 1H), 3.79 (t, 5.8 Hz, 2H), 3.74 (t, J=6.2 Hz, 2H), 3.60 (t, J=6.6 Hz, 2H), 2.97 (t, J=7.9 Hz, 2H), 2.50–1.80 (br, 2H), 2.17–1.91 (m, 4H).

EXAMPLE 25(1)–25(5)

The following compounds were obtained by the same procedure as a series of reaction of Example 25, using a corresponding thiol.

EXAMPLE 25(1)

8-(3-Hydroxypropyl)-4-isobutylthio-(5-trifluoromethyl-1,2,4-triazolo)[4,3-a]quinoxaline

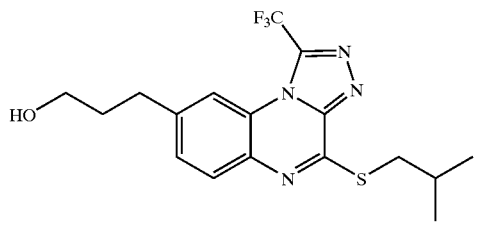

TLC: Rf 0.53 (Hexane:Ethyl acetate=1:1);

NMR (CDCl3): δ7.97 (d, J=8.1 Hz, 1H), 7.93 (brs, 1H), 7.54 (d, J=8.1 Hz, 1H), 3.75 (t, J=6.0 Hz, 2H), 3.36 (d, J=6.6 Hz, 2H), 2.96 (t, J=7.5 Hz, 2H), 2.22–2.02 (m, 1H), 2.04–1.94 (m, 2 H), 1.46 (brs,1H), 1.13 (d, J=6.6 Hz, 6H).

EXAMPLE 25(2)

4-Cyclohexylthio-8-(3-hydroxypropyl)-(5-trifluoromethyl-1,2,4-triazolo)[4,3-a]quinoxaline

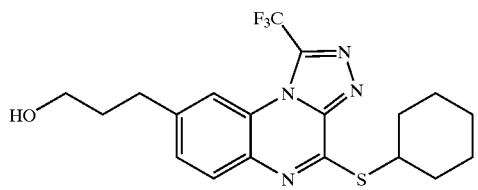

TLC: Rf 0.36 (Toluene:Ethyl acetate=4:1);

NMR (CDCl3): δ7.98 (d, J=8.4 Hz, 1H), 7.93 (s, 1H), 7.54 (dd, J=8.4, 1.4 Hz, 1H), 4.35–4.20 (m, 1H), 3.74 (t, J=6.2 Hz, 2H), 2.96 (t, J=7.7 Hz, 2H), 2.27–2.10 (m, 2H), 2.05–1.20 (m, 11 H).

EXAMPLE 25(3)

4-Butylthio-8-(3-hydroxypropyl)-(5-trifluoromethyl-1,2,4-triazolo)[4,3-a]quinoxaline

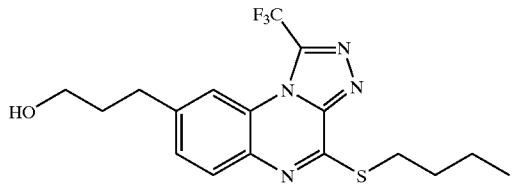

TLC: Rf 0.28 (Toluene:Ethyl acetate=4:1);

NMR (CDCl3): δ7.98 (d, J=8.0 Hz, 1H), 7.94 (s, 1H), 7.54 (dd, J=8.0, 1.6 Hz, 1H), 3.75 (t, J=6.2 Hz, 2H), 3.45 (t, J=6.6 Hz, 2H), 2.96 (t, J=7.9 Hz, 2H), 2.06–1.50 (m, 7H), 1.00 (t, J=7.4 Hz, 3H).

EXAMPLE 25(4)

4-(4-Fluorophenyl)thio-8-(3-hydroxypropyl)-(5-trifluoromethyl-1,2,4-triazolo)[4,3-a]quinoxaline

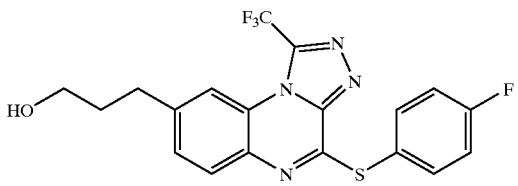

TLC: Rf 0.31 (Toluene:Ethyl acetate=4:1);

NMR (CDCl3): δ7.94 (s, 1H), 7.76–7.65 (m, 3H), 7.47 (dd, J=8.4, 1.8 Hz, 1H), 7.19 (dd, J=8.8 Hz, 1H), 3.72 (t, J=6.2 Hz, 2H), 2.95 (t, J=7.2 Hz, 2H), 2.04–1.90 (m, 2H), 1.90–1.40 (br, 1H).

EXAMPLE 25(5)

4-Cyclopentylthio-8-(3-hydroxypropyl)-(5-trifluoromethyl-1,2,4-triazolo)[4,3-a]quinoxaline

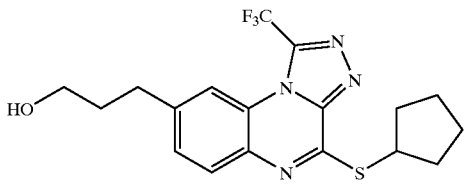

TLC: Rf 0.51 (Toluene:Ethyl acetate=1:1)

NMR (CDCl3): δ7.98 (d, J=8.0 Hz, 1H), 7.93 (s, 1H), 7.54 (dd, J=8.0, 1.8 Hz, 1H), 4.43–4.30 (m, 1H), 3.74 (t, J=6.2 Hz, 2H), 2.96 (t, J=7.4 Hz, 2H), 2.48–2.23 (m, 2H), 2.05–1.20 (m, 9H).

Reference Example 10

8-Carbamoyl-4-chloro-(5-trifluoromethyl-1,2,4-triazolo)[4,3-a]quinoxaline

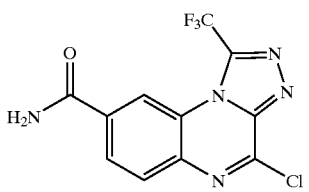

A solution of the compound prepared in Reference Example 1(13) (2.09 g) in thionyl chloride (2 ml) was refluxed with heating for 2 hours. The reaction solution was concentrated, and distilled off an azeotropic mixture with toluene. A solution of the residue in THF was poured into a solution of an aqueous solution of ammonium in THF. Water was added to the solution, the mixture was extracted with chloroform. The organic layer was dried over anhydrous magnesium sulfate and concentrated. The residue was purified by column chromatography on silica gel (toluene:ethyl acetate 4:1→2:1) to give the title compound (0.89 g) having the following physical data.

TLC: Rf 0.55 (Ethyl acetate);

NMR (d6-DMSO): δ8.53 (s, 1H), 8.43 (brs, 1H), 8.05 (d, J=8.4 Hz, 1H), 7.88 (brs, 1H), 7.62 (d, J=8.4 Hz, 1H).

Reference Example 11

4-Chloro-8-nitrile-(5-trifluoromethyl-1,2,4-triazolo)[4,3-a]quinoxaline

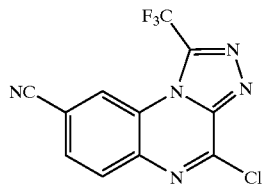

To a solution of the compound prepared in Reference Example 10 (845 mg) in dioxane (10 ml), pyridine (0.5 ml) was added and anhydrous trifluoroacetic acid (0.6 ml) was dropped under cooling with ice. The mixture was stirred for 30 minutes. The reaction solution was diluted with ethyl acetate. The solution was washed with 2N hydrochloric acid and a saturated aqueous solution of sodium chloride, successively, dried over anhydrous magnesium sulfate and concentrated. The precipitate was separated from the solution by filtration, and washed with ether to give the title compound (712 mg) having the following physical data.

TLC: Rf 0.57 (Hexane:Ethyl acetate=2:1);

NMR (d6-DMSO): δ8.38 (d, J=8.4 Hz, 1H), 8.33 (d, J=8.4 Hz, 1H), 8.27 (s, 1H).

Example 26

4-Isobutylthio-8-nitrile-(5-trifluoromethyl-1,2,4-triazolo)[4,3-a]quinoxaline

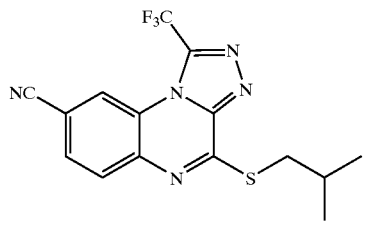

The title compound (134 mg) having the following physical data was obtained by the same procedure as a series of reaction of Example 1, using the compound prepared in Reference Example 11 (318 mg).

TLC: Rf 0.58 (Chloroform)

NMR (CDCl3): δ8.36 (d, J=1.5 Hz , 1H), 8.15 (d, J=8.4 Hz , 1H), 7.93 (dd, J=8.4, 1.5 H, 1H), 3.40 (d, J=6.6H, 2H), 2.24–2.06 (m, 1H), 1.15 (d, J=6.6 Hz, 6H

EXAMPLE 26(1)–26(3)

The following compounds were obtained by the same procedure as a series of reaction of Example 26, using a corresponding thiol.

EXAMPLE 26(1)

4-Isopropylthio-8-nitrile-(5-trifluoromethyl-1,2,4-triazolo)[4,3-a]quinoxaline

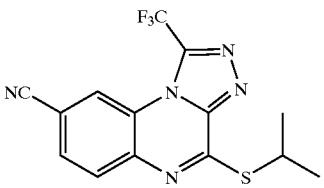

TLC: Rf 0.66 (Hexane:Ethyl acetate=2:1);

NMR (d6-DMSO): δ8.20 (s, 2H), 8.16 (s, 1H), 4.33 (hept, J=6.9 Hz , 1H), 1.52 (d, J=6.9 Hz , 6H).

EXAMPLE 26(2)

4-(4-Hydroxybutyl)thio-8-nitrile-(5-trifluoromethyl-1,2,4-triazolo)[4,3-a]quinoxaline

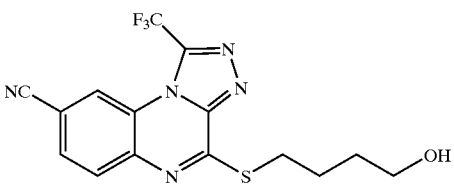

TLC: Rf 0.56 (Chloroform Methanol=9:1);

NMR (CDCl3): δ8.37 (d, J=1.5 Hz , 1H), 8.16 (d, J=8.4 Hz, 1H), 7.94 (dd, J=8.4, 1.5 Hz, 1H), 3.77 (t, J=6.0 Hz, 2H), 3.52 (t, J=7.2 Hz, 2H), 2.05–1.94 (m, 2H), 1.86–1.76 (m, 2H).

EXAMPLE 26(3)

4-(3-Hydroxypropyl)thio-8-nitrile-(5-trifluoromethyl-1,2,4-triazolo)[4,3-a]quinoxaline

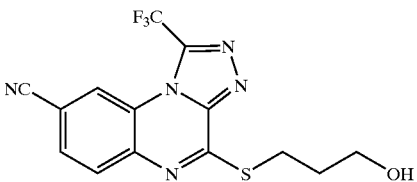

TLC: Rf 0.51 (Chloroform:Methanol=10:1);

NMR (CDCl3) δ8.37 (d, J=1.8 Hz, 1H), 8.14 (d, J=8.4 Hz, 1H), 7.94 (dd, J=8.4, 1.8 Hz , 1H), 3.84 (dt, J=4.8, 7.0 Hz, 2H), 3.63 (t, J=7.2 Hz, 2H), 2.18–2.09 (m, 3H).

EXAMPLE 27

8-Carbamoyl-4-isopropylthio-(5-trifluoromethyl-1,2,4-triazolo)[4,3-a]quinoxaline

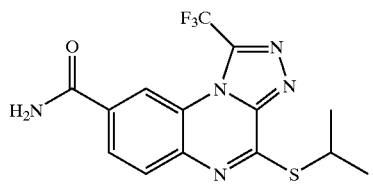

The title compound (131 mg) having the following physical data was obtained by the same procedure as a series of reaction of Example 1, using the compound prepared in Reference Example 10 (176 mg) and a corresponding thiol.

TLC: Rf 0.63 (Ethyl acetate)

NMR (d6-DMSO): δ8.63 (1H, s), 8.33 (1H, brs), 8.24 (1H, d, J=8.4 Hz ), 8.10 (1H, d, J=8.4 Hz), 7.75 (1H, brs), 4.32 (1H, hept, J=6.9 Hz), 1.52 (6H, d, J=6.9 Hz).

EXAMPLE 27(1)–27(8)

The following compounds were obtained by the same procedure as a series of reaction of Example 27, using the compound prepared in Reference Example 10, or the compound prepared by the same procedure as a series of reaction of Example 10 using a corresponding amine instead of the compound in Reference Example 1(13) and a corresponding amine.

EXAMPLE 27(1)

8-(N,N-Dimethylcarbamoyl)-4-phenylthio-(5-trifluoromethyl-1,2,4-triazolo)[4,3-a]quinoxaline

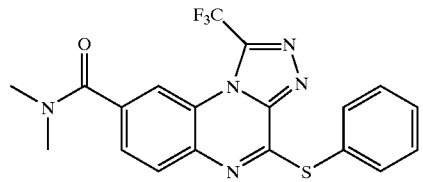

TLC: Rf 0.61 (Ethyl acetate);

NMR (CDCl3): δ8.16 (1H, s), 7.85 (1H, d, J=8.2 Hz), 7.73–7.66 (3H, m), 7.57–7.50 (3H, m), 3.17 (3H, s), 3.03 (3H, s).

EXAMPLE 27(2)

8-Carbamoyl-4-phenylthio-(5-trifluoromethyl-1,2,4-triazolo)[4,3-a]quinoxaline

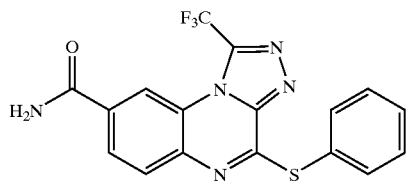

TLC: Rf 0.54 (Ethyl acetate);

NMR (d6-DMSO): δ8.62 (1H, s), 8.32 (1H, brs), 8.16 (1H, d, J=8.2 Hz), 7.78 (1H, d, J=8.2 Hz), 7.76–7.70 (3H, m), 7.65–7.55 (3H, m).

EXAMPLE 27(3)

8-(N-Phenylcarbamoyl)-4-phenylthio-(5-trifluoromethyl-1,2,4-triazolo)[4,3-a]quinoxaline

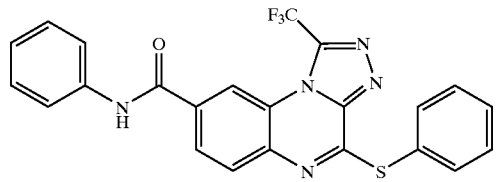

TLC Rf 0.68 (Hexane:Ethyl acetate=1:1);

NMR (d6-DMSO): δ8.65 (1H, s), 8.35 (1H, d, J=8.8 Hz ), 7.87 (1H, d, J=8.8 Hz), 7.85–7.73 (5H, m), 7.63–7.58 (3H, m), 7.38 (2H, t, J=7.6 Hz), 7.14 (1H, t, J=7.6 Hz ).

EXAMPLE 27(4)

4-Isopropylthio-8-(N-phenylcarbamoyl)-(5-trifluoromethyl-1,2,4-triazolo)[4,3-a]quinoxaline

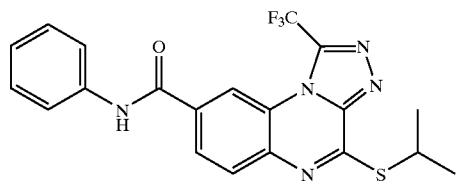

TLC: Rf 0.46 (Hexane:Ethyl acetate=2:1);

NMR (CDCl3): δ8.75 (1H, brs), 8.16 (1H, d, J=8.8 Hz ), 8.09 (1H, dd, J=8.8, 1.8 H), 7.89 (1H, brs), 7.69 (2H, d, J=8.8 Hz), 7.43 (2H, dd, J=8.8, 8.8 Hz), 7.22 (1H, t, J=8.8 Hz), 4.42 (1H, hept, J=7.0 Hz), 1.59 (6H, d, J=7.0 Hz).

EXAMPLE 27(5)

8-(N,N-Dimethylcarbamoyl)-4-isopropylthio-(5-trifluoromethyl-1,2,4-triazolo)[4,3-a]quinoxaline

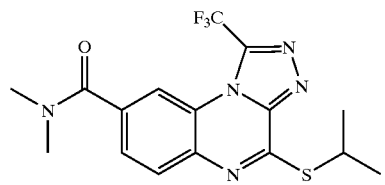

TLC: Rf 0.69 (Ethyl acetate);

NMR (d6-DMSO): δ8.09 (1H, d, J=8.1 Hz), 7.97 (1H, s), 7.82 (1H, d, J=8.1 Hz), 4.32 (1H, hept, J=6.9 Hz), 3.04 (3H, s), 2.99 (3H, s), 1.51 (6H, d, J=6.9 Hz).

EXAMPLE 27(6)

7-Carbamoyl-4-isopropylthio-(5-trifluoromethyl-1,2,4-triazolo)[4,3-a]quinoxaline

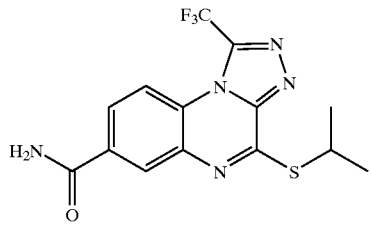

TLC: Rf 0.65 (Ethyl acetate);

NMR (d6-DMSO): δ8.54 (d, J=1.8 Hz, 1H), 8.35 (brs, 1H), 8.21 (dd, J=8.7, 1.8 Hz, 1H), 8.05 (d, J=8.7 Hz, 1H), 7.67 (brs, 1H), 4.32 (hept, J=6.9 Hz, 1H), 1.53 (d, J=6.9 Hz, 6H).

EXAMPLE 27(7)

8-[N-(2-Hydroxyethyl)carbamoyl]-4-isopropylthio-(5-trifluoromethyl-1,2,4-triazolo)[4,3-a]quinoxaline

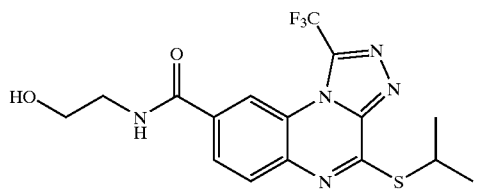

TLC: Rf 0.44 (Chloroform:Methanol=9:1);

NMR (d6-DMSO): δ8.83 (t, J=6.0 Hz, 1H), 8.61 (s, 1H), 8.25 (d, J=8.4 Hz, 1H), 8.12 (d, J=8.4 Hz, 1H), 4.77 (t, J=6.0 Hz, 1H), 4.32 (hept, J=6.9 Hz, 1H), 3.55 (dt, J=6.0, 5.7 Hz, 2H), 3.39 (dt, J=6.0, 5.7 Hz, 2H), 1.52 (d, J=6.9 Hz, 6H).

EXAMPLE 27(8)

4-Isopropylthio-8-[N-(2-morpholinoethyl)carbamoyl]-(5-trifluoromethyl-1,2,4-triazolo)[4,3-a]quinoxaline

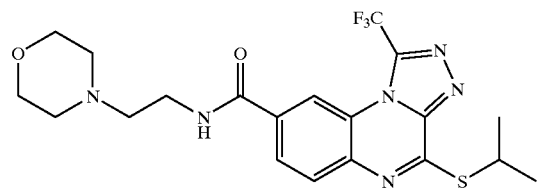

TLC: Rf 0.51 (Chloroform:Methanol=5:1);

NMR (CDCl3): δ8.56 (s, 1H), 8.12 (d, J=8.4 Hz, 1H), 8.08 (d, J=8.4 Hz, 1H), 7.01 (brs, 1H), 4.41 (hept, J=6.9 Hz, 1H), 3.76 (t, J=4.8 Hz, 4H), 3.63 (dt, J=6.0 5.4 Hz, 2H), 2.67 (t, J=6.0 Hz, 2H), 2.56 (t, J=4.8 Hz, 4H), 1.58 (d, J=6.9 Hz, 6H).

EXAMPLE 28

8-[N-(Dimethylaminomethylene)carbamoyl]-4-isopropylthio-(5-trifluoromethyl-1,2,4-triazolo)[4,3-a]quinoxaline

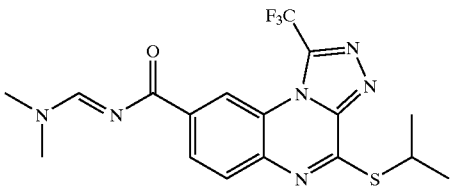

To the compound prepared in Example 27 (519 mg), thionyl chloride (1 ml) was dropped, and one drop of DMF was added. The mixture was stirred for 6 hours at 80° C. The reaction solution was concentrated the residue was diluted with chloroform, washed with a saturated aqueous solution of sodium chloride, dried over anhydrous magnesium sulfate and concentrated. The residue was purified by column chromatography on silica gel (toluene:ethyl acetate=1:1)to give the title compound (128 mg) having the following physical data and the same compound (329 mg) prepared in Example 26.

TLC: Rf 0.70 (Ethyl acetate)

NMR (CDCl3): δ9.32 (s, 1H), 8.72 (s, 1H), 8.50 (d, J=8.7 Hz, 1H), 8.06 (d, J=8.7 Hz, 1H), 4.41 (hept, J=6.6 Hz, 1H), 3.30 (s, 3H), 3.27 (s, 3H), 1.58 (d J=6.6 Hz, 6H).

EXAMPLE 29

7-Bromomethyl-4-isobutylthio-(5-trifluoromethyl-1,2,4-triazolo)[4,3-a]pyrazine

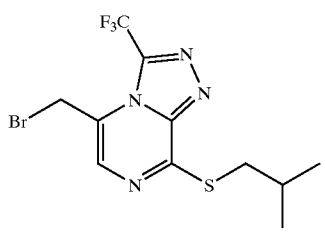

N-Bromo succinimide (197 mg) and benzoyl peroxide (30 mg) were added to a solution of the compound prepared in Example 3(32) (308 mg) in carbon tetrachloride (10 ml). The mixture was refluxed with heating overnight. The cooled reaction solution was diluted with chloroform, washed with water and a saturated aqueous solution of sodium chloride, successively, dried over anhydrous magnesium sulfate and concentrated. The residue was purified by column chromatography on silica gel (Hexane:Ethyl acetate=9:1) to give the title compound (201 mg) having the following physical data.

TLC: Rf 0.58 (Toluene:Ethyl acetate=9:1);

NMR (CDCl3): δ7.92 (s, 1H), 4.82 (s, 2H), 3.28 (d, J=6.9 Hz, 2H), 2.15–2.01 (m, 1H), 1.11 (d, J=6.6 Hz, 6H).

EXAMPLE 30

7-Hydroxymethyl-4-isobutylthio-(5-trifluoromethyl-1,2,4-triazolo)[4,3-a]pyrazine

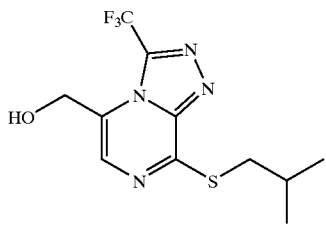

Distilled water (1 ml) and calcium carbonate (161 mg) were added to a solution of the compound prepared in Example 29 (195 mg) in dioxane (1 ml). The mixture was refluxed with heating for 90 minutes. The cooled reaction solution was diluted with ethyl acetate, and filtered. The filtrate was washed with water and a saturated aqueous solution of sodium chloride, successively, dried overanhydrous magnesium sulfate and concentrated. The residue was purified by column chromatography on silica gel (Hexane:Ethyl acetate=5:1) to give the title compound (68.6 mg) having the following physical data.

TLC: Rf 0.19 (Hexane:Ethyl acetate=4:1);

NMR (CDCl3): δ7.96 (brs, 1H), 5.03 (d, J=5.7 Hz, 2H), 3.28 (d, J=6.6 Hz, 2H), 2.20 (t, J=5.7 H, 1H), 2.14–2.00 (m, 1H), 1.10 (d, J=6.9 Hz, 6H).

EXAMPLE 31

4-isobutylthio-7-phenoxymethyl-(5-trifluoromethyl-1,2,4-triazolo)[4,3-a]pyrazine

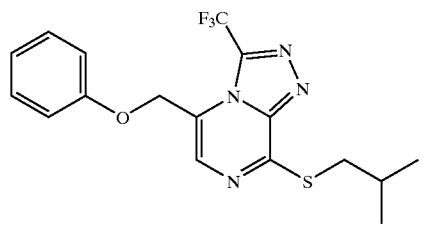

Triphenyl phosphine (206.8 mg) and diethyl azodicarboxylate (0.130 ml) were added to a solution of the compound prepared in Example 30 (203.3 mg) and phenol (75.2 mg) in THF (3 ml) under an atmosphere of argon. The mixture was stirred for 40 minutes at room temperature, and concentrated. The residue was purified by column chromatography on silica gel (Hexane:Ethyl acetate=9:1) to give the title compound (122.3 mg) having the following physical data.

TLC: Rf 0.20 (Hexane:Ethyl acetate=9:1);

NMR (CDCl3): δ7.97 (brs, 1H), 7.39–7.31 (m, 2H), 7.10–7.03 (m, 1H), 6.99–6.93 (m, 2H), 5.31 (s, 2H), 3.29 (d, J=6.9 Hz, 2H), 2.16–2.02 (m, 1H), 1.11 d, J=6.6 Hz, 6H).

EXAMPLE 32

7-Formyl-4-isobutylthio-(5-trifluoromethyl-1,2,4-triazolo)[4,3-a]pyrazine

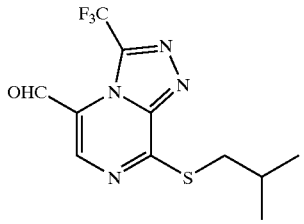

The title compound having the following physical data was obtained by the same procedure as a series of reaction of Example 13, using the compound prepared in Example 30.

TLC: Rf 0.61 (Hexane:Ethyl acetate=2:1);

NMR (CDCl3): δ10.06 (s, 1H), 8.38 (s, 1H), 3.38 (d, J=6.6 Hz, 2H), 2.21–2.03 (m, 1H), 1.13 (d, J=6.9 Hz, 6H).

EXAMPLE 33

7-Carboxy-4-isobutylthio-(5-trifluoromethyl-1,2,4-triazolo)[4,3-a]pyrazine

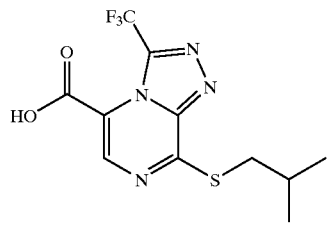

2-Methyl-2-butene (0.310 ml), sodium dihydrogenphosphate bihydrate (116.5 mg) and hypochlorous acid (80% active ingredient) (225.2 mg) were added to a solution of the compound prepared in Example 32 (206.1 mg) in butanol/water (3:1; 6 ml). The mixture was stirred for 30 minutes at room temperature. Hydrochloric acid was added to the reaction solution under cooling with ice. The solution was extracted with chloroform. The organic layer was dried over anhydrous magnesium sulfate and concentrated. The residue was purified by column chromatography on silica gel (Chloroform Methanol=9:1) to give the title compound (162.6 mg) having the following physical data.

TLC: Rf 0.43 (Chloroform:Methanol=4:1);

NMR (CDCl3): δ8.37 (s, 1H), 3.33 (d, J=6.3 Hz, 2H), 2.16–2.02 (m, 1H), 1.11 (d, J=6.6 Hz, 6H).

EXAMPLE 34

7-Carbamoyl-4-isobutylthio-(5-trifluoromethyl-1,2,4-triazolo)[4,3-a]pyrazine

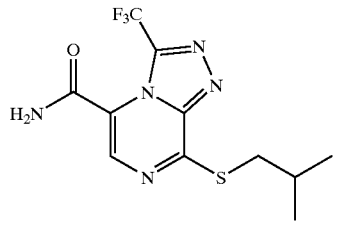

A solution of the compound prepared in Example 33 (464.4 mg) in thionyl chloride (4 ml) was refluxed with heating for 2 hours. The reaction solution was concentrated. The residue was distilled off an azeotropic mixture with toluene. A solution of the residue in THF was poured into an aqueous solution of ammonium in THF under cooling with ice. Water was added to the solution, and the solution was extracted with chloroform. The organic layer was dried over anhydrous magnesium sulfate and concentrated.

The residue was purified by column chromatography on silica gel (toluene ethyl acetate=4:1 →2:1) to give the title compound (404.4 mg) having the following physical data.

TLC: Rf 0.39 (Toluene:Ethyl acetate=1:1);

NMR (CDCl3): δ8.05 (s, 1H), 3.30 (d, J=6.6 Hz, 2H), 2.15–2.01 (m, 1H), 1.10 d,J=6.6 Hz, 6H).

EXAMPLE 35

4-Isobutylthio-7-nitrile-(5-trifluoromethyl -1,2,4-triazolo) [4,3-a]pyrazine

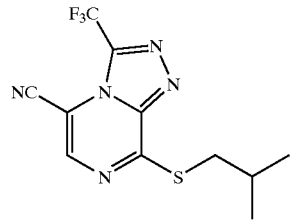

The title compound (209.9 mg) having the following physical data was obtained by the same procedure as a series of reaction of Reference Example 11, using the compound prepared in Example 34 (232.1 mg).

TLC: Rf 0.31 (Hexane:Ethyl acetate=4:1);

NMR (CDCl3): δ8.27 (s, 1H), 3.36 (d, J=6.8 Hz, 2H), 2.24–1.97 (m, 1H), 1.12 (d, J=6.6 Hz, 6H).

EXAMPLE 36(1)–36(3)

The following compounds were obtained by the same procedure as a series of reaction of Example 14, using the compound prepared in Example 32 and a corresponding compound instead of trimethyl phosphonoacetate.

EXAMPLE 36(1)

4-Isobutylthio-7-(2-nitrileethenyl)-(5-trifluoromethyl-1,2,4-triazolo)[4,3-a]pyrazine

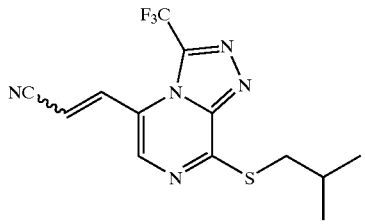

TLC: Rf 0.37 and 0.33 (Hexane:Ethyl acetate 4:1);

NMR (CDCl3): δ8.35 (d, J=0.6 Hz, 0.3H), 7.96 (d, J=1.2 Hz, 0.7H), 7.59 (dt, J=16.2, 1.2 Hz, 0.7H), 7.36 (brd, J=12.0 Hz, 0.3H), 6.07 (d, J=16.2 Hz, 0.7H), 5.88 (d, J=12.0 Hz, 0.3H), 3.33 (d, J=6.6 Hz, 0.6H), 3.31 (d, J=6.6 Hz, 1.4H), 2.17–2.03 (m, 1H), 1.12 (d, J=6.6 Hz, 1.8H), 1.11 (d, J=6.6 Hz, 4.2H).

EXAMPLE 36(2)

7-(2-trans-Ethoxycarbonylethenyl)-4-isobutylthio-(5-trifluoromethyl-1,2,4-triazolo)[4,3-a]pyrazine

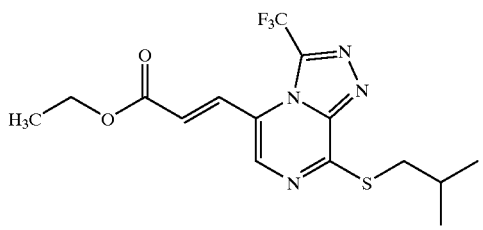

TLC: Rf 0.66 (Hexane:Ethyl acetate 2:1);

NMR (CDCl3): δ8.00 (d, J=0.9 Hz, 1H), 7.91 (dt, J=15.3, 0.9 Hz, 1H), 6.54 (d, J=15.3 Hz, 1H), 4.33 (q, J=7.2 Hz, 2H), 3.31 (d, J=6.6 Hz, 2H), 2.16–2.02 (m, 1H), 1.37 (t, J=7.2 Hz, 3H), 1.11 (d, J=6.6 Hz, 6H).

EXAMPLE 36(3)

7-(2-trans-Acetylethenyl)-4-isobutylthio-(5-trifluoromethyl-1,2,4-triazolo)[4,3-a]pyrazine

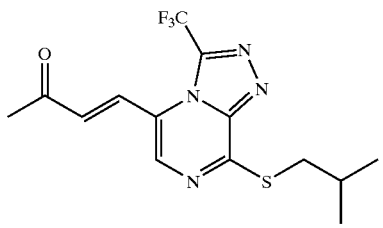

TLC: Rf 0.21 (Hexane Ethyl acetate=4:1);

NMR (CDCl3): δ8.03 (brs, 1H), 7.72 (brd, J=15.6 Hz, 1H), 6.76 (d, J=15.6 Hz, 1H), 3.32 (d, J=7.0 Hz, 2H), 2.45 (s, 3H), 2.19–1.98 (m, 1H), 1.11 (d, J=6.6 Hz 6).

EXAMPLE 37

7-(2, 2-Dinitrileethenyl)-4-isobutylthio-(5-trifluoromethyl-1,2,4-triazolo)[4,3-a]pyrazine

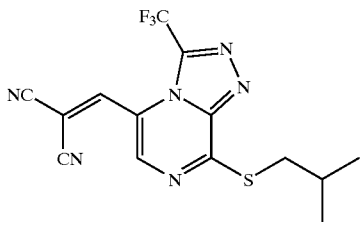

Malononitrile (66.0 mg) and piperidine (a catalytic amount) were added to a solution of the compound prepared in Example 32 (201.8 mg) in ethanol (5 ml). The mixture was stirred for 30 minutes at room temperature. The reaction solution was concentrated. The residue was purified by column chromatography on silica gel (ethyl acetate) to give the title compound (126.9 mg) having the following physical data.

TLC: Rf 0.68 (Toluene:Ethyl acetate=4:1);

NMR (CDCl3): δ8.56 (d, J=0.9 Hz, 1H), 7.93 (brs, 1H), 3.39 (d, J=6.9 Hz, 2H), 2.19–2.05 (m, 1H), 1.13 (d, J=6.6 Hz, 6H).

EXAMPLE 38

7-(2,2-Dichloroethenyl)-4-isobutylthio-(5-trifluoromethyl-1,2,4-triazolo)[4,3-a]pyrazine

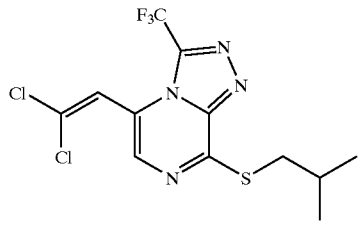

A solution of carbon tetrachloride (190 µl) in methylene chloride (1 ml) was added to a solution of triphenylphosphine (1.02 g) in methylene chloride (3 ml) under an atmosphere of argon, under cooling with ice. The mixture was stirred for 30 minutes at room temperature. The compound prepared in Example 32 (207.7 mg) was added to the solution. The mixture was stirred for 2 hours at room temperature. Methanol was added to the reaction solution under cooling with ice, and the mixture was stirred. The mixture was diluted with ethyl acetate, washed with water and a saturated aqueous solution of sodium chloride, successively, dried over anhydrous magnesium sulfate and concentrated. The residue was purified by column chromatography on silica gel (toluene) to give the title compound (144.5 mg) having the following physical data.

TLC: Rf 0.38 (Toluene);

NMR (CDCl3): δ7.94 (d, J=1.5 Hz, 1H), 6.90 (t, J=1.5 Hz, 1H), 3.30 (d, J=6.9 Hz, 2H), 2.16–2.02 (m, 1H), 1.11 (d, J=6.6 Hz, 6H).

Formulation Example 1

The following components were admixed in conventional method and punched out to obtain 100 tablets each containing 50 mg of active ingredient.

| | |
|---|---|
| 4-Isopropylthio-(5-trifluoromethyl-1,2,4-triazolo)[3,4-c]1,4,5-triazanaphthalene | 5.0 g |
| Carboxymethyl Cellulose calcium (disintegrating agent) | 0.2 g |
| Magnesium stearate (lubricating agent) | 0.1 g |
| Microcrystalline cellulose | 4.7 g |

Formulation Example 2

The following components were admixed in conventional method. The solution was sterilized in conventional manner, placed 5 ml portions into ampoules and freeze-dried to obtain 100 ampoules each containing 20 mg of the active ingredient.

| | |
|---|---|
| 4-Isopropylthio-(5-trifluoromethyl-1,2,4-triazolo)[3,4-c]1,4,5-triazanaphthalene | 5.0 g |
| mannitol | 20 g |
| distilled water | 500 ml |

What is claimed is:

1. A method of treating disorders mediated by cellular adhesion comprising administering an effective amount of a composition comprising fused pyrazine derivatives of the formula (I):

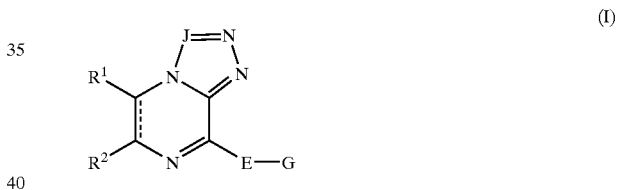

wherein $R^1$ and $R^2$ each, independently, is (i) hydrogen, (ii) C1–8 alkyl, (iii) C1–8 alkoxy, (iv) C1–8 alkylthio, (v) Cyc1, (vi) nitrile, (vii) formyl, (viii) —COOR$^{14}$, in which $R^{14}$ is hydrogen or C1–8 alkyl, (ix) —CONR$^{15}$R$^{16}$, in which $R^{15}$ and $R^{16}$ each, independently, is hydrogen, C1–8 or phenyl, (x) C1–8 alkyl or C2–8 alkenyl substituted by 1 or 2 of hydroxy, C1–4 alkoxy, phenoxy, halogen atom, nitrile, C2–5 acyl, —COOR$^{14}$, —CONR$^{15}$R$^{16}$, or —NR$^{17}$R$^{18}$, in which $R^{17}$ and $R^{18}$ each, independently, is hydrogen, C1–8 alkyl or acetyl, (xi) C1–8 alkyl, C1–8 alkoxy or C1–8 alkylthio substituted by Cyc1, or $R^1$ and $R^2$, taken together with carbon atoms which are attached to each of them, is

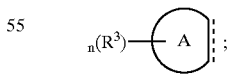

in which Cyc1 is C3–15 mono-, bi- or tri-carbocyolic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —NR$^{101}$R$^{102}$, in which $R^{101}$ and $R^{102}$ each, independently, is hydrogen or C1–8 alkyl (ix) —COOR$^{103}$, in which $R^{103}$ is hydrogen or C1–8 alkyl, (x)

trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —NR$^{101}$R$^{102}$ or —COOR$^{103}$,

is C3–7 mono-carbocyclic ring or 3–7 membered mono-heterocyclic ring containing 1–4 of nitrogen(s), 1–2 of oxygen(s) and/or 1 of sulfur;

R$^3$ is
1) hydrogen,
2) C1–8 alkyl,
3) C2–8 alkenyl,
4) C1–8 alkoxy,
5) C1–8 alkylthio,
6) halogen atom,
7) nitro,
8) cyano,
9) hydroxy,
10) formyl,
11) C2–5 acyl,
12) —NR$^4$R$^5$, in which R$^4$ and R$^5$ each, independently, is hydrogen, C1–8 alkyl or acetyl,
13) —COOR$^6$, in which R$^6$ is hydrogen or C1–8 alkyl,
14) —CONR$^{19}$R$^{20}$, in which R$^{19}$ and R$^{20}$ each, independently, is hydrogen, C1–8 alkyl, phenyl, or C1–4 alkyl substituted by hydroxy, 5–7 membered mono-heterocyclic ring containing 1–2 of nitrogen (s), or 1 of nitrogen and 1 of oxygen, or R$^{19}$ and R$^{20}$, taken together is =CH—NR$^{21}$R$^{22}$, in which R$^{21}$ and R$^{22}$ each, independently, is hydrogen or C1–4 alkyl,
15) trihalomethyl,
16) trihalomethoxy,
17) phenyl,
18) phenyloxy,
19) phenylthio, or
20) C1–8 alkyl, C1–8 alkoxy, C1–8 alkylthio or C1–8 alkylamino substituted by phenyl, or
21) C1–8 alkyl or C2–8 alkenyl substtuted ny 1 or 2 of hydroxy, C1 –4 alkoxy, phenoxy, halogen atom, nitrile, C2–5 acyl, —COOR$^6$—CONR$^{19}$R$^{20}$ or —NR$^4$R$^5$;

n is 0 or 1–5;
J is C—CF$^3$
E is a single bond, C1–4 alkylene, oxygen atom, sulfur atom, —SO—, —SO$_2$—, C1–4 alkylene-M—, with the proviso that alkylene bond to ring and M is bond to G;
M is oxygen atom, sulfur atom, —SO—, —SO$_2$—;
G is
1) C1–8 alkyl,
2) C2–8 alkenyl,
3) C2–8 alkynyl,
4) Cyc3, or
5) C1–8 alkyl substituted by —OR$^8$, —SR$^8$, —NR$^9$R$^{10}$, —COR$^{11}$ or Cyc3, with the proviso that (i) one carbon atom in C1–8 alkyl, which is a component atom of cycloalkyl, may represent 3–7 membered cycloalkyl, or (ii) neighboring two carbon atom in C1–8 alkyl, which are component atoms of cycloalkyl, may represent 3–7 membered cycloalkyl;
in which Cyc3 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1 –8 alkyl, (ii) C1–8 alkoxy, (iii) nitro, (iv) halogen atom, (v) nitrile, (vi) hydroxy, (vii) benzyloxy, (viii) —NR$^{301}$R$^{302}$, in which R$^{301}$ and R$^{302}$ each, independently, is hydrogen or C1–8 alkyl, (ix) —COOR$^{303}$, in which R$^{303}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —NR$^{301}$R$^{302}$ or —COOR$^{303}$, R$^8$ is hydrogen, C1–8 alkyl, C2–8 alkenyl, C1–8 alkyl substituted by phenyl or C1–8 alkoxy, or —S—(C1–8 alkylene)-OR$^{23}$, in which R$^{23}$ is hydrogen or C1–8 alkyl; with the proviso that (i) one carbon atom in C1–8 alkylene, which is a component atom of cycloalkyl, may represent 3–7 membered cycloalkyl , or (ii) neighboring two carbon atom in C1–8 alkylene, which are component atoms of cycloalkyl, may represent 3–7 membered cycloalkyl;

R$^9$ is hydrogen, C1–8 alkyl, C2–8 alkenyl, C1–8 alkyl substituted by phenyl or C1–8 alkoxy;

R$^{10}$ is hydrogen, C1–8 alkyl, C2–8 alkenyl, C1–8 alkyl substituted by phenyl, or C2–5 acyl;

R$^{11}$ is (i) C1–8 alkyl, (ii) C1–8 alkoxy, (iii) hydroxy, (iv) C1–8 alkyl or C1–8 alkoxy substituted by phenyl, or (v) —NR$^{12}$R$^{13}$, in which R$^{12}$ and R$^{13}$ each, independently, is hydrogen, C1–8 alkyl or C1–8 alkyl substituted by phenyl;

=== is a single bond or a double bond;

with the proviso that the compounds in which R$^2$ is C1–8 alkyl, E is a single bond or C1–4 alkylene and G is C1–8 alkyl are excluded;

or non-toxic acid thereof as active ingredient.

2. Novel fused pyrazine derivatives of the formula (I):

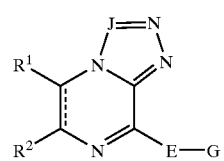

wherein R$^1$ and R$^2$ each, independently, is (i) hydrogen, (ii) C1–8 alkyl, (iii) C1–8 alkoxy, (iv) C1–8 alkylthio, (v) Cyc1, (vi) nitrile, (vii) formyl, (viii) —COOR$^{14}$, in which R$^{14}$ is hydrogen or C1–8 alkyl, (ix) —CONR$^{15}$R$^{16}$, in which R$^{15}$ and R$^{16}$ each, independently, is hydrogen, C1–8 alkyl or phenyl, (x) C1–8 alkyl or C2–8 alkenyl substituted by 1 or 2 of hydroxy, C1–4 alkoxy, phenoxy, halogen atom, nitrile, C2–5 acyl, —COOR$^{14}$, —CONR$^{15}$R$^{16}$ or —NR$^{17}$R$^{18}$, in which R$^{17}$ and R$^{18}$ each, independently, is hydrogen, C1–8 alkyl or acetyl, (xi) C1–8 alkyl, C1–8 alkoxy or C1–8 alkylthio substituted by Cyc1, or R$^1$ and R$^2$, taken together with carbon atoms which are attached to each of them, is

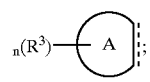

in which Cyc1 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —NR$^{101}$R$^{102}$, in which R$^{101}$ and R$^{102}$ each, independently, is hydrogen or C1–8 alkyl (ix) —COOR$^{103}$, in which R$^{103}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —NR$^{101}$R$^{102}$ or —COOR$^{103}$;

is C3–7 mono-carbocyclic ring or 3–7 membered mono-heterocyclic ring containing 1–4 of nitrogen(s), 1–2 of oxygen(s) and/or 1 of sulfur;

R$^3$ is
1) hydrogen,
2) C1–8 alkyl,
3) C2–8 alkenyl,
4) C1–8 alkoxy,
5) C1–8 alkylthio,
6) halogen atom,
7) nitro,
8) cyano,
9) hydroxy,
10 formyl,
11) C2–5 acyl,
12) —NR$^4$R$^5$, in which R$^4$ and R$^5$ each, independenily, is hydrogen, C1–8 alkyl or acetyl,
13) —COOR$^6$, in which R$^6$ is hydrogen or C1–8 alkyl,
14) —CONR$^{19}$R$^{20}$ in which R$^{19}$ and R$^{20}$ each, independently, is hydrogen, C1–8 alkyl, phenyl, or C1–4 alkyl substituted by hydroxy, 5–7 membered mono-heterocyclic ring containing 1–2 of nitrogen (s), or 1 of nitrogen and 1 of oxygen, or R$^{19}$ and R$^{20}$, taken together is =CH—NR$^{21}$R$^{22}$, in which R$^{21}$ and R$^{22}$ each, independently, is hydrogen or C1–4 alkyl,
15) trihalomethyl,
16) trihalomethoxy,
17) phenyl,
18) phenyloxy,
19) phenylthio, or
20) C1–8 alkyl, C1–8 alkoxy, C1–8 alkylthio or C1–8 alkylamino substituted by phenyl, or
21) C1–8 alkyl or C2–8 alkenyl substituted by 1 or 2 of hydroxy, C1–4 alkoxy, phenoxy, halogen atom, nitrile, C2–5 acyl, —COOR , —CONR $^{19}$R$^{20}$ or —NR$^4$R$^5$;

n is 0 or 1–5;

J is C—CF$^3$

E is a single bond, C1–4 alkylene, oxygen atom, sulfur atom, —SO—, —SO$_2$—, C1–4 alkylene-M—, with the proviso that alkylene bond to ring and M is bond to G;

M is oxygen atom, sulfur atom, —SO—, —SO$_2$;

G is
1) C1–8 alkyl,
2) C2–8 alkenyl,
3) C2–8 alkynyl,
4) Cyc3, or
5) C1–8 alkyl substituted by —OR$^8$, —SR$^8$, —NR$^9$R$^{10}$, —COR$^{11}$ or Cyc3, with the proviso that (i) one carbon atom in C1–8 alkyl, which is a component atom of cycloalkyl, may represent 3–7 membered cycloalkyl, or (ii) neighboring two carbon atom in C1–8 alkyl, which are component atoms of cycloalkyl, may represent 3–7 membered cycloalkyl;

in which Cyc3 is C3–15 mono-, bi- or tri-carbocyclic ring or 5–18 membered mono-, bi- or tri-heterocyclic ring containing 1–4 of nitrogen(s), 1–2 of oxygen(s) and/or 1 of sulfur, the above carbocyclic ring or heterocyclic ring may be substituted by one or more of (i) C1–8 alkyl, (ii) C1–8 alkoxy, (iii) nitro, (iv) halogen atom, (v) nitrile, (vi) hydroxy, (vii) benzyloxy, (viii) —NR$^{301}$R$^{302}$, in which R$^{301}$ and R$^{302}$ each, independently, is hydrogen or C1–8 alkyl, (ix) —COOR$^{303}$, in which R$^{303}$ is hydrogen or C1–8 alkyl, (x) trihalomethyl, (xi) trihalomethoxy, (xii) phenyl, (xiii) phenyloxy, (xiv) C1–8 alkyl or C1–8 alkoxy substituted by phenyl, phenyloxy, hydroxy, —NR$^{301}$R$^{302}$ or —COOR$^{303}$;

R is hydrogen, C1–8 alkyl, C2–8 alkenyl, C1–8 alkyl substituted by phenyl or C1–8 alkoxy, or —S—(C1–8 alkylene)-OR$^{23}$, in which R$^{23}$ is hydrogen or C1–8 alkyl; with the proviso that (i) one carbon atom in C1–8 alkylene, which is a component atom of cycloalkyl, may represent 3–7 membered cycloalkyl, or (ii) neighboring two carbon atom in C1–8 alkylene, which are component atoms of cycloalkyl, may represent 3–7 membered cycloalkyl;

R$^9$ is hydrogen, C1–8 alkyl, C2–8 alkenyl, C1–8 alkyl substituted by phenyl or C1–8 alkoxy;

R$^{10}$ is hydrogen, C1–8 alkyl, C2–8 alkenyl, C1–8 alkyl substituted by phenyl, or C2–5 acyl;

R$^{11}$ is (i) C1–8 alkyl, (ii) C1–8 alkoxy, (iii) hydroxy, (iv) C1–8 alkyl or C1–8 alkoxy substituted by phenyl, or (v) —NR$^{12}$R$^{13}$, in which R$^{12}$ and R$^{13}$ each, independently, is hydrogen, C1–8 alkyl or C1–8 alkyl substituted by phenyl;

=== is a single bond or a double bond;

with the proviso that the compounds in which R$^2$ is C1–8 alkyl, E is a single bond or C1–4 alkylene and G is C1–8 alkyl and the following compounds are excluded;

(1) 4-Phenylthio-8-chloro(5-trifluoromethyl-1,2,4-triazolo)-[4,3-a]quinoxaline,
(2) 4-(4-Chlorophenyl)thio(5-trifluoromethyl-1,2,4-triazolo)-[4,3-a]quinoxaline,
(3) 4-Phenylmethylthio(5-trifluoromethyl-1,2,4-triazolo)-[4,3-a]quinoxaline,
(4) 4-(Pyridin-2-yl)thio(5-trifluoromethyl-1,2,4-triazolo)-[4,3-a]quinoxaline,
(5) 4-Phenylthio(5-trifluoromethyl-1,2,4-triazolo)-[4,3-a]quinoxaline,
(6) 4-(4-Methoxyphenyl)thio(5-trifluoromethyl-1,2,4-triazolo)-[4,3-a]quinoxaline.

3. A compound according to claim 2, wherein R$^1$ and R$^2$ each, independently, is (i) hydrogen, (ii) C1–8 alkyl, (iii) C1–8 alkoxy, (iv) C1–8 alkylthio, (v) Cyc1, (vi) nitrile, (vii) formyl, (viii) —COOR$^{14}$, (ix) —CONR$^{15}$R$^{16}$, (x) C1–8 alkyl or C2–8 alkenyl substituted by 1 or 2 of hydroxy, C1–4 alkoxy, phenoxy, halogen atom, nitrile, C2–5 acyl, —COOR$^{14}$, —CONR$^{15}$R$^{16}$, or —NR$^{17}$R$^{18}$, (xi) C1–8 alkyl, C1–8 alkoxy or C1–8 alkylthio substituted by Cyc1.

4. A compound according to claim 2, wherein R$^1$ and R$^2$, taken together with carbon atoms which are attached to each of them, is

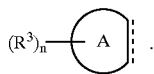

5. A compound according to claim 2, which is selected from
(1) 4-Phenylthio-(5-trifluoromethyl-1,2,4-triazolo)[4,3-a]pyrazine,
(2) 4-Allylthio-(5-trifluoromethyl-1,2,4-triazolo)[4,3-a]pyrazine,
(3) 4-(3-Allylthiopropyl)thio-(5-trifluoromethyl-1,2,4-triazolo)[4,3-a]pyrazine,
(4) 4-Phenylthio-6,7-dimethyl-(5-trifluoromethyl-1,2,4-triazolo)[4,3-a]pyrazine,
(5) 4-Isopropylthio-6-phenyl-(5-trifluoromethyl-1,2,4-triazolo)[4,3-a]pyrazine,
(6) 4-Isobutylthio-7-methyl-(5-trifluoromethyl-1,2,4-triazolo)[4,3-a]pyrazine,
(7) 4-Isobutylthio-6-methyl-(5-trifluoromethyl-1,2,4-triazolo)[4,3-a]pyrazine,
(8) 7-Ethyl-4-isobutylthio-(5-trifluoromethyl-1,2,4-triazolo)[4,3-a]pyrazine,
(9) 4-(4-Hydroxybutyl)thio-7-methyl-(5-trifluoromethyl-1,2,4-triazolo)[4,3-a]pyrazine,
(10) 4-Isobutylthio-(5-trifluoromethyl-1,2,4-triazolo)[4,3-a]pyrazine,
(11) 6,7-Dimethyl-4-isobutylthio-(5-trifluoromethyl-1,2,4-triazolo)[4,3-a]pyrazine,
(12) 4-Isobutylthio-7-propyl-(5-trifluoromethyl-1,2,4-triazolo)[4,3-a]pyrazine,
(13) 7-Butyl-4-isobutylthio-(5-trifluoromethyl-1,2,4-triazolo)[4,3-a]pyrazine,
(14) 4-Isobutylthio-7-pentyl-(5-trifluoromethyl-1,2,4-triazolo)[4,3-a]pyrazine,
(15) 7-Bromomethyl-4-isobutyl-(5-trifluoromethyl-1,2,4-triazolo)[4,3-a]pyrazine,
(16) 7-Hydroxymethyl-4-isobutyl-(5-trifluoromethyl-1,2,4-triazolo)[4,3-a]pyrazine,
(17) 4-Isobutyl-7-phenoxymethyl-(5-trifluoromethyl-1,2,4-triazolo)[4,3-a]pyrazine,
(18) 7-Formyl-4-isobutyl-(5-trifluoromethyl-1,2,4-triazolo)[4,3-a]pyrazine,
(19) 7-Carboxy-4-isobutyl-(5-trifluoromethyl-1,2,4-triazolo)[4,3-a]pyrazine,
(20) 7-Carbamoyl-4-isobutyl-(5-trifluoromethyl-1,2,4-triazolo)[4,3-a]pyrazine,
(21) 4-Isobutyl-7-nitrile-(5-trifluoromethyl-1,2,4-triazolo)[4,3-a]pyrazine,
(22) 4-Isobutyl-7-(2-nitrileethenyl)-(5-trifluoromethyl-1,2,4-triazolo)[4,3-a]pyrazine,
(23) 7-(2-trans-Ethoxycarbonylethenyl)-4-isobutyl-(5-trifluoromethyl-1,2,4-triazolo)[4,3-a]pyrazine,
(24) 7-(2-trans-Acetylethenyl)-4-isobutyl-(5-trifluoromethyl-1,2,4-triazolo)[4,3-a]pyrazine,
(25) 7-(2,2-Dinitrileethenyl)-4-isobutyl-(5-trifluoromethyl-1,2,4-triazolo)[4,3-a]pyrazine, or
(26) 7-(2,2-Dichloroethenyl)-4-isobutyl-(5-trifluoromethyl[4,3-a]pyrazine.

6. A compound according to claim 2, which is selected from
(1) 4-Isopropylthio-(5-trifluoromethyl-1,2,4-triazolo)[4,3-a]quinoxaline,
(2) 4-Phenyloxy-(5-trifluoromethyl-1,2,4-triazolo)[4,3-a]quinoxaline,
(3) 4-(Pyrimidin-2-yl)thio-(5-trifluoromethyl-1,2,4-triazolo)[4,3-a]quinoxaline,
(4) 4-Allylthio-(5-trifluoromethyl-1,2,4-triazolo)[4,3-a]quinoxaline,
(5) 4-(Thiophen-2-yl)thio-(5-trifluoromethyl-1,2,4-triazolo)[4,3-a]quinoxaline,
(6) 4-Cyclohexylthio-(5-trifluoromethyl-1,2,4-triazolo)[4,3-a]quinoxaline,
(7) 4-(4-Trifluoromethylphenyl)thio-(5-trifluoromethyl-1,2,4-triazolo)[4,3-a]quinoxaline,
(8) 4-(4-Trifluoromethoxyphenyl)thio-(5-trifluoromethyl-1,2,4-triazolo)[4,3-a]quinoxaline,
(9) 4-(Pyridin-4-yl)thio-(5-trifluoromethyl-1,2,4-triazolo)[4,3-a]quinoxaline,
(10) 4-(Pyridin-4-yl)thio-(5-trifluoromethyl-1,2,4-triazolo)[4,3-a]quinoxaline hydrochloride,
(11) 4-(2-Methoxyphenyl)thio-(5-trifluoromethyl-1,2,4-triazolo)[4,3-a]quinoxaline,
(12) 4-(3-Methoxyphenyl)thio-(5-trifluoromethyl-1,2,4-triazolo)[4,3-a]quinoxaline,
(13) 4-(2-Chlorophenyl)thio-(5-trifluoromethyl-1,2,4-triazolo)[4,3-a]quinoxaline,
(14) 4-(3-Chlorophenyl)thio-(5-trifluoromethyl-1,2,4-triazolo)[4,3-a]quinoxaline,
(15) 4-(2-Aminophenyl)thio-(5-trifluoromethyl-1,2,4-triazolo)[4,3-a]quinoxaline,
(16) 4-(2-Aminophenyl)thio-(5-trifluoro methyl-1,2,4-triazolo)[4,3-a]quinoxaline hydrochloride,
(17) 4-(3-Carboxyphenyl)thio-(5-trifluoromethyl-1,2,4-triazolo)[4,3-a]quinoxaline,
(18) 4-(4-Carboxyphenyl)thio-(5-trifluoromethyl-1,2,4-triazolo)[4,3-a]quinoxaline,
(19) 4-(4-Aminophenyl)thio-(5-trifluoromethyl-1,2,4-triazolo)[4,3-a]quinoxaline,
(20) 4-(4-Aminophenyl)thio-(5-trifluoromeThyl-1,2,4-triazolo)[4,3-a]quinoxaline hydrochloride,
(21) 4-(4-(2-Carboxyethyl)phenyl)thio-(5-trifluoromethyl-1,2,4-triazolo)[4,3-a]quinoxaline,
(22) 4-(N,N-Dimethylamino)ethylthio-(5-trifluoromethyl-1,2,4-triazolo)[4,3-a]quinoxaline,
(23) 4-(N,N-Dimethylamino)ethylthio-(5-trifluoromethyl-1,2,4-triazolo)[4,3-a]quinoxaline hydrochloride,
(24) 4-(3-Methoxycarbonylphenyl)thio-(5-trifluoromethyl-1,2,4-triazolo)[4,3-a]quinoxaline,
(25) 4-(4-Methoxycarbonylphenyl)thio-(5-trifluoromethyl-1,2,4-triazolo)[4,3-a]quinoxaline,
(26) 4-(4-(2-Methoxycarbonylethyl)phenyl)thio-(5-trifluoromethyl-1,2,4-triazolo)[4,3-a]quinoxaline,
(27) 4-(3-Aminophenyl)thio-(5-trifluoromethyl-1,2,4-triazolo)[4,3-a]quinoxaline,
(28) 4-(3-Aminophenyl)thio-(5-trifluoromethyl-1,2,4-triazolo)[4,3-a]quinoxaline hydrochloride,
(29) 4-Isopropyloxy-(5-trifluoromethyl-1,2,4-triazolo)[4,3-a]quinoxaline,
(30) 4-Allyloxy-(5-trifluoromethyl-1,2,4-triazolo)[4,3-a]quinoxaline,
(31) 4-Methoxycarbonylmethylthio-(5-trifluoromethyl-1,2,4-triazolo)[4,3-a]quinoxaline,
(32) 4-(1-Ethoxycarbonylethyl)thio-(5-trifluoromethyl-1,2,4-triazolo)[4,3-a]quinoxaline,
(33) 4-(2-Thiazolin-2-yl)thio-(5-trifluoromethyl-1,2,4-triazolo)[4,3-a]quinoxaline,
(34) 4-(Thiazol-2-yl)thio-(5-trifluoromethyl-1,2,4-triazolo)[4,3-a]quinoxaline,
(35) 4-(1-Methyltetrazol-5-yl)thio-(5-trifluoromethyl-1,2,4-triazolo)[4,3-a]quinoxaline,
(36) 4-(1-Phenyltetrazol-5-yl)thio-(5-trifluoromethyl-1,2,4-triazolo)[4,3-a]quinoxaline,
(37) 4-(2-Hydroxyethyl)thio-(5-trifluoromethyl-1,2,4-triazolo)[4,3-a]quinoxaline,

(38) 4-(2-Hydroxypropyl)thio-(5-trifluoromethyl-1,2,4-triazolo)[4,3-a]quinoxaline,
(39) 4-(3-Hydroxypropyl)thio-(5-trifluoromethyl-1,2,4-triazolo)[4,3-a]quinoxaline,
(40) 4-(2-Methylfuran-3-yl)thio-(5-trifluoromethyl-1,2,4-triazolo)[4,3-a]quinoxaline,
(41) 4-(6-Methyl-4H,5H-1,3-thiadine)thio-(5-trifluoromethyl-1,2,4-triazolo)[4,3-a]quinoxaline,
(42) 4-(Imidazol-2-yl)thio-(5-trifluoromethyl-1,2,4-triazolo)[4,3-a]quinoxaline,
(43) 4-[3-(Methoxymethoxy)propyl]thio-(5-trifluoromethyl-1,2,4-triazolo)[4,3-a]quinoxaline,
(44) 4-(3-Methylthiopropoxy)-(5-trifluoromethyl-1,2,4-triazolo)[4,3-a]quinoxaline,
(45) 4-(3-Methoxypropyl)thio-(5-trifluoromethyl-1,2,4-triazolo)[4,3-a]quinoxaline,
(46) 4-(2-Methoxyethyl)thio-(5-trifluoromethyl-1,2,4-triazolo)[4,3-a]quinoxaline,
(47) (±)-4-(2-Methoxypropyl)thio-(5-trifluoromethyl-1,2,-4-triazolo)[4,3-a]quinoxaline,
(48) 4-[2-(Methoxymethoxy)ethyl]thio-(5-trifluoromethyl-1,2,4-triazolo)[4,3-a]quinoxaline,
(49) (±)-4-[2-(Methoxymethoxy)propyl]thio-(5-trifluoromethyl-1,2,4-triazolo)[4,3-a]quinoxaline,
(50) 4-(2-Ethoxyethoxy)-(5-trifluoromethyl-1,2,4-triazolo)[4,3-a]quinoxaline,
(51) 4-(3-Hydroxypropoxy)-(5-trifluoromethyl-1,2,4-triazolo)[4,3-a]quinoxaline,
(52) 4-Cyclopentyloxy-(5-trifluoromethyl-1,2,4-triazolo)[4,3-a]quinoxaline,
(53) 4-Cyclopentylmethyloxy-(5-trifluoromethyl-1,2,4-triazolo)[4,3-a]quinoxaline,
(54) 4-Cyclobutyloxy-(5-trifluoromethyl-1,2,4-triazolo)[4,3-a]quinoxaline,
(55) 4-Cyclohexylmethyloxy-(5-trifluoromethyl-1,2,4-triazolo)[4,3-a]quinoxaline,
(56) 4-Cyclopropylmethyloxy-(5-trifluoromethyl-1,2,4-triazolo)[4,3-a]quinoxaline,
(57) 4-Cycloheptyloxy-(5-trifluoromethyl-1,2,4-triazolo)[4,3-a]quinoxaline,
(58) 4-(4-Fluorophenoxy)-(5-trifluoromethyl-1,2,4-triazolo)[4,3-a]quinoxaline,
(59) 4-(4-Chlorophenoxy)-(5-trifluoromethyl-1,2,4-triazolo)[4,3-a]quinoxaline,
(60) 4-(2-Hydroxyethoxy)-(5-trifluoromethyl-1,2,4-triazolo)[4,3-a]quinoxaline
(61) 4-(3-Hydroxy-3-methylbutyl)thio-(5-trifluoromethyl-1,2,4-triazolo)[4,3-a]quinoxaline,
(62) (±)-4-(3-Hydroxybutyl)thio-(5-trifluoromethyl-1,2,4-triazolo)[4,3-a]quinoxaline,
(63) 4-(3-Hydroxy-2,2-dimethylpropyl)thio-(5-trifluoromethyl-1,2,4-triazolo)[4,3-a[quinoxaline,
(64) 4-(2-Hydroxy-2-methylpropyl)thio-(5-trifluoromethyl-1,2,4-triazolo)[4,3-a]quinoxaline,
(65) 4-(4-Hydroxybutyl)thio-(5-trifluoromethyl-1,2,4-triazolo)[4,3-a]quinoxaline,
(66) 4-(5-Hydroxypentyl)thio-(5-trifluoromethyl-1,2,4-triazolo)[4,3-a]quinoxaline,
(67) 4-(6-Hydroxyhexyl)thio-(5-trifluoromethyl-1,2,4-triazolo)[4,3-a]quinoxaline,
(68) 4-[1-(Hydroxymethyl)cyclopropyl-1-yl]methylthio-(5-trifluoromethyl-1,2,4-triazolo)[4,3-a]quinoxaline,
(69) (±)-4-(3-Hydroxy-2-methylpropyl)thio-(5-trifluoromethyl-1,2,4-triazolo)[4,3-a]quinoxaline
(70) (±)-4-(4-Hydroxy-2-butyl)thio-(5-trifluoromethyl-1,2,4-triazolo)[4,3-a]quinoxaline,
(71) (±)-4-(3-Hydroxy-2-propyl)thio-(5-trifluoromethyl-1,2,4-triazolo)[4,3-a]quinoxaline,
(72) (±)-4-(1-Hydroxy-2-butyl)thio-(5-trifluoromethyl-1,2,4-triazolo)[4,3-a]quinoxaline,
(73) (±)-4-(1-Hydroxy-3-pentyl)thio-(5-trifluoromethyl-1,2,4-triazolo)[4,3-a]quinoxaline,
(74) (±)-4-(2-Hydroxybutyl)thio-(5-trifluoromethyl-1,2,4-triazolo)[4,3-a]quinoxaline,
(75) (±)-4-(4-Hydroxypentyl)thio-(5-trifluoromethyl-1,2,4-triazolo)[4,3-a]quinoxaline,
(76) (±)-4-(1-Hydroxy-3-methylbutyl)thio-(5-trifluoromethyl-1,2,4-triazolo)[4,3-a]quinoxaline,
(77) (±)-cis-4-[2-(Hydroxymethyl)cyclopropylmethyl]thio-(5-trifluoromethyl-1,2,4-triazolo)[4,3-a]quinoxaline,
(78) 4-(Cyclopropylmethyl)thio-(5-trifluoromethyl-1,2,4-triazolo)[4,3-a]quinoxaline,
(79) (+)-4-(2,2-Dimethyl-1,3-dioxolan-4-yl)methylthio-(5-trifluoromethyl-1,2,4-triazolo)[4,3-a]quinoxaline,
(80) (±)-4-(2,3-Dihydroxypropyl)thio-(5-trifluoromethyl-1,2,4-triazolo)[4,3-a]quinoxaline,
(81) (±)-trans-4-[2-(Hydroxymethyl)cyclopropyl]methylthio-(5-trifluoromethyl-1,2,4-triazolo)[4,3-a]quinoxaline,
(82) (±)-4-(2-Hydroxymethylbutyl)thio-(5-trifluoromethyl-1,2,4-triazolo)[4,3-a]quinoxaline,
(83) 4-Phenylthio-(5-trifluoromethyl-1,2,4-triazolo)(3,4-c]1,4,5-triazanaphthalene,
(84) 4-Phenylthio-7-nitro-(5-trifluoromethyl-1,2,4-triazolo)[4,3-a]quinoxaline,
(85) 4-Phenylthio-7,8-dimethoxy-(5-trifluoromethyl-1,2,4-triazolo)[4,3-a]quinoxaline,
(86) 4-Phenylthio-7,8-dichloro-(5-trifluoromethyl-1,2,4-triazolo)[4,3-a]quinoxaline,
(87) 4-Phenylthio-7-methoxycarbonyl-(5-trifluoromethyl-1,2,4-triazolo)[4,3-a]quinoxaline,
(88) 4-Phenyloxy-7-methoxycarbonyl-(5-trifluoromethyl-1,2,4-triazolo)[4,3-a]quinoxaline,
(89) 4-Phenylthio-6,7,8,9-tetrahydro-(5-trifluoromethyl-1,2,4-triazolo)[4,3-a]quinoxaline,
(90) 4-Phenylthio-8-nitro-(5-trifluoromethyl-1,2,4-triazolo)[4,3-a]quinoxaline,
(91) 4,8-Diphenylthio-(5-trifluoromethyl-1,2,4-triazoio)[4,3-a]quinoxaline,
(92) 8-Methoxycarbonyl-4-phenylthio-(5-trifluoromethyl-1,2,4-triazolo)[4,3-a]quinoxaline,
(93) 8-Methoxycarbonyl-4-phenoxy-(5-trifluoromethyl-1,2,4-triazolo)[4,3-a]quinoxaline,
(94) 4-Isopropylthio-(5-trifluoromethyl-1,2,4-triazolo)[3,4-c]1,4,5-triazanaphthalene,
(95) 4-Isobutylthio-(5-trifluoromethyl-1,2,4-triazolo)[3,4-c]1,4,5-triazanaphthalene,
(96) 4-Butylthio-(5-trifluoromethyl-1,2,4-triazolo)[3,4-c]1,4,5-triazanaphthalene,
(97) 4-Cyclopentylthio-(5-trifluoromethyl-1,2,4-triazolo)[3,4-c]1,4,5-triazanaphthalene,
(98) 6-Nitro-4-phenylthio-(5-trifluoromethyl-1,2,4-triazolo)[4,3-a]quinoxaline,
(99) 6-Ethoxycarbonyl-4-phenylthio-(5-trifluoromethyl-1,2,4-triazolo)[4,3-a]quinoxaline,
(100) 6-Ethoxycarbonyl-4-isopropylthio-(5-trifluoromethyl-1,2,4-triazolo)[4,3-a]quinoxaline,
(101) 8-Carboxy-4-phenylthio-(5-trifluoromethyl-1,2,4-triazolo)[4,3-a]quinoxaline,
(102) 8-Carboxy-4-isopropylthio-(5-trifluoromethyl-1,2,4-triazolo)[4,3-a]quinoxaline,
(103) 4-Isopropylthio-8-methoxycarbonyl-(5-trifluoromethyl-1,2,4-triazolo)[4,3-a]quinoxaline,
(104) 4-(4-Fluorophenyl)thio-8-methoxycarbonyl-(5-trifluoromethyl-1,2,4-triazolo)[4,3-a]quinoxaline, (105) 4-(3-Hydroxypropyl)thio-8-methoxycarbonyl-(5-trifluoromethyl-1,2,4-triazolo)[4,3-a]quinoxaline,
(106) 4-(Imidazol-2-yl)thio-8-methoxycarbonyl-(5-trifluoromethyl-1,2,4-triazolo)[4,3-a]quinoxaline,
(107) 7-Chloro-4-isopropylthio-(5-trifluoromethyl-1,2,4-triazolo)[4,3-a]quinoxaline,
(108) 8-Chloro-4-isopropylthio-(5-trifluoromethyl-1,2,4-triazolo)[4,3-a]quinoxaline,
(109) 4-(4-Fluorophenyl)thio-(5-trifluoromethyl-1,2,4-triazolo)[3,4-c]1,4,5-triazanaphthalene,
(110) 4-(3-Hydroxypropyl)thio-(5-trifluoromethyl-1,2,4-triazolo)[3,4-c]1,4,5-triazanaphthalene,
(111) 8-Chloro-4-(4-fluorophenyl)thio-(5-trifluoromethyl-1,2,4-triazolo)[4,3-a]quinoxaline,
(112) 8-Chloro-4-(3-hydroxypropyl)thio-(5-trifluoromethyl-1,2,4-triazolo)[4,3-a]quinoxaline,
(113) 4-Isobutyloxy-(5-trifluoromethyl-1,2,4-triazolo)[3,4-c]1,4,5-triazanaphthalene,
(114) 6-Chloro-4-isobutylthio-(5-trifluoromethyl-1,2,4-triazolo)[4,3-a]quinoxaline,
(115) 6,8-Dichloro-4-isobutylthio-(5-trifluoromethyl-1,2,4-triazolo)[4,3-a]quinoxaline,
(116) 4-Isobutylthio-8-trifluoromethyl-(5-trifluoromethyl-1,2,4-triazolo)[4,3-a]quinoxaline,
(117) 8-Fluoro-4-isobutylthio-(5-trifluoromethyl-1,2,4-triazolo)[4,3-a]quinoxaline,
(118) 6,8-Dibromo-4-isobutylthio-(5-trifluoromethyl-1,2,4-triazolo)[4,3-a]quinoxaline,
(119) 4-(4-Fluorophenyl)thio-8-fluoro-(5-trifluoromethyl-1,2,4-triazolo)[4,3-a]quinoxaline,
(120) 8-Fluoro-4-(3-hydroxypropyl)thio-(5-trifluoromethyl-1,2,4-triazolo)[4,3-a]quinoxaline,
(121) 4-(3-Hydroxy-3-methylbutyl)thio-(5-trifluoromethyl-1,2,4-triazolo)[3,4-c]1,4,5-triazanaphthalene,
(122) 8-Chloro-4-(3-hydroxy-3-methylbutyl)thio-(5-trifluoromethyl-1,2,4-triazolo)[4,3-a]quinoxaline,
(123) (±)-8-Chloro-4-(3-hydroxybutyl)thio-(5-trifluoromethyl-1,2,4-triazolo)[4,3-a]quinoxaline,
(124) 8-Chloro-4-(3-hydroxy-2,2-dimethylpropyl)thio-(5-trifluoromethyl-1,2,4-triazolo)[4,3-a]quinoxaline,
(125) 8-Chloro-4-(2-hydroxy-2-methylpropyl)thio-(5-trifluoromethyl-1,2,4-triazolo)[4,3-a]quinoxaline,
(126) 8-Chloro-4-isobutylthio-6-methoxycarbonyl-(5-trifluoromethyl-1,2,4-triazolo)[4,3-a]quinoxaline,
(127) 8-Chloro-4-(4-fluorophenyl)thio-6-methoxycarbonyl-(5-trifluoromethyl-1,2,4-triazolo)[4,3-a]quinoxaline,
(128) 8-Chloro-4-(4-hydroxybutyl)thio-(5-trifluoromethyl-1,2,4-triazolo)[4,3-a]quinoxaline,
(129) 8-Chloro-4-[[1-[[1-(hydroxymethyl)cyclopropy-1-yl]methylsulfanyl methyl]cyclopropyl-1-yl]methyloxy]-(5-trifluoromethyl-1,2,4-triazolo)[4,3-a]quinoxaline,
(130) 4-[1-(Hydroxy)cyclopropyl-1-yl]methylthio-(5-trifluoromethyl-1,2,4-triazolo)[4,3-a]quinoxaline,
(131) 4-[1-(Hydroxy)cyclopropyl-1-yl]methylthio-8-chloro-(5-trifluoromethyl-1,2,4-triazolo)[4,3-a]quinoxaline,
(132) 4-(3-Hydroxy-2,2-dimethylpropyl)thio-(5-trifluoromethyl-1,2,4-triazolo)[3,4-c]1,4,5-triazanaphthalene,
(133) 4-(4-Hydroxybutyl)thio-(5-trifluoromethyl-1,2,4-triazolo)[3,4-c]1,4,5-triazanaphthalene,
(134) (±)-4-(3-Hydroxybutyl)thio-(5-trifluoromethyl-1,2,4-triazolo)[3,4-c]1,4,5-triazanaphthalene,
(135) 4-Isobutylthio-6,7,8,9-tetrahydro-(5-trifluoromethyl-1,2,4-triazolo)[4,3-a]quinoxaline,
(136) 4-(4-Hydroxybutyl)thio-6,7,8,9-tetrahydro-(5-trifluoromethyl-1,2,4-triazolo)[4,3-a]quinoxaline,
(137) 8-Fluoro-4-(4-hydroxybutyl)thio-(5-trifluoromethyl-1,2,4-triazolo)[4,3-a]quinoxaline,
(138) 8-Fluoro-4-(2-hydroxyethyl)thio-(5-trifluoromethyl-1,2,4-triazolo)[4,3-a]quinoxaline,
(139) (±)-4-(3-Hydroxy-2-methylpropyl)thio-(5-triflororomethyl-1,2,4-triazolo)[3,4-c]1,4,5-triazanaphthalene,
(140) 4-Isobutylthio-8-nitro-(5-trifluoromethyl-1,2,4-triazolo)[4,3-a]quinoxaline,
(141) 4-(3-Hydroxypropyl)thio-8-nitro-(5-trifluoromethyl-1,2,4-triazolo)[4,3-a]quinoxaline,
(142) 4-(4-Hydroxybutyl)thio-8-nitro-(5-trifluoromethyl-1,2,4-triazolo)[4,3-a]quinoxaline,
(143) 4-(5-Hydroxypentyl)thio-(5-trifluoromethyl-1,2,4-triazolo)[3,4-c]1,4,5-triazanaphthalene,
(144) 4-(6-Hydroxyhexyl)thio-(5-trifluoromethyl-1,2,4-triazolo)[3,4-c]1,4,5-triazanaphthalene,
(145) 8-Chloro-4-(5-hydroxypentyl)thio-(5-trifluoromethyl-1,2,4-triazolo)[4,3-a]quinoxaline,
(146) 8-Chloro-4-(6-hydroxyhexyl)thio-(5-trifluoromethyl-1,2,4-triazolo)[4,3-a]quinoxaline,
(147) 4-[1-(Hydroxymethyl)cyclopropyl-1-yl]methylthio-(5-trifluoromethyl-1,2,4-triazolo)[3,4-c]1,4,5-triazanaphthalene,
(148) 8-Fluoro-4-(5-hydroxypentyl)thio-(5-trifluoromethyl-1,2,4-triazolo)[4,3-a]quinoxaline,
(149) 8-Fluoro-4-(6-hydroxyhexyl)thio-(5-trifluoromethyl-1,2,4-triazolo)[4,3-a]quinoxaline,
(150) 4-Isobutylthio-7-methoxycarbonyl-(5-trifluoromethyl-1,2,4-triazolo)[4,3-a]quinoxaline,
(151) 8-Hydroxymethyl-4-isobutylthio-(5-trifluoromethyl-1,2,4-triazolo)[4,3-a]quinoxaline,
(152) 8-Hydroxymethyl-4-(3-hydroxypropyl)thio-(5-trifluoromethyl-1,2,4-triazolo)[4,3-a]quinoxaline,
(153) 8-Chloro-4-[1-(hydroxymethyl)cyclopropyl-1-yl]methylthio-(5-trifluoromethyl-1,2,4-triazolo)[4,3-a]quinoxaline,
(154) (±)-8-Chloro-4-(3-hydroxy-2-methylpropyl)thio-(5-trifluoromethyl-1,2,4-triazolo)[4,3-a]quinoxaline,
(155) 8-Bromo-4-isobutylthio-(5-trifluoromethyl-1,2,4-triazolo)[4,3-a]quinoxaline,
(156) 8-Bromo-4-(3-hydroxypropyl)thio-(5-trituoromethyl-1,2,4-triazolo)[4,3-a]quinoxaline,
(157) 8-Bromo-4-(4-hydroxybutyl)thio-(5-trifuoro methyl-1,2,4-triazolo)[4,3-a]quinoxaline,
(158) 4-Isobutylthio-(5-trifluoromethyl-1,2,4-triazolo([4,3-a]1,4,5-triazanaphthalene,
(159) 4-Cyclopentylthio-6-hydroxymethyl-(5-trifluoromethyl-1,2,4-triazolo)[4,3-a]quinoxaline,
(160) 4-Cyclohexylthio-6-hydroxymethyl-(5-trifluoromethyl-1,2,4-triazolo)[4,3-a]quinoxaline,
(161) (±)-8-Fluoro-4-(2-hydroxypropyl)thio-(5-trifluoromethyl-1,2,4-triazolo)[4,3-a]quinoxaline,
(162) (±)-8-Fluoro-4-(3-hydroxy-2-methylpropyl)thio-(5-trifluoromethyl-1,2,4-triazolo)[4,3-a]quinoxaline,
(163) 4-Butylthio-6-hydroxymethyl-(5-trifluoromethyl-1,2,4-triazolo)[4,3-a]quinoxaline,
(164) 4-(4-Fluorophenyl)thio-6-hydroxymethyl-(5-trifluoromethyl-1,2,4-triazolo)[4,3-a]quinoxaline,
(165) 4-Butylthio-8-chloro-6-hydroxymethyl-(5-trifluoromethyl-1,2,4-triazolo)[4,3-a]quinoxaline,
(166) 8-Chloro-4-cyclohexylthio-6-hydroxymethyl-(5-trifluoromethyl-1,2,4-triazolo)[4,3-a]quinoxaline,
(167) (±)-8-Chloro-4-(2-hydroxypropyl)thio-(5-trifluoromethyl-1,2,4-triazolo)[4,3-a]quinoxaline,
(168) (±)-4-(2-Hydroxypropyl)thio-(5-trifluoromethyl-1,2,4-triazolo)[3,4-c]1,4,5-triazanaphthalene, (169) 6-Hydroxymethyl-4-isobutylthio-(5-trifluoromethyl-1,2,4-triazolo)[4,3-a]quinoxaline,
(170) 8-Chloro-4-(4-fluorophenyl)thio-6-hydroxymethyl-(5-trifluoromethyl-1,2,4-triazolo)[4,3-a]quinoxaline,
(171) 8-Chloro-4-cyclopentylthio-6-hydroxymethyl-(5-trifluoromethyl-1,2,4-triazolo)[4,3-a]quinoxaline,
(172) 4-(4-Hydroxypropyl)thio-8-trifluoromethyl-(5-trifluoromethyl-1,2,4-triazolo)[4,3-a]quinoxaline,
(173) 4-(4-Hydroxybutyl)thio-8-trifluoromethyl-(5-trifluoromethyl-1,2,4-triazolo)[4,3-a]quinoxaline,
(174) 4-(4-Hydroxypentyl)thio-8-trifluoromethyl-(5-trifluoromethyl-1,2,4-triazolo)[4,3-a]quinoxaline,
(175) (±)-cis-8-Fluoro-4-[2-(hydroxymethyl)cyclopropyl]methylthio-(5-trifluoromethyl-1,2,4-triazolo)[4,3-a]quinoxaline,
(176) (±)-cis-8-Chloro-4-[2-(hydroxymethyl)cyclopropyl]methylthio-(5-trifluoromethyl-1,2,4-triazolo)[4,3-a]quinoxaline,
(177) 4-Cyclohexylthio-8-fluoro-6-hydroxymethyl-(5-trifluoromethyl-1,2,4-triazolo)[4,3-a]quinoxaline,
(178) 4-Butylthio-8-fluoro-6-hydroxymethyl-(5-trifluoromethyl-1,2,4-triazolo)[4,3-a]quinoxaline,
(179) 4-Cyclopentylthio-8-fluoro-6-hydroxymethyl-(5-trifluoromethyl-1,2,4-triazolo)[4,3-a]quinoxaline,
(180) 8-Fluoro-4-(4-fluorophenyl)thio-6-hydroxymethyl-(5-trifluoromethyl-1,2,4-triazolo)[4,3-a]quinoxaline,
(181) 8-Fluoro-6-hydroxymethyl-4-isobutylthio-(5-trifluoromethyl-1,2,4-triazolo)[4,3-a]quinoxaline,
(182) 8-Chloro-4-allylthio-(5-trifluoromethyl-1,2,4-triazolo)[4,3-a]quinoxaline,
(183) 4-Allylthio-8-fluoro-(5-trifluoromethyl-1,2,4-triazolo)[4,3-a]quinoxaline,
(184) 4-Allylthio-(5-trifluoromethyl-1,2,4-triazolo)[3,4-c]1,4,5-triazanaphthalene,
(185) (±)-cis-4-[2-(Hydroxymethyl)cyclopropyl]methylthio-(5-trifluoromethyl-1,2,4-triazolo)[3,4-c]1,4,5-triazanaphthalene,
(186) (±)-trans-8-Fluoro-4-[2-(hydroxymethyl)cyclopropyl]methylthio-(5-trifluoromethyl-1,2,4-triazolo)[4,3-a]quinoxaline,
(187) (±)-trans-8-Chloro-4-[2-(hydroxymethyl)cyclopropyl]methylthio-(5-trifluoromethyl-1,2,4-triazolo)[4,3-a]quinoxaline,
(188) (±)-trans-4-[2-(Hydroxymethyl)cyclopropyl]methylthio-(5-trifluoromethyl-1,2,4-triazolo)[3,4-c]1,4,5-triazanaphthalene,
(189) 4-Cyclopropylmethylthio-8-hydroxymethyl-(5-trifluoromethyl-1,2,4-triazolo)[4,3-a]quinoxaline,
(190) (±)-8-Fluoro-4-(2-hydroxymethylbutyl)thio-(5-trifluoromethyl-1,2,4-triazolo)[4,3-a]quinoxaline,
(191) (±)-8-Chloro-4-(2-hydroxymethylbutyl)thio-(5-trifluoromethyl-1,2,4-triazolo)[4,3-a]quinoxaline,
(192) (±)-4-(2-Hydroxymethylbutyl)thio-(5-trifluoromethyl-1,2,4-triazolo)[3,4-c]1,4,5-triazanaphthalene,
(193) 4-(Cyclopropylmethyl)thio-7-methoxycarbonyl-(5-trifluoromethyl-1,2,4-triazolo)[3,4-c]1,4,5-triazanaphthalene,
(194) 4-Cyclopentylthio-8-hydroxymethyl-(5-trifluoromethyl-1,2,4-triazolo)[4,3-a]quinoxaline,
(195) 4-Cyclohexylthio-8-hydroxymethyl-(5-trifluoromethyl-1,2,4-triazolo)[4,3-a]quinoxaline,
(196) 4-Butylthio-8-hydroxymethyl-(5-trifluoromethyl-1,2,4-triazolo)[4,3-a]quinoxaline,
(197) 8-Chloro-4-(cyclopropylmethyl)thio-(5-trifluoromethyl-1,2,4-triazolo)[4,3-a]quinoxaline,
(198) 4-(Cyclopropylmethyl)thio-8-fluoro-(5-trifluoromethyl-1,2,4-triazolo)[4,3-a]quinoxaline,
(199) 4-(Cyclopropylmethyl)thio-(5-trifluoromethyl-1,2,4-triazolo)[3,4-c]1,4,5-triazanaphthalene,
(200) 4-Cyclopropylmethylthio-8-fluoro-6-hydroxymethyl-(5-trifluoromethyl-1,2,4-triazolo)[4,3-a]quinoxaline,
(201) 4-Phenylthio-7-amino-(5-trifluoromethyl-1,2,4-triazolo)[4,3-a]quinoxaline,
(202) 6-Amino-4-phenylthio-(5-trifluoromethyl-1,2,4-triazolo)[4,3-a]quinoxaline,
(203) 8-Amino-4-phenylthio-(5-trifluoromethyl-1,2,4-triazolo)[4,3-a]quinoxaline,
(204) 4-Benzyl-(5-trifluoromethyl-1,2,4-triazolo)[4,3-a]quinoxaline,
(205) 4-Isobutyl-(5-trifluoromethyl-1,2,4-triazolo)[4,3-a]quinoxaline,
(206) 4-Methyl-(5-trifluoromethyl-1,2,4-triazolo)[4,3-a]quinoxaline,
(207) 4-Isopropyl-(5-trifluoromethyl-1,2,4-triazolo)[4,3-a]quinoxaline,
(208) 4-Phenyl-(5-trifluoromethyl-1,2,4-triazolo)[4,3-a]quinoxaline,
(209) 4-(Thiophen-3-yl)-(5-trifluoromethyl-1,2,4-triazolo)[4,3-a]quinoxaline,
(210) 4-(Furan-3-yl)-(5-trifluoromethyl-1,2,4-triazolo)[4,3-a]quinoxaline,
(211) 4-(4-Dimethylaminophenyl)-(5-trifluoromethyl-1,2,4-triazolo)[4,3-a]quinoxaline,
(212) 4-Phenylsulfinyl-(5-trifluoromethyl-1,2,4-triazolo)[4,3-a]quinoxaline,
(213) 4-Isopropylsulfinyl-(5-trifluoromethyl-1,2,4-triazolo)[3,4-c]1,4,5-triazanaphthalene,
(214) 6-t-Butylamino-4-phenylthio-(5-trifluoromethyl-1,2,4-triazolo)[4,3-a]quinoxaline,
(215) 6-Acetylamino-4-phenylthio-(5-trifluoromethyl-1,2,4-triazolo)[4,3-a]quinoxaline,
(216) 6-Methylamino-4-phenylthio-(5-trifluoromethyl-1,2,4-triazolo)[4,3-a]quinoxaline,
(217) 8-Methylamino-4-phenylthio-(5-trifluoromethyl-1,2,4-triazolo)[4,3-a]quinoxaline,
(218) 4-Isopropylthiomethyl-(5-trifluoromethyl-1,2,4-triazolo)[4,3-a]quinoxaline,
(219) 4-Cyclopentylthiomethyl-(5-trifluoromethyl-1,2,4-triazolo)[4,3-a]quinoxaline,
(220) 4-Phenylthiomethyl-(5-trifluoromethyl-1,2,4-triazolo)[4,3-a]quinoxaline,
(221) 8-Hydroxymethyl-4-isopropylthio-(5-trifluoromethyl-1,2,4-triazolo)[4,3-a]quinoxaline,
(222) 7-Hydroxymethyl-4-phenoxy-(5-trifluoromethyl-1,2,4-triazolo)[4,3-a]quinoxaline,
(223) 8-Hydroxymethyl-4-phenoxy-(5-trifluoromethyl-1,2,4-triazolo)[4,3-a]quinoxaline,
(224) 7-Hydroxymethyl-4-phenylthio-(5-trifluoromethyl-1,2,4-triazolo)[4,3-a]quinoxaline,
(225) 8-Hydroxymethyl-4-phenylthio-(5-trifluoromethyl-1,2,4-triazolo)[4,3-a]quinoxaline,
(226) 6-Hydroxymethyl-4-isopropylthio-(5-trifluoromethyl-1,2,4-triazolo)[4,3-a]quinoxaline,
(227) 6-Hydroxymethyl-4-phenylthio-(5-trifluoromethyl-1,2,4-triazolo)[4,3-a]quinoxaline,
(228) 6-Hydroxymethyl-4-isopropylthio-(5-trifluoromethyl-1,2,4-triazolino)[4,3-a]quinoxaline,
(229) 4-(4-Fluorophenyl)thio-8-hydroxymethyl-(5-trifluoromethyl-1,2,4-triazolo)[4,3-a]quinoxaline,
(230) 8-Chloro-6-hydroxymethyl-4-isobutylthio-(5-trifluoromethyl-1,2,4-triazolo)[4,3-a]quinoxaline,
(231) 7-Hydroxymethyl-4-isobutylthio-(5-trifluoromethyl-1,2,4-triazolo)[4,3-a]quinoxaline,
(232) 4-(Cyclopropylmethyl)thio-7-hydroxymethyl-(5-trifluoromethyl-1,2,4-triazolo)[3,4-c]1,4,5-triazanaphthalene, (233) 8-Formyl-4-isopropylthio-(5-trifluoromethyl-1,2,4-triazolo)[4,3-a]quinoxaline,
(234) 8-Formyl-4-isobutylthio-(5-trifluoromethyl-1,2,4-triazolo)[4,3-a]quinoxaline,
(235) 4-Isopropylthio-8-(2-methoxycarbonylethenyl)-(5-trifluoromethyl-1,2,4-triazolo)[4,3-a]quinoxaline,
(236) 4-Isobutylthio-8-(3-oxo-1-butenyl)-(5-trifluoromethyl-1,2,4-triazolo)[4,3-a]quinoxaline,
(237) 8-(3-Hydroxy-1-propenyl)-4-isopropylthio-(5-triflueromethyl-1,2,4-triazolo)[4,3-a]quinoxaline,
(238) 8-Vinyl-4-isobutylthio-(5-trifluoromethyl-1,2,4-triazolo)[4,3-a]quinoxaline,
(239) 8-(2-Hydroxyethyl)-4-isobutylthio-(5-trifluoromethyl-1,2,4-triazolo)[4,3-a]quinoxaline,
(240) 8-(1-Hydroxyethyl)-4-isobutylthio-(5-trifluoromethyl-1,2,4-triazolo)[4,3-a]quinoxaline,
(241) 6-(2-Hydroxyethyl)-4-isobutylthio-(5-trifluoromethyl-1,2,4-triazolo)[4,3-a]quinoxaline,
(242) 4-Cyclopentylthio-8-(2-hydroxyethyl)-(5-trifluoromethyl-1,2,4-triazolo)[4,3-a]quinoxaline,
(243) 4-Cyclohexylthio-8-(2-hydroxyethyl)-(5-trifluoromethyl-1,2,4-triazolo)[4,3-a]quinoxaline,
(244) 4-Butylthio-8-(2-hydroxyethyl)-(5-trifluoromethyl-1,2,4-triazolo)[4,3-a]quinoxaline,
(245) 8-Acetyl-4-isobutylthio-(5-trifluoromethyl-1,2,4-triazolo)[4,3-a]quinoxaline,
(246) 6-Bromomethyl-4-isopropylthio-(5-trifluoromethyl-1,2,4-triazolo)[4,3-a]quinoxaline,
(247) 6-Aminomethyl-4-isopropylthio-(5-trifluoromethyl-1,2,4-triazolo)[4,3-a]quinoxaline,
(248) 8-Aminomethyl-4-isopropylthio-(5-trifluoromethyl-1,2,4-triazolo)[4,3-a]quinoxaline,
(249) 6-Dimethylaminomethyl-4-isopropylthio-(5-trifluoromethyl-1,2,4-triazolo)[4,3-a]quinoxaline,
(250) 8-Dimethylaminomethyl-4-isopropylthio-(5-trifluoromethyl-1,2,4-triazolo)(4,3-a]quinoxaline,
(251) 4-Methoxy-8-methoxycarbonyl-(5-trifluoromethyl-1,2,4-triazolo)[4,3-a]quinoxaline,
(252) 4-Methoxy-8-(2-methoxycarbonylethenyl)-(5-trifluoromethyl-1,2,4-triazolo)[4,3-a]quinoxaline,
(253) 4-Methoxy-8-(2-methoxycarbonylethyl)-(5-trifluoromethyl-1,2,4-triazolo)[4,3-a]quinoxaline,
(254) 4-Isobutyl-8-(2-methoxycarbonylethyl)-(5-trifluoromethyl-1,2,4-triazolo)[4,3-a]quinoxaline,
(255) 8-(3-Hydroxypropyl)-4-(3-hydroxypropyl)thio-(5-trifluoromethyl-1,2,4-triazolo[4,3-a]quinoxaline,
(256) 8-(3-Hydroxypropyl)-4-isobutylthio-(5-trifluoromethyl-1,2,4-triazolo)[4,3-a]quinoxaline,
(257) 4-Cyclohexylthio-8-(3-hydroxypropyl)-(5-trifluoromethyl-1,2,4-triazolo)[4,3-a]quinoxaline,
(258) 4-Butylthio-8-(3-hydroxypropyl)-(5-trifluoromethyl-1,2,4-triazolo)[4,3-a]quinoxaline,
(259) 4-(4-Fluorophenyl)thio-8-(3-hydroxypropyl)-(5-trifluoromethyl-1,2,4-triazolo)[4,3-a]quinoxaline,
(260) 4-Cyclopentylthio-8-(3-hydroxypropyl)-(5-trifluoromethyl-1,2,4-triazolo)[4,3-a]quinoxaline,
(261) 4-Isobutylthio-8-nitrile-(5-trifluoromethyl-1,2,4-triazolo)[4,3-a]quinoxaline,
(262) 4-Isopropylthio-8-nitrile-(5-trifluoromethyl-1,2,4-triazolo)[4,3-a]quinoxaline,
(263) 4-(4-hydroxybutyl)thio-8-nitrile-(5-trifluoromethyl-1,2,4-triazolo)[4,3-a]quinoxaline,
(264) 4-(3-Hydroxypropyl)thio-8-nitrile-(5-trifluoromethyl-1,2,4-triazolo)[4,3-a]quinoxaline,
(265) 8-Carbamoyl-4-isopropyltnio-(5-trifluoromethyl-1,2,4-triazolo)[4,3-a]quinoxaline,
(266) 8-(N,N-Dimethylcarbamoyl)-4-phenylthio-(5-trifluoromethyl-1,2,4-triazolo)[4,3-a]quinoxaline,
(267) 8-Carbamoyl-4-phenylthio-(5-trifluoromethyl-1,2,4-triazolo)[4,3-a]quinoxaline,
(268) 8-(N-Phenylcarbamoyl)-4-phenylthio-(5-trifluoromethyl-1,2,4-triazolo)[4,3-a]quinoxaline,
(269) 4-Isopropylthio-8-(N-phenylcarbamoyl)-(5-trifluoromethyl-1,2,4-triazolo)[4,3-a]quinoxaline,
(270) 8-(N,N-Dimethylcarbamoyl)-4-isopropylthio-(5-trifluoromethyl-1,2,4-triazolo)[4,3-a]quinoxaline,
(271) 7-Carbamoyl-4-isopropylthio-(5-trifluoromethyl-1,2,4-triazolo)[4,3-a]quinoxaline,
(272) 8-[N-(2-Hydroxyethyl)carbamoyl]-4-isopropylthio-(5-trifluoromethyl-1,2,4-triazolo)[4,3-a]quinoxaline,
(273) 4-Isopropylthio-8-[N-(2-morpholinoethyl)carbamoyl]-(5-trifluoromethyl-1,2,4-triazolo)[4,3-a]quinoxaline, or
(274) 8-[N-(Dimethylaminomethylene) carbamoyl]-4-isopropylthio-(5-trifluoro methyl-1,2,4-triazolo)[4,3-a]quinoxaline.

7. A method according to claim 1, wherein the disorders mediated by cellular adhesion are selected from the group consisting of inflammation, rheumatoid arthritis, allergies, asthma, atopic dermatitis psoriasis, suppression of ischemia reperfusion injury, nephritis, hepatitis, multiple sclerosis, ulcerative colitis, adult respiratory distress syndrome, suppression of transplant rejection, sepsis, diabetes, autoimmune diseases, tumor metastasis, arteriosclerosis and AIDS.

8. A method of preventing and treating disorders mediated by cellular adhesion according to claim 1, wherein the fused pyrazine derivative of formula (I) is selected from:
(1) 4-Phenylthio-8-chloro(5-trifluoromethyl-1,2,4-triazolo)-[4,3-a]quinoxaline,
(2) 4-(4-Chlorophenyl)thio(5-trifluoromethyl-1,2,4-triazolo)-[4,3-a]quinoxaline,
(3) 4-Phenylmethylthio(5-trifluoromethyl-1,2,4-triazolo)-[4,3-a]quinoxaline,
(4) 4-(Pyridin-2-yl)thio(5-trifluoromethyl-1,2,4-triazolo)-[4,3-a]quinoxaline,
(5) 4-Phenylthio(5-trifluoromethyl-1,2,4-triazolo)-[4,3-a]quinoxaline,
(6) 4-(4-Methoxyphenyl)thio(5-trifluoromethyl-1,2,4-triazolo)-[4,3-a]quinoxaline,
or non-toxic salts thereof as active ingredient.

* * * * *